(12) United States Patent
Zhuo et al.

(10) Patent No.: US 11,859,215 B2
(45) Date of Patent: Jan. 2, 2024

(54) POLYNUCLEOTIDES ENCODING ORNITHINE TRANSCARBAMYLASE FOR THE TREATMENT OF UREA CYCLE DISORDERS

(71) Applicant: ModernaTX, Inc., Cambridge, MA (US)

(72) Inventors: Zhijian Zhuo, Andover, MA (US); Andrea Lea Frassetto, Haverhill, MA (US); Paolo G. V. Martini, Boston, MA (US); Vladimir Presnyak, Manchester, NH (US); Patrick Finn, Franklin, MA (US)

(73) Assignee: ModernaTX, Inc., Cambridge, MA (US)

(*) Notice: Subject to any disclaimer, the term of this patent is extended or adjusted under 35 U.S.C. 154(b) by 576 days.

(21) Appl. No.: 16/765,604

(22) PCT Filed: Nov. 21, 2018

(86) PCT No.: PCT/US2018/062226
§ 371 (c)(1),
(2) Date: May 20, 2020

(87) PCT Pub. No.: WO2019/104152
PCT Pub. Date: May 31, 2019

(65) Prior Publication Data
US 2020/0299652 A1 Sep. 24, 2020

Related U.S. Application Data

(60) Provisional application No. 62/765,354, filed on Aug. 20, 2018, provisional application No. 62/590,157, filed on Nov. 22, 2017.

(51) Int. Cl.
| A61P 7/00 | (2006.01) |
| C12N 9/10 | (2006.01) |
| A61K 9/00 | (2006.01) |
| A61K 9/51 | (2006.01) |

(52) U.S. Cl.
CPC .......... *C12N 9/1018* (2013.01); *A61K 9/0019* (2013.01); *A61K 9/5123* (2013.01); *A61P 7/00* (2018.01); *C12Y 201/03003* (2013.01)

(58) Field of Classification Search
CPC ....... C12N 9/1018; A61P 7/00; A61K 9/0019; A61K 9/5123; C12Y 201/03003
See application file for complete search history.

(56) References Cited

U.S. PATENT DOCUMENTS

| 6,165,763 A | 12/2000 | Brown et al. |
| 8,691,966 B2 | 4/2014 | Kariko et al. |
| 9,821,114 B2 | 11/2017 | Aquino et al. |
| 2010/0047261 A1 | 2/2010 | Hoerr et al. |
| 2013/0259924 A1* | 10/2013 | Bancel .................... A61P 31/10 530/358 |
| 2018/0126003 A1 | 5/2018 | Hoerr et al. |
| 2018/0311379 A1 | 11/2018 | Fotin-Mleczek |

FOREIGN PATENT DOCUMENTS

| JP | 2015518705 | 7/2015 |
| JP | 2017512466 | 5/2017 |
| JP | 2017537613 | 12/2017 |
| WO | WO2009127230 | 10/2009 |
| WO | WO2011068810 | 6/2011 |
| WO | WO2012075040 | 6/2012 |
| WO | WO2012170889 | 12/2012 |
| WO | WO2013149140 | 10/2013 |
| WO | WO2013149141 | 10/2013 |
| WO | WO2013151666 | 10/2013 |
| WO | WO-2013151666 A2 * | 10/2013 ............. A61K 38/17 |
| WO | WO2013185067 | 12/2013 |
| WO | WO2013185069 | 12/2013 |
| WO | WO2014144196 | 9/2014 |
| WO | WO2014152513 | 9/2014 |
| WO | WO2015017519 | 2/2015 |
| WO | WO2015021448 | 2/2015 |
| WO | WO2015061467 | 4/2015 |
| WO | WO2015138348 | 9/2015 |

(Continued)

OTHER PUBLICATIONS

Bell et al., "Effects of self-complementarity, Codon optimization, transgene, and dose on liver transduction with AAV8", Human Gene Therapy Methods, Nov. 2016, 27(6):228-237.
Brandt et al., "Messenger RNA (mRNA) delivery to the liver corrects ornithine transcarbamylase deficiency in a mouse disease model", Molecular Genetics and Metabolism, Feb. 2017, 120(1-2):D31.
Caldovic et al., "Genotype-Phenotype Correlations in Ornithine Transcarbamylase Deficiency: A Mutation Update", Journal of Genetics and Genomics, 2015, 45(5):181-194.
Hanson et al., "Codon optimality, bias and used in translation and mRNA decay", Nat. Rev. Mol. Cell Biol., Oct. 2017, 19(1):20-30.
International Preliminary Report on Patentability in International Application No. PCT/US2018/062226, dated Jun. 4, 2020, 16 pages.

(Continued)

*Primary Examiner* — Neil P Hammell
*Assistant Examiner* — Kyle Thomas Rega
(74) *Attorney, Agent, or Firm* — Fish & Richardson P.C.

(57) ABSTRACT

This disclosure relates mRNA therapy for the treatment of ornithine transcarbamylase deficiency (OTCD). mRNAs for use in the invention, when administered in vivo, encode human ornithine transcarbamylase (OTC), isoforms thereof, functional fragments thereof, and fusion proteins comprising OTC. mRNAs of the invention are preferably encapsulated in lipid nanoparticles (LNPs) to effect efficient delivery to cells and/or tissues in subjects, when administered thereto. mRNA therapies of the invention increase and/or restore deficient levels of OTC expression and/or activity in subjects. mRNA therapies of the invention further decrease levels of toxic ammonia associated with deficient OTC activity in subjects.

29 Claims, 20 Drawing Sheets
Specification includes a Sequence Listing.

(56) References Cited

FOREIGN PATENT DOCUMENTS

| WO | WO2015138357 | 9/2015 |
|---|---|---|
| WO | WO2016070166 | 5/2016 |
| WO | WO2016118697 | 7/2016 |
| WO | WO2017049245 | 3/2017 |
| WO | WO2017100551 | 6/2017 |
| WO | WO2017153936 | 9/2017 |
| WO | WO2017167910 | 10/2017 |
| WO | WO2017177169 | 10/2017 |
| WO | WO2017191274 | 11/2017 |
| WO | WO2017201349 | 11/2017 |
| WO | WO2017218524 | 12/2017 |
| WO | WO2018035377 | 2/2018 |
| WO | WO2018089846 | 5/2018 |
| WO | WO2018126084 | 7/2018 |
| WO | WO2018127382 | 7/2018 |
| WO | WO2018157133 | 8/2018 |
| WO | WO2018157141 | 8/2018 |
| WO | WO2018157153 | 8/2018 |
| WO | WO2018165257 | 9/2018 |

OTHER PUBLICATIONS

International Search Report and Written Opinion in International Application No. PCT/US2018/062226, dated May 17, 2019, 29 pages.
Tavernier et al., "mRNA as gene therapeutic: How to control protein expression", Journal of Controlled Release, Oct. 2010, 150(3):238-247.
Yamamoto et al., "Current prospects for mRNA gene delivery", European Journal of Pharmaceutics and Biopharmaceutics, Oct. 2008, 71(3):484-489.
Youn et al., "Modified mRNA as an alternative to plasmid DNA (pDNA) for transcript replacement and vaccination therapy", Expert Opinion on Biological Therapy, Jun. 2015, 15(9):1337-1348.
Prieve et al., "Correction of Ornithine Transcarbamylase Deficiency Following Treatment with PhaseRx's Hybrid mRNA Technology™ Delivery System and Safety Evaluation in Rats and Non-Human Primates," Molecular Therapy, May 2017,25(5):191.
Prieve et al., "Targeted mRNA Therapy for Ornithine Transcarbamylase Deficiency," Molecular Therapy, Mar. 2018, 26(3):801-813.

* cited by examiner

| Group | Mouse Genotype | Treatment | Dose Level | N (28 days) | N (24 hours) |
|---|---|---|---|---|---|
| 1 | Spf-ash | eGFP | 1 mg/kg | 10 | 4 |
| 2 | Spf-ash | OTC | 0.05 mg/kg | 10 | 4 |
| 3 | Spf-ash | OTC | 0.2 mg/kg | 10 | 4 |
| 4 | Spf-ash | OTC | 0.5 mg/kg | 10 | 4 |
| 5 | Spf-ash | OTC | 1 mg/kg | 10 | 4 |

Animals:
Spf-ash

ROA:
IV bolus mRNA:
OTC 12

Formulation:
Compound II/DMG (PBS)

Dosing Schedule:
Single Dose

Measurements: Bodyweight, survival, plasma NH3, liver expression and activity

FIGURE 10

POLYNUCLEOTIDES ENCODING ORNITHINE TRANSCARBAMYLASE FOR THE TREATMENT OF UREA CYCLE DISORDERS

CROSS-REFERENCE TO RELATED APPLICATIONS

This application claims priority to U.S. Provisional Appl. No. 62/590,157, filed Nov. 22, 2017, and U.S. Provisional Appl. No. 62/765,354, filed Aug. 20, 2018. The content of both applications are incorporated by reference herein in their entirety.

SEQUENCE LISTING

This application contains a Sequence Listing that has been submitted electronically as an ASCII text file named "SequenceListing.txt." The ASCII text file, created on Feb. 11, 2019, is 153,238 bytes in size. The material in the ASCII text file is hereby incorporated by reference in its entirety.

BACKGROUND

Ornithine transcarbamylase deficiency (OTCD) is a rare, X-linked recessive disorder caused by mutations in ornithine transcarbamylase (OTC) that eliminate or reduce OTC function. OTCD is responsible for nearly half of all inherited disorders that affect the urea cycle. Caldovic et al., J. Genet. Genomics 42(5):181-194 (2015). OTCD symptoms can vary substantially. OTC defects can cause hyperammonemic episodes. The toxic effects of ammonia in the brain can lead to recurrent vomiting, neurobehavioral changes, seizures, and even death. Most patients with OTCD are hemizygous males lacking or severely deficient for OTC in the liver, who present with acute hyperammonemia, ataxia, and lethargy within the first week following birth. Heterozygous females and males with partial defects in OTC can present with symptoms later in life, including in adulthood. OTCD is estimated to have a prevalence of about 1:62,000 to 1:77,000 in the United States.

OTC is a mitochondrial urea cycle enzyme that catalyzes a reaction between carbamyl phosphate and ornithine to form citrulline and phosphate. This is essential for the conversion of ammonia, a neurotoxic product of protein catabolism, into non-toxic urea. Human OTC (NM_000531.5) encodes a protein (NP_000522.3) that is 354 amino acids in length. It is expressed in the liver, and localizes within the mitochondria and cytosol of cells. An N-terminal leader sequence is removed in the mitochondria, to form a 322 amino acid mature protein. OTC is a homotrimer with three active sites.

OTC patients exhibit elevated levels of plasma ammonia, elevated plasma glutamine, low or absent plasma citrulline, and elevated urinary orotic acid. These biochemical markers can be used to distinguish OTCD from other urea cycle disorders. Treatment options are limited for OTCD, as there are no commercial therapeutics for the disease, and only liver transplantation is considered curative.

In view of the significant problems associated with existing OTCD treatments, there is an unmet need for improved treatment for OTCD.

SUMMARY

The present invention provides messenger RNA (mRNA) therapeutics for the treatment of ornithine transcarbamylase deficiency (OTCD) and urea cycle disorders. The mRNA therapeutics of the invention are particularly well-suited for the treatment of OTCD as the technology provides for the intracellular delivery of mRNA encoding OTC followed by de novo synthesis of functional OTC protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modification to reduce the innate immune response and sequence optimization, in particular, within the open reading frame (ORF) of therapeutic mRNAs encoding OTC to enhance protein expression.

In further embodiments, the mRNA therapeutic technology of the instant invention also features delivery of mRNA encoding OTC via a lipid nanoparticle (LNP) delivery system. The instant invention features ionizable lipid-based LNPs, which have improved properties when combined with mRNA encoding OTC and administered in vivo, for example, cellular uptake, intracellular transport and/or endosomal release or endosomal escape. The LNP formulations of the invention also demonstrate reduced immunogenicity associated with the in vivo administration of LNPs.

In certain aspects, the invention relates to compositions and delivery formulations comprising a polynucleotide, e.g., a ribonucleic acid (RNA), e.g., a mRNA, encoding OTC and methods for treating OTCD in a human subject in need thereof by administering the same.

The present disclosure provides a pharmaceutical composition comprising a lipid nanoparticle encapsulated mRNA that comprises an open reading frame (ORF) encoding an OTC polypeptide, wherein the composition is suitable for administration to a human subject in need of treatment for OTCD.

The present disclosure further provides a pharmaceutical composition comprising: (a) a mRNA that comprises (i) an open reading frame (ORF) encoding an OTC polypeptide, wherein the ORF comprises at least one chemically modified nucleobase, sugar, backbone, or any combination thereof and (ii) an untranslated region (UTR) comprising a microRNA (miRNA) binding site; and (b) a delivery agent, wherein the pharmaceutical composition is suitable for administration to a human subject in need of treatment for OTC.

In one aspect, the disclosure features a pharmaceutical composition comprising an mRNA comprising an open reading frame (ORF) encoding an ornithine transcarbamylase (OTC) polypeptide, wherein the composition when administered as a single intravenous dose to a human subject in need thereof is sufficient to:
  (i) increase the level of OTC activity in liver tissue to within at least 2%, at least 5%, at least 10%, at least 20%, at least 30%, at least 40%, at least 50%, at least 60%, at least 70%, at least 80%, at least 90%, or at least 100% of normal OTC activity level for at least 12 hours, at least 24 hours, at least 48 hours, at least 72 hours, at least 96 hours, at least 120 hours, at least 1 week, at least 2 weeks, at least 3 weeks, or at least 4 weeks post-administration;
  (ii) increase the level of OTC activity in liver tissue at least 1.5-fold, at least 2-fold, at least 3-fold, at least 4-fold, at least 5-fold, at least 10-fold, at least 20-fold, or at least 50-fold compared to the subject's baseline OTC activity level or a reference OTC activity level in a human subject having ornithine transcarbamylase deficiency (OTCD) for at least 12 hours, at least 24 hours, at least 48 hours, at least 72 hours, at least 96 hours, at least 120 hours, at least 1 week, at least 2 weeks, at least 3 weeks, or at least 4 weeks post-administration;

(iii) reduce RBC, plasma, serum and/or liver levels of ammonia at least 20%, at least 30%, at least 40%, at least 50%, at least 60%, at least 70%, at least 80%, at least 90%, or at least 100% compared to the subject's baseline RBC, plasma, serum and/or liver ammonia level or a reference RBC, plasma, serum and/or liver ammonia level in a human subject having ornithine transcarbamylase deficiency (OTCD) for at least 12 hours, at least 24 hours, at least 48 hours, at least 72 hours, at least 96 hours, at least 120 hours, at least 1 week, at least 2 weeks, at least 3 weeks, or at least 4 weeks post-administration;

(iv) reduce plasma, serum, and/or urine levels of orotic acid at least 20%, at least 30%, at least 40%, at least 50%, at least 60%, at least 70%, at least 80%, at least 90%, or at least 100% compared to the subject's baseline plasma, serum, or urine orotic acid level or a reference plasma, serum, or urine orotic level in a human subject having ornithine transcarbamylase deficiency (OTCD) for at least 12 hours, at least 24 hours, at least 48 hours, at least 72 hours, at least 96 hours, at least 120 hours, at least 1 week, at least 2 weeks, at least 3 weeks, or at least 4 weeks post-administration;

(v) reduce RBC, plasma, serum and/or liver levels of ammonia at least 1.5-fold, at least 2-fold, at least 5-fold, at least 10-fold, at least 20-fold, or at least 50-fold as compared to the subject's baseline RBC, plasma, serum and/or liver ammonia level or a reference RBC, plasma, serum and/or liver ammonia level in a patient with ornithine transcarbamylase deficiency (OTCD) for at least 12 hours, at least 24 hours, at least 48 hours, at least 72 hours, at least 96 hours, at least 120 hours, at least 1 week, at least 2 weeks, at least 3 weeks, or at least 4 weeks post-administration;

(vi) reduce plasma, serum, and/or urine level of orotic acid at least 1.5-fold, at least 2-fold at least 5-fold, at least 10-fold, at least 20-fold or at least 50-fold as compared to the subject's baseline plasma, serum, and/or urine orotic acid level or a reference plasma, serum, and/or urine orotic acid level in a patient with ornithine transcarbamylase deficiency (OTCD) for at least 12 hours, at least 24 hours, at least 48 hours, at least 72 hours, at least 96 hours, at least 120 hours, at least 1 week, at least 2 weeks, at least 3 weeks, or at least 4 weeks post-administration;

(vii) increase body weight of the human subject by at least 2%, at least 5%, at least 10%, at least 15%, at least 20%, at least 25%, or at least 30% of pre-treatment body weight by at least 12 hours, at least 24 hours, at least 48 hours, at least 72 hours, at least 96 hours, at least 5 days, at least 7 days, at least 14 days, at least 24 days, at least 48 days, or at least days post-administration; and/or (viii) maintain body weight of the human subject to within at least 80%, at least 85%, at least 90%, at least 95%, at least 98%, or at least 99% of pre-treatment body weight for at least 12 hours, at least 24 hours, at least 48 hours, at least 72 hours, at least 96 hours, at least 5 days, at least 7 days, at least 14 days, at least 24 days, at least 48 days, or at least days post-administration.

In some embodiments of this aspect, the pharmaceutical composition comprises a delivery agent. In some instances, the delivery agent comprises a lipid nanoparticle comprising: (i) Compound II, (ii) Cholesterol, and (iii) PEG-DMG or Compound I; (i) Compound VI, (ii) Cholesterol, and (iii) PEG-DMG or Compound I; (i) Compound II, (ii) DSPC or DOPE, (iii) Cholesterol, and (iv) PEG-DMG or Compound I; or (i) Compound VI, (ii) DSPC or DOPE, (iii) Cholesterol, and (iv) PEG-DMG or Compound I.

In some embodiments of this aspect, the OTC polypeptide comprises the amino acid sequence set forth in SEQ ID NO:1.

In some embodiments of this aspect, the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs:2 and 5-29.

In some embodiments of this aspect, the mRNA comprises a microRNA (miR) binding site. In certain instances, the microRNA is expressed in an immune cell of hematopoietic lineage or a cell that expresses TLR7 and/or TLR8 and secretes pro-inflammatory cytokines and/or chemokines. In some instances, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof. In certain instances, the microRNA binding site is for a microRNA selected from the group consisting of miR126-3p, miR-142-3p, miR-142-5p, miR-155, or any combination thereof. In one instance, the microRNA binding site is a miR-142-3p binding site. In some instances, the microRNA binding site is located in the 3' UTR of the mRNA.

In some embodiments of this aspect, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:4.

In some embodiments of this aspect, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:4, SEQ ID NO:111, SEQ ID NO:150, SEQ ID NO:175, SEQ ID NO:177, SEQ ID NO:178, SEQ ID NO:198, or SEQ ID NO:199.

In some embodiments of this aspect, the mRNA comprises a 5' UTR comprising a nucleic acid sequence at least 90%, at least about 95%, at least about 96%, at least about 97%, at least about 98%, at least about 99%, or 100% identical to a 5' UTR sequence of SEQ ID NO:3.

In some embodiments of this aspect, the mRNA comprises a 5' UTR comprising a nucleic acid sequence at least 90%, at least about 95%, at least about 96%, at least about 97%, at least about 98%, at least about 99%, or 100% identical to a 5' UTR sequence of SEQ ID NO:3, SEQ ID NO:191, SEQ ID NO:196, or SEQ ID NO:197.

In some embodiments of this aspect, the mRNA comprises a 5' terminal cap. In certain instances, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azi-doguanosine, Cap2, Cap4, 5' methylG cap, or an analog thereof In some embodiments, the mRNA comprises a poly-A region. In certain instances, the poly-A region is at least about 10, at least about 20, at least about 30, at least about at least about 50, at least about 60, at least about 70, at least about 80, at least about nucleotides in length, or at least about 100 nucleotides in length. In some instances, the poly-A region has about 10 to about 200, about 20 to about 180, about 50 to about 160, about 70 to about 140, or about 80 to about 120 nucleotides in length.

In some embodiments, the mRNA comprises at least one chemically modified nucleobase, sugar, backbone, or any combination thereof. In certain instances, the at least one chemically modified nucleobase is selected from the group consisting of pseudouracil (ψ), N1 methylpseudouracil (m1ψ), 1-ethylpseudouracil, 2-thiouracil (s2U), 4'-thiouracil, 5-methyluracil, 5-methoxyuracil, and any combination thereof. In some instances, at least about 25%, at least about 30%, at least about 40%, at least about 50%, at least about 60%, at least about 70%, at least about 80%, at least about 90%, at least about 95%, at least about 99%, or 100% of the uracils are chemically modified to N1-methylpseudouracils.

In some embodiments, at least about 25%, at least about 30%, at least about 40%, at least about 50%, at least about 60%, at least about 70%, at least about 80%, at least about 90%, at least about 95%, at least about 99%, or 100% of the guanines are chemically modified.

In some embodiments, at least about 25%, at least about 30%, at least about 40%, at least about 50%, at least about 60%, at least about 70%, at least about 80%, at least about 90%, at least about 95%, at least about 99%, or 100% of the cytosines are chemically modified.

In some embodiments, at least about 25%, at least about 30%, at least about 40%, at least about 50%, at least about 60%, at least about 70%, at least about 80%, at least about 90%, at least about 95%, at least about 99%, or 100% of the adenines are chemically modified.

In some embodiments, the human subject has ornithine transcarbamylase deficiency (OTCD).

In another aspect, the disclosure features a polynucleotide comprising an mRNA comprising: (i) a 5' UTR; (ii) an open reading frame (ORF) encoding a human ornithine transcarbamylase (OTC) polypeptide, wherein the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs:2 and 5-29; (iii) a stop codon; and (iv) a 3' UTR. In some embodiments, the OTC polypeptide comprises or consists of the amino acid sequence of SEQ ID NO:1.

In another aspect, the disclosure features a polynucleotide comprising an mRNA comprising: (i) a 5' UTR; (ii) an open reading frame (ORF) encoding a human OTC polypeptide, wherein the ORF comprises a nucleic acid sequence selected from the group consisting of SEQ ID NOs:2 and 5-29; (iii) a stop codon; and (iv) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF has at least 80% sequence identity to SEQ ID NO:14; and (iii) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF has at least 85% sequence identity to SEQ ID NO:14; and (iii) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF has at least 90% sequence identity to SEQ ID NO:14; and (iii) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF has at least 95% sequence identity to SEQ ID NO:14; and (iii) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF has at least 97% sequence identity to SEQ ID NO:14; and (iii) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF has at least 98% sequence identity to SEQ ID NO:14; and (iii) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF has at least 99% sequence identity to SEQ ID NO:14; and (iii) a 3' UTR.

In one aspect, the disclosure features a polynucleotide comprising an mRNA comprising: (i) a 5' UTR; (ii) an open reading frame (ORF) encoding a human OTC polypeptide (e.g., SEQ ID NO:1), wherein the ORF comprises SEQ ID NO:14; and (iii) a 3' UTR.

In some embodiments, the polynucleotide comprises a microRNA (miR) binding site. In some embodiments, the microRNA is expressed in an immune cell of hematopoietic lineage or a cell that expresses TLR7 and/or TLR8 and secretes pro-inflammatory cytokines and/or chemokines. In certain instances, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof. In some instances, the microRNA binding site is for a microRNA selected from the group consisting of miR126-3p, miR-142-3p, miR-142-5p, miR-155, or any combination thereof. In one instance, the microRNA binding site is a miR-142-3p binding site. In certain instances, the microRNA binding site is located in the 3' UTR of the mRNA.

In some embodiments, the 3' UTR comprises a nucleic acid sequence at least about 90%, at least about 95%, at least about 96%, at least about 97%, at least about 98%, at least about 99%, or 100% identical to a 3' UTR of SEQ ID NO: 4.

In some embodiments of this aspect, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:4, SEQ ID NO:111, SEQ ID NO:150, SEQ ID NO:175, SEQ ID NO:177, SEQ ID NO:178, SEQ ID NO:198, or SEQ ID NO:199.

In some embodiments, the 5' UTR comprises a nucleic acid sequence at least about 90%, at least about 95%, at least about 96%, at least about 97%, at least about 98%, at least about 99%, or 100% identical to a 3' UTR of SEQ ID NO: 3.

In some embodiments of this aspect, the mRNA comprises a 5' UTR comprising a nucleic acid sequence at least about 90%, at least about 95%, at least about 96%, at least about 97%, at least about 98%, at least about 99%, or 100% identical to a 5' UTR sequence of SEQ ID NO:3, SEQ ID NO:191, SEQ ID NO:196, or SEQ ID NO:197.

In some embodiments, the polynucleotide comprises a 5' terminal cap. In certain instances, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the polynucleotide comprises a poly-A region. In certain instances, the poly-A region is at least about 10, at least about 20, at least about 30, at least about 40, at least about 50, at least about 60, at least about 70, at least about 80, at least about 90 nucleotides in length, or at least about 100 nucleotides in length. In other instances, the poly-A region has about 10 to about 200, about 20 to about 180, about 50 to about 160, about 70 to about 140, or about 80 to about 120 nucleotides in length.

In certain embodiments, the polynucleotide comprises at least one chemically modified nucleobase, sugar, backbone, or any combination thereof. In some instances, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some instances, at least about 25%, at least about 30%, at least about 40%, at least about 50%, at least about 60%, at least about 70%, at least about 80%, at least about 90%, at least about 95%, at least about 99%, or 100% of the uracils are chemically modified to N1-methylpseudouracils.

In certain embodiments, the polynucleotide comprises a nucleic acid sequence selected from the group consisting of SEQ ID NO:30-55.

In another aspect the disclosure features a polynucleotide comprising an mRNA comprising: (i) a 5'-terminal cap; (ii) a 5' UTR comprising the nucleic acid sequence of SEQ ID NO:3; (iii) an open reading frame (ORF) encoding a human ornithine transcarbamylase (OTC) polypeptide, wherein the ORF comprises a sequence selected from the group consisting of SEQ ID NOs:2 and 5-29; (iv) a 3' UTR comprising the nucleic acid sequence of SEQ ID NO:4; and (v) a poly-A-region.

In another aspect the disclosure features a polynucleotide comprising an mRNA comprising: (i) a 5'-terminal cap; (ii) a 5' UTR comprising the nucleic acid sequence of SEQ ID NO:3, SEQ ID NO:191, SEQ ID NO:196, or SEQ ID NO:197; (iii) an open reading frame (ORF) encoding a human ornithine transcarbamylase (OTC) polypeptide, wherein the ORF comprises a sequence selected from the group consisting of SEQ ID NOs:2 and 5-29; (iv) a 3' UTR comprising the nucleic acid sequence of SEQ ID NO:4, SEQ ID NO:111, SEQ ID NO:150, SEQ ID NO:175, SEQ ID NO:177, SEQ ID NO:178, SEQ ID NO:198, or SEQ ID NO:199; and (v) a poly-A-region.

In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the poly-A region is at least about 10, at least about 20, at least about 30, at least about 40, at least about 50, at least about 60, at least about 70, at least about 80, at least about 90 nucleotides in length, or at least about 100 nucleotides in length. In certain instances, the poly-A region has about 10 to about 200, about 20 to about 180, about 50 to about 160, about 70 to about 140, or about 80 to about 120 nucleotides in length.

In certain embodiments, the mRNA comprises at least one chemically modified nucleobase, sugar, backbone, or any combination thereof. In some instances, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

In certain embodiments, the polynucleotide comprises a nucleic acid sequence selected from the group consisting of SEQ ID NO: 30-55. In certain instances, the 5' terminal cap comprises Cap1 and all of the uracils of the polynucleotide are N1-methylpseudouracils. In certain instances, the poly-A-region is 100 nucleotides in length.

In another aspect the disclosure provides a pharmaceutical composition comprising a polynucleotide described herein and a delivery agent.

In certain embodiments, the delivery agent comprises a lipid nanoparticle comprising: (i) Compound II, (ii) Cholesterol, and (iii) PEG-DMG or Compound I; (i) Compound VI, (ii) Cholesterol, and (iii) PEG-DMG or Compound I; (i) Compound II, (ii) DSPC or DOPE, (iii) Cholesterol, and (iv) PEG-DMG or Compound I; or (i) Compound VI, (ii) DSPC or DOPE, (iii) Cholesterol, and (iv) PEG-DMG or Compound I.

In another aspect, the disclosure features a method of expressing an ornithine transcarbamylase (OTC) polypeptide in a human subject in need thereof. The method involves administering to the subject an effective amount of a pharmaceutical composition or a polynucleotide described herein.

In another aspect, the disclosure features a method of treating, preventing, or delaying the onset and/or progression of ornithine transcarbamylase deficiency (OTCD) in a human subject in need thereof. The method involves administering to the subject an effective amount of a pharmaceutical composition or a polynucleotide described herein.

In another aspect, the disclosure features a method of reducing ammonia blood levels in a human subject in need thereof. The method involves administering to the subject an effective amount of a pharmaceutical composition or a polynucleotide described herein.

In another aspect, the disclosure features a method of reducing urinary orotic acid levels in a human subject in need thereof. The method involves administering to the subject an effective amount of a pharmaceutical composition or a polynucleotide described herein.

In certain embodiments of the above methods:
(i) the ammonia RBC, plasma, serum and/or liver level is reduced at least 20%, at least 30%, at least 40%, at least 50%, at least 60%, at least 70%, at least 80%, at least 90%, or at least 100% as compared to the subject's baseline ammonia RBC, plasma, serum and/or liver level or a reference ammonia RBC, plasma, serum and/or liver level in a patient with OTCD, for at least 12 hours, at least 24 hours, at least 48 hours, at least 72 hours, at least 96 hours, at least 120 hours, at least 6 days, at least 1 week, at least 8 days, at least 9 days, at least 10 days, at least 11 days, at least 12 days, at least 2 weeks, at least 3 weeks, or at least 4 weeks after a single administration;
(ii) the orotic acid plasma, serum, and/or urine level is reduced at least 20%, at least 30%, at least 40%, at least 30%, at least 40%, at least 50%, at least 60%, at least 70%, at least 80%, at least 90%, or at least 100% as compared to the subject's baseline orotic acid plasma, serum, and/or urine level or a reference orotic acid plasma, serum, and/or urine level in a patient with OTCD, for at least 12 hours, at least 24 hours, at least 48 hours, at least 72 hours, at least 96 hours, at least 120 hours, at least 6 days, at least 1 week, at least 8 days, at least 9 days, at least 10 days, at least 11 days, at least 12 days, at least 2 weeks, at least 3 weeks, or at least 4 weeks after a single administration;

(iii) the ammonia RBC, plasma, serum and/or liver level is reduced to at least within 1.5-fold, at least within 2-fold, at least within 5-fold, at least within 10-fold, at least within or at least within 50-fold as compared to a normal ammonia RBC, plasma, serum and/or liver level within at least 12 hours, at least 24 hours, at least 48 hours, at least 72 hours, at least 96 hours, at least 120 hours, at least 6 days, at least 1 week, at least 8 days, at least 9 days, at least 10 days, at least 11 days, at least 12 days, at least 2 weeks, at least 3 weeks, or at least 4 weeks after a single administration;

(iv) the orotic acid plasma, serum, and/or urine level is reduced to at least within 1.5-fold, at least within 2-fold, at least within 5-fold, at least within 10-fold, at least within 20-fold, or at least within 50-fold as compared to a normal orotic acid plasma, serum, and/or urine level, for at least 12 hours, at least 24 hours, at least 48 hours, at least 72 hours, at least 96 hours, at least 120 hours, at least 6 days, at least 1 week, at least 8 days, at least 9 days, at least 10 days, at least 11 days, at least 12 days, at least 2 weeks, at least 3 weeks, or at least 4 weeks after a single administration;

(v) the body weight of the human subject is increased by at least 2%, at least 5%, at least 10%, at least 15%, at least 20%, at least 25%, or at least 30% of pre-treatment body weight by at least 12 hours, at least 24 hours, at least 48 hours, at least 72 hours, at least 96 hours, at least 5 days, at least 7 days, at least 14 days, at least 24 days, at least 48 days, or at least 60 days post-administration; and/or (vi) the body weight of the human subject is maintained to within at least 80%, at least 85%, at least 90%, at least 95%, at least 98%, or at least 99% of pre-treatment body weight for at least 12 hours, at least 24 hours, at least 48 hours, at least 72 hours, at least 96 hours, at least 5 days, at least 7 days, at least 14 days, at least 24 days, at least 48 days, or at least 60 days post-administration.

In another aspect, the disclosure features a method of increasing OTC activity in a human subject in need thereof. The method involves administering to the subject an effective amount of a pharmaceutical composition or a polynucleotide described herein.

In certain embodiments of the above methods:
(i) the level of OTC activity in the subject is increased at least 1.5-fold, at least 2-fold, at least 5-fold, at least 10-fold, at least 20-fold, or at least 50-fold as compared to a reference OTC activity level in a subject having OTCD for at least 12 hours, at least 24 hours, at least 48 hours, at least 72 hours, at least 96 hours, at least 120 hours, at least 6 days, at least 1 week, at least 8 days, at least 9 days, at least 10 days, at least 11 days, at least 12 days, at least 2 weeks, at least 3 weeks, or at least 4 weeks after a single administration; and/or (ii) 12 hours after a single administration of the pharmaceutical composition or polynucleotide is administered to the subject, the OTC activity in the subject is increased at least 2%, at least 5%, at least 10%, at least 20%, at least 30%, at least 40%, at least 50%, at least 60%, at least 70%, at least 80%, at least 90%, at least 100%, at least 150%, at least 200%, at least 300%, at least 400%, at least 500%, or at least 600% compared to the subject's baseline OTC activity.

In certain embodiments, the OTC activity is increased in the liver of the subject.

In some embodiments, the administration to the subject is about once a week, about once every two weeks, or about once a month.

In certain embodiments, the pharmaceutical composition or polynucleotide is administered intravenously. In some instances, the pharmaceutical composition or polynucleotide is administered at a dose of 0.1 mg/kg to 2.0 mg/kg. In some instances, the pharmaceutical composition or polynucleotide is administered at a dose of 0.1 mg/kg to 1.5 mg/kg. In some instances, the pharmaceutical composition or polynucleotide is administered at a dose of 0.1 mg/kg to 1.0 mg/kg. In some instances, the pharmaceutical composition or polynucleotide is administered at a dose of 0.1 mg/kg to 0.5 mg/kg.

BRIEF DESCRIPTION OF THE DRAWINGS/FIGURES

FIG. 1A includes a Western blot showing the expression of human OTC in HeLa cells 24 hours post transfection.

Figure 8A:
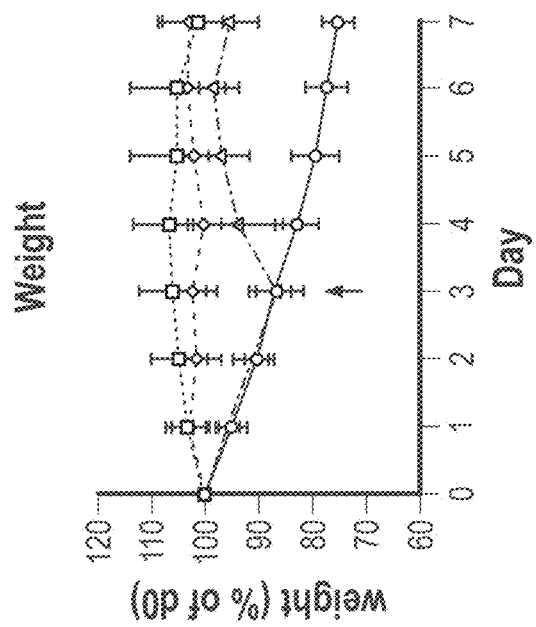
FIG. 8A shows the percent survival of wild type mice and spf$^{ash}$ mice fed a high protein diet over the course of 7 days. The spf$^{ash}$ mice were administered a human OTC mRNA construct at day 0 or day 3 of being fed the high protein diet.
Figure 8B:
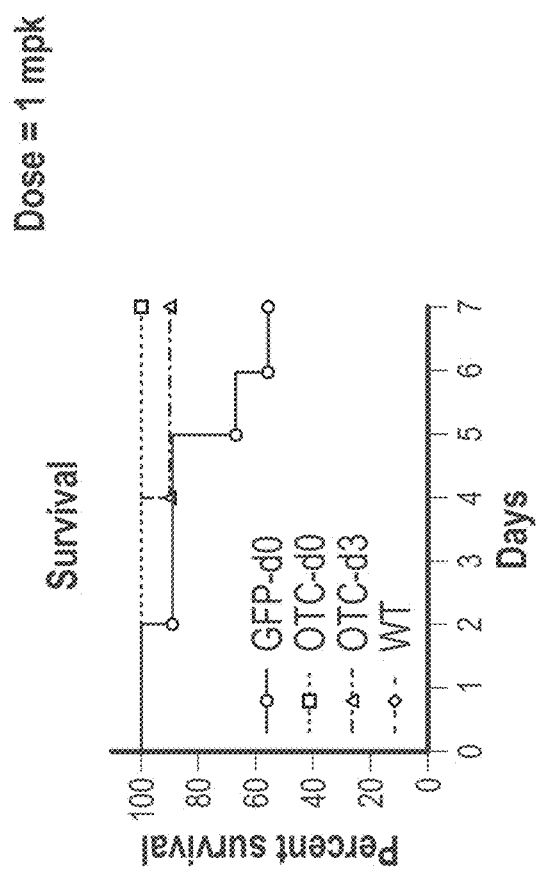
FIG. 8B shows the body weight of wild type and spf$^{ash}$ mice fed a high protein diet over the course of 7 days. The spf$^{ash}$ mice were administered a human OTC mRNA construct at day 0 or day 3 of being fed the high protein diet.
Figure 8C:
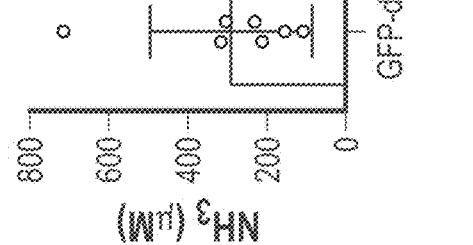

FIG. 8C shows the plasma ammonia levels of wild type and spf$^{ash}$ mice after 3 days of being fed a high protein diet. The spf$^{ash}$ mice were administered a human OTC mRNA construct at day 0 or day 3 of being fed the high protein diet.

Figure 8D:
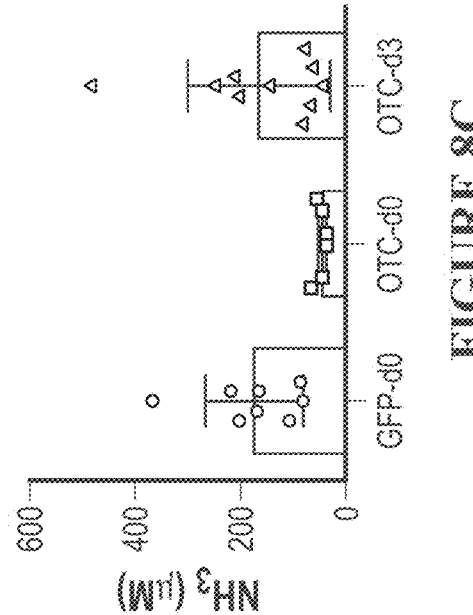

FIG. 8D shows the plasma ammonia levels of wild type and spf$^{ash}$ mice after 7 days of being fed a high protein diet. The spf$^{ash}$ mice were administered a human OTC mRNA construct at day 0 or day 3 of being fed the high protein diet.

Figure 9:
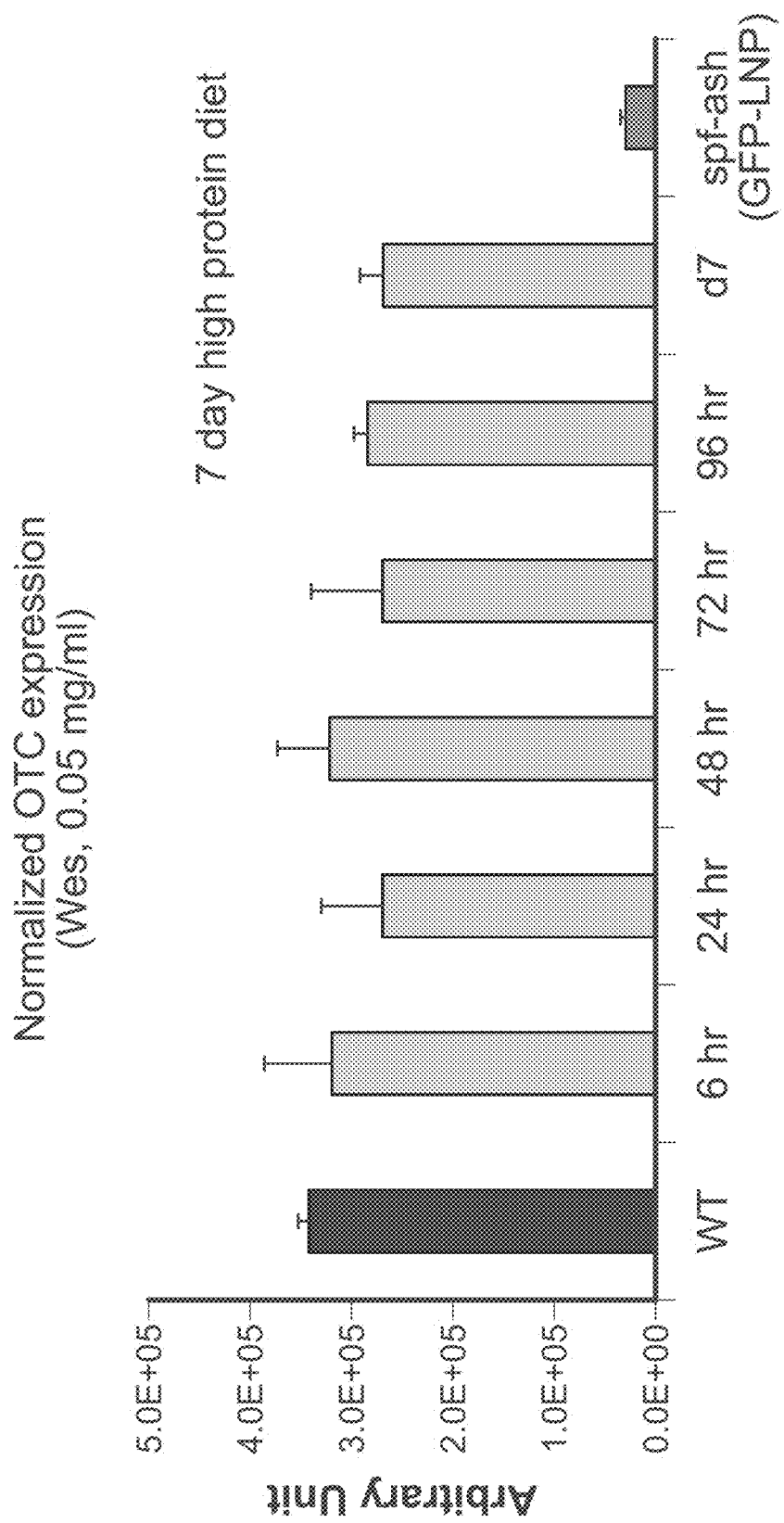

FIG. 9 shows the levels of OTC expression in liver lysates from spf$^{ash}$ mice fed a high protein diet at 6 hours, 1 day, 2 days, 3 days, 4 days, and 7 days following the administration of a human OTC mRNA construct.

FIG. 10 provides the experimental design of a study to determine if administering a single dose of human OTC mRNA can increase the body weight and improve the survival of spf$^{ash}$ mice fed a high protein diet by increasing OTC expression and function.

Figure 11A:
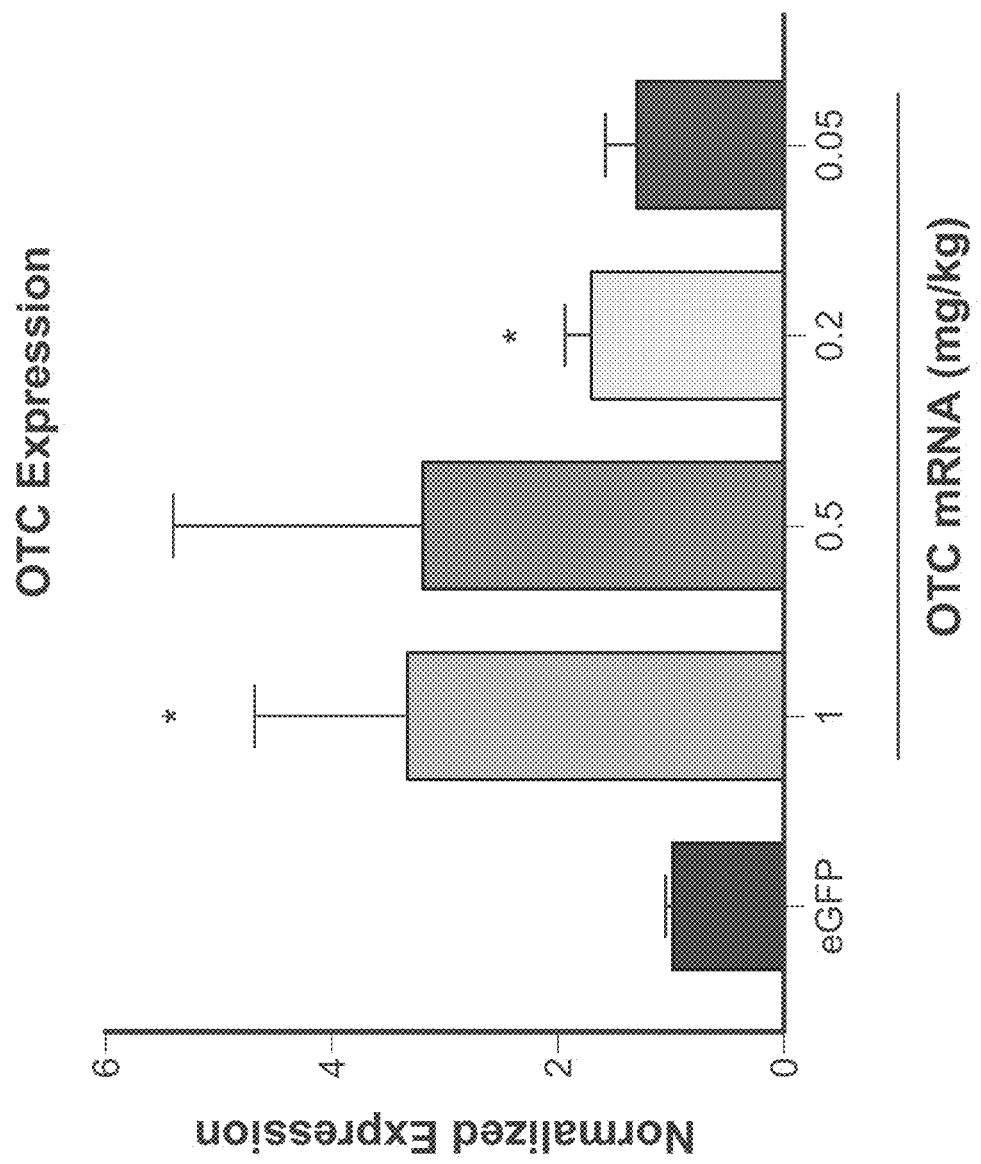

FIG. 11A shows the expression of human OTC in spf$^{ash}$ mouse liver homogenates one day after the mice were administered OTC mRNA at a single 0.05, 0.2, 0.5, or 1 mg/kg dose, as determined by capillary electrophoresis (CE). Citrate synthase (a mitochondrial protein marker) was used as loading control for normalization. Error bars are standard deviation (SD). Significance was determined by Student's paired, two-tailed t-Test comparing the expression levels in cells with OTC mRNA to expression levels in cells with the eGFP control mRNA.

Figure 11B:
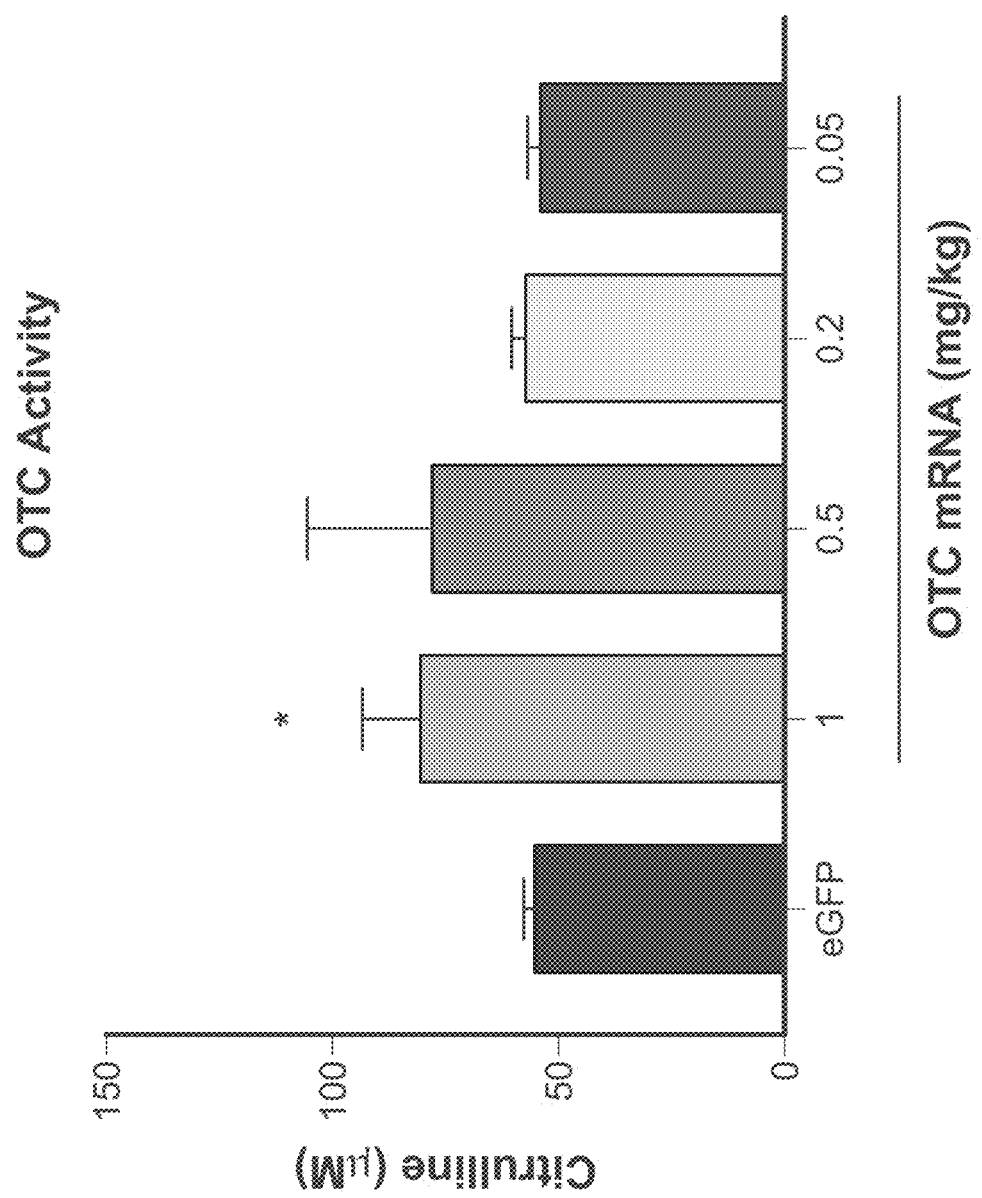

FIG. 11B shows the activity of human OTC in spf$^{ash}$ mouse liver mitochondrial lysates one day after the mice were administered OTC mRNA at a single 0.05, 0.2, 0.5, or 1 mg/kg dose, as measured using a colorimetric assay for L-citrulline. Error bars are standard deviation (SD). Significance was determined by Student's paired, two-tailed t-Test comparing the activity levels in cells with OTC mRNA to activity levels in cells with the eGFP control mRNA.

Figure 12A:
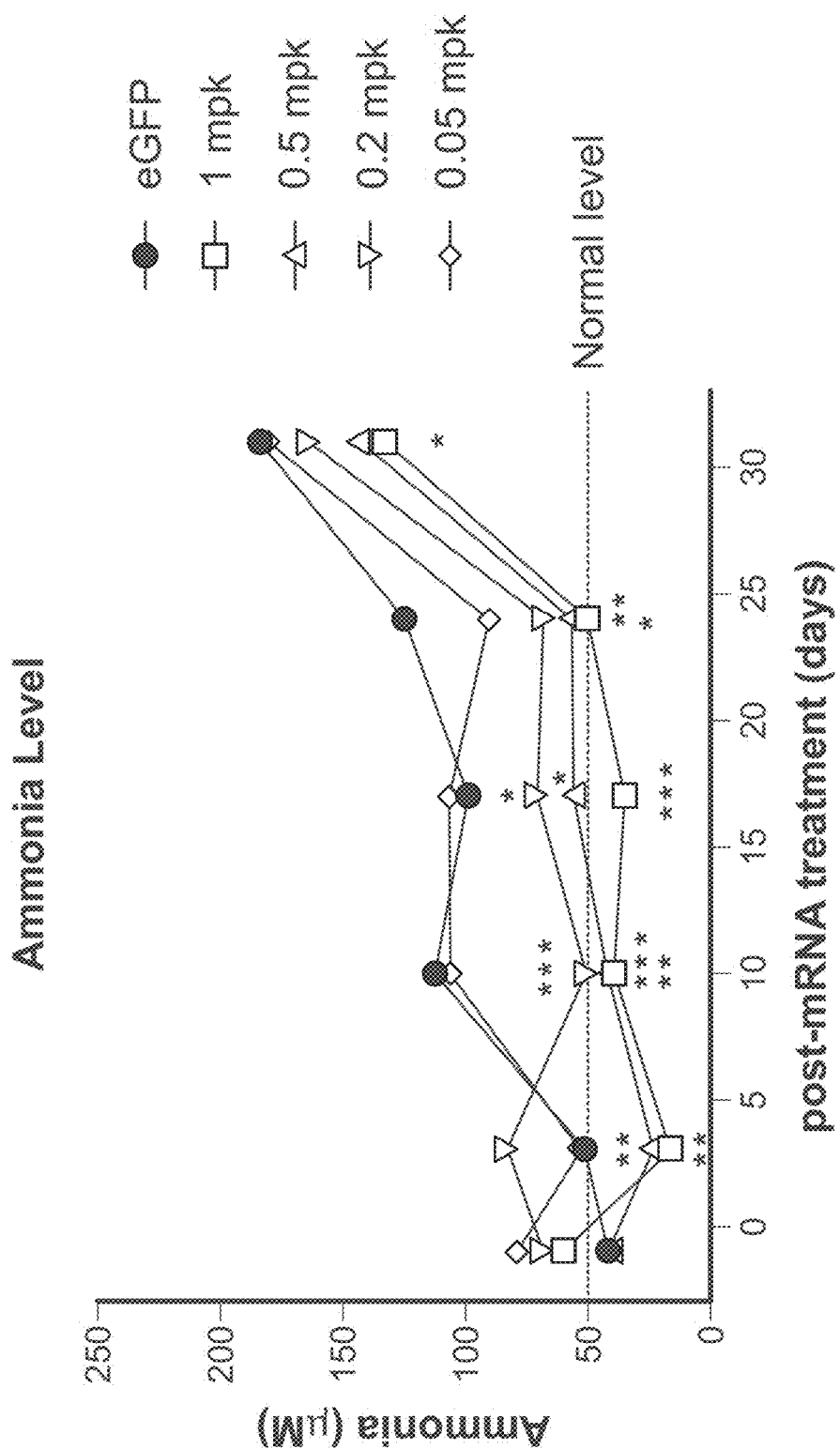

FIG. 12A shows plasma ammonia levels in spf$^{ash}$ mice fed a high protein diet and administered a single 0.05, 0.2, 0.5, or 1 mg/kg dose of OTC mRNA or eGFP mRNA over the course of one month. The dotted line represents the plasma ammonia levels in wild-type mice. Error bars are omitted for the sake of clarity. Significance was determined by Student's paired, two-tailed t-Test comparing the ammonia levels in plasma from mice injected with OTC mRNA to the ammonia levels in plasma from mice injected with eGFP control mRNA at same time point.

Figure 12B:
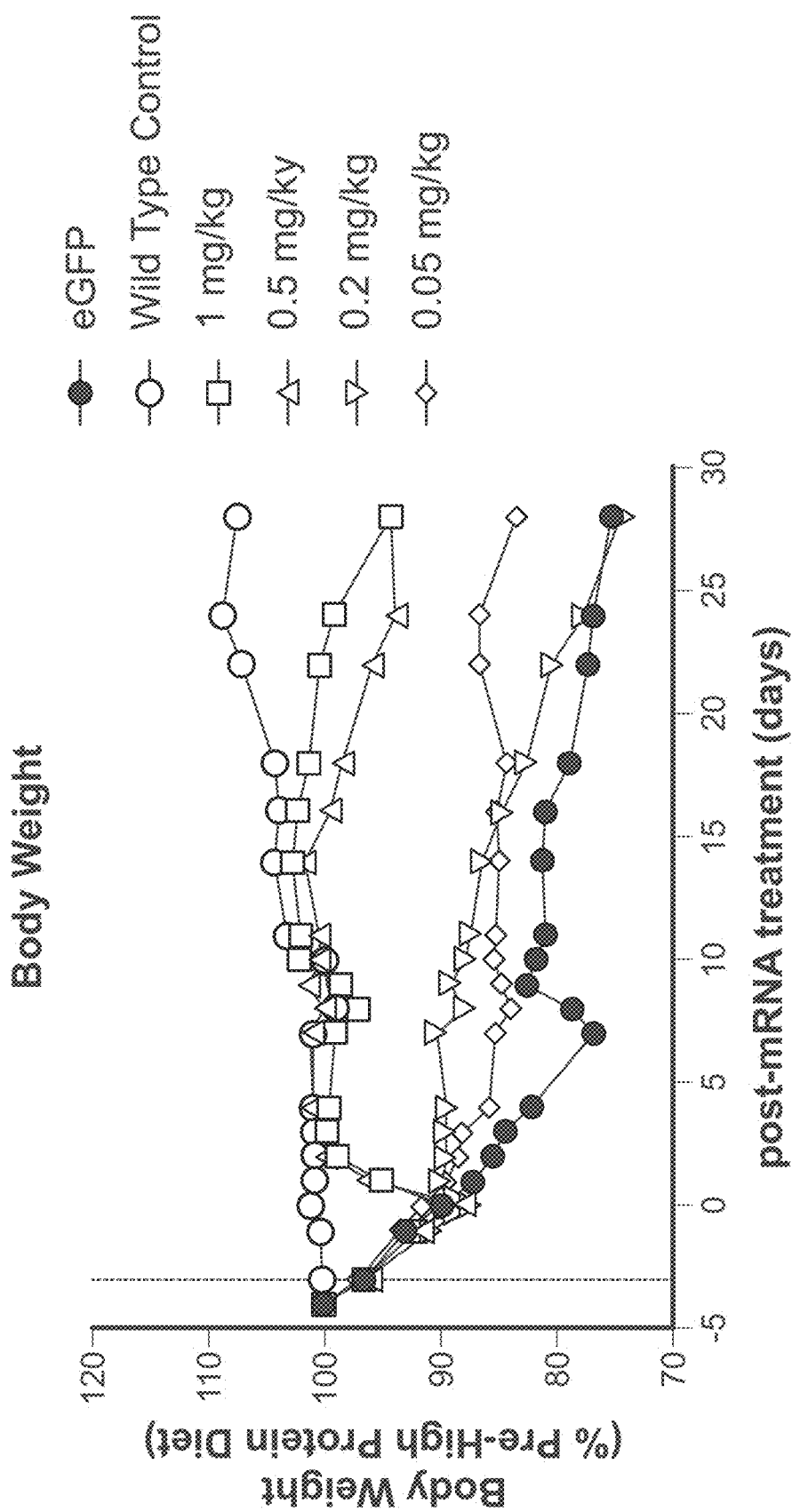

FIG. 12B shows the body weight of spf$^{ash}$ mice fed a high protein diet and administered a single 0.05, 0.2, 0.5, or 1 mg/kg dose of OTC mRNA or eGFP mRNA over the course of one month. Error bars and statistical significance are omitted for the sake of clarity.

Figure 13:
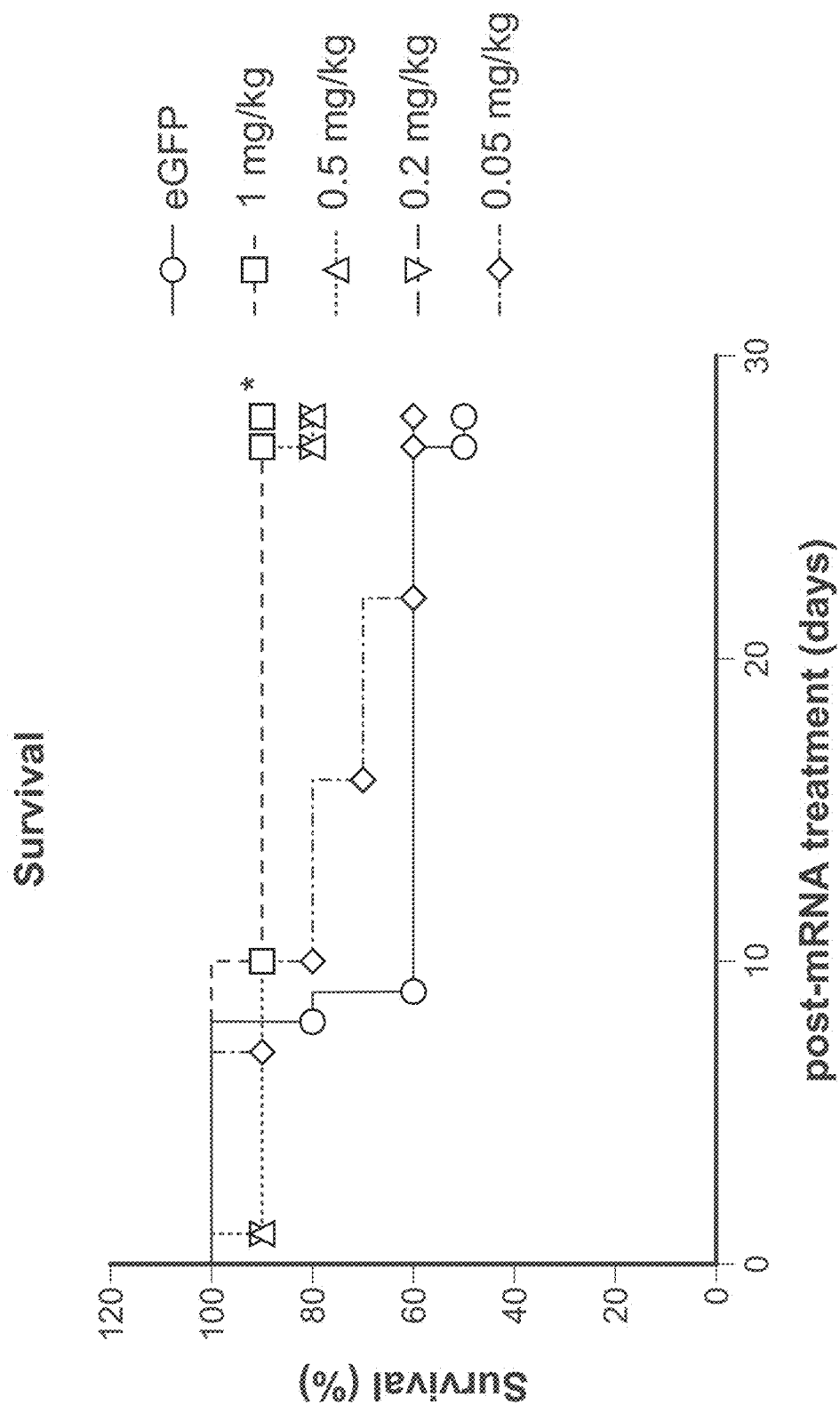

FIG. 13 shows the percentage of spf$^{ash}$ mice fed a high protein diet and administered a single 0.05, 0.2, 0.5, or 1 mg/kg dose of OTC mRNA that survive over the course of one month. Significance was determined by Log-rank (Mantel-Cox) and Gehan-Breslow-Wilsoxon tests.

Figure 14:
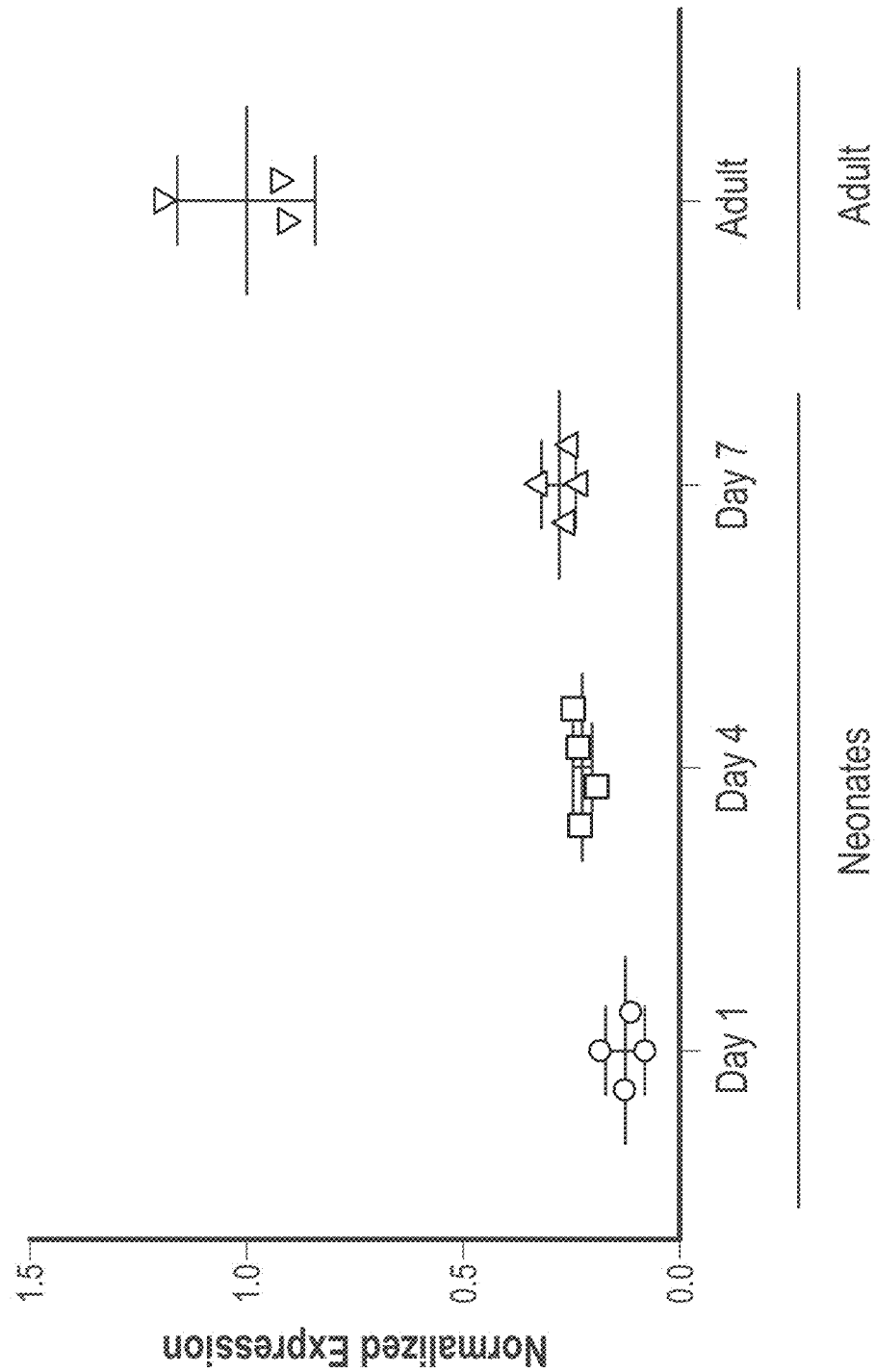

FIG. 14 shows the expression of Low-Density Lipoprotein Receptor (LDLR) (normalized to ERP72) in day 1, day 4 and day 7 neonatal mouse liver homogenates relative to LDLR expression in adult mice.

Figure 15:
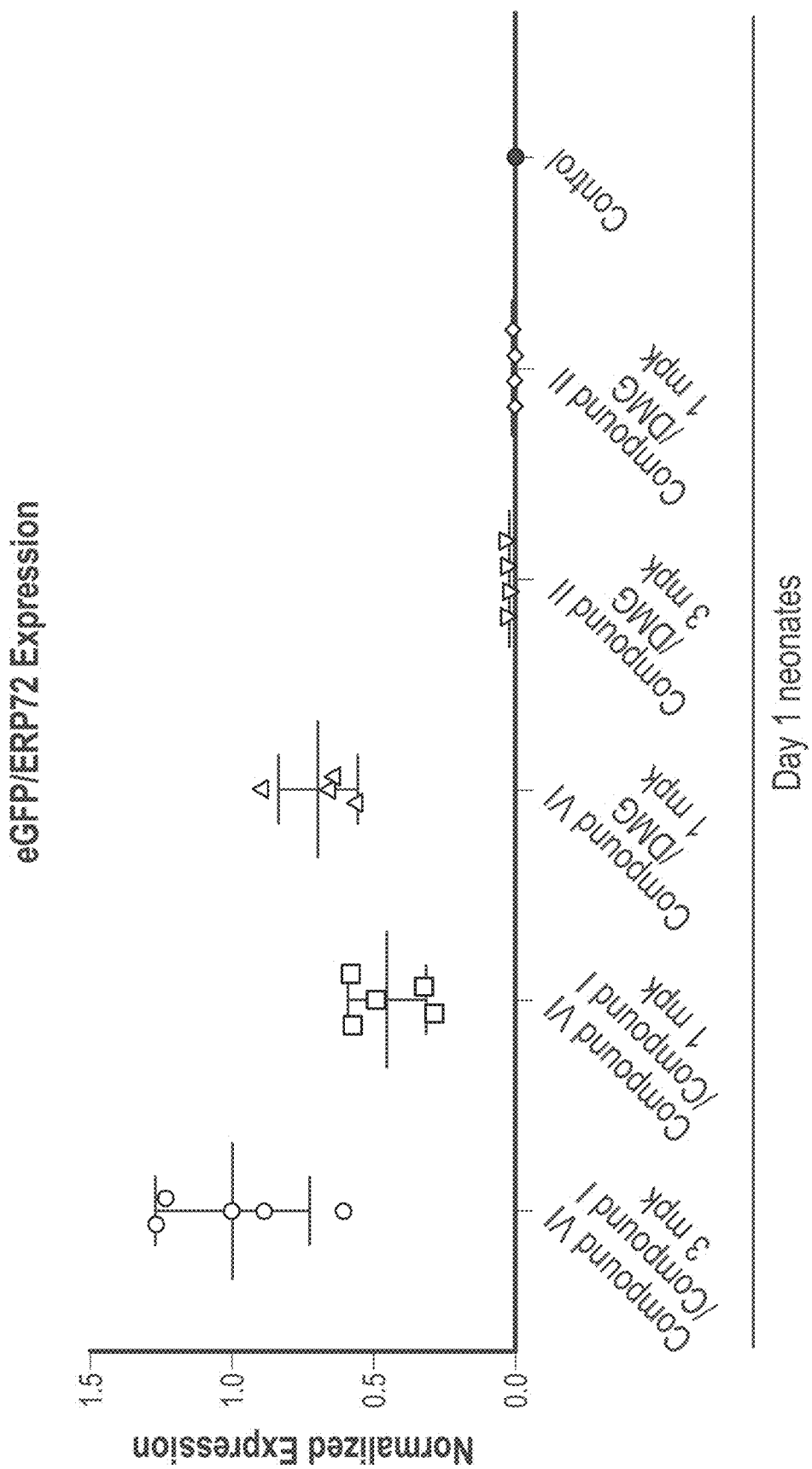

FIG. 15 shows expression of eGFP in one-day-old neonatal mouse (day 1) liver homogenates following administration of a single dose of eGFP mRNA formulated in Compound VI/Compound I, Compound VI/PEG-DMG, or Compound II/PEG-DMG lipid nanoparticles (LNPs) at birth (day 0).

Figure 16:
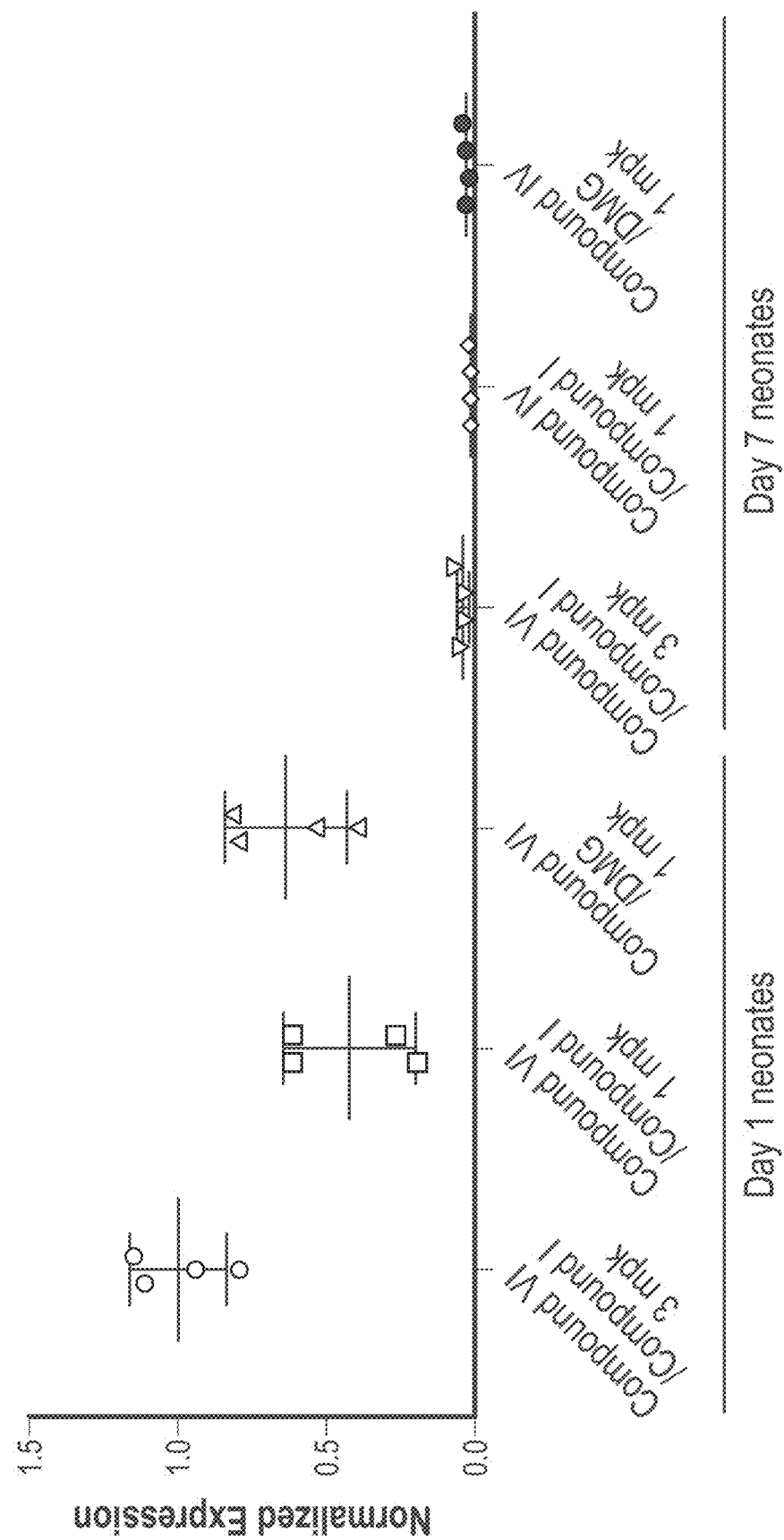

FIG. 16 shows expression of eGFP in one-day-old (day 1) and seven-day-old (day 7) neonatal mouse liver homogenates following administration of a single dose of eGFP mRNA formulated in Compound VI/Compound I or Compound VI/PEG-DMG lipid nanoparticles at birth (day 0).

DETAILED DESCRIPTION

The present invention provides mRNA therapeutics for the treatment of ornithine transcarbamylase deficiency (OTCD). OTCD is an X-linked recessive urea cycle disorder affecting the ability to convert ammonia, which is neurotoxic, into urea. OTCD is caused by mutations in the OTC gene, which codes for the enzyme ornithine transcarbamylase (OTC). Without OTC, ammonia accumulates abnormally, and can cause hyperammonemia. mRNA therapeutics are particularly well-suited for the treatment of OTCD as the technology provides for the intracellular delivery of mRNA encoding OTC followed by de novo synthesis of functional OTC protein within target cells. After delivery of mRNA to the target cells, the desired OTC protein is expressed by the cells' own translational machinery, and hence, fully functional OTC protein replaces the defective or missing protein.

One challenge associated with delivering nucleic acid-based therapeutics (e.g., mRNA therapeutics) in vivo stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution and a strong type I interferon (type I IFN) response. This disclosure features the incorporation of different modified nucleotides within therapeutic mRNAs to minimize the immune activation and optimize the translation efficiency of mRNA to protein. Particular aspects feature a combination of nucleotide modification to reduce the innate immune response and sequence optimization, in particular, within the open reading frame (ORF) of therapeutic mRNAs encoding OTC to enhance protein expression. Certain embodiments of the mRNA therapeutic technology of the instant disclosure also feature delivery of mRNA encoding OTC via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features ionizable lipid-based LNPs combined with mRNA encoding OTC which have improved properties when administered in vivo. Without being bound in theory, it is believed that the ionizable lipid-based LNP formulations of the invention have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient enzymes (e.g., OTC) in a therapeutic context. This is because repeat administration of mRNA therapeutics is in most instances essential to maintain necessary levels of enzyme in target tissues in subjects (e.g., subjects suffering from OTCD.) Repeat dosing challenges can be addressed on multiple levels. mRNA engineering and/or efficient delivery by LNPs can result in increased levels and or enhanced duration of protein (e.g., OTC) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the disclosure in one aspect, combats the ABC phenomenon. Moreover, LNPs can be engineered to avoid immune sensing and/or recognition and can thus further avoid ABC upon subsequent or repeat dosing. An exemplary aspect of the disclosure features LNPs which have been engineered to have reduced ABC.

1. Ornithine Transcarbamylase (OTC)

Ornithine transcarbamylase (OTC; EC 2.1.3.3) is an enzyme of the urea cycle and of the bacterial arginine biosynthesis pathway. OTC catalyzes the reaction between carbamyl phosphate and ornithine to form citrulline and phosphate. OTC exists as a homotrimer within the cell.

Ornithine transcarbamylase deficiency (OTCD) is an X-linked urea cycle disorder associated with OTC function, wherein ammonia is insufficiently converted into urea, causing ammonia to accumulate and leading to hyperammonemia in severe cases. A variety of mutations can affect OTC function and activity in humans. Large deletions, frameshift, nonsense, and missense mutations can abolish OTC enzymatic activity or folding, causing severe neonatal onset disease in hemizygous males and OTCD symptoms in heterozygous females. Missense mutations that retain OTC activity but destabilize the protein, reduce enzymatic activity, or decrease substrate affinity can lead to late onset disease in hemizygous males. Female carriers of hypomorphic alleles can also present with OTCD symptoms.

The wild type OTC canonical mRNA sequence is described at the NCBI Reference Sequence database (RefSeq) under accession number NM_000531.5 ("*Homo sapiens* ornithine carbamoyltransferase (OTC), mRNA"). The wild type OTC canonical protein sequence is described at the RefSeq database under accession number NP_000522.3 ("ornithine carbamoyltransferase, mitochondrial precursor [*Homo sapiens*]"). The OTC protein is 354 amino acids long, and has a molecule weight of 39.9 kDa. An N-terminal leader sequence is removed in the mitochondria to form a 322 amino acid mature protein. It is noted that the specific nucleic acid sequences encoding the reference protein sequence in the Ref Seq sequences are the coding sequence as indicated in the respective RefSeq database entry.

The amino acid sequence of human OTC is provided in SEQ ID NO:1.

In certain aspects, the disclosure provides a polynucleotide (e.g., an RNA, e.g., an mRNA) comprising a nucleotide sequence (e.g., an open reading frame (ORF)) encoding an OTC polypeptide. In some embodiments, the OTC polypeptide of the invention is a wild type full length OTC protein. In some embodiments, the OTC polypeptide of the invention is a variant, a peptide or a polypeptide containing a substitution, and insertion and/or an addition, a deletion and/or a covalent modification with respect to a wild-type OTC sequence. In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of an OTC sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

OTC protein fragments, functional protein domains, variants, and homologous proteins (orthologs) are also within the scope of the OTC polypeptides of the invention. A nonlimiting example of a polypeptide encoded by the polynucleotides of the invention is shown in SEQ ID NO:1.

Certain compositions and methods presented in this disclosure refer to the protein or polynucleotide sequences of wild type human OTC. Such disclosures are equally applicable to any other variants of OTC known in the art.

2. Polynucleotides and Open Reading Frames (ORFs)

The instant invention features mRNAs for use in treating or preventing ornithine transcarbamylase deficiency (OTCD). The mRNAs featured for use in the invention are administered to subjects and encode human ornithine transcarbamylase (OTC) protein in vivo. Accordingly, the invention relates to polynucleotides, e.g., mRNA, comprising an open reading frame of linked nucleosides encoding human OTC (SEQ ID NO:1), isoforms thereof, functional fragments thereof, and fusion proteins comprising OTC. In some embodiments, the open reading frame is sequence-optimized. In particular embodiments, the invention provides sequence-optimized polynucleotides comprising nucleotides encoding the polypeptide sequence of human OTC, or sequence having high sequence identity with those sequence optimized polynucleotides.

In certain aspects, the invention provides polynucleotides (e.g., a RNA such as an mRNA) that comprise a nucleotide sequence (e.g., an ORF) encoding one or more OTC polypeptides. In some embodiments, the encoded OTC polypeptide of the invention can be selected from:

(i) a full length OTC polypeptide (e.g., having the same or essentially the same length as wild-type OTC);
(ii) a functional fragment of OTC described herein (e.g., a truncated (e.g., deletion of carboxy, amino terminal, or internal regions) sequence shorter than OTC; but still retaining OTC enzymatic activity);
(iii) a variant thereof (e.g., full length or truncated OTC protein in which one or more amino acids have been replaced, e.g., variants that retain all or most of the OTC activity of the polypeptide with respect to a reference protein (such as any natural or artificial variants known in the art)); or
(iv) a fusion protein comprising (i) a full length OTC protein (e.g., SEQ ID NO:1), a functional fragment or a variant thereof, and (ii) a heterologous protein.

In certain embodiments, the encoded OTC polypeptide is a mammalian OTC polypeptide, such as a human OTC polypeptide, a functional fragment or a variant thereof.

In some embodiments, the polynucleotide (e.g., a RNA, e.g., an mRNA) of the invention increases OTC protein expression levels and/or detectable OTC enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to OTC protein expression levels and/or detectable OTC enzymatic activity levels in the cells prior to the administration of the polynucleotide of the invention. OTC protein expression levels and/or OTC enzymatic activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the invention comprise a nucleotide sequence (e.g., an ORF) that encodes a wild-type human OTC, e.g., SEQ ID NO: 1.

In some embodiments, the polynucleotide (e.g., a RNA, e.g., an mRNA) of the invention comprises a codon optimized nucleic acid sequence, wherein the open reading frame (ORF) of the codon optimized nucleic acid sequence is derived from a wild-type OTC sequence (e.g., wild-type human OTC). For example, for polynucleotides of invention comprising a sequence optimized ORF encoding OTC, the corresponding wild type sequence is the native OTC. Similarly, for a sequence optimized mRNA encoding a functional fragment of OTC, the corresponding wild type sequence is the corresponding fragment from OTC.

In some embodiments, the polynucleotides (e.g., a RNA, e.g., an mRNA) of the invention comprise a nucleotide sequence encoding OTC having the full length sequence of human OTC (i.e., including the initiator methionine and an N-terminal leader sequence that is removed upon import of the protein into mitochondria; amino acids 1-354). In some embodiments, the polynucleotide (e.g., a RNA, e.g., an mRNA) of the invention comprising a nucleotide sequence encoding full length human OTC is sequence optimized.

In some embodiments, the polynucleotides (e.g., a RNA, e.g., an mRNA) of the invention comprise a nucleotide sequence (e.g., an ORF) encoding a mutant OTC polypeptide. In some embodiments, the polynucleotides of the invention comprise an ORF encoding an OTC polypeptide that comprises at least one point mutation in the OTC sequence and retains OTC enzymatic activity. In some embodiments, the mutant OTC polypeptide has an OTC activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the OTC activity of the corresponding wild-type OTC (i.e., the same OTC but without the mutation(s)). In some embodiments, the polynucleotide (e.g., a RNA, e.g., an mRNA) of the invention comprising an ORF encoding a mutant OTC polypeptide is sequence optimized.

In some embodiments, the polynucleotide (e.g., a RNA, e.g., an mRNA) of the invention comprises a nucleotide sequence (e.g., an ORF) that encodes an OTC polypeptide with mutations that do not alter OTC enzymatic activity. Such mutant OTC polypeptides can be referred to as function-neutral. In some embodiments, the polynucleotide comprises an ORF that encodes a mutant OTC polypeptide comprising one or more function-neutral point mutations.

In some embodiments, the mutant OTC polypeptide has higher OTC enzymatic activity than the corresponding wild-type OTC. In some embodiments, the mutant OTC polypeptide has an OTC activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type OTC (i.e., the same OTC but without the mutation(s)).

In some embodiments, the polynucleotides (e.g., a RNA, e.g., an mRNA) of the invention comprise a nucleotide sequence (e.g., an ORF) encoding a functional OTC fragment, e.g., where one or more fragments correspond to a polypeptide subsequence of a wild type OTC polypeptide and retain OTC enzymatic activity. In some embodiments, the OTC fragment has an OTC activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the OTC activity of the corresponding full length OTC. In some embodiments, the polynucleotides (e.g., a RNA, e.g., an mRNA) of the invention comprising an ORF encoding a functional OTC fragment is sequence optimized.

In some embodiments, the polynucleotide (e.g., a RNA, e.g., an mRNA) of the invention comprises a nucleotide sequence (e.g., an ORF) encoding an OTC fragment that has higher OTC enzymatic activity than the corresponding full length OTC. Thus, in some embodiments the OTC fragment has an OTC activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the OTC activity of the corresponding full length OTC.

In some embodiments, the polynucleotide (e.g., a RNA, e.g., an mRNA) of the invention comprises a nucleotide sequence (e.g., an ORF) encoding an OTC fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type OTC.

In some embodiments, the polynucleotide (e.g., a RNA, e.g., an mRNA) of the invention comprises a nucleotide sequence (e.g., an ORF) encoding an OTC polypeptide (e.g., the wild-type sequence, functional fragment, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:62.

In some embodiments, the polynucleotide (e.g., a RNA, e.g., an mRNA) of the invention comprises a nucleotide sequence (e.g., an ORF) encoding an OTC polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 2 and In some embodiments, the polynucleotide (e.g., a RNA, e.g., an mRNA) of the invention comprises a nucleotide sequence (e.g., an ORF) encoding an OTC polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 2 and 5-29.

In some embodiments, the polynucleotide (e.g., a RNA, e.g., an mRNA) of the invention comprises an ORF encoding an OTC polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 2, and 5-29.

In some embodiments the polynucleotide (e.g., a RNA, e.g., an mRNA) of the invention comprises a nucleotide sequence (e.g., an ORF) encoding an OTC polypeptide (e.g., the wild-type sequence, functional fragment, or variant thereof), wherein the nucleotide sequence is between 70% and 90% identical; between 75% and 85% identical; between 76% and 84% identical; between 77% and 83% identical, between 77% and 82% identical, or between 78% and 81% identical to a sequence selected from the group consisting of SEQ ID NO: 2 or 5-29.

In some embodiments, the polynucleotide (e.g., a RNA, e.g., an mRNA) of the invention comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,187 to 1,200, from 1,187 to 1,400, from 1,187 to 1,600, from 1,187 to 1,800, from 1,187 to 2,000, from 1,187 to 3,000, from 1,187 to 5,000, from 1,187 to 7,000, from 1,187 to 10,000, from 1,187 to from 1,187 to 50,000, from 1,187 to 70,000, or from 1,187 to 100,000).

In some embodiments, the polynucleotide of the invention (e.g., a RNA, e.g., an mRNA) comprises a nucleotide sequence (e.g., an ORF) encoding an OTC polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,100, 1,187, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,300, 5,400, 5,500, 5,600, 5,700, 5,800, 5,900, 6,000, 7,000, 8,000, 9,000, 10,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding an OTC polypeptide (e.g., the wild-type sequence, functional fragment, or variant thereof) further comprises at least one nucleic acid sequence that is noncoding, e.g., a microRNA binding site. In some embodiments, the polynucleotide (e.g., a RNA, e.g., an mRNA) of the invention further comprises a 5'-UTR (e.g., selected from the sequences of SEQ ID NOs: 3, 88-102, or 165-167 or selected from SEQ ID NO:3, SEQ ID NO:191, SEQ ID NO:196, and SEQ ID NO:197) and a 3'UTR (e.g., selected from the sequences of SEQ ID NOs: 4, 104-112, or 150 or selected from SEQ ID NO:4, SEQ ID NO:111, SEQ ID NO:150, SEQ ID NO:175, SEQ ID NO:177, SEQ ID NO:178, SEQ ID NO:198, and SEQ ID NO:199). In some embodiments, the polynucleotide (e.g., a RNA, e.g., an mRNA) of the invention comprises a sequence selected from the group consisting of SEQ ID NOs: 2 and 5-29 In a further embodiment, the polynucleotide (e.g., a RNA, e.g., an mRNA) comprises a 5' terminal cap (e.g., Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In a further embodiment, the polynucleotide (e.g., a RNA, e.g., an mRNA) a comprises a 3' UTR comprising a nucleic acid sequence selected from the group consisting of SEQ ID NOs: 4, 111, or 112 or any combination thereof. In some embodiments, the mRNA comprises a 3' UTR comprising a nucleic acid sequence of SEQ ID NO: 111. In some embodiments, the mRNA comprises a 3' UTR comprising a nucleic acid sequence of SEQ ID NO: 4. In some embodiments, the mRNA comprises a 3' UTR comprising a nucleic acid sequence of any of SEQ ID NO:4, SEQ ID NO:111, SEQ ID NO:150, SEQ ID NO:175, SEQ ID NO:177, SEQ ID NO:178, SEQ ID NO:198, or SEQ ID NO:199. In some embodiments, the mRNA comprises a polyA tail. In some instances, the poly A tail is 50-150, 75-150, 85-150, 90-150, 90-120, 90-130, or 90-150 nucleotides in length. In some instances, the poly A tail is 100 nucleotides in length.

In some embodiments, the polynucleotide of the invention (e.g., a RNA, e.g., an mRNA) comprises a nucleotide sequence (e.g., an ORF) encoding an OTC polypeptide is single stranded or double stranded.

In some embodiments, the polynucleotide of the invention comprising a nucleotide sequence (e.g., an ORF) encoding an OTC polypeptide (e.g., the wild-type sequence, functional fragment, or variant thereof) is DNA or RNA. In some embodiments, the polynucleotide of the invention is RNA. In some embodiments, the polynucleotide of the invention is, or functions as, an mRNA. In some embodiments, the mRNA comprises a nucleotide sequence (e.g., an ORF) that encodes at least one OTC polypeptide, and is capable of being translated to produce the encoded OTC polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding an OTC polypeptide (e.g., the wild-type sequence, functional fragment, or variant thereof, see, e.g., see e.g., SEQ ID NOs.; 2 and 5-29), wherein the polynucleotide comprises at least one chemically modified nucleobase, e.g., N1-methylpseudouracil or 5-methoxyuracil. In certain embodiments, all uracils in the polynucleotide are N1-methylpseudouracils. In other embodiments, all uracils in the polynucleotide are 5-methoxyuracils. In some embodiments, the polynucleotide further comprises a miRNA binding site, e.g., a miRNA binding site that binds to miR-142 and/or a miRNA binding site that binds to miR-126.

In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or "helper lipid") (e.g., 5-10, 10-15, or 15-20 mol % phospholipid (or related suitable phospholipid or "helper lipid")), about 20 to about 50 mol % cholesterol (or related sterol or "non-cationic" lipid) (e.g., about 20-30, 30-35, 35-40, 40-45, or 45-50 mol % cholesterol (or related sterol or "non-cationic" lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or 50:10:38.5:1.5. In certain instances, an exemplary delivery agent can comprise mole ratios of, for example, 47.5:10.5:39.0:3; 47.5:10:39.5:3; 47.5:11:39.5:2; 47.5:10.5:39.5:2.5; 47.5:11:39:2.5; 48.5:10: 38.5:3; 48.5:10.5:39:2; 48.5:10.5:38.5:2.5; 48.5:10.5:39.5: 1.5; 48.5:10.5:38.0:3; 47:10.5:39.5:3; 47:10:40.5:2.5; 47:11: 40:2; 47:10.5:39.5:3; 48:10.5:38.5:3; 48:10:39.5:2.5; 48:11: 39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 50:10:38.5:1.5.

In some embodiments, the polynucleotide of the disclosure is an mRNA that comprises a 5'-terminal cap (e.g., Cap 1), a 5'UTR (e.g., SEQ ID NO:3), an ORF sequence selected from the group consisting of SEQ ID NOs.: 2 and 5-29, a 3'UTR (e.g., SEQ ID NO:4), and a poly A tail (e.g., about 100 nt in length), wherein all uracils in the polynucleotide are N1-methylpseudouracils. In some embodiments, the delivery agent comprises Compound II or Compound VI as the ionizable lipid and PEG-DMG or Compound I as the PEG lipid.

In some embodiments, the polynucleotide of the disclosure is an mRNA that comprises a 5'-terminal cap (e.g., Cap 1), a 5'UTR (e.g., SEQ ID NO:3, SEQ ID NO:191, SEQ ID NO:196, or SEQ ID NO:197), an ORF sequence selected from the group consisting of SEQ ID NOs.: 2 and 5-29, a 3'UTR (e.g., SEQ ID NO:4, SEQ ID NO:111, SEQ ID NO:150, SEQ ID NO:175, SEQ ID NO:177, SEQ ID NO:178, SEQ ID NO:198, or SEQ ID NO:199), and a poly A tail (e.g., about 100 nt in length), wherein all uracils in the polynucleotide are N1-methylpseudouracils. In some embodiments, the delivery agent comprises Compound II or Compound VI as the ionizable lipid and PEG-DMG or Compound I as the PEG lipid.

3. Signal Sequences

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes an OTC polypeptide described herein.

In some embodiments, the "signal sequence" or "signal peptide" is a polynucleotide or polypeptide, respectively, which is from about 30-210, e.g., about 45-80 or 15-60 nucleotides (e.g., about 20, 30, 40, 50, 60, or 70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired sit.

In some embodiments, the polynucleotide of the invention comprises a nucleotide sequence encoding an OTC polypeptide, wherein the nucleotide sequence further comprises a 5' nucleic acid sequence encoding a heterologous signal peptide.

4. Fusion Proteins

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding an OTC polypeptide, a functional fragment, or a variant thereof. However, in some embodiments, the polynucleotide of the invention can comprise more than one ORF, for example, a first ORF encoding an OTC polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a G$_4$S (SEQ ID NO: 86) peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding a OTC polypeptide and a second nucleic acid sequence (e.g., a second ORF) encoding a second polypeptide of interest.

Linkers and Cleavable Peptides

In certain embodiments, the mRNAs of the disclosure encode more than one OTC domain (e.g., OTC catalytic domain, OTC tetramerization domain) or a heterologous domain, referred to herein as multimer constructs. In certain embodiments of the multimer constructs, the mRNA further encodes a linker located between each domain. The linker can be, for example, a cleavable linker or protease-sensitive linker. In certain embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) PLoS ONE 6:e18556). In certain embodiments, the linker is an F2A linker. In certain embodiments, the linker is a GGGS linker. In certain embodiments, the linker is a (GGGS)n linker, wherein n=2, 3,4, or 5 (SEQ ID NO:206). In certain embodiments, the multimer construct contains three domains with intervening linkers, having the structure: domain-linker-domain-linker-domain e.g., OTC domain-linker-OTC domain.

In one embodiment, the cleavable linker is an F2A linker (e.g., having the amino acid sequence GSGVKQTLNFDLLKLAGDVESNPGP (SEQ ID NO:207)). In other embodiments, the cleavable linker is a T2A linker (e.g., having the amino acid sequence GSGEGRGSLLTCGDVEENPGP (SEQ ID NO:208)), a P2A linker (e.g., having the amino acid sequence GSGATNFSLLKQAGDVEENPGP (SEQ ID NO:209)) or an E2A linker (e.g., having the amino acid sequence GSGQCTNYALLKLAGDVESNPGP (SEQ ID NO:210)). The skilled artisan will appreciate that other art-recognized linkers may be suitable for use in the constructs of the invention (e.g., encoded by the polynucleotides of the invention). The skilled artisan will likewise appreciate that other multicistronic constructs may be suitable for use in the invention. In exemplary embodiments, the construct design yields approximately equimolar amounts of intrabody and/or domain thereof encoded by the constructs of the invention.

In one embodiment, the self-cleaving peptide may be, but is not limited to, a 2A peptide. A variety of 2A peptides are known and available in the art and may be used, including e.g., the foot and mouth disease virus (FMDV) 2A peptide, the equine rhinitis A virus 2A peptide, the Thosea asigna virus 2A peptide, and the porcine teschovirus-1 2A peptide. 2A peptides are used by several viruses to generate two proteins from one transcript by ribosome-skipping, such that a normal peptide bond is impaired at the 2A peptide sequence, resulting in two discontinuous proteins being produced from one translation event. As a non-limiting example, the 2A peptide may have the protein sequence of SEQ ID NO:188, fragments or variants thereof. In one embodiment, the 2A peptide cleaves between the last glycine and last proline. As another non-limiting example, the polynucleotides of the present invention may include a polynucleotide sequence encoding the 2A peptide having the protein sequence of fragments or variants of SEQ ID NO:200. One example of a polynucleotide sequence encoding the 2A peptide is: GGAAGCGGAGCUACUAAC-UUCAGCCUGCUGAAGCAGGCUGGAGACGUGGA GGAGAACCCUGGACCU (SEQ ID NO:188). In one illustrative embodiment, a 2A peptide is encoded by the following sequence: 5'-UCCGGACUCAGAUCCGGGGAUCU-CAAAAUUGUCGCUCCUGUCAAACAAACU CUUAACUUUGAUUUACUCAAACUGGCUGGGGAU-GUAGAAAGCAAUCCAGGT CCACUC-3' (SEQ ID NO:200). The polynucleotide sequence of the 2A peptide may be modified or codon optimized by the methods described herein and/or are known in the art.

In one embodiment, this sequence may be used to separate the coding regions of two or more polypeptides of interest. As a non-limiting example, the sequence encoding the F2A peptide may be between a first coding region A and a second coding region B (A-F2Apep-B). The presence of the F2A peptide results in the cleavage of the one long protein between the glycine and the proline at the end of the F2A peptide sequence (NPGP is cleaved to result in NPG and P) thus creating separate protein A (with 21 amino acids of the F2A peptide attached, ending with NPG) and separate protein B (with 1 amino acid, P, of the F2A peptide attached). Likewise, for other 2A peptides (P2A, T2A and E2A), the presence of the peptide in a long protein results in cleavage between the glycine and proline at the end of the 2A peptide sequence (NPGP is cleaved to result in NPG and P). Protein A and protein B may be the same or different peptides or polypeptides of interest (e.g., a OTC polypeptide such as full length human OTC or a truncated version thereof comprising the catalytic and tetramerization domain of OTC). In particular embodiments, protein A and protein B are a OTC catalytic domain, and a OTC tetramerization domain, in either order. In certain embodiments, the first coding region and the second coding region encode a OTC catalytic domain and a OTC tetramerization domain, in either order.

5. Sequence Optimization of Nucleotide Sequence Encoding an OTC Polypeptide

In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding an OTC polypeptide, optionally, a nucleotide sequence (e.g, an ORF) encoding another polypeptide of interest, a 5'-UTR, a 3'-UTR, the 5' UTR or 3' UTR optionally comprising at least one microRNA binding site, optionally a nucleotide sequence encoding a linker, a polyA tail, or any combination thereof), in which the ORF(s) are sequence optimized.

A sequence-optimized nucleotide sequence, e.g., a codon-optimized mRNA sequence encoding an OTC polypeptide, is a sequence comprising at least one synonymous nucleobase substitution with respect to a reference sequence (e.g., a wild type nucleotide sequence encoding an OTC polypeptide).

A sequence-optimized nucleotide sequence can be partially or completely different in sequence from the reference sequence. For example, a reference sequence encoding polyserine uniformly encoded by UCU codons can be sequence-optimized by having 100% of its nucleobases substituted (for each codon, U in position 1 replaced by A, C in position 2 replaced by G, and U in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

Codon options for each amino acid are given in TABLE 1.

TABLE 1

Codon Options

| Amino Acid | Single Letter Code | Codon Options |
|---|---|---|
| Isoleucine | I | AUU, AUC, AUA |
| Leucine | L | CUU, CUC, CUA, CUG, UUA, UUG |
| Valine | V | GUU, GUC, GUA, GUG |
| Phenylalanine | F | UUU, UUC |
| Methionine | M | AUG |
| Cysteine | C | UGU, UGC |
| Alanine | A | GCU, GCC, GCA, GCG |
| Glycine | G | GGU, GGC, GGA, GGG |
| Proline | P | CCU, CCC, CCA, CCG |
| Threonine | T | ACU, ACC, ACA, ACG |
| Serine | S | UCU, UCC, UCA, UCG, AGU, AGC |
| Tyrosine | Y | UAU, UAC |
| Tryptophan | W | UGG |
| Glutamine | Q | CAA, CAG |
| Asparagine | N | AAU, AAC |
| Histidine | H | CAU, CAC |
| Glutamic acid | E | GAA, GAG |
| Aspartic acid | D | GAU, GAC |
| Lysine | K | AAA, AAG |
| Arginine | R | CGU, CGC, CGA, CGG, AGA, AGG |
| Selenocysteine | Sec | UGA in mRNA in presence of Selenocysteine insertion element (SECIS) |
| Stop codons | Stop | UAA, UAG, UGA |

In some embodiments, a polynucleotide (e.g., a RNA, e.g., an mRNA) of the invention comprises a sequence-optimized nucleotide sequence (e.g., an ORF) encoding an OTC polypeptide, a functional fragment, or a variant thereof, wherein the OTC polypeptide, functional fragment, or a variant thereof encoded by the sequence-optimized nucleotide sequence has improved properties (e.g., compared to an OTC polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence (e.g., an ORF) is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g, an ORF) encoding an OTC polypeptide, a nucleotide sequence (e.g, an ORF) encoding another polypeptide of interest, a 5'-UTR, a 3'-UTR, a microRNA binding site, a nucleic acid sequence encoding a linker, or any combination thereof) that is sequence-optimized according to a method comprising:

(i) substituting at least one codon in a reference nucleotide sequence (e.g., an ORF encoding an OTC polypeptide) with an alternative codon to increase or decrease uridine content to generate a uridine-modified sequence;

(ii) substituting at least one codon in a reference nucleotide sequence (e.g., an ORF encoding an OTC polypeptide) with an alternative codon having a higher codon frequency in the synonymous codon set;

(iii) substituting at least one codon in a reference nucleotide sequence (e.g., an ORF encoding an OTC polypeptide) with an alternative codon to increase G/C content; or (iv) a combination thereof.

In some embodiments, the sequence-optimized nucleotide sequence (e.g., an ORF encoding an OTC polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the OTC polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR, a 3' UTR and/or a microRNA binding site. In some embodiments, the polynucleotide comprises two or more 5' UTRs and/or 3' UTRs, which can be the same or different sequences. In some embodiments, the polynucleotide comprises two or more microRNA binding sites, which can be the same or different sequences. Any portion of the 5' UTR, 3' UTR, and/or microRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, *neurospora*, maize, *drosophila*, etc. where high copy plasmid-like or chromosome structures occur by methods described herein.

6. Sequence-Optimized Nucleotide Sequences Encoding OTC Polypeptides

In some embodiments, the polynucleotide of the invention comprises a sequence-optimized nucleotide sequence encoding an OTC polypeptide disclosed herein. In some embodiments, the polynucleotide of the invention comprises an open reading frame (ORF) encoding an OTC polypeptide, wherein the ORF has been sequence optimized.

Exemplary sequence-optimized nucleotide sequences encoding human OTC are set forth as SEQ ID NOs: 2 and 5-29 (OTC-02, OTC-03, OTC-04, OTC-05, OTC-06, OTC-07, OTC-08, OTC-09, OTC-10, OTC-11, OTC-12, OTC-13, OTC-14, OTC-15, OTC-16, OTC-17, OTC-18, OTC-19, OTC-20, OTC-21, OTC-22, OTC-02-001, OTC-03-001, OTC-01-023, OTC-01-024, and OTC-01-25, respectively). In some embodiments, the sequence optimized OTC sequences, fragments, and variants thereof are used to practice the methods disclosed herein. In some embodiments, the sequence optimized OTC sequences set forth in SEQ ID NOs: 2 and 5-29, fragments and variants thereof, are combined with or alternatives to the wild-type OTC sequence.

In some embodiments, a polynucleotide of the present disclosure, for example a polynucleotide comprising an mRNA nucleotide sequence encoding an OTC polypeptide, comprises from 5' to 3' end:
(i) a 5' cap provided herein, for example, Cap1;
(ii) a 5' UTR, such as the sequences provided herein, for example, SEQ ID NO: 3;
(iii) an open reading frame encoding an OTC polypeptide, e.g., a sequence optimized nucleic acid sequence encoding OTC set forth as SEQ ID NOs: 2 and 5-29;
(iv) at least one stop codon;
(v) a 3' UTR, such as the sequences provided herein, for example, SEQ ID NO: 4; and
(vi) a poly-A tail provided above.

In some embodiments, a polynucleotide of the present disclosure, for example a polynucleotide comprising an mRNA nucleotide sequence encoding an OTC polypeptide, comprises from 5' to 3' end:
(i) a 5' cap provided herein, for example, Cap1;
(ii) a 5' UTR, such as the sequences provided herein, for example, SEQ ID NO:3, SEQ ID NO:191, SEQ ID NO:196, or SEQ ID NO:197;
(iii) an open reading frame encoding an OTC polypeptide, e.g., a sequence optimized nucleic acid sequence encoding OTC set forth as SEQ ID NOs: 2 and 5-29;
(iv) at least one stop codon;
(v) a 3' UTR, such as the sequences provided herein, for example, SEQ ID NO:4, SEQ ID NO:111, SEQ ID NO:150, SEQ ID NO:175, SEQ ID NO:177, SEQ ID NO:178, SEQ ID NO:198, or SEQ ID NO:199; and
(vi) a poly-A tail provided above.

In certain embodiments, all uracils in the polynucleotide are N1-methylpseudouracil (G5). In certain embodiments, all uracils in the polynucleotide are 5-methoxyuracil (G6).

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding an OTC polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

Methods for optimizing codon usage are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

7. Characterization of Sequence Optimized Nucleic Acids

In some embodiments of the invention, the polynucleotide (e.g., a RNA, e.g., an mRNA) comprising a sequence optimized nucleic acid disclosed herein encoding an OTC polypeptide can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding an OTC polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding an OTC polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the invention, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half life by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the invention, the desired property of the polynucleotide is the level of expression of an OTC polypeptide encoded by a sequence optimized sequence disclosed herein. Protein expression levels can be measured using one or more expression systems. In some embodiments, expression can be measured in cell culture systems, e.g., CHO cells, HEK293 cells, or HeLa cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the invention, the sequence optimization of a nucleic acid sequence disclosed herein, e.g., a nucleic acid sequence encoding an OTC polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding an OTC polypeptide or a functional fragment thereof can trigger an immune response, which could be caused by (i) the therapeutic agent (e.g., an mRNA encoding an OTc polypeptide), or (ii) the expression product of such therapeutic agent (e.g., the OTC polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding an OTC polypeptide or by the expression product of OTC encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon 7-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (I1-13), interferon α (IFN-α), etc.

8. Modified Nucleotide Sequences Encoding OTC Polypeptides

In some embodiments, the polynucleotide (e.g., a RNA, e.g., an mRNA) of the invention comprises a chemically modified nucleobase, for example, a chemically modified uracil, e.g., pseudouracil, N1-methylpseudouracil, 5-methoxyuracil, or the like. In some embodiments, the mRNA is a uracil-modified sequence comprising an ORF encoding a OTC polypeptide, wherein the mRNA comprises a chemically modified nucleobase, for example, a chemically modified uracil, e.g., pseudouracil, N1-methylpseudouracil, or 5-methoxyuracil.

In certain aspects of the invention, when the modified uracil base is connected to a ribose sugar, as it is in polynucleotides, the resulting modified nucleoside or nucleotide is referred to as modified uridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% modified uracil. In one embodiment, uracil in the polynucleotide is at least 95% modified uracil. In another embodiment, uracil in the polynucleotide is 100% modified uracil.

In embodiments where uracil in the polynucleotide is at least 95% modified uracil overall uracil content can be adjusted such that an mRNA provides suitable protein expression levels while inducing little to no immune response. In some embodiments, the uracil content of the ORF is between about 100% and about 150%, between about 100% and about 110%, between about 105% and about 115%, between about 110% and about 120%, between about 115% and about 125%, between about 120% and about 130%, between about 125% and about 135%, between about 130% and about 140%, between about 135% and about 145%, between about 140% and about 150% of the theoretical minimum uracil content in the corresponding wild-type ORF (% $U_{TM}$). In other embodiments, the uracil content of the ORF is between about 121% and about 136% or between 123% and 134% of the % $U_{TM}$. In some embodiments, the uracil content of the ORF encoding a OTC polypeptide is about 115%, about 120%, about 125%, about 130%, about 135%, about 140%, about 145%, or about 150% of the % $U_{TM}$. In this context, the term "uracil" can refer to modified uracil and/or naturally occurring uracil.

In some embodiments, the uracil content in the ORF of the mRNA encoding a OTC polypeptide of the invention is less than about 30%, about 25%, about 20%, about 15%, or about 10% of the total nucleobase content in the ORF. In some embodiments, the uracil content in the ORF is between about 10% and about 20% of the total nucleobase content in the ORF. In other embodiments, the uracil content in the ORF is between about 10% and about 25% of the total nucleobase content in the ORF. In one embodiment, the uracil content in the ORF of the mRNA encoding a OTC polypeptide is less than about 20% of the total nucleobase content in the open reading frame. In this context, the term "uracil" can refer to modified uracil and/or naturally occurring uracil.

In further embodiments, the ORF of the mRNA encoding a OTC polypeptide having modified uracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the OTC polypeptide (% $G_{TMX}$; % $C_{TMX}$, or % $G/C_{TMX}$). In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a OTC polypeptide of the invention comprises modified uracil and has an adjusted uracil content containing less uracil pairs (UU) and/or uracil triplets (UUU) and/or uracil quadruplets (UUUU) than the corresponding wild-type nucleotide sequence encoding the OTC polypeptide. In some embodiments, the ORF of the mRNA encoding a OTC polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the OTC polypeptide. In a particular embodiment, the ORF of the mRNA encoding the OTC polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the OTC polypeptide contains no non-phenylalanine uracil pairs and/or triplets.

In further embodiments, the ORF of the mRNA encoding a OTC polypeptide of the invention comprises modified uracil and has an adjusted uracil content containing less uracil-rich clusters than the corresponding wild-type nucleotide sequence encoding the OTC polypeptide. In some embodiments, the ORF of the mRNA encoding the OTC polypeptide of the invention contains uracil-rich clusters that are shorter in length than corresponding uracil-rich clusters in the corresponding wild-type nucleotide sequence encoding the OTC polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the OTC polypeptide-encoding ORF of the modified uracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the OTC polypeptide is substituted with an alternative codon having a codon frequency lower than the codon frequency of the substituted codon in the synonymous codon set.

In some embodiments, the adjusted uracil content, OTC polypeptide-encoding ORF of the modified uracil-comprising mRNA exhibits expression levels of OTC when administered to a mammalian cell that are higher than expression levels of OTC from the corresponding wild-type mRNA. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, OTC is expressed a a level higher than expression levels of OTC from the corresponding wild-type mRNA when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or 0.2 mg/kg or about 0.5 mg/kg. In some embodiments, the mRNA is administered intravenously or intramuscularly. In other embodiments, the OTC polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, OTC polypeptide-encoding ORF of the modified uracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, serum, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a OTC polypeptide but does not comprise modified uracil under the same conditions, or relative to the immune response induced by an mRNA that encodes for a OTC polypeptide and that comprises modified uracil but that does not have adjusted uracil content under the same conditions. The innate immune response can be manifested by increased expression of pro-inflammatory cytokines, activation of intracellular PRRs (RIG-I, MDA5, etc), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a OTC polypeptide but does not comprise modified uracil, or to an mRNA that encodes a OTC polypeptide and that comprises modified uracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a OTC polypeptide but does not comprise modified uracil, or an mRNA that encodes for a OTC polypeptide and that comprises modified uracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

9. Methods for Modifying Polynucleotides

The disclosure includes modified polynucleotides comprising a polynucleotide described herein (e.g., a polynucleotide, e.g. mRNA, comprising a nucleotide sequence encoding an OTC polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding an OTC polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

In some embodiments, a polynucleotide of the present invention (e.g., a polynucleotide comprising a nucleotide sequence encoding an OTC polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

Therapeutic compositions of the present disclosure comprise, in some embodiments, at least one nucleic acid (e.g., RNA) having an open reading frame encoding at least one OTC polypeptide, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

In some embodiments, at least one RNA (e.g., mRNA) of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise N1-methylpseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises N1-methylpseudouridine (m1ψ) substitutions at one or more or all uridine positions of the nucleic acid.

In some embodiments, a RNA nucleic acid of the disclosure comprises N1-methylpseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with N1-methylpseudouridine, meaning that all uridine residues in the mRNA sequence are replaced with N1-methylpseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

10. Untranslated Regions (UTRs)

Translation of a polynucleotide comprising an open reading frame encoding a polypeptide can be controlled and regulated by a variety of mechanisms that are provided by various cis-acting nucleic acid structures. For example, naturally-occurring, cis-acting RNA elements that form hairpins or other higher-order (e.g., pseudoknot) intramolecular mRNA secondary structures can provide a translational regulatory activity to a polynucleotide, wherein the RNA element influences or modulates the initiation of polynucleotide translation, particularly when the RNA element is positioned in the 5' UTR close to the 5'-cap structure (Pelletier and Sonenberg (1985) Cell 40(3):515-526; Kozak (1986) Proc Natl Acad Sci 83:2850-2854).

Untranslated regions (UTRs) are nucleic acid sections of a polynucleotide before a start codon (5' UTR) and after a stop codon (3' UTR) that are not translated. In some embodiments, a polynucleotide (e.g., a ribonucleic acid (RNA), e.g., a messenger RNA (mRNA)) of the invention comprising an open reading frame (ORF) encoding an OTC polypeptide further comprises UTR (e.g., a 5'UTR or functional fragment thereof, a 3'UTR or functional fragment thereof, or a combination thereof).

Cis-acting RNA elements can also affect translation elongation, being involved in numerous frameshifting events (Namy et al., (2004) Mol Cell 13(2):157-168). Internal ribosome entry sequences (IRES) represent another type of cis-acting RNA element that are typically located in 5' UTRs, but have also been reported to be found within the coding region of naturally-occurring mRNAs (Holcik et al. (2000) Trends Genet 16(10):469-473). In cellular mRNAs, IRES often coexist with the 5'-cap structure and provide mRNAs with the functional capacity to be translated under conditions in which cap-dependent translation is compromised (Gebauer et al., (2012) Cold Spring Harb Perspect Biol 4(7):a012245). Another type of naturally-occurring cis-acting RNA element comprises upstream open reading frames (uORFs). Naturally-occurring uORFs occur singularly or multiply within the 5' UTRs of numerous mRNAs and influence the translation of the downstream major ORF, usually negatively (with the notable exception of GCN4 mRNA in yeast and ATF4 mRNA in mammals, where uORFs serve to promote the translation of the downstream major ORF under conditions of increased eIF2 phosphorylation (Hinnebusch (2005) Annu Rev Microbiol 59:407-450)). Additional exemplary translational regulatory activities provided by components, structures, elements, motifs, and/or specific sequences comprising polynucleotides (e.g., mRNA) include, but are not limited to, mRNA stabilization or destabilization (Baker & Parker (2004) Curr Opin Cell Biol 16(3):293-299), translational activation (Villalba et al., (2011) Curr Opin Genet Dev 21(4):452-457), and translational repression (Blumer et al., (2002) Mech Dev 110(1-2):97-112). Studies have shown that naturally-occurring, cis-acting RNA elements can confer their respective functions when used to modify, by incorporation into, heterologous polynucleotides (Goldberg-Cohen et al., (2002) J Biol Chem 277(16):13635-13640).

Modified Polynucleotides Comprising Functional RNA Elements

The present disclosure provides synthetic polynucleotides comprising a modification (e.g., an RNA element), wherein the modification provides a desired translational regulatory activity. In some embodiments, the disclosure provides a polynucleotide comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a polynucleotide, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich element), by RNA secondary structure formed by the element (e.g. stem-loop), by the location of the element within the RNA molecule (e.g., located within the 5' UTR of an mRNA), by the biological function and/or activity of the element (e.g., "translational enhancer element"), and any combination thereof.

In some aspects, the disclosure provides an mRNA having one or more structural modifications that inhibits leaky scanning and/or promotes the translational fidelity of mRNA translation, wherein at least one of the structural modifications is a GC-rich RNA element. In some aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In other aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is [CCG]n, wherein n=1 to 10, n=2 to 8, n=3 to 6, or n=4 to 5. In some embodiments, the sequence comprises a repeating GC-motif [CCG]n, wherein n=1, 2, 3, 4 or 5. In some embodiments, the sequence comprises a repeating GC-motif [CCG]n, wherein n=1, 2, or 3. In some embodiments, the sequence comprises a repeating GC-motif [CCG]n, wherein n=1. In some embodiments, the sequence comprises a repeating GC-motif [CCG]n, wherein n=2. In some embodiments, the sequence comprises a repeating GC-motif [CCG]n, wherein n=3. In some embodiments, the sequence comprises a repeating GC-motif [CCG]n, wherein n=4. In some embodiments, the sequence comprises a repeating GC-motif [CCG]n, wherein n=5.

In another aspect, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element comprises any one of the sequences set forth in Table 2. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In other aspects, the disclosure provides a modified mRNA comprising at least one modification, wherein at least one modification is a GC-rich RNA element comprising the sequence V1 [CCCCGGCGCC (SEQ ID NO: 194)] as set forth in Table 2, or derivatives or analogs thereof, preceding a Kozak consensus sequence in the 5' UTR of the mRNA. In some embodiments, the GC-rich element comprises the sequence V1 as set forth in Table 2 located immediately adjacent to and upstream of the Kozak consensus sequence in the 5' UTR of the mRNA. In some embodiments, the GC-rich element comprises the sequence V1 as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence V2 [CCCCGGC (SEQ ID NO: 195)] as set forth in Table 2, or derivatives or analogs thereof, preceding a Kozak consensus sequence in the 5' UTR of the mRNA. In some embodiments, the GC-rich element comprises the sequence V2 as set forth in Table 2 located immediately adjacent to and upstream of the Kozak consensus sequence in the 5' UTR of the mRNA. In some embodiments, the GC-rich element comprises the sequence V2 as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V2 as set forth in Table 2 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence EK [GCCGCC (SEQ ID NO: 193)] as set forth in Table 2, or derivatives or analogs thereof, preceding a Kozak consensus sequence in the 5' UTR of the mRNA. In some embodiments, the GC-rich element comprises the sequence EK as set forth in Table 2 located immediately adjacent to and upstream of the Kozak consensus sequence in the 5' UTR of the mRNA. In some embodiments, the GC-rich element comprises the sequence EK as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence EK as set forth in Table 2 located 1-3, 3-5, 5-7, 7-9, 9-12, or 12-15 bases upstream of the Kozak consensus sequence in the 5' UTR of the mRNA.

In yet other aspects, the disclosure provides a modified mRNA comprising at least one modification, wherein at least one modification is a GC-rich RNA element comprising the sequence V1 [CCCCGGCGCC (SEQ ID NO: 194)] as set forth in Table 2, or derivatives or analogs thereof, preceding a Kozak consensus sequence in the 5' UTR of the mRNA, wherein the 5' UTR comprises the following sequence shown in Table 2:

GGGAAAUAAGAGAGAAAAGAAGAGUA AGAAGAAAUAUAAGA (SEQ ID NO: 85). The skilled artisan will of course recognize that all Us in the RNA sequences described herein will be Ts in a corresponding template DNA sequence, for example, in DNA templates or constructs from which mRNAs of the disclosure are transcribed, e.g., via IVT.

In some embodiments, the GC-rich element comprises the sequence V1 as set forth in Table 2 located immediately adjacent to and upstream of the Kozak consensus sequence in the 5' UTR sequence shown in Table 2. In some embodiments, the GC-rich element comprises the sequence V1 as set forth in Table 2 located 1, 2, 3, 4, 5, 6, 7, 8, 9 or 10 bases upstream of the Kozak consensus sequence in the 5' UTR of the mRNA, wherein the 5' UTR comprises the following sequence shown in Table 2:

```
                                        (SEQ ID NO: 85)
   GGGAAAUAAGAGAGAAAAGAAGAGUAAGAAGAAAUAUAAGA.
```

In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA, wherein the 5' UTR comprises the following sequence shown in Table 2:

```
                                        (SEQ ID NO: 85)
   GGGAAAUAAGAGAGAAAAGAAGAGUAAGAAGAAAUAUAAGA.
```

In some embodiments, the 5' UTR comprises the following sequence set forth in Table 2:

```
                                       (SEQ ID NO: 191)
   GGGAAAUAAGAGAGAAAAGAAGAGUAAGAAGAAAUAUAAGACCCCG
   GCGCCGCCACC
```

TABLE 2

| 5'UTRs | 5'UTR Sequence |
|---|---|
| Standard | GGGAAAUAAGAGAGAAAAGAAGAGUAAGAAG AAAUAUAAGAGCCACC (SEQ ID NO: 3) |
| V1-UTR | GGGAAAUAAGAGAGAAAAGAAGAGUAAGAAG AAAUAUAAGACCCCGGCGCCGCCACC (SEQ ID NO: 191) |
| V2-UTR | GGGAAAUAAGAGAGAAAAGAAGAGUAAGAAG AAAUAUAAGACCCCGGCGCCACC (SEQ ID NO: 190) |
| GC-Rich RNA Elements | Sequence |
| K0 (Traditional Kozak consensus) | [GCCA/GCC] (SEQ ID NO: 192) |
| EK | [GCCGCC] (SEQ ID NO: 193) |
| V1 | [CCCCGGCGCC] (SEQ ID NO: 194) |
| V2 | [CCCCGGC] (SEQ IDNO: 195) |
| $(CCG)_n$, where n = 1-10 | $[CCG]_n$ |
| $(GCC)_n$, where n = 1-10 | $[GCC]_n$ |

In another aspect, the disclosure provides a modified mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream of the Kozak consensus sequence. In another embodiment, the stable RNA secondary structure is located about 30, about 25, about 20, about 15, about 10, or about 5 nucleotides upstream of the Kozak consensus sequence. In another embodiment, the stable RNA secondary structure is located about 20, about 15, about 10 or about 5 nucleotides upstream of the Kozak consensus sequence. In another embodiment, the stable RNA secondary structure is located about 5, about 4, about 3, about 2, about 1 nucleotides upstream of the Kozak consensus sequence. In another embodiment, the stable RNA secondary structure is located about 15-30, about 15-20, about 15-25, about 10-15, or about 5-10 nucleotides upstream of the Kozak consensus sequence. In another embodiment, the stable RNA secondary structure is located 12-15 nucleotides upstream of the Kozak consensus sequence. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to ~10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

RNA elements that provide a desired translational regulatory activity as described herein can be identified and characterized using known techniques, such as ribosome profiling. Ribosome profiling is a technique that allows the determination of the positions of PICs and/or ribosomes bound to mRNAs (see e.g., Ingolia et al., (2009) Science 324(5924):218-23, incorporated herein by reference). The technique is based on protecting a region or segment of mRNA, by the PIC and/or ribosome, from nuclease digestion. Protection results in the generation of a 30-bp fragment of RNA termed a 'footprint'. The sequence and frequency of RNA footprints can be analyzed by methods known in the art (e.g., RNA-seq). The footprint is roughly centered on the A-site of the ribosome. If the PIC or ribosome dwells at a particular position or location along an mRNA, footprints generated at these position would be relatively common. Studies have shown that more footprints are generated at positions where the PIC and/or ribosome exhibits decreased processivity and fewer footprints where the PIC and/or ribosome exhibits increased processivity (Gardin et al., (2014) eLife 3:e03735). In some embodiments, residence time or the time of occupancy of the PIC or ribosome at a discrete position or location along a polynucleotide comprising any one or more of the RNA elements described herein is determined by ribosome profiling.

A UTR can be homologous or heterologous to the coding region in a polynucleotide. In some embodiments, the UTR is homologous to the ORF encoding the OTC polypeptide. In some embodiments, the UTR is heterologous to the ORF encoding the OTC polypeptide. In some embodiments, the polynucleotide comprises two or more 5'UTRs or functional fragments thereof, each of which has the same or different nucleotide sequences. In some embodiments, the polynucleotide comprises two or more 3'UTRs or functional fragments thereof, each of which has the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., N1-methylpseudouracil or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5' UTR or 3' UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG (SEQ ID NO: 87), where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5' UTR and the 3' UTR can be heterologous. In some embodiments, the 5' UTR can be derived from a different species than the 3' UTR. In some embodiments, the 3' UTR can be derived from a different species than the 5' UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more and/or 3'UTR derived from the nucleic acid sequence of: a globin, such as an α- or β-globin (e.g., a Xenopus, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial H⁺-ATP synthase); a growth hormone e (e.g., bovine (bGH) or human (hGH)); an elongation factor (e.g., elongation factor 1 al (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5' UTR is selected from the group consisting of a β-globin 5' UTR; a 5'UTR containing a strong Kozak translational initiation signal; a cytochrome b-245 α polypeptide (CYBA) 5' UTR; a hydroxysteroid (17-(3) dehydrogenase (HSD17B4) 5' UTR; a Tobacco etch virus (TEV) 5' UTR; a Venezuelen equine encephalitis virus (TEEV) 5' UTR; a 5' proximal open reading frame of rubella virus (RV) RNA encoding nonstructural proteins; a Dengue virus (DEN) 5' UTR; a heat shock protein 70 (Hsp70) 5' UTR; a eIF4G 5' UTR; a GLUT1 5' UTR; functional fragments thereof and any combination thereof.

In some embodiments, the 3' UTR is selected from the group consisting of a β-globin 3' UTR; a CYBA 3' UTR; an albumin 3' UTR; a growth hormone (GH) 3' UTR; a VEEV 3' UTR; a hepatitis B virus (HBV) 3' UTR; α-globin 3'UTR; a DEN 3' UTR; a PAV barley yellow dwarf virus (BYDV-PAV) 3' UTR; an elongation factor 1 al (EEF1A1) 3' UTR; a manganese superoxide dismutase (MnSOD) 3' UTR; a13 subunit of mitochondrial H(+)-ATP synthase (β-mRNA) 3' UTR; a GLUT1 3' UTR; a MEF2A 3' UTR; a β-F1-ATPase 3' UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, the contents of which are incorporated herein by reference in their entirety.

UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5' UTR or 3' UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5' UTR and/or a 3' UTR selected from any of the UTRs disclosed herein. In some embodiments, the 5' UTR comprises:

5' UTR-001 (Upstream UTR)
                                    (SEQ ID NO:3)
(GGGAAAUAAGAGAGAAAAGAAGAGUAAGAAGAAAUAUAAGAGCCACC);

5' UTR-002 (Upstream UTR)
                                    (SEQ ID NO: 89)
(GGGAGAUCAGAGAGAAAAGAAGAGUAAGAAGAAAUAUAAGAGCCACC);

5' UTR-003 (Upstream UTR) (See WO2016/100812);

5' UTR-004 (Upstream UTR)
                                    (SEQ ID NO: 90)
(GGGAGACAAGCUUGGCAUUCCGGUACUGUUGGUAAAGCCACC);

5' UTR-005 (Upstream UTR)
                                    (SEQ ID NO: 89)
(GGGAGAUCAGAGAGAAAAGAAGAGUAAGAAGAAAUAUAAGAGCCACC);

5' UTR-006 (Upstream UTR) (See WO2016/100812);

5' UTR-007 (Upstream UTR)
                                    (SEQ ID NO: 90)
(GGGAGACAAGCUUGGCAUUCCGGUACUGUUGGUAAAGCCACC);

5' UTR-008 (Upstream UTR)
                                    (SEQ ID NO: 93)
(GGGAAUUAACAGAGAAAAGAAGAGUAAGAAGAAAUAUAAGAGCCACC);

5' UTR-009 (Upstream UTR)
                                    (SEQ ID NO: 94)
(GGGAAAUUAGACAGAAAAGAAGAGUAAGAAGAAAUAUAAGAGCCACC);

5' UTR-010, Upstream
                                    (SEQ ID NO: 95)
(GGGAAAUAAGAGAGUAAAGAACAGUAAGAAGAAAUAUAAGAGCCACC);

5' UTR-011 (Upstream UTR)
                                    (SEQ ID NO: 96)
(GGGAAAAAAGAGAGAAAAGAAGACUAAGAAGAAAUAUAAGAGCCACC);

5' UTR-012 (Upstream UTR)
                                    (SEQ ID NO: 97)
(GGGAAAUAAGAGAGAAAAGAAGAGUAAGAAGAUAUAUAAGAGCCACC);

5' UTR-013 (Upstream UTR)
                                    (SEQ ID NO: 98)
(GGGAAAUAAGAGACAAAACAAGAGUAAGAAGAAAUAUAAGAGCCACC);

5' UTR-014 (Upstream UTR)
                                    (SEQ ID NO: 99)
(GGGAAAUUAGAGAGUAAAGAACAGUAAGUAGAAUUAAAAGAGCCACC);

5' UTR-15 (Upstream UTR)
                                    (SEQ ID NO: 100)
(GGGAAAUAAGAGAGAAUAGAAGAGUAAGAAGAAAUAUAAGAGCCACC);

5' UTR-016 (Upstream UTR)
                                    (SEQ ID NO: 101)
(GGGAAAUAAGAGAGAAAAGAAGAGUAAGAAGAAAUUAAGAGCCACC);

5' UTR-017 (Upstream UTR);
                                    (SEQ ID NO:102)
(GGGAAAUAAGAGAGAAAAGAAGAGUAAGAAGAAAUUUAAGAGCCACC);
or 5' UTR-018 (Upstream UTR) 5' UTR
                                    (SEQ ID NO: 88)
(UCAAGCUUUUGGACCCUCGUACAGAAGCUAAUACGACUCACUAUAGGGA
AAUAAGAGAGAAAAGAAGAGUAAGAAGAAAUAUAAGAGCCACC).

In some embodiments, the 3' UTR comprises:

142-3p 3' UTR (UTR including miR142-3p binding site)
                                    (SEQ ID NO: 162)
(UGAUAAUAGUCCAUAAAGUAGGAAACACUACAGCUGGAGCCUCGGUGGC
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);

142-3p 3' UTR (UTR including miR142-3p binding site)
                                    (SEQ ID NO: 163)
(UGAUAAUAGGCUGGAGCCUCGGUGGCUCCAUAAAGUAGGAAACACUACA
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);
or 142-3p 3' UTR (UTR including miR142-3p binding site)
                                    (SEQ ID NO: 170)
(UGAUAAUAGGCUGGAGCCUCGGUGGCCAUGCUUCUUGCCCCUUCCAUAA
AGUAGGAAACACUACAUGGGCCUCCCCCCAGCCCCUCCUCCCCUUCCUGC
ACCCGUACCCCCGUGGUCUUUGAAUAAAGUCUGAGUGGGCGGC);

142-3p 3' UTR (UTR including miR142-3p binding site)
                                    (SEQ ID NO: 171)
(UGAUAAUAGGCUGGAGCCUCGGUGGCCAUGCUUCUUGCCCCUUGGGCCU
CCCCCCAGUCCAUAAAGUAGGAAACACUACACCCCUCCUCCCCUUCCUGC
ACCCGUACCCCCGUGGUCUUUGAAUAAAGUCUGAGUGGGCGGC);

142-3p 3' UTR (UTR including miR142-3p binding site)
                                    (SEQ ID NO: 172)
(UGAUAAUAGGCUGGAGCCUCGGUGGCCAUGCUUCUUGCCCCUUGGGCCU
CCCCCCAGCCCCUCCUCCCCUUCUCCAUAAAGUAGGAAACACUACACUGC
ACCCGUACCCCCGUGGUCUUUGAAUAAAGUCUGAGUGGGCGGC);

142-3p 3' UTR (UTR including miR142-3p binding site)
                                    (SEQ ID NO: 151)
(UGAUAAUAGGCUGGAGCCUCGGUGGCCAUGCUUCUUGCCCCUUGGGCCU
CCCCCCAGCCCCUCCUCCCCUUCCUGCACCCGUACCCCCUCCAUAAAGUA
GGAAACACUACAGUGGUCUUUGAAUAAAGUCUGAGUGGGCGGC).

142-3p 3' UTR (UTR including miR142-3p binding site)
                                    (SEQ ID NO: 173)
(UGAUAAUAGGCUGGAGCCUCGGUGGCCAUGCUUCUUGCCCCUUGGGCCU
CCCCCCAGCCCCUCCUCCCCUUCCUGCACCCGUACCCCCGUGGUCUUUGA
AUAAAGUUCCAUAAAGUAGGAAACACUACACUGAGUGGGCGGC);

3' UTR-018 (See SEQ ID NO: 150;

3' UTR (miR142 and miR126 binding sites variant 1)
                                    (SEQ ID NO: 111)
(UGAUAAUAGUCCAUAAAGUAGGAAACACUACAGCUGGAGCCUCGGUGGC
CAUGCUUCUUGCCCCUUGGGCCUCCCCCCAGCCCCUCCUCCCCUUCCUGC
ACCCGUACCCCCGCAUUAUUACUCACGGUACGAGUGGUCUUUGAAUAAA
GUCUGAGUGGGCGGC)

-continued

3' UTR (miR142 and miR126 binding sites variant 2)
(SEQ ID NO: 112)
(UGAUAAUAGUCCAUAAAGUAGGAAACACUACAGCUGGAGCCUCGGUGGC

CUAGCUUCUUGCCCCUUGGGCCUCCCCCCAGCCCCUCCUCCCCUUCCUGC

ACCCGUACCCCCCGCAUUAUUACUCACGGUACGAGUGGUCUUUGAAUAAA

GUCUGAGUGGGCGGC);
or

3'UTR (miR142-3p binding site variant 3)
(SEQ ID NO: 4)
UGAUAAUAGGCUGGAGCCUCGGUGGCCUAGCUUCUUGCCCCUUGGGCCUC

CCCCCAGCCCCUCCUCCCCUUCCUGCACCCGUACCCCUCCAUAAAGUAG

GAAACACUACAGUGGUCUUUGAAUAAAGUCUGAGUGGGCGGC.

In certain embodiments, the 5' UTR and/or 3' UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5' UTR sequences comprising any of SEQ ID NOs: 3, 88-102, or 165-167 and/or 3' UTR sequences comprises any of SEQ ID NOs:4, 104-112, or 150, and any combination thereof.

In certain embodiments, the 5' UTR and/or 3' UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5' UTR sequences comprising any of SEQ ID NO:3, SEQ ID NO:191, SEQ ID NO:196, or SEQ ID NO:197 and/or 3' UTR sequences comprises any of SEQ ID NO:4, SEQ ID NO:111, SEQ ID NO:150, SEQ ID NO:175, SEQ ID NO:177, SEQ ID NO:178, SEQ ID NO:198, or SEQ ID NO:199, and any combination thereof.

In some embodiments, the 5' UTR comprises an amino acid sequence set forth in Table 4B (SEQ ID NO:3, SEQ ID NO:191, SEQ ID NO:196, or SEQ ID NO:197). In some embodiments, the 3' UTR comprises an amino acid sequence set forth in Table 4B (SEQ ID NO:4, SEQ ID NO:111, SEQ ID NO:150, SEQ ID NO:175, SEQ ID NO:177, SEQ ID NO:178, SEQ ID NO:198, or SEQ ID NO:199). In some embodiments, the 5' UTR comprises an amino acid sequence set forth in Table 4B (SEQ ID NO:3, SEQ ID NO:191, SEQ ID NO:196, or SEQ ID NO:197) and the 3' UTR comprises an amino acid sequence set forth in Table 4B (SEQ ID NO:4, SEQ ID NO:111, SEQ ID NO:150, SEQ ID NO:175, SEQ ID NO:177, SEQ ID NO:178, SEQ ID NO:198, or SEQ ID NO:199).

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5' UTR sequence. In some embodiments, the polynucleotide comprises an ORF and a viral capsid sequence. In some embodiments, the polynucleotide comprises a synthetic 5' UTR in combination with a non-synthetic 3' UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can be located between the transcription promoter and the start codon. In some embodiments, the 5' UTR comprises a TEE.

In one aspect, a TEE is a conserved element in a UTR that can promote translational activity of a nucleic acid such as, but not limited to, cap-dependent or cap-independent translation.

11. MicroRNA (miRNA) Binding Sites

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences".

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

The present invention also provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a polypeptide. In some embodiments, the polynucleotide further comprises a miRNA binding site, e.g., a miRNA binding site that binds A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5' UTR and/or 3' UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide long miRNA sequence, to a 19-23 nucleotide long miRNA sequence, or to a 22 nucleotide long miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/1eu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5' UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5' UTR and/or 3' UTR of a polynucleotide of the invention.

To further drive the selective degradation and suppression in APCs and macrophage, a polynucleotide of the invention can include a further negative regulatory element in the 5' UTR and/or 3' UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. mMiRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-5480-3p, miR-5480-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008,18, 610-621; Goff L A et al., PLoS One, 2009, 4:e7192; Bar M et al., Stem cells, 2008, 26, 2496-2505, the content of each of which is incorporated herein by reference in its entirety).

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) PLoS One 9:e102259; Landgraf, P. et al. (2007) Cell 129:1401-1414; Bissels, U. et al. (2009) RNA 15:2375-2384. Any one miR-site incorporation in the 3' UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plamacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of a polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g, reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miRNA binding site. In certain embodiments, use of three copies of the same miR binding site can exhibit beneficial properties as compared to use of a single miRNA binding site. Non-limiting examples of sequences for 3' UTRs containing three miRNA bindings sites are shown in SEQ ID NO: 155 (three miR-142-3p binding sites) and SEQ ID NO: 157 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 111 (one miR-142-3p binding site and one miR-126-3p binding site), SEQ ID NO: 158 (two miR-142-5p binding sites and one miR-142-3p binding sites), and SEQ ID NO: 161 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences 123. In some embodiments, the miRNA binding site comprises a nucleotide sequence at least 80%, at least 85%, at least 90%, at least 95%, or 100% identical to SEQ ID NO: 121 or SEQ ID NO: 123.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO: 98 or 163.

TABLE 3 miR-142, miR-126, and miR-142 and miR-126 binding sites

| SEQ ID NO. | Description | Sequence |
|---|---|---|
| 114 | miR-142 | GACAGUGCAGUCACCCAUAAAGUAGAAAGCACUACUAA CAGCACUGGAGGGUGUAGUGUUUCCUACUUUAUGGAUG AGUGUACUGUG |
| 115 | miR-142-3p | UGUAGUGUUUCCUACUUUAUGGA |
| 116 | miR-142-3p binding site | UCCAUAAAGUAGGAAACACUACA |
| 117 | miR-142-5p | CAUAAAGUAGAAAGCACUACU |
| 118 | miR-142-5p binding site | AGUAGUGCUUUCUACUUUAUG |
| 1119 | miR-126 | CGCUGGCGACGGGACAUUAUUACUUUUGGUACGCGCUG UGACACUUCAAACUCGUACCGUGAGUAAUAAUGCGCCG UCCACGGCA |
| 120 | miR-126-3p | uCGUACCGUGAGUAAUAAUGCG |
| 121 | miR-126-3p binding site | CGCAUUAUUACUCACGGUACGA |
| 122 | miR-126-5p | CAUUAUUACUUUUGGUACGCG |
| 123 | miR-126-5p binding site | CGCGUACCAAAAGUAAUAAUG | selected from Table 3, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from Table 3, including any combination thereof.

In some embodiments, the miRNA binding site binds to miR-142 or is complementary to miR-142. In some embodiments, the miR-142 comprises SEQ ID NO:114. In some embodiments, the miRNA binding site binds to miR-142-3p or miR-142-5p. In some embodiments, the miR-142-3p binding site comprises SEQ ID NO:116. In some embodiments, the miR-142-5p binding site comprises SEQ ID NO:118. In some embodiments, the miRNA binding site comprises a nucleotide sequence at least 80%, at least 85%, at least 90%, at least 95%, or 100% identical to SEQ ID NO:116 or SEQ ID NO:118.

In some embodiments, the miRNA binding site binds to miR-126 or is complementary to miR-126. In some embodiments, the miR-126 comprises SEQ ID NO: 119. In some embodiments, the miRNA binding site binds to miR-126-3p or miR-126-5p. In some embodiments, the miR-126-3p binding site comprises SEQ ID NO: 121. In some embodiments, the miR-126-5p binding site comprises SEQ ID NO:

In some embodiments, a miRNA binding site is inserted in the polynucleotide of the invention in any position of the polynucleotide (e.g., the 5' UTR and/or 3' UTR). In some embodiments, the 5' UTR comprises a miRNA binding site. In some embodiments, the 3' UTR comprises a miRNA binding site. In some embodiments, the 5' UTR and the 3' UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

In some embodiments, a miRNA binding site is inserted within the 3' UTR immediately following the stop codon of the coding region within the polynucleotide of the invention, e.g., mRNA. In some embodiments, if there are multiple copies of a stop codon in the construct, a miRNA binding site is inserted immediately following the final stop codon. In some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 162, 163, and 164, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 165, 166, and 167, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3' UTR comprises more than one miRNA bindingsite (e.g., 2-4 miRNA binding sites), wherein there can be a spacer region (e.g., of 10-100, 20-70 or 30-50 nucleotides in length) between each miRNA bindingsite. In another embodiment, the 3' UTR comprises a spacer region between the end of the miRNA bindingsite(s) and the poly A tail nucleotides. For example, a spacer region of 10-100, 20-70 or 30-50 nucleotides in length can be situated between the end of the miRNA bindingsite(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5' UTR comprises more than one miRNA bindingsite (e.g., 2-4 miRNA binding sites), wherein there can be a spacer region (e.g., of 10-100, 20-70 or 30-50 nucleotides in length) between each miRNA bindingsite.

In one embodiment, the 3' UTR comprises more than one stop codon, wherein at least one miRNA bindingsite is positioned downstream of the stop codons. For example, a 3' UTR can comprise 1, 2 or 3 stop codons. Non-limiting examples of triple stop codons that can be used include: UGAUAAUAG (SEQ ID NO:124), UGAUAGUAA (SEQ ID NO:125), UAAUGAUAG (SEQ ID NO:126), UGAUAAUAA (SEQ ID NO:127), UGAUAGUAG (SEQ ID NO:128), UAAUGAUGA (SEQ ID NO:129), UAAUAGUAG (SEQ ID NO:130), UGAUGAUGA (SEQ ID NO:131), UAAUAAUAA (SEQ ID NO:132), and UAGUAGUAG (SEQ ID NO:133). Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID NOs: 151, 162, 163, and 164.

TABLE 4A

5' UTRs, 3' UTRs, miR sequences, and miR binding sites

| SEQ ID NO: | Sequence |
|---|---|
| 134 | GCUGGAGCCUCGGUGGCCAUGCUUCUUGCCCCUUGGGCCUCCCCCCAGCCCC UCCUCCCCUUCCUGCACCCGUACCCCCUCCAUAAAGUAGGAAACACUACAGU GGUCUUUGAAUAAAGUCUGAGUGGGCGGC<br>(3' UTR with miR 142-3p binding site) |
| 116 | UCCAUAAAGUAGGAAACACUACA<br>(miR 142-3p binding site) |
| 115 | UGUAGUGUUUCCUACUUUAUGGA<br>(miR 142-3p sequence) |
| 117 | CAUAAAGUAGAAAGCACUACU<br>(miR 142-5p sequence) |
| 135 | CCUCUGAAAUUCAGUUCUUCAG<br>(miR 146-3p sequence) |
| 136 | UGAGAACUGAAUUCCAUGGGUU<br>(miR 146-5p sequence) |
| 137 | CUCCUACAUAUUAGCAUUAACA<br>(miR 155-3p sequence) |
| 138 | UUAAUGCUAAUCGUGAUAGGGGU<br>(miR 155-5p sequence) |
| 120 | UCGUACCGUGAGUAAUAAUGCG<br>(miR 126-3p sequence) |
| 122 | CAUUAUUACUUUUGGUACGCG<br>(miR 126-5p sequence) |
| 139 | CCAGUAUUAACUGUGCUGCUGA<br>(miR 16-3p sequence) |
| 140 | UAGCAGCACGUAAAUAUUGGCG<br>(miR 16-5p sequence) |
| 141 | CAACACCAGUCGAUGGGCUGU<br>(miR 21-3p sequence) |
| 142 | UAGCUUAUCAGACUGAUGUUGA<br>(miR 21-5p sequence) |
| 143 | UGUCAGUUUGUCAAAUACCCCA<br>(miR 223-3p sequence) |
| 144 | CGUGUAUUUGACAAGCUGAGUU<br>(miR 223-5p sequence) |
| 145 | UGGCUCAGUUCAGCAGGAACAG<br>(miR 24-3p sequence) |
| 146 | UGCCUACUGAGCUGAUAUCAGU<br>(miR 24-5p sequence) |
| 147 | UUCACAGUGGCUAAGUUCCGC<br>(miR 27-3p sequence) |
| 148 | AGGGCUUAGCUGCUUGUGAGCA<br>(miR 27-5p sequence) |
| 121 | CGCAUUAUUACUCACGGUACGA<br>(miR 126-3p binding site) |
| 149 | UGAUAAUAGGCUGGAGCCUCGGUGGCCAUGCUUCUUGCCCCUUGGGCCUCCC CCCAGCCCCUCCUCCCCUUCCUGCACCCGUACCCCC<u>CGCAUUAUUACUCACG GUACGA</u>GUGGUCUUUGAAUAAAGUCUGAGUGGGCGGC<br>(3' UTR with miR 126-3p binding site) |
| 150 | UGAUAAUAGGCUGGAGCCUCGGUGGCCAUGCUUCUUGCCCCUUGGGCCUCCC CCCAGCCCCUCCUCCCCUUCCUGCACCCGUACCCCGUGGUCUUUGAAUAAA GUCUGAGUGGGCGGC<br>(3' UTR, no miR binding sites) |

TABLE 4A-continued

5' UTRs, 3' UTRs, miR sequences, and miR binding sites

| SEQ ID NO: | Sequence |
|---|---|
| 151 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCCUCCAUAAAGUAGGAAA<br>CACUACAGUGGUCUUUGAAUAAAGUCUGAGUGGGCGGC<br>(3' UTR with miR 142-3p binding site) |
| 111 | UGAUAAUAGUCCAUAAAGUAGGAAACACUACAGCUGGAGCCUCGGUGGCCAU<br>GCUUCUUGCCCCUUGGGCCUCCCCCAGCCCCUCCUCCCCUUCCUGCACCCG<br>UACCCCCCGCAUUAUUACUCACGGUACGAGUGGUCUUUGAAUAAAGUCUGAG<br>UGGGCGGC<br>(3' UTR with miR 142-3p and miR 126-3p binding sites variant 1) |
| 153 | UUAAUGCUAAUUGUGAUAGGGGU<br>(miR 155-5p sequence) |
| 154 | ACCCCUAUCACAAUUAGCAUUAA<br>(miR 155-5p binding site) |
| 155 | UGAUAAUAGUCCAUAAAGUAGGAAACACUACAGCUGGAGCCUCGGUGGCCAU<br>GCUUCUUGCCCCUUGGGCCUCCAUAAAGUAGGAAACACUACAUCCCCCCAGC<br>CCCUCCUCCCCUUCCUGCACCCGUACCCCCUCCAUAAAGUAGGAAACACUAC<br>AGUGGUCUUUGAAUAAAGUCUGAGUGGGCGGC<br>(3' UTR with 3 miR 142-3p binding sites) |
| 156 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC AGUAGUGCUUUCUACU<br>UUAUG GUGGUCUUUGAAUAAAGUCUGAGUGGGCGGC<br>(3' UTR with miR 142-5p binding sites) |
| 157 | UGAUAAUAG AGUAGUGCUUUCUACUUUAUG GCUGGAGCCUCGGUGGCCAUGC<br>UUCUUGCCCCUUGGGCC AGUAGUGCUUUCUACUUUAUG UCCCCCCAGCCCCU<br>CCUCCCCUUCCUGCACCCGUACCCCC AGUAGUGCUUUCUACUUUAUG GUGGU<br>CUUUGAAUAAAGUCUGAGUGGGCGGC<br>(3' UTR with 3 miR 142-5p binding sites) |
| 158 | UGAUAAUAG AGUAGUGCUUUCUACUUUAUG GCUGGAGCCUCGGUGGCCAUGC<br>UUCUUGCCCCUUGGGCC UCCAUAAAGUAGGAAACACUAC UCCCCCCAGCCC<br>CUCCUCCCCUUCCUGCACCCGUACCCCC AGUAGUGCUUUCUACUUUAUG GUG<br>GUCUUUGAAUAAAGUCUGAGUGGGCGGC<br>(3' UTR with 2 miR 142-5p binding sites and 1 miR 142-3p binding site) |
| 159 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC ACCCCUAUCACAAUUA<br>GCAUUAA GUGGUCUUUGAAUAAAGUCUGAGUGGGCGGC<br>(3' UTR with miR 155-5p binding site) |
| 160 | UGAUAAUAG ACCCCUAUCACAAUUAGCAUUAA GCUGGAGCCUCGGUGGCCAU<br>GCUUCUUGCCCCUUGGGCC ACCCCUAUCACAAUUAGCAUUAA UCCCCCCAGC<br>CCCUCCUCCCCUUCCUGCACCCGUACCCCC ACCCCUAUCACAAUUAGCAUUA<br>AGUGGUCUUUGAAUAAAGUCUGAGUGGGCGGC<br>(3' UTR with 3 miR 155-5p binding sites) |

TABLE 4A-continued

5' UTRs, 3' UTRs, miR sequences, and miR binding sites

| SEQ ID NO: | Sequence |
|---|---|
| 161 | UGAUAAUAGACCCCUAUCACAAUUAGCAUUAAGCUGGAGCCUCGGUGGCCAU<br><br>GCUUCUUGCCCCUUGGGCCUCCAUAAAGUAGGAAACACUACAUCCCCCCAGC<br><br>CCCUCCUCCCCUUCCUGCACCCGUACCCCACCCCUAUCACAAUUAGCAUUA<br><br>AGUGGUCUUUGAAUAAAGUCUGAGUGGGCGGC<br><br>(3' UTR with 3 miR 155-5p binding sites and 1 miR 142-3p binding site) |
| 162 | UGAUAAUAGUCCAUAAAGUAGGAAACACUACAGCUGGAGCCUCGGUGGCCAU<br>GCUUCUUGCCCCUUGGGCCUCCCCCCAGCCCCUCCUCCCCUUCCUGCACCCG<br>UACCCCGUGGUCUUUGAAUAAAGUCUGAGUGGGCGGC<br>(3' UTR with miR 142-3p binding site, P1 insertion) |
| 163 | UGAUAAUAGGCUGGAGCCUCGGUGGCUCCAUAAAGUAGGAAACACUACACAU<br>GCUUCUUGCCCCUUGGGCCUCCCCCAGCCCCUCCUCCCCUUCCUGCACCCG<br>UACCCCGUGGUCUUUGAAUAAAGUCUGAGUGGGCGGC<br>(3' UTR with miR 142-3p binding site, P2 insertion) |
| 164 | UGAUAAUAGGCUGGAGCCUCGGUGGCCAUGCUUCUUGCCCCUUGGGCCUCCA<br>UAAAGUAGGAAACACUACAUCCCCCAGCCCCUCCUCCCCUUCCUGCACCCG<br>UACCCCGUGGUCUUUGAAUAAAGUCUGAGUGGGCGGC<br>(3' UTR with miR 142-3p binding site, P3 insertion) |
| 118 | AGUAGUGCUUUCUACUUUAUG<br>(miR-142-5p binding site) |
| 114 | GACAGUGCAGUCACCCAUAAAGUAGAAAGCACUACUAACAGCACUGGAGGGU<br>GUAGUGUUUCCUACUUUAUGGAUGAGUGUACUGUG<br>(miR-142) |
| 3 | GGGAAAUAAGAGAGAAAAGAAGAGUAAGAAGAAAUAUAAGAGCCACC<br>(5' UTR) |
| 165 | GGGAAAUAAGAGUCCAUAAAGUAGGAAACACUACAAGAAAAGAAGAGUAAGA<br>AGAAAUAUAAGAGCCACC<br>(5' UTR with miR142-3p binding site at position p1) |
| 166 | GGGAAAUAAGAGAGAAAAGAAGAGUAAUCCAUAAAGUAGGAAACACUACAGA<br>AGAAAUAUAAGAGCCACC<br>(5' UTR with miR142-3p binding site at position p2) |
| 167 | GGGAAAUAAGAGAGAAAAGAAGAGUAAGAAGAAAUAUAAUCCAUAAAGUAGG<br>AAACACUACAGAGCCACC<br>(5' UTR with miR142-3p binding site at position p3) |
| 169 | UGAUAAUAGAGUAGUGCUUUCUACUUUAUGGCUGGAGCCUCGGUGGCCAUGC<br><br>UUCUUGCCCCUUGGGCCAGUAGUGCUUUCUACUUUAUGUCCCCCCAGCCCCU<br><br>CUCCCCUUCCUGCACCCGUACCCCAGUAGUGCUUUCUACUUUAUGGUGGUC<br><br>UUUGAAUAAAGUCUGAGUGGGCGGC<br><br>(3' UTR with 3 miR 142-5p binding sites) |
| 170 | UGAUAAUAGGCUGGAGCCUCGGUGGCCAUGCUUCUUGCCCCUUCCAUAAAGU<br>AGGAAACACUACAUGGGCCUCCCCCAGCCCCUCCUCCCCUUCCUGCACCCG<br>UACCCCGUGGUCUUUGAAUAAAGUCUGAGUGGGCGGC<br>(3'UTR including miR142-3p binding site) |
| 171 | UGAUAAUAGGCUGGAGCCUCGGUGGCCAUGCUUCUUGCCCCUUGGGCCUCCC<br>CCCAGUCCAUAAAGUAGGAAACACUACACCCCUCCUCCCCUUCCUGCACCCG<br>UACCCCGUGGUCUUUGAAUAAAGUCUGAGUGGGCGGC<br>(3'UTR including miR142-3p binding site) |
| 172 | UGAUAAUAGGCUGGAGCCUCGGUGGCCAUGCUUCUUGCCCCUUGGGCCUCCC<br>CCCAGCCCCUCCUCCCCUUCUCCAUAAAGUAGGAAACACUACACUGCACCCG<br>UACCCCGUGGUCUUUGAAUAAAGUCUGAGUGGGCGGC<br>(3'UTR including including miR142-3p binding site) |

TABLE 4A-continued

5' UTRs, 3' UTRs, miR sequences, and miR binding sites

| SEQ ID NO: | Sequence |
|---|---|
| 173 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCGUGGUCUUUGAAUAAA<br>GUUCCAUAAAGUAGGAAACACUACACUGAGUGGGCGGC<br>(3'UTR including including miR142-3p binding site) |
| 112 | UGAUAAUAGUCCAUAAAGUAGGAAACACUACAGCUGGAGCCUCGGUGGCCUA<br>GCUUCUUGCCCCUUGGGCCUCCCCCCAGCCCCUCCUCCCCUUCCUGCACCCG<br>UACCCCCGCAUUAUUACUCACGGUACGAGUGGUCUUUGAAUAAAGUCUGAG<br>UGGGCGGC<br>(3' UTR with miR 142-3p and miR 126-3p binding sites variant 2) |
| 175 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCGUGGUCUUUGAAUAAA<br>GUCUGAGUGGGCGGC<br>(3' UTR, no miR binding sites variant 2) |
| 4 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCUCCAUAAAGUAGGAAA<br>CACUACAGUGGUCUUUGAAUAAAGUCUGAGUGGGCGGC<br>(3' UTR with miR 142-3p binding site variant 3) |
| 177 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCCGCAUUAUUACUCACG<br>GUACGAGUGGUCUUUGAAUAAAGUCUGAGUGGGCGGC<br>(3' UTR with miR 126-3p binding site variant 3) |
| 178 | UGAUAAUAGUCCAUAAAGUAGGAAACACUACAGCUGGAGCCUCGGUGGCCUA<br>GCUUCUUGCCCCUUGGGCCUCCAUAAAGUAGGAAACACUACAUCCCCCCAGC<br>CCCUCCUCCCCUUCCUGCACCCGUACCCCCUCCAUAAAGUAGGAAACACUAC<br>AGUGGUCUUUGAAUAAAGUCUGAGUGGGCGGC<br>(3' UTR with 3 miR 142-3p binding sites variant 2) |
| 179 | UGAUAAUAGUCCAUAAAGUAGGAAACACUACAGCUGGAGCCUCGGUGGCCUA<br>GCUUCUUGCCCCUUGGGCCUCCCCCCAGCCCCUCCUCCCCUUCCUGCACCCG<br>UACCCCGUGGUCUUUGAAUAAAGUCUGAGUGGGCGGC<br>(3'UTR with miR 142-3p binding site, P1 insertion variant 2) |
| 180 | UGAUAAUAGGCUGGAGCCUCGGUGGCUCCAUAAAGUAGGAAACACUACACUA<br>GCUUCUUGCCCCUUGGGCCUCCCCCCAGCCCCUCCUCCCCUUCCUGCACCCG<br>UACCCCGUGGUCUUUGAAUAAAGUCUGAGUGGGCGGC<br>(3'UTR with miR 142-3p binding site, P2 insertion variant 2) |
| 181 | UGAUAAUAGGCUGGAGCCUCGGUGGCCUAGCUUCUUGCCCCUUGGGCCUCCA<br>UAAAGUAGGAAACACUACAUCCCCCCAGCCCCUCCUCCCCUUCCUGCACCCG<br>UACCCCGUGGUCUUUGAAUAAAGUCUGAGUGGGCGGC<br>(3'UTR with miR 142-3p binding site, P3 insertion variant 2) |
| 182 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCACCCCUAUCACAAUUA<br>GCAUUAAGUGGUCUUUGAAUAAAGUCUGAGUGGGCGGC<br>(3'UTR with miR 155-5p binding site variant 2) |
| 183 | UGAUAAUAGACCCCUAUCACAAUUAGCAUUAAGCUGGAGCCUCGGUGGCCUA<br>GCUUCUUGCCCCUUGGGCCACCCCUAUCACAAUUGCAUUAAUCCCCCCAGC<br>CCCUCCUCCCCUUCCUGCACCCGUACCCCACCCCUAUCACAAUUAGCAUUA<br>AGUGGUCUUUGAAUAAAGUCUGAGUGGGCGGC<br>(3' UTR with 3 miR 155-5p binding sites variant 2) |
| 184 | UGAUAAUAGACCCCUAUCACAAUUAGCAUUAAGCUGGAGCCUCGGUGGCCUA<br>GCUUCUUGCCCCUUGGGCCUCCAUAAAGUAGGAAACACUACAUCCCCCCAGC<br>CCCUCCUCCCCUUCCUGCACCCGUACCCCACCCCUAUCACAAUUAGCAUUA |

TABLE 4A-continued

5' UTRs, 3' UTRs, miR sequences, and miR binding sites

| SEQ ID NO: | Sequence |
|---|---|
| | AGUGGUCUUUGAAUAAAGUCUGAGUGGGCGGC |
| | (3'UTR with 2 miR 155-5p binding sites and 1 miR 142-3p binding site variant 2) |

Stop codon = bold
miR 142-3p binding site = underline
miR 126-3p binding site = bold underline
miR 155-5p binding site = shaded
miR 142-5p binding site = shaded and bold underline

TABLE 4B

Exemplary Preferred UTRs

| SEQ ID NO: | Sequence |
|---|---|
| 5' UTR (v1) (SEQ ID NO: 3) | GGGAAAUAAGAGAGAAAAGAAGAGUAAGAAGAAAUAUAAGAGCCACC |
| 5' UTR (v1 A) (SEQ ID NO: 196) | AGGAAAUAAGAGAGAAAAGAAGAGUAAGAAGAAAUAUAAGAGCCACC |
| 5' UTR (v1.1) (SEQ ID NO: 191) | GGGAAAUAAGAGAGAAAAGAAGAGUAAGAAGAAAUAUAAGACCCCGGCGCCGCCACC |
| 5' UTR (v1.1 A) (SEQ ID NO: 197) | <u>AGGAAAUAAGAGAGAAAAGAAGAGUAAGAAGAAAUAUAAGACCCCGGCGCCGCCACC</u> |
| 3' UTR (v1) (SEQ ID NO: 150) | UGAUAAUAGGCUGGAGCCUCGGUGGCCAUGCUUCUUGCCCCUUGGGCCUCCCCCAGCCCCUCCUCCCCUUCCUGCACCCGUACCCCCGUGGUCUUUGAAUAAAGUCUGAGUGGGCGGC |
| 3' UTR (v1.1) (SEQ ID NO: 175) | UGAUAAUAGGCUGGAGCCUCGGUGGCCUAGCUUCUUGCCCCUUGGGCCUCCCCCAGCCCCUCCUCCCCUUCCUGCACCCGUACCCCCGUGGUCUUUGAAUAAAGUCUGAGUGGGCGGC |
| 3' UTR (miR122) (SEQ ID NO: 198) | UGAUAAUAGGCUGGAGCCUCGGUGGCCAUGCUUCUUGCCCCUUGGGCCUCCCCCAGCCCCUCCUCCCCUUCCUGCACCCGUACCCCCCAAACACCAUUGUCACACUCCAGUGGUCUUUGAAUAAAGUCUGAGUGGGCGGC |
| 3' UTR (v1.1 miR122) (SEQ ID NO: 198) | UGAUAAUAGGCUGGAGCCUCGGUGGCCUAGCUUCUUGCCCCUUGGGCCUCCCCCAGCCCCUCCUCCCCUUCCUGCACCCGUACCCCCCAAACACCAUUGUCACACUCCAGUGGUCUUUGAAUAAAGUCUGAGUGGGCGGC |
| 3' UTR (v1.1 miR142-3p) (SEQ ID NO: 4) | UGAUAAUAGGCUGGAGCCUCGGUGGCCUAGCUUCUUGCCCCUUGGGCCUCCCCCAGCCCCUCCUCCCCUUCCUGCACCCGUACCCCCUCCAUAAAGUAGGAAACACUACAGUGGUCUUUGAAUAAAGUCUGAGUGGGCGGC |
| 3' UTR (v1.1 miR 126-3p) (SEQ ID NO: 177) | UGAUAAUAGGCUGGAGCCUCGGUGGCCUAGCUUCUUGCCCCUUGGGCCUCCCCCAGCCCCUCCUCCCCUUCCUGCACCCGUACCCCCCGCAUUAUUACUCACGGUACGAGUGGUCUUUGAAUAAAGUCUGAGUGGGCGGC |
| 3' UTR (mir-126, miR-142-3p) (SEQ ID NO: 111) | UGAUAAUAGUCCAUAAAGUAGGAAACACUACAGCUGGAGCCUCGGUGGCCAUGCUUCUUGCCCCUUGGGCCUCCCCCAGCCCCUCCUCCCCUUCCUGCACCCGUACCCCCCGCAUUAUUACUCACGGUACGAGUGGUCUUUGAAUAAAGUCUGAGUGGGCGGC |
| 3' UTR (v1.1 3x miR142-3p) (SEEQ ID NO: 178) | UGAUAAUAGUCCAUAAAGUAGGAAACACUACAGCUGGAGCCUCGGUGGCCUAGCUUCUUGCCCCUUGGGCCUCCAUAAAGUAGGAAACACUACAUCCCCCAGCCCCUCCUCCCCUUCCUGCACCCGUACCCCCUCCAUAAAGUAGGAAACACUACAGUGGUCUUUGAAUAAAGUCUGAGUGGGCGGC |

In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO: 116. In one embodiment, the 3' UTR of the mRNA comprising the miR-142-3p microRNA binding site comprises the sequence shown in SEQ ID NO: 134.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 121. In one embodiment, the 3' UTR of the mRNA of the invention comprising the miR-126-3p microRNA binding site comprises the sequence shown in SEQ ID NO: 149.

Non-limiting exemplary sequences for miRs to which a microRNA binding site(s) of the disclosure can bind include the following: miR-142-3p (SEQ ID NO: 115), miR-142-5p (SEQ ID NO: 117), miR-146-3p (SEQ ID NO: 135), miR-146-5p (SEQ ID NO: 136), miR-155-3p (SEQ ID NO: 137), miR-155-5p (SEQ ID NO: 138), miR-126-3p (SEQ ID NO: 120), miR-126-5p (SEQ ID NO: 122), miR-16-3p (SEQ ID NO: 139), miR-16-5p (SEQ ID NO: 140), miR-21-3p (SEQ ID NO: 141), miR-21-5p (SEQ ID NO: 142), miR-223-3p (SEQ ID NO: 143), miR-223-5p (SEQ ID NO: 144), miR-24-3p (SEQ ID NO: 145), miR-24-5p (SEQ ID NO: 146), miR-27-3p (SEQ ID NO: 147) and miR-27-5p (SEQ ID NO: 148). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA bindingsite to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA bindingsite for modulating tissue expression of an encoded protein of interest.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the is necessary for miRNA mediated gene expression (Meijer H A et al., Science, 2013, 340, 82-85, herein incorporated by reference in its entirety). The polynucleotides of the invention can further include this structured 5'UTR in order to enhance microRNA mediated gene regulation.

At least one miRNA binding site can be engineered into the 3'UTR of a polynucleotide of the invention. In this context, at least two, at least three, at least four, at least five, at least six, at least seven, at least eight, at least nine, at least ten, or more miRNA binding sites can be engineered into a 3'UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., myeloid cells, endothelial cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In some embodiments, the expression of a polynucleotide of the invention can be controlled by incorporating at least one sensor sequence in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising a ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment the miRNA sequence in the 5'UTR can be used to stabilize a polynucleotide of the invention described herein.

In another embodiment, a miRNA sequence in the 5'UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include mir-142-5p, mir-142-3p, mir-146a-5p, and mir-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding an OTC polypeptide (e.g., the wild-type sequence, functional fragment, or variant thereof) and (ii) a miRNA binding site (e.g., a miRNA binding site that binds to miR-142) and/or a miRNA binding site that binds to miR-126.

12. 3' UTRs

In certain embodiments, a polynucleotide of the present invention (e.g., a polynucleotide comprising a nucleotide sequence encoding an OTC polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the invention comprises a binding site for regulatory proteins or microRNAs.

In certain embodiments, the 3' UTR useful for the polynucleotides of the invention comprises a 3' UTR selected from the group consisting of SEQ ID NO: 4 and 104 to 113, or any combination thereof. In some embodiments, the 3' UTR comprises a nucleic acid sequence selected from the group consisting of SEQ ID NOs: 111, 112, or 113 or any combination thereof. In some embodiments, the 3' UTR comprises a nucleic acid sequence selected from the group consisting of SEQ ID NOs: 4, 111, 150, 175, 177, 178, 198, or 199, or any combination thereof. In some embodiments, the 3'UTR comprises a nucleic acid sequence of SEQ ID NO:4. In some embodiments, the 3' UTR comprises a nucleic acid sequence of SEQ ID NO: 111. In some embodiments, the 3' UTR comprises a nucleic acid sequence of SEQ ID NO: 112. In some embodiments, the 3' UTR comprises a nucleic acid sequences of SEQ ID NO: 113. In some embodiments, the 3' UTR comprises a nucleic acid sequence of SEQ ID NO: 150. In some embodiments, the 3' UTR comprises a nucleic acid sequence of SEQ ID NO: 175. In some embodiments, the 3' UTR comprises a nucleic acid sequence of SEQ ID NO: 177. In some embodiments, the 3' UTR comprises a nucleic acid sequence of SEQ ID NO: 178. In some embodiments, the 3' UTR comprises a nucleic acid sequence of SEQ ID NO: 198. In some embodiments, the 3' UTR comprises a nucleic acid sequence of SEQ ID NO: 199.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NOs: 4 and 104 to 113, or any combination thereof.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NOs: 4, 111, 150, 175, 177, 178, 198, and 199, or any combination thereof.

13. Regions Having a 5' Cap

The invention also includes a polynucleotide that comprises both a 5' Cap and a polynucleotide of the present invention (e.g., a polynucleotide comprising a nucleotide sequence encoding an OTC polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding an OTC polypeptide) incorporate a cap moiety.

In some embodiments, polynucleotides of the present invention (e.g., a polynucleotide comprising a nucleotide sequence encoding an OTC polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides. Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m 7 G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m 7 Gm-ppp-G).

In some embodiments, the cap is a dinucleotide cap analog. As a non-limiting example, the dinucleotide cap analog can be modified at different phosphate positions with a boranophosphate group or a phosphoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m$^{3'-O}$G(5)ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous structures of nucleic acids produced by the endogenous, cellular transcription machinery, can lead to reduced translational competency and reduced cellular stability.

Polynucleotides of the invention (e.g., a polynucleotide comprising a nucleotide sequence encoding an OTC polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other analog structures known in the art. Cap structures include, but are not limited to, 7mG(5')ppp(5')N,pN2p (cap 0), 7mG(5')ppp(5')N1mpNp (cap 1), and 7mG(5')-ppp(5')N1mpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

14. Poly-A Tails

In some embodiments, the polynucleotides of the present disclosure (e.g., a polynucleotide comprising a nucleotide sequence encoding an OTC polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about to about 3,000 nucleotides (e.g., from 30 to 50, from 30 to 100, from 30 to 250, from to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 2,500, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

15. Start Codon Region

The invention also includes a polynucleotide that comprises both a start codon region and the polynucleotide described herein (e.g., a polynucleotide comprising a nucleotide sequence encoding an OTC polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/ UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miRNA binding site. The perfect complement of a miRNA binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

16. Stop Codon Region

The invention also includes a polynucleotide that comprises both a stop codon region and the polynucleotide described herein (e.g., a polynucleotide comprising a nucleotide sequence encoding an OTC polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA. In another embodiment, the polynucleotides of the present invention include three consecutive stop codons, four stop codons, or more.

17. Polynucleotide Comprising an mRNA Encoding a OTC Polypeptide

In certain embodiments, a polynucleotide of the present disclosure, for example a polynucleotide comprising an mRNA nucleotide sequence encoding an OTC polypeptide, comprises from 5' to 3' end:
  (i) a 5' cap provided above;
  (ii) a 5' UTR, such as the sequences provided above;
  (iii) an open reading frame encoding an OTC polypeptide, e.g., a sequence optimized nucleic acid sequence encoding OTC disclosed herein;
  (iv) at least one stop codon;
  (v) a 3' UTR, such as the sequences provided above; and
  (vi) a poly-A tail provided above.

In some embodiments, the polynucleotide further comprises a miRNA binding site, e.g., a miRNA binding site that binds to miRNA-142. In some embodiments, the 5' UTR comprises the miRNA binding site. In some embodiments, the 3' UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type human OTC (SEQ ID NO:1).

In some embodiments, a polynucleotide of the present disclosure, for example a polynucleotide comprising an mRNA nucleotide sequence encoding a polypeptide, comprises (1) a 5' cap provided above, for example, CAP1, (2) a 5' UTR, (3) a nucleotide sequence ORF selected from the group consisting of SEQ ID NOs: 2 and 5-29, (3) a stop codon, (4) a 3' UTR, and (5) a poly-A tail provided above, for example, a poly-A tail of about 100 residues.

Exemplary OTC nucleotide constructs are described below:

SEQ ID NO: 30 consists from 5' to 3' end: 5' UTR of SEQ ID NO: 3, OTC nucleotide ORF of SEQ ID NO: 2, and 3' UTR of SEQ ID NO: 4.

SEQ ID NO: 31 consists from 5' to 3' end: 5' UTR of SEQ ID NO: 3, OTC nucleotide ORF of SEQ ID NO: 5, and 3' UTR of SEQ ID NO: 4.

SEQ ID NO: 32 consists from 5' to 3' end: 5' UTR of SEQ ID NO: 3, OTC nucleotide ORF of SEQ ID NO: 6, and 3' UTR of SEQ ID NO: 4.

SEQ ID NO: 33 consists from 5' to 3' end: 5' UTR of SEQ ID NO: 3, OTC nucleotide ORF of SEQ ID NO: 7, and 3' UTR of SEQ ID NO: 4.

SEQ ID NO: 34 consists from 5' to 3' end: 5' UTR of SEQ ID NO: 3, OTC nucleotide ORF of SEQ ID NO: 8, and 3' UTR of SEQ ID NO: 4.

SEQ ID NO: 35 consists from 5' to 3' end: 5' UTR of SEQ ID NO: 3, OTC nucleotide ORF of SEQ ID NO: 9, and 3' UTR of SEQ ID NO: 4.

SEQ ID NO: 36 consists from 5' to 3' end: 5' UTR of SEQ ID NO: 3, OTC nucleotide ORF of SEQ ID NO: 10, and 3' UTR of SEQ ID NO: 4.

SEQ ID NO: 37 consists from 5' to 3' end: 5' UTR of SEQ ID NO: 3, OTC nucleotide ORF of SEQ ID NO: 11, and 3' UTR of SEQ ID NO: 4.

SEQ ID NO: 38 consists from 5' to 3' end: 5' UTR of SEQ ID NO: 3, OTC nucleotide ORF of SEQ ID NO: 12, and 3' UTR of SEQ ID NO: 4.

SEQ ID NO: 39 consists from 5' to 3' end: 5' UTR of SEQ ID NO: 3, OTC nucleotide ORF of SEQ ID NO: 13, and 3' UTR of SEQ ID NO: 4.

SEQ ID NO: 40 consists from 5' to 3' end: 5' UTR of SEQ ID NO: 3, OTC nucleotide ORF of SEQ ID NO: 14, and 3' UTR of SEQ ID NO: 4.

SEQ ID NO: 41 consists from 5' to 3' end: 5' UTR of SEQ ID NO: 3, OTC nucleotide ORF of SEQ ID NO: 15, and 3' UTR of SEQ ID NO: 4.

SEQ ID NO: 42 consists from 5' to 3' end: 5' UTR of SEQ ID NO: 3, OTC nucleotide ORF of SEQ ID NO: 16, and 3' UTR of SEQ ID NO: 4.

SEQ ID NO: 43 consists from 5' to 3' end: 5' UTR of SEQ ID NO: 3, OTC nucleotide ORF of SEQ ID NO: 17, and 3' UTR of SEQ ID NO: 4.

SEQ ID NO: 44 consists from 5' to 3' end: 5' UTR of SEQ ID NO: 3, OTC nucleotide ORF of SEQ ID NO: 18, and 3' UTR of SEQ ID NO: 4.

SEQ ID NO: 45 consists from 5' to 3' end: 5' UTR of SEQ ID NO: 3, OTC nucleotide ORF of SEQ ID NO: 19, and 3' UTR of SEQ ID NO: 4.

SEQ ID NO: 46 consists from 5' to 3' end: 5' UTR of SEQ ID NO: 3, OTC nucleotide ORF of SEQ ID NO: 20, and 3' UTR of SEQ ID NO: 4.

SEQ ID NO: 47 consists from 5' to 3' end: 5' UTR of SEQ ID NO: 3, OTC nucleotide ORF of SEQ ID NO: 21, and 3' UTR of SEQ ID NO: 4.

SEQ ID NO: 48 consists from 5' to 3' end: 5' UTR of SEQ ID NO: 3, OTC nucleotide ORF of SEQ ID NO: 22, and 3' UTR of SEQ ID NO: 4.

SEQ ID NO: 49 consists from 5' to 3' end: 5' UTR of SEQ ID NO: 3, OTC nucleotide ORF of SEQ ID NO: 23, and 3' UTR of SEQ ID NO: 4.

SEQ ID NO: 50 consists from 5' to 3' end: 5' UTR of SEQ ID NO: 3, OTC nucleotide ORF of SEQ ID NO: 24, and 3' UTR of SEQ ID NO: 4.

SEQ ID NO: 51 consists from 5' to 3' end: 5' UTR of SEQ ID NO: 3, OTC nucleotide ORF of SEQ ID NO: 25, and 3' UTR of SEQ ID NO: 4.

SEQ ID NO: 52 consists from 5' to 3' end: 5' UTR of SEQ ID NO: 3, OTC nucleotide ORF of SEQ ID NO: 26, and 3' UTR of SEQ ID NO: 4.

SEQ ID NO: 53 consists from 5' to 3' end: 5' UTR of SEQ ID NO: 3, OTC nucleotide ORF of SEQ ID NO: 27, and 3' UTR of SEQ ID NO: 4.

SEQ ID NO: 54 consists from 5' to 3' end: 5' UTR of SEQ ID NO: 3, OTC nucleotide ORF of SEQ ID NO: 28, and 3' UTR of SEQ ID NO: 150.

SEQ ID NO: 55 consists from 5' to 3' end: 5' UTR of SEQ ID NO: 3, OTC nucleotide ORF of SEQ ID NO: 29, and 3' UTR of SEQ ID NO: 4.

In certain embodiments, in constructs with SEQ ID NOs.: 30 to 55, all uracils therein are replaced by N1-methylpseudouracil. In certain embodiments, in constructs with SEQ ID NOs.: 30 to 55, all uracils therein are replaced by 5-methoxyuracil.

In some embodiments, a polynucleotide of the present disclosure, for example a polynucleotide comprising an mRNA nucleotide sequence encoding a OTC polypeptide, comprises (1) a 5' cap provided above, for example, CAP1, (2) a nucleotide sequence selected from the group consisting of SEQ ID NO:30 to 55, and (3) a poly-A tail provided above, for example, a poly A tail of ~100 residues. In certain embodiments, in constructs with SEQ ID NOs.:30 to 55, all uracils therein are replaced by N1-methylpseudouracil. In certain embodiments, in constructs with SEQ ID NOs.:30 to 55, all uracils therein are replaced by 5-methoxyuracil.

TABLE 5

Modified mRNA constructs including ORFs encoding human OTC (each of constructs #1 to #26 comprises a Cap1 5' terminal cap and a 3' terminal PolyA region)

| | | OTC ORF | | |
|---|---|---|---|---|
| OTC mRNA construct | 5' UTR SEQ ID NO | Name (Chemistry) | SEQ ID NO | 3' UTR SEQ ID NO: |
| #1 (SEQ ID NO: 30) | 3 | OTC_02 (G5) | 2 | 4 |
| #2 (SEQ ID NO: 31) | 3 | OTC_03 (G5) | 5 | 4 |
| #3 (SEQ ID NO: 32) | 3 | OTC_04 (G5) | 6 | 4 |
| #4 (SEQ ID NO: 33) | 3 | OTC_05 (G5) | 7 | 4 |
| #5 (SEQ ID NO: 34) | 3 | OTC_06 (G5) | 8 | 4 |
| #6 (SEQ ID NO: 35) | 3 | OTC_07 (G5) | 9 | 4 |
| #7 (SEQ ID NO: 36) | 3 | OTC_08 (G5) | 10 | 4 |

TABLE 5-continued

Modified mRNA constructs including ORFs encoding human OTC (each of constructs #1 to #26 comprises a Cap1 5' terminal cap and a 3' terminal PolyA region)

| OTC mRNA construct | 5' UTR SEQ ID NO | OTC ORF Name (Chemistry) | SEQ ID NO | 3' UTR SEQ ID NO: |
|---|---|---|---|---|
| #8 (SEQ ID NO: 37) | 3 | OTC_09 (G5) | 11 | 4 |
| #9 (SEQ ID NO: 38) | 3 | OTC_10 (G5) | 12 | 4 |
| #10 (SEQ ID NO: 39) | 3 | OTC_11 (G5) | 13 | 4 |
| #11 (SEQ ID NO: 40) | 3 | OTC_12 (G5) | 14 | 4 |
| #12 (SEQ ID NO: 41) | 3 | OTC_13 (G5) | 15 | 4 |
| #13 (SEQ ID NO: 42) | 3 | OTC_14 (G6) | 16 | 4 |
| #14 (SEQ ID NO: 43) | 3 | OTC_15 (G6) | 17 | 4 |
| #15 (SEQ ID NO: 44) | 3 | OTC_16 (G6) | 18 | 4 |
| #16 (SEQ ID NO: 45) | 3 | OTC_17 (G6) | 19 | 4 |
| #17 (SEQ ID NO: 46) | 3 | OTC_18 (G6) | 20 | 4 |
| #18 (SEQ ID NO: 47) | 3 | OTC_19 (G6) | 21 | 4 |
| #19 (SEQ ID NO: 48) | 3 | OTC_20 (G6) | 22 | 4 |
| #20 (SEQ ID NO: 49) | 3 | OTC_21 (G6) | 23 | 4 |
| #21 (SEQ ID NO: 50) | 3 | OTC_22 (G6) | 24 | 4 |
| #22 (SEQ ID NO: 51) | 3 | OTC 2-001 (G5) | 25 | 4 |
| #23 (SEQ ID NO: 52) | 3 | OTC 3-001 (G5) | 26 | 4 |
| #24 (SEQ ID NO: 53) | 3 | OTC 1-023 (G5) | 27 | 4 |
| #25 (SEQ ID NO: 54) | 3 | OTC 1-024 (G5) | 28 | 150 |
| #26 (SEQ ID NO: 55) | 3 | OTC 01-025 (G5) | 29 | 4 |

18. Methods of Making Polynucleotides

The present disclosure also provides methods for making a polynucleotide of the invention (e.g., a polynucleotide comprising a nucleotide sequence encoding an OTC polypeptide) or a complement thereof.

In some aspects, a polynucleotide (e.g., a RNA, e.g., an mRNA) disclosed herein, and encoding an OTC polypeptide, can be constructed using in vitro transcription. In other aspects, a polynucleotide (e.g., a RNA, e.g., an mRNA) disclosed herein, and encoding an OTC polypeptide, can be constructed by chemical synthesis using an oligonucleotide synthesizer.

In other aspects, a polynucleotide (e.g., a RNA, e.g., an mRNA) disclosed herein, and encoding an OTC polypeptide is made by using a host cell. In certain aspects, a polynucleotide (e.g., a RNA, e.g., an mRNA) disclosed herein, and encoding an OTC polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding an OTC polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding an OTC polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L6991, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, and/or deletional variants.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of E. coli, Bacillus DNA polymerase I, Therms aquaticus (Taq) DNA polymerases, and the T7 RNA and DNA polymerases, is among the best studied of these families. Another large family is DNA polymerase a (pol a) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present invention is a Syn5 RNA polymerase. (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 185 as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention. For example, polymerase chain reaction (PCR), strand displacement amplification (SDA), nucleic acid sequence-based amplification (NASBA), also called transcription mediated amplification (TMA), and/or rolling-circle amplification (RCA) can be utilized in the manufacture of one or more regions of the polynucleotides of the present invention. Assembling polynucleotides or nucleic acids by a ligase is also widely used.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding an OTC polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. Nos. U.S. Pat. No. 8,999,380 or U.S. Pat. No. 8,710,200, all of which are herein incorporated by reference in their entireties.

c. Purification of Polynucleotides Encoding OTC

Purification of the polynucleotides described herein (e.g., a polynucleotide comprising a nucleotide sequence encoding an OTC polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding an OTC polypeptide) removes impurities that can reduce or remove an unwanted immune response, e.g., reducing cytokine activity.

In some embodiments, the polynucleotide of the invention (e.g., a polynucleotide comprising a nucleotide sequence encoding an OTC polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence an OTC polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded OTC protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding an OTC polypeptide comprising one or more of the point mutations known in the art.

In some embodiments, the use of RP-HPLC purified polynucleotide increases OTC protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of OTC protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional OTC protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of OTC protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable OTC activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional OTC in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding OTC

In some embodiments, the polynucleotides of the present invention (e.g., a polynucleotide comprising a nucleotide sequence encoding an OTC polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

19. Pharmaceutical Compositions and Formulations

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes an OTC polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes an OTC polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in *Remington: The Science and Practice of Pharmacy* 21$^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding an OTC polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound II, DSPC, Cholesterol, and Compound I or PEG-DMG, e.g., with a mole ratio of about 47.5:10.5:39.0:3.0. In some embodiments, the delivery agent comprises Compound VI, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio of about 47.5:10.5:39.0:3.0.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, M D, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN080], sorbitan monopalmitate [SPAN040], glyceryl monooleate, polyoxyethylene esters, polyethylene glycol fatty acid esters (e.g., CREMOPHOR®), polyoxyethylene ethers (e.g., polyoxyethylene lauryl ether [BRIJ030]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, ascorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

20. Delivery Agents a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:

(a) a polynucleotide comprising a nucleotide sequence encoding an OTC polypeptide; and (b) a delivery agent.

Lipid Nanoparticle Formulations

In some embodiments, nucleic acids of the invention (e.g. OTC mRNA) are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the invention can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Nucleic acids of the present disclosure (e.g. OTC mRNA) are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

Ionizable Lipids

In some aspects, the ionizable lipids of the present disclosure may be one or more of compounds of Formula (I):

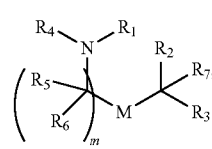

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —N(R)S(O)$_2$R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H; M and M' are independently selected from —C(O)O—, —OC(O)—, —OC(O)-M"-C(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13; and wherein when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In certain embodiments, a subset of compounds of Formula (I) includes those of Formula (IA):

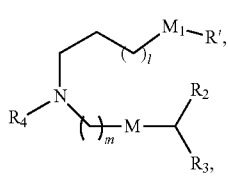

(IA)

or its N-oxide, or a salt or isomer thereof, wherein 1 is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or —$(CH_2)_nQ$, in which Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —OC(O)-M''-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —$NHC(S)N(R)_2$, or —$NHC(O)N(R)_2$. For example, Q is —$N(R)C(O)R$, or —$N(R)S(O)_2R$.

In certain embodiments, a subset of compounds of Formula (I) includes those of Formula (IB):

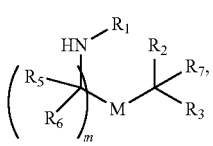

(IB)

or its N-oxide, or a salt or isomer thereof in which all variables are as defined herein. For example, m is selected from 5, 6, 7, 8, and 9; $R_4$ is hydrogen, unsubstituted $C_{1-3}$ alkyl, or —$(CH_2)_nQ$, in which Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —OC(O)-M''-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —$NHC(S)N(R)_2$, or —$NHC(O)N(R)_2$. For example, Q is —$N(R)C(O)R$, or —$N(R)S(O)_2R$.

In certain embodiments, a subset of compounds of Formula (I) includes those of Formula (II):

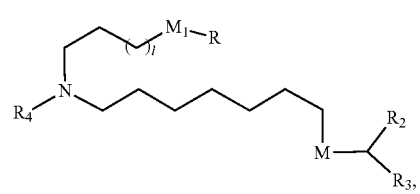

(II)

or its N-oxide, or a salt or isomer thereof, wherein 1 is selected from 1, 2, 3, 4, and 5; $M_1$ is a bond or M'; $R_4$ is hydrogen, unsubstituted $C_{1-3}$ alkyl, or —$(CH_2)_nQ$, in which n is 2, 3, or 4, and Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —OC(O)-M''-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In one embodiment, the compounds of Formula (I) are of Formula (IIa),

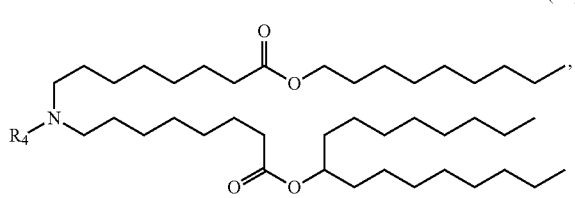

(IIa)

or their N-oxides, or salts or isomers thereof, wherein $R_4$ is as described herein.

In another embodiment, the compounds of Formula (I) are of Formula (IIb),

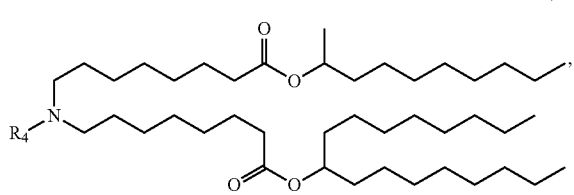

(IIb)

or their N-oxides, or salts or isomers thereof, wherein $R_4$ is as described herein.

In another embodiment, the compounds of Formula (I) are of Formula (IIc) or (IIe):

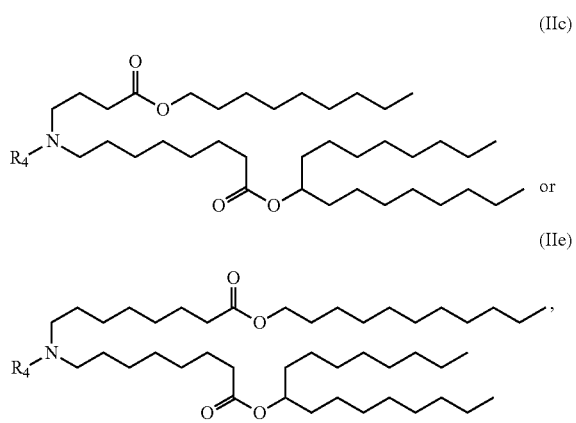

(IIc)

or (IIe)

or their N-oxides, or salts or isomers thereof, wherein $R_4$ is as described herein.

In another embodiment, the compounds of Formula (I) are of Formula OM:

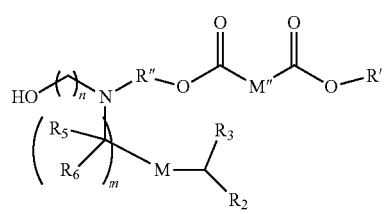

(IIf)

or their N-oxides, or salts or isomers thereof, wherein M is —C(O)O— or —OC(O)—, M″ is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (I) are of Formula (Hd),

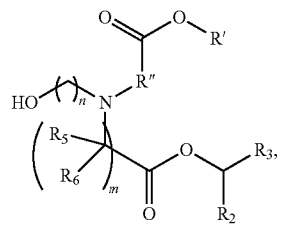

(IId)

or their N-oxides, or salts or isomers thereof, wherein n is 2, 3, or 4; and m, R', R″, and $R_2$ through $R_6$ are as described herein. For example, each of $R_2$ and $R_3$ may be independently selected from the group consisting of $C_{5-14}$ alkyl and $C_{5-14}$ alkenyl.

In a further embodiment, the compounds of Formula (I) are of Formula (IIg),

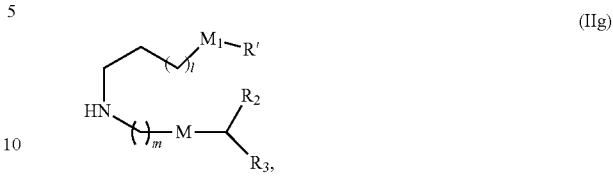

(IIg)

or their N-oxides, or salts or isomers thereof, wherein l is selected from 1, 2, 3, 4, and 5; m is selected from 5, 6, 7, 8, and 9; $M_1$ is a bond or M'; M and M' are independently selected from —C(O)O—, —OC(O)—, —OC(O)-M″-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, M″ is $C_{1-6}$ alkyl (e.g., $C_{1-4}$ alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is

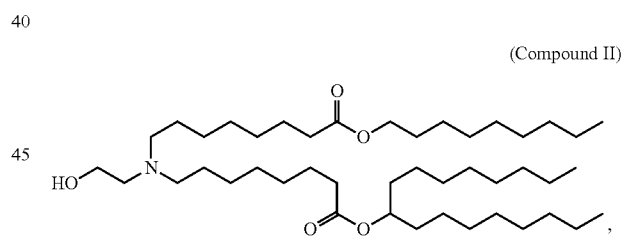

(Compound II)

or a salt thereof.

In some embodiments, the ionizable lipid is

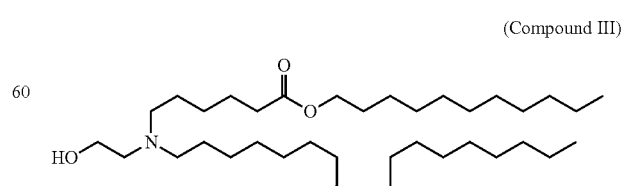

(Compound III)

or a salt thereof.

In some embodiments, the ionizable lipid is

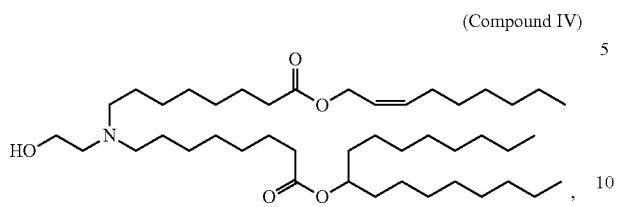

(Compound IV)

or a salt thereof.

In some embodiments, the ionizable lipid is

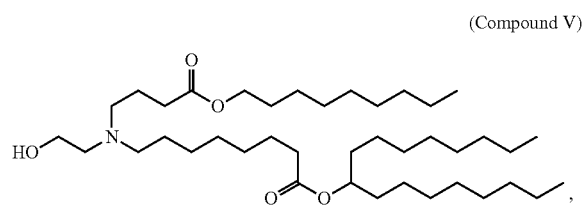 [SMILES: CCCCCCCCCOC(=O)CCCN(CCO)CCCCCCCC(=O)OC(CCCCCCCC)CCCCCCCC]

(Compound V)

or a salt thereof.

The central amine moiety of a lipid according to Formula (I), (IA), (IB), (II), (IIa), (IIb), (IIc), (IId), (IIe), (IIf), or (IIg) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

In some aspects, the ionizable lipids of the present disclosure may be one or more of compounds of formula (III),

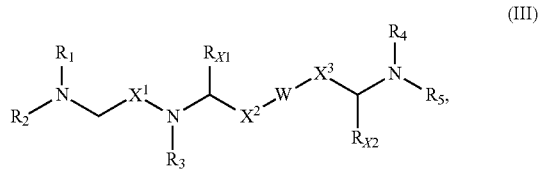

(III)

or salts or isomers thereof, wherein
W is

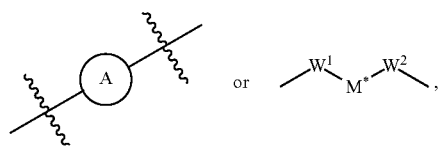

ring A is

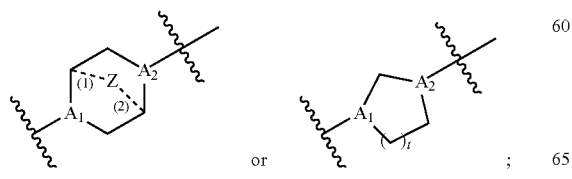

t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
$R_{X1}$ and $R_{X2}$ are each independently H or $C_{1-3}$ alkyl;
each M is independently selected from the group consisting
of —C(O)O—, —OC(O)—, —OC(O)O—, —C(O)N(R')—, —N(R')C(O)—, —C(O)—, —C(S)—, —C(S)S—, —S C(S)—,
—CH(OH)—, —P(O)(OR')O—, —S(O)$_2$—, —C(O)S—, —SC(O)—, an aryl group, and a heteroaryl group;
M* is $C_1$-$C_6$ alkyl,
$W^1$ and $W^2$ are each independently selected from the group consisting of —O— and —N($R_6$)—;
each $R_6$ is independently selected from the group consisting of H and $C_{1-5}$ alkyl;
$X^1$, $X^2$, and $X^3$ are independently selected from the group consisting of a bond, —$CH_2$—, —($CH_2$)$_2$—, —CHR—, —CHY—, —C(O)—, —C(O)O—, —OC(O)—, —($CH_2$)$_n$—C(O)—, —C(O)—($CH_2$)$_n$—, —($CH_2$)$_n$—C(O)O—, —OC(O)—($CH_2$)$_n$—, —($CH_2$)$_n$—OC(O)—, —C(O)O—($CH_2$)$_n$—, —CH(OH)—, —C(S)—, and —CH(SH)—;
each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H;
each R" is independently selected from the group consisting of $C_{3-12}$ alkyl, $C_{3-12}$ alkenyl and —R*MR'; and
n is an integer from 1-6;
wherein when ring A is

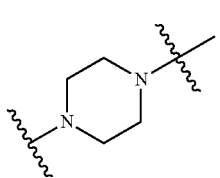

then
i) at least one of $X^1$, $X^2$, and $X^3$ is not —$CH_2$—; and/or
ii) at least one of $R_1$, $R_2$, $R_3$, $R_4$, and $R_5$ is —R"MR'.

In some embodiments, the compound is of any of formulae (IIIa1)-(IIIa8):

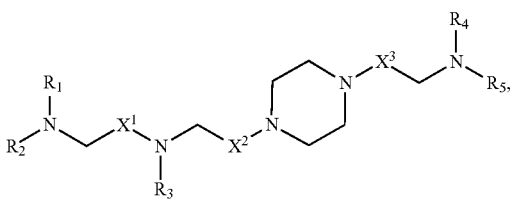

(IIIa1)

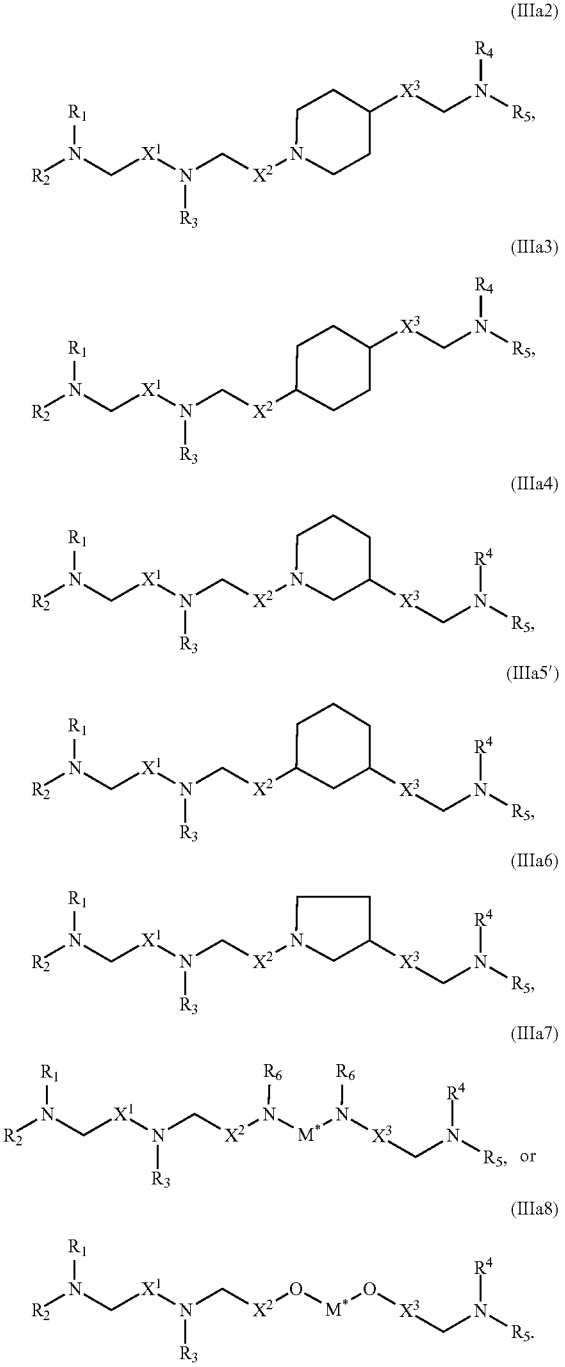

In some embodiments, the ionizable lipids are one or more of the compounds described in U.S. Application Nos. 62/271,146, 62/338,474, 62/413,345, and 62/519,826, and PCT Application No. PCT/US2016/068300.

In some embodiments, the ionizable lipids are selected from Compounds 1-156 described in U.S. Application No. 62/519,826.

In some embodiments, the ionizable lipids are selected from Compounds 1-16, 42-66, 68-76, and 78-156 described in U.S. Application No. 62/519,826.

The central amine moiety of a lipid according to Formula (III), (IIIa1), (IIIa2), (IIIa3), (IIIa4), (IIIa5), (IIIa6), (IIIa7), or (IIIa8) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Phospholipids

The lipid composition of the lipid nanoparticle composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid of the invention comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine,1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof In certain embodiments, a phospholipid useful or potentially useful in the present invention is an analog or variant of DSPC. In certain embodiments, a phospholipid useful or potentially useful in the present invention is a compound of Formula (IV):

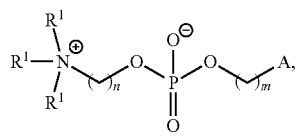

(IV)

or a salt thereof, wherein:
each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;
n is 1, 2, 3, 4, 5, 6, 7, 8, 9, or 10;
m is 0, 1, 2, 3, 4, 5, 6, 7, 8, 9, or 10;
A is of the formula:

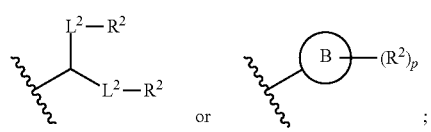

each instance of L 2 is independently a bond or optionally substituted $C_{1-6}$ alkylene, wherein one methylene unit of the optionally substituted $C_{1-6}$ alkylene is optionally replaced with 0, $N(R^N)$, S, C(O), $C(O)N(R^N)$, $NR^NC(O)$, C(O)O, OC(O), OC(O)O, $OC(O)N(R^N)$, —$NR^NC(O)O$, or $NR^NC(O)N(R^N)$;
each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, —$NR^NC(O)N(R^N)$, C(O)O, OC(O), OC(O)O, $OC(O)N(R^N)$, $NR^NC(O)O$, C(O)S, SC(O), —$C(=NR^N)$, $C(=NR^N)N(R^N)$, $NR^NC(=NR^N)$, $NR^NC(=NR^N)N(R^N)$, C(S), $C(S)N(R^N)$, —$NR^NC(S)$, $NR^NC(S)N(R^N)$, S(O), OS(O), S(O)O, OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, —$N(R^N)S(O)_2$, $S(O)_2N(R^N)$, $N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group; Ring B is optionally substituted carbocyclyl, optionally substituted heterocyclyl, optionally substituted aryl, or optionally substituted heteroaryl; and
p is 1 or 2;
provided that the compound is not of the formula:

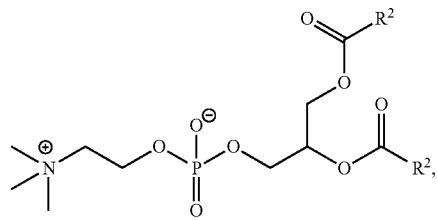

wherein each instance of $R^2$ is independently unsubstituted alkyl, unsubstituted alkenyl, or unsubstituted alkynyl.

In some embodiments, the phospholipids may be one or more of the phospholipids described in U.S. Application No. 62/520,530.

i) Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IV), at least one of $R^1$ is not methyl. In certain embodiments, at least one of $R^1$ is not hydrogen or methyl. In certain embodiments, the compound of Formula (IV) is of one of the following formulae:

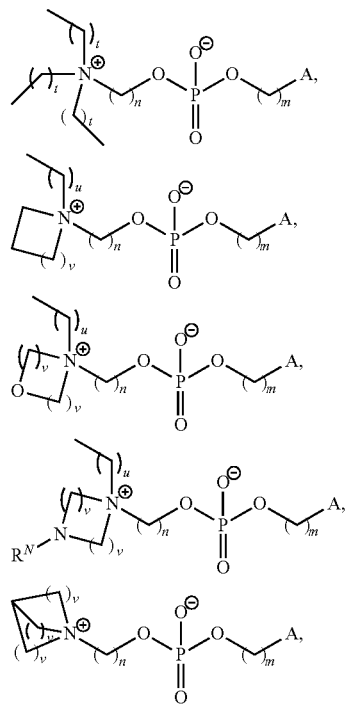

or a salt thereof, wherein:

each t is independently 1, 2, 3, 4, 5, 6, 7, 8, 9, or 10;
each u is independently 0, 1, 2, 3, 4, 5, 6, 7, 8, 9, or 10; and
each v is independently 1, 2, or 3.

In certain embodiments, a compound of Formula (IV) is of Formula (IV-a):

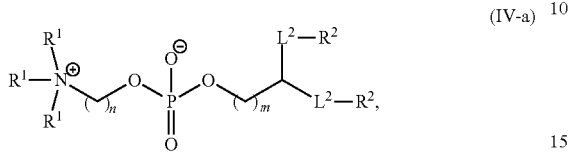

(IV-a)

or a salt thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IV) is of Formula (IV-b):

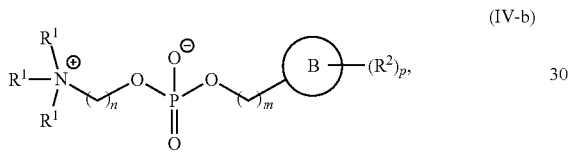

(IV-b)

or a salt thereof.

(ii) Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IV) is of Formula (IV-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, N($R^N$), O, S, C(O), C(O)N($R^N$), NR$^N$C(O), —NR$^N$C(O)N($R^N$), C(O)O, OC(O), OC(O)O, OC(O)N($R^N$), NR$^N$C(O)O, C(O)S, SC(O), —C(=NR$^N$), C(=NR$^N$)N($R^N$), NR$^N$C(=NR$^N$), NR$^N$C(=NR$^N$)N($R^N$), C(S), C(S)N($R^N$), —NR$^N$C(S), NR$^N$C(S)N($R^N$), S(O), OS(O), S(O)O, OS(O)O, OS(O)$_2$, S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, —N($R^N$)S(O)$_2$, S(O)$_2$N($R^N$), N($R^N$)S(O)$_2$N($R^N$), OS(O)$_2$N($R^N$), or N($R^N$)S(O)$_2$O.

In certain embodiments, the compound of Formula (IV) is of Formula (IV-c):

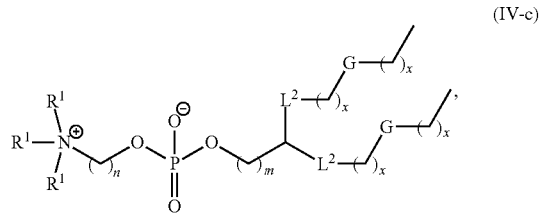

(IV-c)

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, N($R^N$), O, S, C(O), C(O)N($R^N$), NR$^N$C(O), —NR$^N$C(O)N($R^N$), C(O)O, OC(O), OC(O)O, OC(O)N($R^N$), NR$^N$C(O)O, C(O)S, SC(O), —C(=NR$^N$), C(=NR$^N$)N($R^N$), NR$^N$C(=NR$^N$), NR$^N$C(=NR$^N$)N($R^N$), C(S), C(S)N($R^N$), —NR$^N$C(S), NR$^N$C(S)N($R^N$), S(O), OS(O), S(O)O, OS(O)O, OS(O)$_2$, S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, —N($R^N$)S(O)$_2$, S(O)$_2$N($R^N$), N($R^N$)S(O)$_2$N($R^N$), OS(O)$_2$N($R^N$), or N($R^N$)S(O)$_2$O. Each possibility represents a separate embodiment of the present invention.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IV), wherein n is 1, 3, 4, 5, 6, 7, 8, 9, or 10. For example, in certain embodiments, a compound of Formula (IV) is of one of the following formulae:

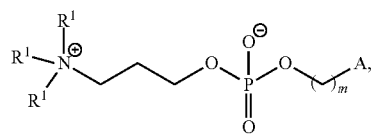

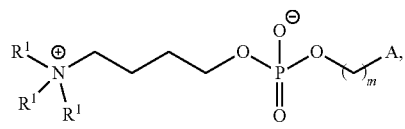

or a salt thereof.

Alternative Lipids

In certain embodiments, an alternative lipid is used in place of a phospholipid of the present disclosure.

In certain embodiments, an alternative lipid of the invention is oleic acid.

In certain embodiments, the alternative lipid is one of the following:

As used herein, the term "structural lipid" refers to sterols and also to lipids containing sterol moieties.

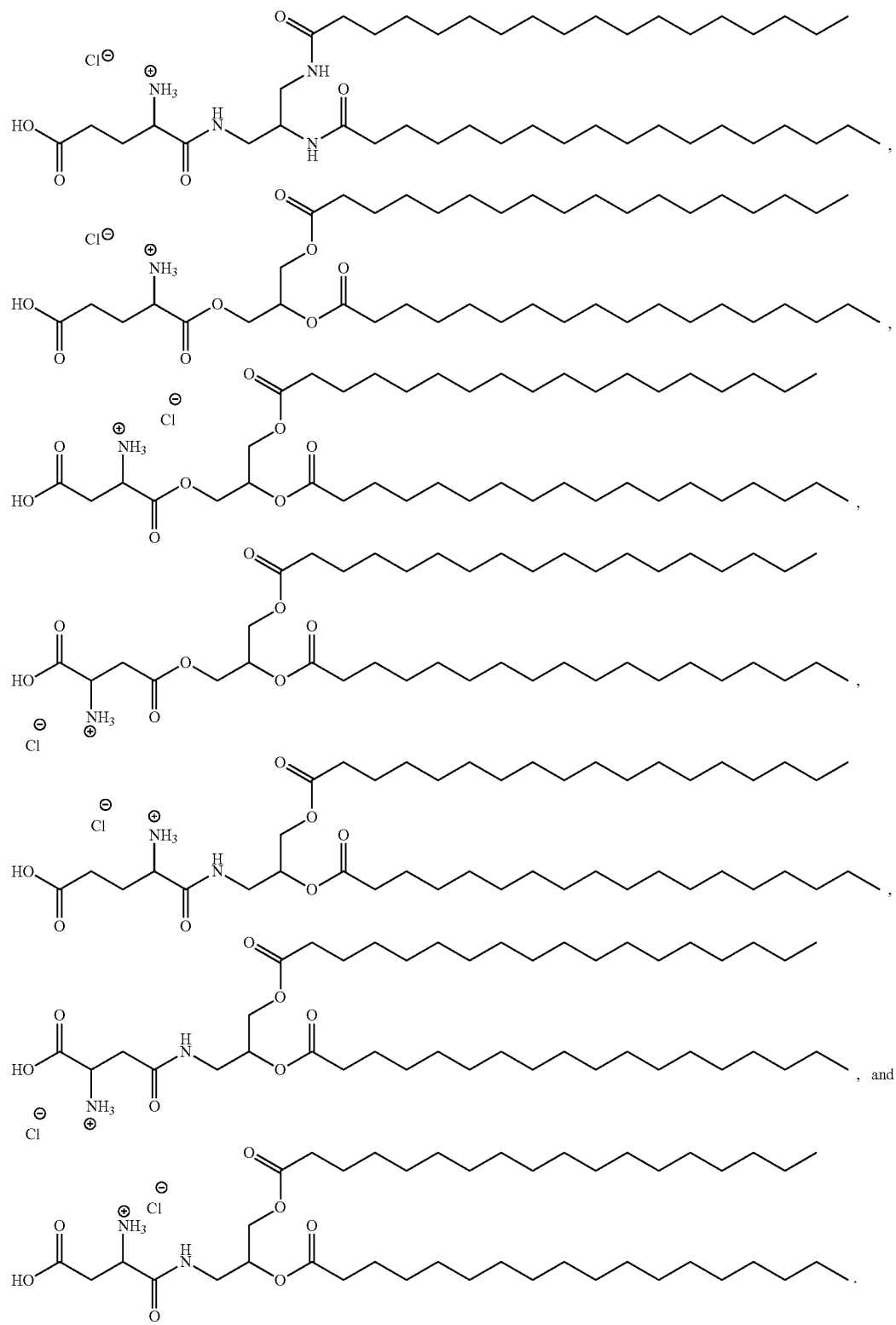

Structural Lipids

The lipid composition of a pharmaceutical composition disclosed herein can comprise one or more structural lipids. Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. Application No. 62/520,530.

Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about C14 to about C16. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

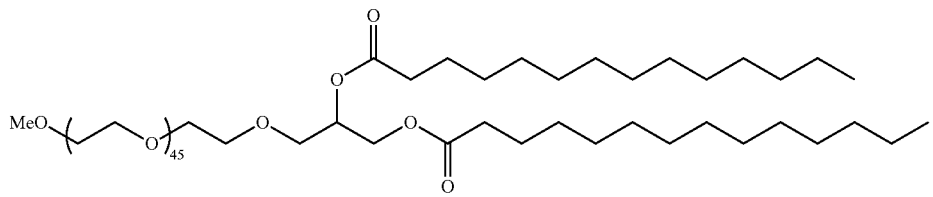

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (V). Provided herein are compounds of Formula (V):

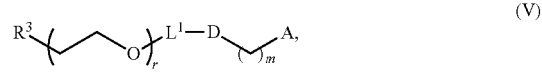

or salts thereof, wherein:

$R^3$ is —$OR^O$;

$R^O$ is hydrogen, optionally substituted alkyl, or an oxygen protecting group;

r is an integer between 1 and 100, inclusive;

L¹ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, N($R^N$), S, C(O), C(O)N($R^N$), $NR^NC(O)$, C(O)O, OC(O), OC(O)O, OC(O)N($R^N$), $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

A is of the formula:

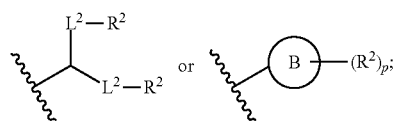

each instance of L 2 is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), $NR^NC(O)$, C(O)O, OC(O), OC(O)O, OC(O)N($R^N$), —$NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, N($R^N$), O, S, C(O), C(O)N($R^N$), $NR^NC(O)$, —$NR^NC(O)N(R^N)$, C(O)O, OC(O), OC(O)O, OC(O)N($R^N$), $NR^NC(O)O$, C(O)S, SC(O), —C(=$NR^N$), C(=$NR^N$)N($R^N$), $NR^NC(=NR^N)$, $NR^NC(=NR^N)N(R^N)$, C(S), C(S)N($R^N$), —$NR^NC(S)$, $NR^NC(S)N(R^N)$, S(O), OS(O), S(O)O, OS(O)O, OS(O)$_2$, S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, —N($R^N$)S(O)$_2$, S(O)$_2$N($R^N$), N($R^N$)S(O)$_2$N($R^N$), OS(O)$_2$N($R^N$), or N($R^N$)S(O)$_2$O;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (V) is a PEG-OH lipid (i.e., $R^3$ is —$OR^O$, and $R^O$ is hydrogen). In certain embodiments, the compound of Formula (V) is of Formula (V—OH):

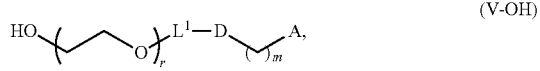

or a salt thereof.

In certain embodiments, a PEG lipid useful in the present invention is a PEGylated fatty acid. In certain embodiments, a PEG lipid useful in the present invention is a compound of Formula (VI). Provided herein are compounds of Formula (VI):

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of R 5 are replaced with optionally substituted carbocyclylene, optionally substituted heterocyclylene, optionally substituted arylene, optionally substituted heteroarylene, —N($R^N$), O, S, C(O), C(O)N($R^N$), $NR^NC(O)$, $NR^NC(O)N(R^N)$, C(O)O, OC(O), OC(O)O, OC(O)N($R^N$), $NR^NC(O)O$, C(O)S, SC(O), C(=$NR^N$), C(=$NR^N$)N($R^N$), $NR^NC(=NR^N)$, —$NR^NC(=NR^N)N(R^N)$, C(S), C(S)N($R^N$), $NR^NC(S)$, $NR^NC(S)N(R^N)$, S(O), OS(O), S(O)O, OS(O)O, OS(O)$_2$, S(O)$_2$O, OS(O)$_2$O, N($R^N$)S(O), S(O)N($R^N$), N($R^N$)S(O)N($R^N$), —OS(O)N($R^N$), N($R^N$)S(O)O, S(O)$_2$, N($R^N$)S(O)$_2$, S(O)$_2$N($R^N$), N($R^N$)S(O)$_2$N($R^N$), —OS(O)$_2$N($R^N$), or N($R^N$)S(O)$_2$O; and each instance of $R^N$ is independently hydrogen, optionally substituted alkyl, or a nitrogen protecting group.

In certain embodiments, the compound of Formula (VI) is of Formula (VI-OH):

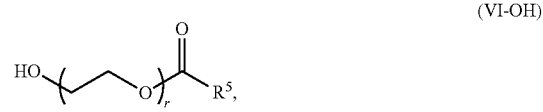

or a salt thereof. In some embodiments, r is 45.

In yet other embodiments the compound of Formula (VI) is:

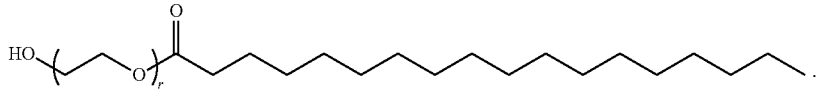

or a salt thereof.

In one embodiment, the compound of Formula (VI) is

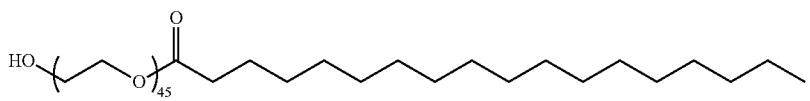

(Compound I).

In some aspects, the lipid composition of the pharmaceutical compositions disclosed herein does not comprise a PEG-lipid.

In some embodiments, the PEG-lipids may be one or more of the PEG lipids described in U.S. Application No. 62/520,530.

In some embodiments, a PEG lipid of the invention comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a LNP of the invention comprises an ionizable cationic lipid of any of Formula I, II or III, a phospholipid comprising DSPC, a structural lipid, and a PEG lipid comprising PEG-DMG.

In some embodiments, a LNP of the invention comprises an ionizable cationic lipid of any of Formula I, II or III, a phospholipid comprising DSPC, a structural lipid, and a PEG lipid comprising a compound having Formula VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid having Formula IV, a structural lipid, and a PEG lipid comprising a compound having Formula VI.

In some embodiments, a LNP of the invention comprises an ionizable cationic lipid of

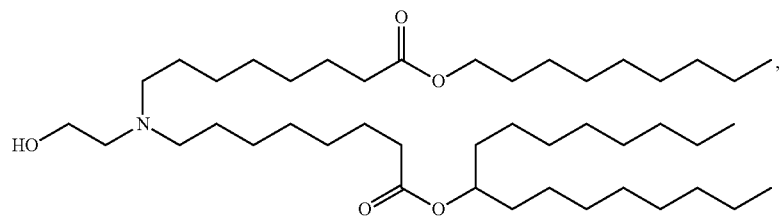 [SMILES: CCCCCCCCCOC(=O)CCCCCCCN(CCO)CCCCCCCC(=O)OC(CCCCCCCC)CCCCCCCC]

and a PEG lipid comprising Formula VI.

In some embodiments, a LNP of the invention comprises an ionizable cationic lipid of

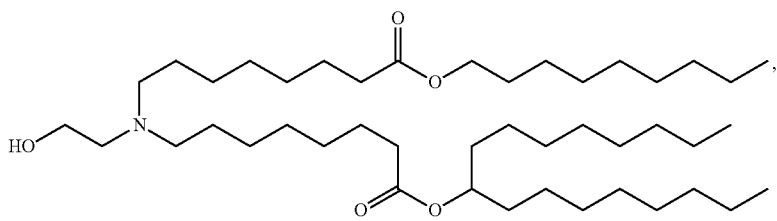 [SMILES: CCCCCCCCCOC(=O)CCCCCCCN(CCO)CCCCCCCC(=O)OC(CCCCCCCC)CCCCCCCC]

and an alternative lipid comprising oleic acid.

In some embodiments, a LNP of the invention comprises an ionizable cationic lipid of

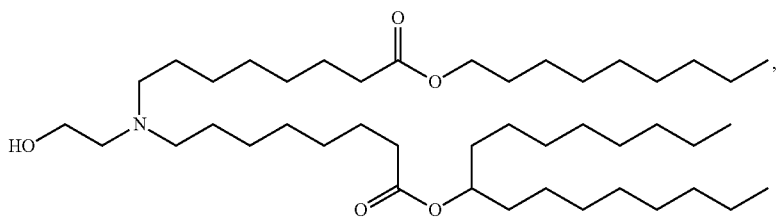 [SMILES: CCCCCCCCCOC(=O)CCCCCCCN(CCO)CCCCCCCC(=O)OC(CCCCCCCC)CCCCCCCC]

an alternative lipid comprising oleic acid, a structural lipid comprising cholesterol, and a PEG lipid comprising a compound having Formula VI.

In some embodiments, a LNP of the invention comprises an ionizable cationic lipid of

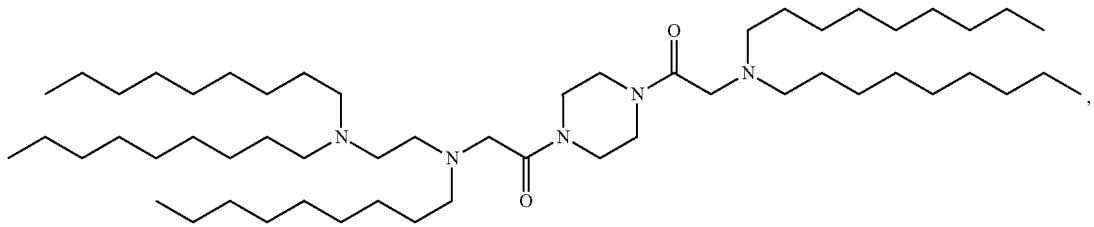 [SMILES: CCCCCCCCCN(CCCCCCCCC)CCN(CCCCCCCCC)CC(=O)N1CCN(C(=O)CN(CCCCCCCCC)CCCCCCCCC)CC1]

a phospholipid comprising DOPE, a structural lipid comprising cholesterol, and a PEG lipid comprising a compound having Formula VI.

In some embodiments, a LNP of the invention comprises an ionizable cationic lipid of a phospholipid comprising DOPE, a structural lipid comprising cholesterol, and a PEG lipid comprising a compound having Formula VII.

In some embodiments, a LNP of the invention comprises an N:P ratio of from about 2:1 to about 30:1.

In some embodiments, a LNP of the invention comprises an N:P ratio of about 6:1.

In some embodiments, a LNP of the invention comprises an N:P ratio of about 3:1.

In some embodiments, a LNP of the invention comprises a wt/wt ratio of the ionizable cationic lipid component to the RNA of from about 10:1 to about 100:1.

In some embodiments, a LNP of the invention comprises a wt/wt ratio of the ionizable cationic lipid component to the RNA of about 20:1.

In some embodiments, a LNP of the invention comprises a wt/wt ratio of the ionizable cationic lipid component to the RNA of about 10:1.

In some embodiments, a LNP of the invention has a mean diameter from about 50 nm to about 150 nm.

In some embodiments, a LNP of the invention has a mean diameter from about 70 nm to about 120 nm.

As used herein, the term "alkyl", "alkyl group", or "alkylene" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "C1-14 alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl", "alkenyl group", or "alkenylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "C2-14 alkenyl" means an optionally substituted linear or branched hydrocarbon including 2-14 carbon atoms and at least one carbon-carbon double bond. An alkenyl group may include one, two, three, four, or more carbon-carbon double bonds. For example, C18 alkenyl may include one or more double bonds. A C18 alkenyl group including two double bonds may be a linoleyl group. Unless otherwise specified, an alkenyl group described herein refers to both unsubstituted and substituted alkenyl groups.

As used herein, the term "alkynyl", "alkynyl group", or "alkynylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "C2-14 alkynyl" means an optionally substituted linear or branched hydrocarbon including 2-14 carbon atoms and at least one carbon-carbon triple bond. An alkynyl group may include one, two, three, four, or more carbon-carbon triple bonds. For example, C18 alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "C3-6 carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, the term "heteroalkyl", "heteroalkenyl", or "heteroalkynyl", refers respectively to an alkyl, alkenyl, alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. Unless otherwise specified, heteroalkyls, heteroalkenyls, or heteroalkynyls described herein refers to both unsubstituted and substituted heteroalkyls, heteroalkenyls, or heteroalkynyls, i.e., optionally substituted heteroalkyls, heteroalkenyls, or heteroalkynyls.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR—OC(O)R), an aldehyde (e.g., —C(O)H), a carbonyl (e.g., —C(O)R, alternatively represented by C=O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R'''', in which each OR are alkoxy groups that can be the same or different and R— is an alkyl or alkenyl group), a phosphate (e.g., P(O)43-), a thiol (e.g., —SH), a sulfoxide (e.g., —S(O)R), a sulfinic acid (e.g., —S(O)OH), a sulfonic acid (e.g., —S(O)2OH), a thial (e.g., —C(S)H), a sulfate (e.g., S(O)42-), a sulfonyl (e.g., —S(O)$_2$—), an amide (e.g., —C(O)NR$_2$, or —N(R)C(O)R), an azido (e.g., —N3), a nitro (e.g., —NO2), a cyano (e.g., —CN), an isocyano (e.g., —NC), an acyloxy (e.g., —OC(O)R), an amino (e.g., —NR2, —NRH, or —NH2), a carbamoyl (e.g., —OC(O)NR$_2$, —OC(O)NRH, or —OC(O)NH2), a sulfonamide (e.g., —S(O)$_2$NR$_2$, —S(O)$_2$NRH, —S(O)2NH2, —N(R)S(O)$_2$R, —N(H)S(O)$_2$R, —N(R)S(O) 2H, or —N(H)S(O)$_2$H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N☐O or N+—O—). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-C 6 alkyl, C1-C6 alkenyl, C1-C6 alkynyl, 3-14-membered carbocycle or 3-14-membered heterocycle) derivatives.

About, approximately: As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean+/−10% of the recited value. For instance, a nanoparticle composition including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 21:1, 22:1, 23:1, 24:1, 25:1, 26:1, 27:1, 28:1, 29:1, 30:1, 31:1, 32:1, 33:1, 34:1, 36:1, 37:1, 38:1, 39:1, 40:1, 41:1, 42:1, 43:1, 44:1, 45:1, 46:1, 47:1, 48:1, 49:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about from about 10:1 to about 40:1, from about 10:1 to about 45:1, from about 10:1 to about 50:1, from about 10:1 to about 55:1, from about 10:1 to about 60:1, from about to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as compound as described herein, and (ii) a polynucleotide encoding a OTC polypeptide. In such nanoparticle composition, the lipid composition disclosed herein can encapsulate the polynucleotide encoding a OTC polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid: about 5-25% structural lipid: about 25-55% sterol; and about 0.5-15% PEG-modified lipid.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a OTC polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm.

In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.16, 0.17, 0.18, 0.19, 0.20, 0.21, 0.22, 0.23, 0.24, or 0.25. In some embodiments, the polydispersity index of a nanoparticle composition disclosed herein can be from about to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about mV, from about 0 mV to about 20 mV, from about 0 mV to about 10 mV, from about mV to about 100 mV, from about 10 mV to about 90 mV, from about 10 mV to about mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about mV to about 100 mV, from about 30 mV to about 90 mV, from about 30 mV to about mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1.

In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

21. Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding an OTC polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multi-lamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethylnonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N- dimethylheptacosa-18,21-dien-10-amine, (15Z,18Z)—N,N-dimethyltetracosa-15,18-dien-5-amine, (14Z,17Z)—N,N di methyltri cos a-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacos a-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl] eptadecan-8-amine, 1-[(1 S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2 S)—N,N-dimethyl-1-[(9Z,12Z)-octadeca-9,12-dien-1-yl oxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2 S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxyl]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z, 16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctypoxyl-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, or greater than 99% of the pharmaceutical composition or compound of the invention are encapsulated in the delivery agent.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsevet al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM) from the Institut fur Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about to about 20 nm, about 10 to about 30 nm, about 10 to about 40 nm, about 10 to about nm, about 10 to about 60 nm, about 10 to about 70 nm, about 10 to about 80 nm, about to about 90 nm, about 20 to about 30 nm, about 20 to about 40 nm, about 20 to about nm, about 20 to about 60 nm, about 20 to about 70 nm, about 20 to about 80 nm, about to about 90 nm, about 20 to about 100 nm, about 30 to about 40 nm, about 30 to about nm, about 30 to about 60 nm, about 30 to about 70 nm, about 30 to about 80 nm, about to about 90 nm, about 30 to about 100 nm, about 40 to about 50 nm, about 40 to about nm, about 40 to about 70 nm, about 40 to about 80 nm, about 40 to about 90 nm, about to about 100 nm, about 50 to about 60 nm, about 50 to about 70 nm about 50 to about nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding an OTC polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-SLAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding an OTC polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, or subcutaneously.

d. Nanoparticle Mimics

In some embodiments, the polynucleotides described herein (e.g., a polynucleotide comprising a nucleotide sequence encoding an OTC polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a an OTC polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

f. Cations and Anions

In some embodiments, the compositions or formulations of the present disclosure comprise the polynucleotides described herein (e.g., a polynucleotide comprising a nucleotide sequence encoding an OTC polypeptide) and a cation or anion, such as $Zn^{2+}$, $Ca^{2+}$, $Cu^{2+}$, $Mg^{2+}$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

g. Amino Acid Lipids

In some embodiments, the compositions or formulations of the present disclosure comprise the polynucleotides described herein (e.g., a polynucleotide comprising a nucleotide sequence encoding an OTC polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

h. Interpolyelectrolyte Complexes

In some embodiments, the compositions or formulations of the present disclosure comprise the polynucleotides described herein (e.g., a polynucleotide comprising a nucleotide sequence encoding an OTC polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

i. Crystalline Polymeric Systems

In some embodiments, the compositions or formulations of the present disclosure comprise the polynucleotides described herein (e.g., a polynucleotide comprising a nucleotide sequence encoding an OTC polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

j. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding an OTC polypeptide) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUSO Bio (Madison, WI) and Roche Madison (Madison, WI), PHASERX™ polymer formulations such as, without limitation, SMARTT POLYMER TECHNOLOGY™ (PHASERX®, Seattle, WA), DMRI/DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/ or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

k. Peptides and Proteins

In some embodiments, the compositions or formulations of the present disclosure comprise the polynucleotides described herein (e.g., a polynucleotide comprising a nucleotide sequence encoding an OTC polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

l. Conjugates

In some embodiments, the compositions or formulations of the present disclosure comprise the polynucleotides described herein (e.g., a polynucleotide comprising a nucleotide sequence encoding an OTC polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835.393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

22. Accelerated Blood Clearance

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, fold, 5-10 fold, 6-100 fold, 6-50 fold, 6-40 fold, 6-30 fold, 6-25 fold, 6-20 fold, 6-fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically, by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance, many sensors are located in the spleen and can easily interact with one another. Alternatively, one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance, the LNP may have an altered PC and/or PEG to prevent interactions with sensors. Alternatively, or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance, the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively, agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively, agents that act on the platelets to block its activity once it is activated or on its effectors can be used together with the LNP to avoid ABC.

(i) Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

23. Methods of Use

The polynucleotides, pharmaceutical compositions and formulations described herein are used in the preparation, manufacture and therapeutic use of to treat and/or prevent OTC-related diseases, disorders or conditions. In some embodiments, the polynucleotides, compositions and formulations of the invention are used to treat and/or prevent ornithine transcarbamylase deficiency (OTCD).

In some embodiments, the polynucleotides, pharmaceutical compositions and formulations of the invention are used in methods for reducing the levels of ammonia in a subject in need thereof, e.g., a subject with hyperammonemia. For instance, one aspect of the invention provides a method of alleviating the symptoms of OTCD in a subject comprising the administration of a composition or formulation comprising a polynucleotide encoding OTC to that subject (e.g, an mRNA encoding an OTC polypeptide).

In some embodiments, the administration of an effective amount of a polynucleotide, pharmaceutical composition or formulation of the invention reduces the levels of a biomarker of OTCD, e.g., ammonia, orotic acid, and/or any combination thereof. In some embodiments, the administration of the polynucleotide, pharmaceutical composition or formulation of the invention results in reduction in the level of one or more biomarkers of OTCD, e.g., ammonia, and/or orotic acid, within a short period of time (e.g., within about 6 hours, within about 8 hours, within about 12 hours, within about 16 hours, within about 20 hours, or within about 24 hours) after administration of the polynucleotide, pharmaceutical composition or formulation of the invention.

In some embodiments, the administration of an effective amount of a polynucleotide, pharmaceutical composition or formulation of the invention increases body weight of a human subject. In some embodiments, the administration of the polynucleotide, pharmaceutical composition or formulation of the invention results in an increase in body weight within a short period of time (e.g., within about 12 hours, 24 hours, 48 hours, 72 hours, 96 hours, 5 days, 7 days, 14 days, 24 days, 48 days, or 60 days) after administration of the polynucleotide, pharmaceutical composition or formulation of the invention.

In some embodiments, the administration of an effective amount of a polynucleotide, pharmaceutical composition or formulation of the invention maintains body weight of a human subject.

Replacement therapy is a potential treatment for OTCD. Thus, in certain aspects of the invention, the polynucleotides, e.g., mRNA, disclosed herein comprise one or more sequences encoding an OTC polypeptide that is suitable for use in gene replacement therapy for OTCD. In some embodiments, the present disclosure treats a lack of OTC or OTC activity, or decreased or abnormal OTC activity in a subject by providing a polynucleotide, e.g., mRNA, that encodes an OTC polypeptide to the subject. In some embodiments, the polynucleotide is sequence-optimized. In some embodiments, the polynucleotide (e.g., an mRNA) comprises a nucleic acid sequence (e.g., an ORF) encoding an OTC polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142 and/or a miRNA binding site that binds miRNA-126.

In some embodiments, the administration of a composition or formulation comprising polynucleotide, pharmaceutical composition or formulation of the invention to a subject results in a decrease in ammonia in cells to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the polynucleotide, pharmaceutical composition or formulation of the invention results in expression of OTC in cells of the subject. In some embodiments, administering the polynucleotide, pharmaceutical composition or formulation of the invention results in an increase of OTC expression and/or enzymatic activity in the subject. For example, in some embodiments, the polynucleotides of the present invention are used in methods of administering a composition or formulation comprising an mRNA encoding an OTC polypeptide to a subject, wherein the method results in an increase of OTC expression and/or enzymatic activity in at least some cells of a subject.

In some embodiments, the administration of a composition or formulation comprising an mRNA encoding an OTC polypeptide to a subject results in an increase of OTC expression and/or enzymatic activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the expression and/or activity level expected in a normal subject, e.g., a human not suffering from OTCD.

In some embodiments, the administration of the polynucleotide, pharmaceutical composition or formulation of the invention results in expression of OTC protein in at least some of the cells of a subject that persists for a period of time sufficient to allow significant galactose metabolism to occur.

In some embodiments, the expression of the encoded polypeptide is increased. In some embodiments, the polynucleotide increases OTC expression and/or enzymatic activity levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the OTC expression and/or enzymatic activity level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 2 and 5-29 or a polynucleotide selected from the group of SEQ ID NOs: 30-55, wherein the polynucleotide encodes an OTC polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

In some embodiments, the polynucleotides (e.g., mRNA), pharmaceutical compositions and formulations used in the methods of the invention comprise a uracil-modified sequence encoding a OTC polypeptide disclosed herein and a miRNA binding site disclosed herein, e.g., a miRNA binding site that binds to miR-142 and/or a miRNA binding site that binds to miR-126. In some embodiments, the uracil-modified sequence encoding a OTC polypeptide comprises at least one chemically modified nucleobase, e.g., N1-methylpseudouracil or 5-methoxyuracil. In some embodiments, at least 95% of a type of nucleobase (e.g., uracil) in a uracil-modified sequence encoding a OTC polypeptide of the invention are modified nucleobases. In some embodiments, at least 95% of uracil in a uracil-modified sequence encoding a OTC polypeptide is 1-N-methylpseudouridine or 5-methoxyuridine. In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 47.5:10.5:39.0:3.0 or about 50:10:38.5:1.5. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or "helper lipid") (e.g., 5-10, 10-15, or 15-mol % phospholipid (or related suitable phospholipid or "helper lipid")), about 20 to about 50 mol % cholesterol (or related sterol or "non-cationic" lipid) (e.g., about 20-30, 35-40, 40-45, or 45-50 mol % cholesterol (or related sterol or "non-cationic" lipid)) and about 0.05 to about 10 mol % PEG lipid (or other suitable PEG lipid) (e.g., 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or In certain instances, an exemplary delivery agent can comprise mole ratios of, for example, 47.5:10.5:39.0:3; 47.5:10:39.5:3; 47.5:11:39.5:2; 47.5:10.5:39.5:2.5; 47.5:11:39:2.5; 48.5:10:38.5:3; 48.5:10.5:39:2; 48.5:10.5:38.5:2.5; 48.5:10.5:39.5:1.5; 48.5:10.5:38.0:3; 47:10.5:39.5:3; 47:10:40.5:2.5; 47:11:40.5:2; 47:10.5:39.5:3; 48:10.5:38.5:3; 48:10:39.5:2.5; 48:11:39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 47.5:10.5:39.0:3.0 or about 50:10:38.5:1.5.

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

OTCD is an X-linked recessive disorder that affects the urea cycle, characterized by an impaired or eliminated ability to catalyze a reaction between carbamyl phosphate and ornithine to form citrulline and phosphate. OTCD patients can be asymptomatic carriers of the disorder or suffer from the various symptoms associated with the disease. OTCD patients usually show high levels of ammonia in their blood (plasma, serum, red blood cells (RBCs)), urine, and/or tissue (e.g., liver). An accumulation of ammonia can cause hyperammonemia. OTCD patients can show high levels of orotic acid in their urine, blood (plasma, serum, red blood cells (RBC)), and/or tissue (e.g., liver). Unless otherwise specified, the methods of treating OTCD patients or human subjects disclosed herein include treatment of both asymptomatic carriers and those individuals with abnormal levels of biomarkers e.g., ammonia and/or orotic acid.

OTC Protein Expression Levels

Certain aspects of the invention feature measurement, determination and/or monitoring of the expression level or levels of ornithine transcarbamylase (OTC) protein in a subject, for example, in an animal (e.g., rodents, primates, and the like) or in a human subject. Animals include normal, healthy or wildtype animals, as well as animal models for use in understanding ornithine transcarbamylase deficiency (OTCD) and treatments thereof. Exemplary animal models include rodent models, for example, OTC deficient mice also referred to as OTC mice.

OTC protein expression levels can be measured or determined by any art-recognized method for determining protein levels in biological samples, e.g., from blood samples or a needle biopsy. The term "level" or "level of a protein" as used herein, preferably means the weight, mass or concentration of the protein within a sample or a subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased OTC protein expression levels in the liver tissue of the subject (e.g., 2-fold, 3-fold, 4-fold, 5-fold, 6-fold, 7-fold, 8-fold, 9-fold, 20-fold, 30-fold, 40-fold, 50-fold increase and/or increased to at least 50%, at least 60%, at least 70%, at least 75%, 80%, at least 85%, at least 90%, at least 95%, or at least 100% of normal levels) for at least 6 hours, at least 12 hours, at least 24 hours, at least 36 hours, at least 48 hours, at least 60 hours, at least 72 hours, at least 84 hours, at least 96 hours, at least 108 hours, at least 122 hours, at least 144 hours, at least 168 hours, at least 192 hours, at least 240 hours, at least 288 hours, at least 336 hours, at least 384 hours, at least 432 hours, at least 480 hours, at least 504 hours at least 528 hours, at least 672 hours after administration of a single dose of the mRNA therapy. In some embodiments, an mRNA therapy of the invention (e.g., a single intravenous dose) results in increased OTC protein expression levels in the liver tissue of the subject (e.g., 2-fold, 3-fold, 4-fold, 5-fold, 6-fold, 7-fold, 8-fold, 9-fold, 10-fold, 20-fold, 30-fold, 40-fold, 50-fold increase and/or increased to at least 50%, at least 60%, at least 70%, at least 75%, 80%, at least 85%, at least 90%, at least 95%, or at least 100% of normal levels) for at least 6 hours, at least 12 hours, at least 24 hours, or at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more days after administration of a single dose of the mRNA therapy.

OTC Protein Activity

In OTCD patients, OTC enzymatic activity is reduced compared to a normal physiological activity level. Further aspects of the invention feature measurement, determination and/or monitoring of the activity level(s) (i.e., enzymatic activity level(s)) of OTC protein in a subject, for example, in an animal (e.g., rodent, primate, and the like) or in a human subject. Activity levels can be measured or determined by any art-recognized method for determining enzymatic activity levels in biological samples. The term "activity level" or "enzymatic activity level" as used herein, preferably means the activity of the enzyme per volume, mass or weight of sample or total protein within a sample. In exemplary embodiments, the "activity level" or "enzymatic activity level" is described in terms of units per milliliter of fluid (e.g., bodily fluid, e.g., serum, plasma, urine and the like) or is described in terms of units per weight of tissue or per weight of protein (e.g., total protein) within a sample. Units ("U") of enzyme activity can be described in terms of weight or mass of substrate hydrolyzed per unit time. In certain embodiments of the invention feature OTC activity described in terms of U/ml plasma or U/mg protein (tissue), where units ("U") are described in terms of nmol substrate hydrolyzed per hour (or nmol/hr).

In certain embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of OTC activity in tissue (e.g., liver) between 6 and 12 hours, or between 12 and 24, between 24 and 48, or between 48 and 72 hours post administration (e.g., at 48 or at 72 hours post administration).

In some embodiments, an mRNA therapy of the invention (e.g., a single intravenous dose) results in increased OTC activity levels in the liver tissue of the subject (e.g., 2-fold, 3-fold, 4-fold, 5-fold, 6-fold, 7-fold, 8-fold, 9-fold, 10-fold, 20-fold, 30-fold, 40-fold, 50-fold increase and/or increased to at least 50%, at least 60%, at least 70%, at least 75%, 80%, at least 85%, at least 90%, at least 95%, or at least 100% of normal levels) for at least 6 hours, at least 12 hours, at least 24 hours, or at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more days after administration of a single dose of the mRNA therapy.

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

OTC Biomarkers

Further aspects of the invention feature determining the level (or levels) of a biomarker, e.g., ammonia or orotic acid, determined in a sample as compared to a level (e.g., a reference level) of the same or another biomarker in another sample, e.g., from the same patient, from another patient, from a control and/or from the same or different time points, and/or a physiologic level, and/or an elevated level, and/or a supraphysiologic level, and/or a level of a control. The skilled artisan will be familiar with physiologic levels of biomarkers, for example, levels in normal or wildtype animals, normal or healthy subjects, and the like, in particular, the level or levels characteristic of subjects who are healthy and/or normal functioning. As used herein, the phrase "elevated level" means amounts greater than normally found in a normal or wildtype preclinical animal or in a normal or healthy subject, e.g. a human subject. As used herein, the term "supraphysiologic" means amounts greater than normally found in a normal or wildtype preclinical animal or in a normal or healthy subject, e.g. a human subject, optionally producing a significantly enhanced physiologic response. As used herein, the term "comparing" or "compared to" preferably means the mathematical comparison of the two or more values, e.g., of the levels of the biomarker(s). It will thus be readily apparent to the skilled artisan whether one of the values is higher, lower or identical to another value or group of values if at least two of such values are compared with each other. Comparing or comparison to can be in the context, for example, of comparing to a control value, e.g., as compared to a reference blood plasma, serum, red blood cells (RBC) and/or tissue (e.g., liver) ammonia level, and/or a reference serum, blood plasma, tissue (e.g., liver), and/or urinary orotic acid level, in said subject prior to administration (e.g., in a person suffering from OTCD) or in a normal or healthy subject. Comparing or comparison to can also be in the context, for example, of comparing to a control value, e.g., as compared to a reference blood plasma, serum, red blood cells (RBC) and/or tissue (e.g., liver) ammoniaGal-1-P level, and/or a reference serum, blood plasma, tissue (e.g., liver), and/or urinary orotic acid levelin said subject prior to administration (e.g., in a person suffering from OTCD) or in a normal or healthy subject.

As used herein, a "control" is preferably a sample from a subject wherein the Gal-1 status of said subject is known. In one embodiment, a control is a sample of a healthy patient. In another embodiment, the control is a sample from at least one subject having a known OTCD status, for example, a severe, mild, or healthy OTCD status, e.g. a control patient. In another embodiment, the control is a sample from a subject not being treated for OTCD. In a still further embodiment, the control is a sample from a single subject or a pool of samples from different subjects and/or samples taken from the subject(s) at different time points.

The term "level" or "level of a biomarker" as used herein, preferably means the mass, weight or concentration of a biomarker of the invention within a sample or a subject. Biomarkers of the invention include, for example, ammonia and/or orotic acid (e.g., urinary orotic acid). It will be understood by the skilled artisan that in certain embodiments the sample may be subjected to, e.g., one or more of the following: substance purification, precipitation, separation, e.g. centrifugation and/or HPLC and subsequently subjected to determining the level of the biomarker, e.g. using mass spectrometric analysis. In certain embodiments, LC-MS can be used as a means for determining the level of a biomarker according to the invention.

The term "determining the level" of a biomarker as used herein can mean methods which include quantifying an amount of at least one substance in a sample from a subject, for example, in a bodily fluid from the subject (e.g., serum, plasma, urine, RBC, lymph, fecal, etc.) or in a tissue of the subject (e.g., liver, heart, spleen kidney, etc.).

The term "reference level" as used herein can refer to levels (e.g., of a biomarker) in a subject prior to administration of an mRNA therapy of the invention (e.g., in a person suffering from OTCD) or in a normal or healthy subject.

As used herein, the term "normal subject" or "healthy subject" refers to a subject not suffering from symptoms associated with OTCD. Moreover, a subject will be considered to be normal (or healthy) if it has no mutation of the functional portions or domains of the ornithine transcarbamylase (OTC) gene and/or no mutation of the OTC gene resulting in a reduction of or deficiency of the enzyme OTC (also known as ornithine transcarbamylase) or the activity thereof, resulting in symptoms associated with OTCD. Said mutations will be detected if a sample from the subject is subjected to a genetic testing for such OTC mutations. In certain embodiments of the present invention, a sample from a healthy subject is used as a control sample, or the known or standardized value for the level of biomarker from samples of healthy or normal subjects is used as a control.

In some embodiments, comparing the level of the biomarker in a sample from a subject in need of treatment for OTCD or in a subject being treated for OTCD to a control level of the biomarker comprises comparing the level of the biomarker in the sample from the subject (in need of treatment or being treated for OTCD) to a baseline or reference level, wherein if a level of the biomarker in the sample from the subject (in need of treatment or being treated for OTCD) is elevated, increased or higher compared to the baseline or reference level, this is indicative that the subject is suffering from OTCD and/or is in need of treatment; and/or wherein if a level of the biomarker in the sample from the subject (in need of treatment or being treated for OTCD) is decreased or lower compared to the baseline level this is indicative that the subject is not suffering from, is successfully being treated for OTCD, or is not in need of treatment for OTCD. The stronger the reduction (e.g., at least 1.5-fold, at least 2-fold, at least 3-fold, at least 4-fold, at least 5-fold, at least 6-fold, at least 7-fold, at least 8-fold, at least 10-fold, at least 20-fold, at least-30 fold, at least 40-fold, at least 50-fold reduction and/or at least 10%, at least 20%, at least 30% at least 40%, at least 50%, at least 60%, at least 70%, at least 80%, at least 90%, or at least 100% reduction) of the level of a biomarker, e.g., ammonia and/or orotic acid, within a certain time period, e.g., within 6 hours, within 12 hours, 24 hours, 36 hours, 48 hours, 60 hours, or 72 hours, and/or for a certain duration of time, e.g., 48 hours, 72 hours, 96 hours, 120 hours, 144 hours, 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, etc. the more successful is a therapy, such as for example an mRNA therapy of the invention (e.g., a single dose or a multiple regimen).

A reduction of at least about 20%, at least about 30%, at least about 40%, at least about 50%, at least about 60%, at least about 70%, at least about 80%, at least about 90%, at least 100% or more of the level of biomarker, in particular, in bodily fluid (e.g., plasma, serum, red blood cells (RBC), urine, e.g., urinary sediment) or in tissue(s) in a subject (e.g., liver), for example ammonia and/or orotic acid, within 1, 2, 3, 4, 5, 6 or more days following administration is indicative of a dose suitable for successful treatment OTCD, wherein reduction as used herein, preferably means that the level of biomarker determined at the end of a specified time period (e.g., post-administration, for example, of a single intravenous dose) is compared to the level of the same biomarker determined at the beginning of said time period (e.g., pre-administration of said dose). Exemplary time periods include 12, 24, 48, 72, 96, 120 or 144 hours post administration, in particular 24, 48, 72 or 96 hours post administration.

A sustained reduction in substrate levels (e.g., biomarkers such as ammonia and/or orotic acid) is particularly indicative of mRNA therapeutic dosing and/or administration regimens successful for treatment of OTCD. Such sustained reduction can be referred to herein as "duration" of effect. In exemplary embodiments, a reduction of at least about 20%, at least about 30%, at least about 40%, at least about 50%, at least about 60%, at least about 65%, at least about 70%, at least about 75%, at least about 80%, at least about 85%, at least about 90%, or at least about 95% at least about 96%, at least about 97%, at least about 98%, at least about 99%, at least about 100% or more of the level of biomarker, in particular, in a bodily fluid (e.g., plasma, serum, RBC, urine, e.g., urinary sediment) or in tissue(s) in a subject (e.g., liver), for example ammonia and/or orotic acid, within 1, 2, 3, 4, 5, 6, 7, 8 or more days following administration is indicative of a successful therapeutic approach. In exemplary embodiments, sustained reduction in substrate (e.g., biomarker) levels in one or more samples (e.g., fluids and/or tissues) is preferred. For example, mRNA therapies resulting in sustained reduction in ammonia and/or orotic acid (as defined herein), optionally in combination with sustained reduction of said biomarker in at least one tissue, preferably two, three, four, five or more tissues, is indicative of successful treatment.

In some embodiments, a single dose of an mRNA therapy of the invention is about 0.2 to about 0.8 mpk. about 0.3 to about 0.7 mpk, about 0.4 to about 0.8 mpk, or about 0.5 mpk. In another embodiment, a single dose of an mRNA therapy of the invention is less than 1.5 mpk, less than 1.25 mpk, less than 1 mpk, or less than 0.75 mpk.

24. Compositions and Formulations for Use

Certain aspects of the invention are directed to compositions or formulations comprising any of the polynucleotides disclosed above.

In some embodiments, the composition or formulation comprises:
(i) a polynucleotide (e.g., a RNA, e.g., an mRNA) comprising a sequence-optimized nucleotide sequence (e.g., an ORF) encoding an OTC polypeptide (e.g., the wild-type sequence, functional fragment, or variant thereof), wherein the polynucleotide comprises at least one chemically modified nucleobase, e.g., N1-methylpseudouracil or 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are N1-methypseudouracils or 5-methoxyuracils), and wherein the polynucleotide further comprises a miRNA binding site, e.g., a miRNA binding site that binds to miR-142 (e.g., a miR-142-3p or miR-142-5p binding site) and/or a miRNA binding site that binds to miR-126 (e.g., a miR-126-3p or miR-126-5p binding site); and (ii) a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent is a lipid nanoparticle comprising Compound II, Compound VI, a salt or a stereoisomer thereof, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound II, DSPC, Cholesterol, and Compound I or PEG-DMG, e.g., with a mole ratio of about 47.5:10.5:39.0:3.0. In some embodiments, the delivery agent comprises Compound VI, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio of about 47.5:10.5:39.0:3.0.

In some embodiments, the uracil or thymine content of the ORF relative to the theoretical minimum uracil or thymine content of a nucleotide sequence encoding the OTC polypeptide (% $U_{TM}$ or % $T_{TM}$), is between about 100% and about 150%, e.g., about 100 to about 110%, about 110 to about 120%, about 120% to about 130%, about 130% to about 140%, about 140% to about 150%.

In some embodiments, the polynucleotides, compositions or formulations above are used to treat and/or prevent an OTC-related disease, disorders or conditions, e.g., OTCD.

25. Forms of Administration

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding an OTC polypeptide or a functional fragment or variant thereof) can be delivered to a cell naked. As used herein in, "naked" refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding an OTC polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

26. Kits and Devices a. Kits

The invention provides a variety of kits for conveniently and/or effectively using the claimed nucleotides of the present invention. Typically, kits will comprise sufficient amounts and/or numbers of components to allow a user to perform multiple treatments of a subject(s) and/or to perform multiple experiments.

In one aspect, the present invention provides kits comprising the molecules (polynucleotides) of the invention.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present invention according to single, multi- or split-dosing regimens taught herein. Such devices are taught in, for example, International Application Publ. No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minute period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

27. Definitions

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type OTC sequence) with another amino acid residue. An amino acid can be substituted in a parent or reference sequence (e.g., a wild type OTC polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, symptoms, sequelae, or any effects causing a decrease in the quality of life of a patient of Gal-1 are considered associated with Gal-1 and in some embodiments of the present invention can be treated, ameliorated, or prevented by administering the polynucleotides of the present invention to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode an OTC peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunction modified mRNA can be a chimeric or quimeric molecule comprising, for example, an RNA encoding an OTC peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising an OTC polypeptide, and a second part (e.g., genetically fused to the first part) comprising a second therapeutic protein (e.g., a protein with a distinct enzymatic activity, an antigen binding moiety, or a moiety capable of extending the plasma half life of OTC, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., an OTC deficiency), an effective amount of an agent is, for example, an amount of mRNA expressing sufficient OTC to ameliorate, reduce, eliminate, or prevent the symptoms associated with the OTC deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the invention are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., OTC) wherein N-terminal, and/or C-terminal, and/or internal subsequences have been deleted. In some preferred aspects of the present invention, the fragments of a protein of the present invention are functional fragments.

Functional: As used herein, a "functional" biological molecule is a biological molecule in a form in which it exhibits a property and/or activity by which it is characterized. Thus, a functional fragment of a polynucleotide of the present invention is a polynucleotide capable of expressing a functional OTC fragment. As used herein, a functional fragment of OTC refers to a fragment of wild type OTC (i.e., a fragment of any of its naturally occurring isoforms), or a mutant or variant thereof, wherein the fragment retains at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

OTC Associated Disease: As use herein the terms "OTC-associated disease" or "OTC-associated disorder" refer to diseases or disorders, respectively, which result from aberrant OTC activity (e.g., decreased activity or increased activity). As a non-limiting example, ornithine transcarbamylase deficiency (OTCD) is an OTC associated disease. Numerous clinical variants of OTCD are know in the art. See, e.g., omim.org/entry/311250.

The terms "OTC enzymatic activity," "OTC activity," and "ornithine transcarbamylase activity" are used interchangeably in the present disclosure and refer to OTC's ability to catalyze a reaction between carbamyl phosphate and ornithine to form citrulline and phosphate, essential for the conversion of ammonia into urea. Accordingly, a fragment or variant retaining or having OTC enzymatic activity or OTC activity refers to a fragment or variant that has measurable enzymatic activity in catalyzing a reaction between carbamyl phosphate and ornithine to form citrulline and phosphate. Therefore, a fragment or variant retaining or having OTC enzymatic activity or OTC activity refers to a fragment or variant that has measurable enzymatic activity in converting ammonia to urea.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically, the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (I1-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,16Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs), including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition. In some embodiments, the treatment is needed, required, or received to prevent or decrease the risk of developing acute disease, i.e., it is a prophylactic treatment.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨPC codon (RNA map in which U has been replaced with pseudouridine).

Standard A-T and G-C base pairs form under conditions which allow the formation of hydrogen bonds between the N3-H and $C_4$-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32: 10489-10496 and references cited therein; 2'-deoxy-5-methyl-isocytidine can be prepared by the method of Tor et al., 1993, J. Am. Chem. Soc. 115: 4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine ($\psi$) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$) (also known as N1-methyl-pseudouridine), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, 1-methyl-3-(3-amino-3-carboxypropyl)pseudouridine ($acp^3$ $\psi$), and 2'-O-methyl-pseudouridine ($\psi$m).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragement or a variant thereof. In some embodiments, the reference nucleic acid sequence is a previously sequence optimized nucleic acid sequence.

Salts: In some aspects, the pharmaceutical composition for delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with and/or cannot exhibit symptoms of the disease, disorder, and/or condition but harbors a propensity to develop a disease or its symptoms. In some embodiments, an individual who is susceptible to a disease, disorder, and/or condition (for example, Gal-1) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a liver, a kidney, a lung, a spleen, or a vascular endothelium in vessels (e.g., intra-coronary or intra-femoral). An "off-target tissue" refers to any one or more tissue types in which the expression of the encoded protein does not result in a desired biological and/or pharmacological effect.

The presence of a therapeutic agent in an off-target issue can be the result of: (i) leakage of a polynucleotide from the administration site to peripheral tissue or distant off-target tissue via diffusion or through the bloodstream (e.g., a polynucleotide intended to express a polypeptide in a certain tissue would reach the off-target tissue and the polypeptide would be expressed in the off-target tissue); or (ii) leakage of an polypeptide after administration of a polynucleotide encoding such polypeptide to peripheral tissue or distant off-target tissue via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding an OTC polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence)

Transfection: As used herein, "transfection" refers to the introduction of a polynucleotide (e.g., exogenous nucleic acids into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a disease, e.g., ornithine transcarbamylase deficiency (OTCD). For example, "treating" OTCD can refer to diminishing symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a $\beta$-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in a sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in a sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g, polymorphisms, isoforms, etc) and artificial variants in which at least one amino acid residue in a native or starting sequence (e.g., a wild type sequence) has been removed and a different amino acid inserted in its place at the same position. These variants can de described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

Initiation Codon: As used herein, the term "initiation codon", used interchangeably with the term "start codon", refers to the first codon of an open reading frame that is translated by the ribosome and is comprised of a triplet of linked adenine-uracil-guanine nucleobases. The initiation codon is depicted by the first letter codes of adenine (A), uracil (U), and guanine (G) and is often written simply as "AUG". Although natural mRNAs may use codons other than AUG as the initiation codon, which are referred to herein as "alternative initiation codons", the initiation codons of polynucleotides described herein use the AUG codon. During the process of translation initiation, the sequence comprising the initiation codon is recognized via complementary base-pairing to the anticodon of an initiator tRNA (Met-tRNA$_i^{Met}$) bound by the ribosome. Open reading frames may contain more than one AUG initiation codon, which are referred to herein as "alternate initiation codons".

The initiation codon plays a critical role in translation initiation. The initiation codon is the first codon of an open reading frame that is translated by the ribosome. Typically, the initiation codon comprises the nucleotide triplet AUG, however, in some instances translation initiation can occur at other codons comprised of distinct nucleotides. The initiation of translation in eukaryotes is a multistep biochemical process that involves numerous protein-protein, protein-RNA, and RNA-RNA interactions between messenger RNA molecules (mRNAs), the 40S ribosomal subunit, other components of the translation machinery (e.g., eukaryotic initiation factors; eIFs). The current model of mRNA translation initiation postulates that the pre-initiation complex (alternatively "43S pre-initiation complex"; abbreviated as "PIC") translocates from the site of recruitment on the mRNA (typically the 5' cap) to the initiation codon by scanning nucleotides in a 5' to 3' direction until the first AUG codon that resides within a specific translation-promotive nucleotide context (the Kozak sequence) is encountered (Kozak (1989) J Cell Biol 108:229-241). Scanning by the PIC ends upon complementary base-pairing between nucleotides comprising the anticodon of the initiator Met-tRNA,' transfer RNA and nucleotides comprising the initiation codon of the mRNA. Productive base-pairing between the AUG codon and the Met-tRNA,' anticodon elicits a series of structural and biochemical events that culminate in the joining of the large 60S ribosomal subunit to the PIC to form an active ribosome that is competent for translation elongation.

Kozak Sequence: The term "Kozak sequence" (also referred to as "Kozak consensus sequence") refers to a translation initiation enhancer element to enhance expression of a gene or open reading frame, and which in eukaryotes, is located in the 5' UTR. The Kozak consensus sequence was originally defined as the sequence <u>GCCRCC</u>, where R=a purine, following an analysis of the effects of single mutations surrounding the initiation codon (AUG) on translation of the preproinsulin gene (Kozak (1986) Cell 44:283-292). Polynucleotides disclosed herein comprise a Kozak consensus sequence, or a derivative or modification thereof (Examples of translational enhancer compositions and methods of use thereof, see U.S. Pat. No. 5,807,707 to Andrews et al., incorporated herein by reference in its entirety; U.S. Pat. No. 5,723,332 to Chernajovsky, incorporated herein by reference in its entirety; U.S. Pat. No. 5,891,665 to Wilson, incorporated herein by reference in its entirety.)

Leaky scanning: A phenomenon known as "leaky scanning" can occur whereby the PIC bypasses the initiation codon and instead continues scanning downstream until an alternate or alternative initiation codon is recognized. Depending on the frequency of occurrence, the bypass of the initiation codon by the PIC can result in a decrease in translation efficiency. Furthermore, translation from this downstream AUG codon can occur, which will result in the production of an undesired, aberrant translation product that may not be capable of eliciting the desired therapeutic response. In some cases, the aberrant translation product may in fact cause a deleterious response (Kracht et al., (2017) Nat Med 23(4):501-507).

Modified: As used herein "modified" or "modification" refers to a changed state or a change in composition or structure of a polynucleotide (e.g., mRNA). Polynucleotides may be modified in various ways including chemically, structurally, and/or functionally. For example, polynucleotides may be structurally modified by the incorporation of one or more RNA elements, wherein the RNA element comprises a sequence and/or an RNA secondary structure(s) that provides one or more functions (e.g., translational regulatory activity). Accordingly, polynucleotides of the disclosure may be comprised of one or more modifications (e.g., may include one or more chemical, structural, or functional modifications, including any combination thereof).

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g., binding affinity, nuclease resistance, chemical stability) to a nucleic acid or a portion or segment thereof. Adenine, cytosine, guanine, thymine, and uracil are the nucleobases predominately found in natural nucleic acids. Other natural, non-natural, and/or synthetic nucleobases, as known in the art and/or described herein, can be incorporated into nucleic acids.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

Nucleic acid: As used herein, the term "nucleic acid" is used in its broadest sense and encompasses any compound and/or substance that includes a polymer of nucleotides, or derivatives or analogs thereof. These polymers are often referred to as "polynucleotides". Accordingly, as used herein the terms "nucleic acid" and "polynucleotide" are equivalent and are used interchangeably. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, mRNAs, modified mRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Nucleic Acid Structure: As used herein, the term "nucleic acid structure" (used interchangeably with "polynucleotide structure") refers to the arrangement or organization of atoms, chemical constituents, elements, motifs, and/or sequence of linked nucleotides, or derivatives or analogs thereof, that comprise a nucleic acid (e.g., an mRNA). The term also refers to the two-dimensional or three-dimensional state of a nucleic acid. Accordingly, the term "RNA structure" refers to the arrangement or organization of atoms, chemical constituents, elements, motifs, and/or sequence of linked nucleotides, or derivatives or analogs thereof, comprising an RNA molecule (e.g., an mRNA) and/or refers to a two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Open Reading Frame: As used herein, the term "open reading frame", abbreviated as "ORF", refers to a segment or region of an mRNA molecule that encodes a polypeptide. The ORF comprises a continuous stretch of non-overlapping, in-frame codons, beginning with the initiation codon and ending with a stop codon, and is translated by the ribosome.

Pre-Initiation Complex (PIC): As used herein, the term "pre-initiation complex" (alternatively "43S pre-initiation complex"; abbreviated as "PIC") refers to a ribonucleoprotein complex comprising a 40S ribosomal subunit, eukaryotic initiation factors (eIF1, eIF1A, eIF3, eIF5), and the eIF2-GTP-Met-tRNA$_i^{Met}$ ternary complex, that is intrinsically capable of attachment to the 5' cap of an mRNA molecule and, after attachment, of performing ribosome scanning of the 5' UTR.

RNA element: As used herein, the term "RNA element" refers to a portion, fragment, or segment of an RNA molecule that provides a biological function and/or has biological activity (e.g., translational regulatory activity). Modification of a polynucleotide by the incorporation of one or more RNA elements, such as those described herein, provides one or more desirable functional properties to the modified polynucleotide. RNA elements, as described herein, can be naturally-occurring, non-naturally occurring, synthetic, engineered, or any combination thereof. For example, naturally-occurring RNA elements that provide a regulatory activity include elements found throughout the transcriptomes of viruses, prokaryotic and eukaryotic organisms (e.g., humans). RNA elements in particular eukaryotic mRNAs and translated viral RNAs have been shown to be involved in mediating many functions in cells. Exemplary natural RNA elements include, but are not limited to, translation initiation elements (e.g., internal ribosome entry site (IRES), see Kieft et al., (2001) RNA 7(2):194-206), translation enhancer elements (e.g., the APP mRNA translation enhancer element, see Rogers et al., (1999) J Biol Chem 274(10):6421-6431), mRNA stability elements (e.g., AU-rich elements (AREs), see Garneau et al., (2007) Nat Rev Mol Cell Biol 8(2):113-126), translational repression element (see e.g., Blumer et al., (2002) Mech Dev 110(1-2):97-112), protein-binding RNA elements (e.g., iron-responsive element, see Selezneva et al., (2013) J Mol Biol 425(18):3301-3310), cytoplasmic polyadenylation elements (Villalba et al., (2011) Curr Opin Genet Dev 21(4):452-457), and catalytic RNA elements (e.g., ribozymes, see Scott et al., (2009) Biochim Biophys Acta 1789(9-10):634-641).

Residence time: As used herein, the term "residence time" refers to the time of occupancy of a pre-initiation complex (PIC) or a ribosome at a discrete position or location along an mRNA molecule.

Translational Regulatory Activity: As used herein, the term "translational regulatory activity" (used interchangeably with "translational regulatory function") refers to a biological function, mechanism, or process that modulates (e.g., regulates, influences, controls, varies) the activity of the translational apparatus, including the activity of the PIC and/or ribosome. In some aspects, the desired translation regulatory activity promotes and/or enhances the translational fidelity of mRNA translation. In some aspects, the desired translational regulatory activity reduces and/or inhibits leaky scanning.

28. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| | mRNA Name | ORF Sequence (Amino Acid) | ORF Sequence (Nucleotide) | 5' UTR Sequence | 3' UTR Sequence | Construct Sequence |
|---|---|---|---|---|---|---|
| SEQ ID NO: | | 1 | 2 | 3 | 4 | 30 |
| | OTC-02 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH | AUGCUGUUUAAUCU GAGGAUCCUGUUAA ACAACGCAGCUUUU AGAAACGGUCACAA CUUCAUGGUUCGAA AUUUCGGUGUGGA CAACCACUACAGAA UAAAGUGCAGCUGA AGGGCCGUGACCUU CUCACUUUGAAGAA CUUUACCGGAGAAG AAAUUAAAUAUAU GCUCUGGCUAUCAG CAGAUCUGAAAUUU AGGAUUAAGCAGAA AGGAGAGUAUUGC CUUUAUUGCAAGGG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA | SEQ ID NO: 30 consists from 5' to 3' end: 5' UTR of SEQ ID NO: 3, ORF Sequence of SEQ ID NO: 2, and 3' UTR of SEQ ID NO: 4 |

| CONSTRUCT SEQUENCES |||||||
|---|---|---|---|---|---|
| | By "G-5" is meant that all uracils (U) in the mRNA are replaced by N1-methylpseudouracils. |
| | By "G6" is meant that all uracils (U) in the mRNA are replaced by 5-methoxyuracils. |
| mRNA Name | ORF Sequence (Amino Acid) | ORF Sequence (Nucleotide) | 5' UTR Sequence | 3' UTR Sequence | Construct Sequence |
| | GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AAGUCCUUAGGCAU GAUUUUCGAGAAGA GAAGUACUCGAACA AGAUUGUCUACAGA AACAGGCUUUGCAC UUCUGGGAGGACAU CCUUGUUUUCUUAC CACACAAGAUAUUC AUUUGGGUGUGAAC GAAAGUCUCACGGA CACGGCCCGUGUAU UGUCUAGCAUGGCA GACGCAGUAUUGGC UCGAGUGUAUAAAC AAUCAGAUUUGGAC ACCCUGGCUAAAGA AGCAUCCAUCCCAA UUAUCAACGGGCUG UCAGAUUUGUACCA UCCUAUCCAGAUCC UGGCUGAUUACCUC ACGCUCCAGGAACA CUAUAGCUCUCUGA AAGGUCUUACCCUC AGCUGGAUCGGGGA CGGGAACAAUAUCC UGCACUCCAUCAUG AUGAGCGCAGCGAA AUUCGGAAUGCACC UUCAGGCAGCUACU CCAAAGGGUUACGA GCCGGACGCUAGUG UAACCAAGUUGGCA GAGCAGUACGCCAA AGAGAACGGUACCA AGCUGUUGCUGACA AACGAUCCAUUGGA AGCAGCGCACGGAG GCAACGUAUUAAUU ACAGACACUUGGAU AAGCAUGGGACAAG AAGAGGAGAAGAA GAAGCGGCUCCAGG CUUUCCAAGGUUAC CAGGUUACAAUGAA GACUGCUAAAGUUG CUGCCUCUGACUGG ACAUUCUUACACUG CUUGCCCAGAAAGC CAGAAGAAGUGGAC GACGAAGUCUUUUA UUCUCCUCGAUCAC UAGUGUUCCCAGAG GCAGAGAACAGAAA GUGGACAAUCAUGG CUGUCAUGGUGUCC CUGCUGACAGAUUA CUCACCUCAGCUCC AGAAGCCUAAAUUU | | AACACU ACAGUG GUCUUU GAAUAA AGUCUG AGUGGG CGGC | |
| SEQ ID NO: | 1 | 5 | 3 | 4 | 31 |
| OTC-03 hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV | AUGCUGUUUAACCU GCGGAUCCUCCUGA ACAACGCCGCCUUU CGGAACGGCCACAA CUUCAUGGUGCGGA ACUUCAGGUGUGGU CAGCCUCUGCAGAA CAAGGUGCAGCUUA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC | SEQ ID NO: 31 consists from 5' to 3' end: 5' UTR of SEQ ID NO: 3, |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AAGGCAGAGAUCUG UUGACCCUGAAGAA CUUCACUGGCGAGG AGAUCAAGUACAUG CUCUGGCUGUCCGC AGACCUAAAGUUCC GCAUCAAGCAGAAG GGAGAGUACCUGCC ACUGCUGCAGGGCA AGAGCCUGGGCAUG AUUUUCGAGAAGAG AAGCACAAGGACCA GACUGUCUACAGAG ACAGGAUUUGCCCU GUUGGGAGGACAUC CCUGCUUCCUGACC ACCCAGGAUAUCCA UCUUGGCGUCAACG AGAGCCUGACCGAC ACCGCCAGAGUUCU CUCCAGCAUGGCCG ACGCUGUGCUGGCC CGGGUGUACAAACA AAGCGACCUGGAUA CCCUGGCAAAGGAG GCCAGUAUCCCCAU UAUCAACGGUCUGA GCGAUCUUUACCAU CCCAUACAGAUCCU GGCCGAUUACCUGA CCCUCCAGGAACAC UACAGCAGCCUCAA AGGGCUGACGCUCA GCUGGAUCGGCGAC GGAAACAACAUUCU UCACUCCAUCAUGA UGAGCGCUGCCAAG UUCGGGAUGCACCU GCAGGCCGCCACAC CCAAGGGCUACGAG CCCGACGCUUCGGU CACUAAGCUGGCCG AGCAGUACGCCAAG GAGAACGGCACAAA GCUGCUGCUGACCA ACGAUCCUCUGGAA GCCGCCCACGGCGG CAACGUGCUGAUCA CAGACACUUGGAUC AGCAUGGGCCAGGA GGAGGAGAAGAAG AAGAGACUGCAGGC UUUCCAGGGCUAUC AGGUGACCAUGAAG ACUGCCAAGGUGGC CGCGAGCGACUGGA CCUUCCUGCAUUGU CUGCCUAGAAAGCC CGAGGAGGUGGACG ACGAGGUGUUCUAC UCUCCCAGGUCCCU GGUGUUCCCAGAGG CCGAGAAUAGAAAG UGGACUAUUAUGGC CGUGAUGGUGUCUC UGCUCACCGAUUAU UCCCCUCAGCUGCA GAAGCCAAAGUUU | | UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | ORF Sequence of SEQ ID NO: 5, and 3' UTR of SEQ ID NO: 4 |

-continued

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 6 | 3 | 4 | 32 |
| OTC-04 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUUAACCU CAGGAUCCUGCUGA ACAACGCCGCAUUC AGAAACGGACACAA CUUUAUGGUGAGGA ACUUCCGGUGCGGA CAGCCUCUGCAGAA CAAGGUUCAACUGA AGGGCCGGGACCUG CUGACCCUCAAGAA CUUCACCGGCGAAG AGAUCAAAUACAUG CUCUGGCUGAGCGC CGACCUGAAGUUCA GAAUCAAACAGAAG GGAGAGUACUUGCC CCUGCUUCAGGGAA AGAGCCUCGGCAUG AUCUUUGAGAAGAG GAGCACCCGGACCC GGCUGAGCACCGAG ACGGGUUUUGCCCU CUUGGGCGGUCAUC CCUGCUUUCUCACC ACACAGGACAUCCA CCUGGGUGUGAACG AGAGCCUCACCGAC ACCGCAAGGGUGCU GAGCAGCAUGGCAG ACGCCGUGCUGGCU CGCGUGUAUAAGCA GUCCGAUCUCGAUA CCCUGGCCAAAGAG GCAAGCAUCCCUAU UAUCAACGGCCUGA GCGAUUUGUACCAU CCAAUCCAGAUCCU UGCCGACUAUCUGA CCCUGCAGGAGCAC UACAGCUCCCUGAA GGGGCUCACCCUGU CUUGGAUUGGGGAC GGUAACAAUAUUCU GCACAGCAUCAUGA UGAGUGCCGCCAAG UUCGGCAUGCACCU GCAGGCCGCCACCC CUAAGGGCUACGAG CCUGACGCCUCCGU GACCAAGCUGGCUG AACAGUACGCAAAG GAGAACGGAACCAA GCUUCUGCUCACCA ACGAUCCACUGGAG GCCGCCCACGGCGG CAACGUGCUGAUCA CAGACACCUGGAUU AGCAUGGGGCAGGA GGAGGAGAAGAAG AAGAGACUGCAGGC AUUUCAGGGAUACC AAGUUACCAUGAAG ACCGCCAAGGUGGC CGCUUCAGAUUGGA CAUUCCUGCAUUGC CUGCCACGGAAACC AGAGGAGGUCGACG ACGAGGUGUUCUAC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 32 consists from 5' to 3' end: 5' UTR of SEQ ID NO: 3, ORF Sequence of SEQ ID NO: 6, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCCCCAGAAGCCU CGUGUUCCCCGAGG CUGAGAACAGAAAG UGGACGAUCAUGGC CGUGAUGGUGAGUU UACUGACCGACUAU UCGCCCCAGCUCCA GAAACCAAAGUUC | | | |
| SEQ ID NO: | 1 | 7 | 3 | 4 | 33 |
| OTC-05 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGGAUCCUGCUGA ACAACGCCGCCUUC CGGAACGGCCACAA CUUCAUGGUGCGGA ACUUCCGGUGCGGC CAGCCCCUGCAGAA CAAGGUGCAGCUGA AGGGCCGGGACCUG CUGACCCUGAAGAA CUUCACCGGCGAGG AGAUCAAGUACAUG CUGUGGCUGAGCGC CGACCUGAAGUUCC GGAUCAAGCAGAAG GGCGAGUACCUGCC CCUGCUGCAGGGCA AGAGCCUGGGCAUG AUCUUCGAGAAGCG GAGCACCCGGACCC GGCUGAGCACCGAG ACUGGCUUCGCCCU GCUGGGCGGCCACC CCUGCUUCCUGACC ACCCAGGACAUCCA CCUGGGCGUGAACG AGAGCCUGACCGAC ACCGCCCGGGUGCU GAGCAGCAUGGCCG ACGCCGUGCUGGCC AGAGUGUACAAGCA GAGCGACCUGGACA CCCUGGCCAAGGAG GCCAGCAUCCCCAU CAUCAACGGCUUGA GUGACCUGUACCAC CCCAUCCAGAUCCU GGCCGACUACCUCA CCCUGCAGGAGCAC UACAGCAGCCUCAA GGGGCUGACACUCA GCUGGAUCGGCGAC GGCAACAACAUCCU GCACAGCAUCAUGA UGAGCGCUGCCAAG UUCGGCAUGCACCU GCAGGCCGCCACAC CCAAGGGCUACGAG CCCGACGCCAGCGU GACCAAGCUGGCCG AGCAGUACGCUAAG GAGAACGGCACAAA GCUGCUGCUGACAA ACGACCCACUGGAG GCCGCCCACGGCGG CAACGUGCUGAUCA CAGAUACUUGGAUC AGCAUGGGCCAGGA GGAGGAGAAGAAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 33 consists from 5' to 3' end: 5' UTR of SEQ ID NO: 3, ORF Sequence of SEQ ID NO: 7, and 3' UTR of SEQ ID NO:4 |

-continued

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AAGCGGCUGCAGGC GUUCCAGGGCUACC AGGUGACCAUGAAG ACCGCCAAGGUGGC CGCCAGCGACUGGA CCUUCCUGCACUGC CUGCCCCGGAAGCC CGAGGAGGUGGACG ACGAGGUGUUCUAC AGCCCUCGGAGCCU GGUGUUCCCCGAGG CCGAGAACCGGAAG UGGACCAUCAUGGC CGUGAUGGUGAGUC UGCUGACUGACUAC AGUCCUCAGCUGCA GAAGCCCAAGUUC | | | |

| SEQ ID NO: | 1 | 8 | 3 | 4 | 34 |
|---|---|---|---|---|---|
| OTC-06 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGGAUCCUGCUGA ACAACGCCGCCUUC CGGAACGGCCACAA CUUCAUGGUGCGGA ACUUCCGGUGCGGC CAGCCCCUGCAGAA CAAGGUGCAGCUGA AGGGCCGGGACCUG CUGACCCUGAAGAA CUUCACCGGCGAGG AGAUCAAGUACAUG CUGUGGCUGAGCGC CGACCUGAAGUUCC GGAUCAAGCAGAAG GGCGAGUACCUGCC CCUGCUGCAGGGCA AGAGCCUGGGCAUG AUCUUCGAGAAGCG GAGCACCCGGACCC GGCUGAGCACCGAA ACCGGCUUCGCCCU GCUGGGCGGCCACC CCUGCUUCCUGACC ACCCAGGACAUCCA CCUGGGCGUGAACG AGAGCCUGACCGAC ACCGCCCGGGUGCU GAGCAGCAUGGCCG ACGCCGUGCUGGCU AGGGUGUACAAGCA GAGCGACCUGGACA CCCUGGCCAAGGAG GCCAGCAUCCCCAU CAUCAACGGCCUGU CCGACUUGUACCAC CCCAUCCAGAUCCU GGCCGACUACCUGA CCCUUCAGGAGCAC UACAGCAGCCUGAA AGGUCUGACACUGA GCUGGAUCGGCGAC GGCAACAACAUCCU GCACAGCAUCAUGA UGAGCGCUGCCAAG UUCGGCAUGCACCU GCAGGCCGCCACGC CGAAGGGCUACGAG CCCGACGCCAGCGU GACCAAGCUGGCCG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 34 consists from 5' to 3' end: 5' UTR of SEQ ID NO: 3, ORF Sequence of SEQ ID NO: 8, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCAGUACGCCAAG GAGAACGGCACUAA GCUACUGCUCACCA ACGAUCCCCUGGAG GCCGCCCACGGCGG CAACGUGCUGAUCA CAGACACCUGGAUC AGCAUGGGCCAGGA GGAGGAGAAGAAG AAGCGGCUGCAGGC UUUCCAGGGCUACC AGGUGACCAUGAAG ACCGCCAAGGUGGC CGCCAGCGACUGGA CCUUCCUGCACUGC CUGCCCCGGAAGCC CGAGGAGGUGGACG ACGAGGUGUUCUAC AGCCCACGGAGCCU GGUGUUCCCCGAGG CCGAGAACCGGAAG UGGACCAUCAUGGC CGUGAUGGUGAGCC UCUUGACCGAUUAC UCACCCCAGCUGCA GAAGCCCAAGUUC | | | |

| SEQ ID NO: | 1 | 9 | 3 | 4 | 35 |
|---|---|---|---|---|---|
| OTC-07 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGGAUCCUGCUGA ACAACGCCGCCUUC CGGAACGGCCACAA CUUCAUGGUGCGGA ACUUCCGGUGCGGC CAGCCCCUCCAGAA CAAGGUCCAGCUCA AGGGCCGCGACCUC CUCACCCUCAAGAA CUUCACCGGCGAGG AGAUCAAGUACAUG CUCUGGCUCUCCGG CGACCUCAAGUUCC GCAUCAAGCAGAAG GGCGAGUACCUGCC CCUCCUCCAGGGCA AGUCCCUCGGCAUG AUCUUCGAGAAGCG CUCCACCCGCACCC GCCUCUCCACCGAA ACCGGCUUCGCCCU CCUCGGCGGCCACC CCUGCUUCCUCACC ACCCAGGACAUCCA CCUCGGCGUCAACG AGUCCCUCACCGAC ACCGCCCGCGUCCU CUCCUCCAUGGCCG ACGCCGUCCUGGCU AGAGUGUACAAGCA GUCCGACCUCGACA CCCUCGCCAAGGAG GCCUCCAUCCCCAU CAUCAACGGCCUCA GCGAUCUCUACCAC CCCAUCCAGAUCCU CGCCGACUACUUGA CCCUGCAGGAGCAC UACUCCUCCCUCAA GGGUUUAACGCUGU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 35 consists from 5' to 3' end: 5' UTR of SEQ ID NO: 3, ORF Sequence of SEQ ID NO: 9, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCUGGAUCGGCGAC GGCAACAACAUCCU CCACUCCAUCAUGA UGUCCGCCGCCAAG UUCGGCAUGCACCU CCAGGCCGCCACAC CAAAGGGCUACGAG CCCGACGCCUCCGU CACCAAGCUCGCCG AGCAGUACGCCAAA GAGAACGGCACGAA GCUGCUGCUGACUA ACGAUCCCCUCGAG GCCGCCCACGGCGG CAACGUCCUCAUCA CCGAUACCUGGAUC UCCAUGGGCCAGGA GGAGGAGAAGAAG AAGAGGCUGCAGGC CUUCCAGGGCUACC AGGUCACCAUGAAG ACCGCCAAGGUCGC CGCCUCCGACUGGA CCUUUCUCCACUGC CUGCCUCGCAAGCC CGAGGAGGUCGACG ACGAGGUCUUCUAC UCACCUCGCUCCCU CGUCUUCCCCGAGG CCGAGAACCGCAAG UGGACCAUCAUGGC CGUCAUGGUGUCUC UCCUAACUGACUAC AGUCCCCAGCUCCA GAAGCCCAAGUUC | | | |
| SEQ ID NO: | 1 | 10 | 3 | 4 | 36 |
| OTC-08 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GAGAAUCCUGCUGA ACAACGCCGCCUUC AGAAACGGCCACAA CUUCAUGGUUCGAA AUUUCGGUGUGGA CAACCACUACAGAA CAAAGUGCAGCUGA AGGGCAGAGACCUG CUGACCCUGAAGAA CUUCACCGGCGAGG AGAUCAAGUACAUG CUGUGGCUGAGCGC CGACCUGAAGUUCA GAAUCAAGCAGAAG GGCGAGUAUUUGCC UUUAUUGCAAGGGA AGUCCUUAGGCAUG AUCUUCGAGAAGAG AAGCACCAGAACCA GACUGAGCACCGAG ACCGGCUUCGCCCU GCUGGGCGGCCACC CCUGCUUCCUGACC ACCCAGGACAUCCA CCUGGGCGUGAACG AGAGCCUGACCGAC ACCGCCAGAGUGCU GAGCAGCAUGGCCG ACGCCGUGCUGGCC AGAGUGUACAAGCA GAGCGACCUGGACA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 36 consists from 5' to 3' end: 5' UTR of SEQ ID NO: 3, ORF Sequence of SEQ ID NO: 10, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCCUGGCCAAGGAG | | | |
| | | GCCAGCAUCCCCAU | | | |
| | | CAUCAACGGCCUGA | | | |
| | | GCGACCUGUACCAC | | | |
| | | CCCAUCCAGAUCCU | | | |
| | | GGCCGACUACCUGA | | | |
| | | CCCUGCAGGAGCAC | | | |
| | | UACAGCAGCCUGAA | | | |
| | | GGGCCUGACCCUGA | | | |
| | | GCUGGAUCGGCGAC | | | |
| | | GGCAACAACAUCCU | | | |
| | | GCACAGCAUCAUGA | | | |
| | | UGAGCGCCGCCAAG | | | |
| | | UUCGGCAUGCACCU | | | |
| | | GCAGGCCGCCACUC | | | |
| | | CCAAGGGCUACGAG | | | |
| | | CCCGACGCCAGCGU | | | |
| | | GACCAAGCUGGCCG | | | |
| | | AGCAGUACGCCAAG | | | |
| | | GAGAACGGCACCAA | | | |
| | | GCUGCUGCUGACAA | | | |
| | | ACGAUCCAUUGGAA | | | |
| | | GCAGCGCACGGAGG | | | |
| | | CAACGUGCUGAUCA | | | |
| | | CCGACACCUGGAUC | | | |
| | | AGCAUGGGCCAGGA | | | |
| | | GGAGGAGAAGAAG | | | |
| | | AAGAGACUGCAGGC | | | |
| | | CUUCCAGGGCUACC | | | |
| | | AGGUGACCAUGAAG | | | |
| | | ACCGCCAAGGUGGC | | | |
| | | CGCCAGCGACUGGA | | | |
| | | CCUUCCUGCACUGC | | | |
| | | CUGCCCAGAAAGCC | | | |
| | | CGAGGAGGUGGACG | | | |
| | | ACGAGGUGUUCUAC | | | |
| | | AGCCCCAGAAGCCU | | | |
| | | GGUGUUCCCCGAGG | | | |
| | | CCGAGAACAGAAAG | | | |
| | | UGGACCAUCAUGGC | | | |
| | | CGUGAUGGUGAGCC | | | |
| | | UGCUGACCGACUAC | | | |
| | | AGCCCUCAGCUGCA | | | |
| | | GAAGCCCAAGUUC | | | |
| SEQ ID NO: | 1 | 11 | 3 | 4 | 37 |
| OTC-09 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY | AUGCUGUUCAACCU GAGAAUCCUGA ACAACGCCGCCUUC AGAAACGGCCACAA CUUCAUGGUGAGAA ACUUCCGGUGCGGC CAGCCUCUGCAGAA CAAGGUGCAGCUGA AGGGCAGAGAUCUG CUGACCCUGAAGAA CUUCACCGGCGAGG AGAUCAAGUACAUG CUGUGGCUGAGCGC CGACCUGAAGUUCA GAAUCAAGCAGAAG GGCGAGUACCUGCC UCUGCUGCAGGGCA AGAGCCUGGGCAUG AUCUUCGAGAAGAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG | SEQ ID NO: 37 consists from 5' to 3' end: 5' UTR of SEQ ID NO: 3, ORF Sequence of SEQ ID NO: 11, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | QVTMKTAKVAASD WTFLHCLPRKPEEVD DEVFYSPRSLVFPEAE NRKWTIMAVMVSLL TDYSPQLQKPKF | AAGCACCAGAACCA GACUGAGCACCGAA ACCGGCUUCGCCCU GCUGGGCGGACACC CUUGCUUCCUGACC ACCCAGGACAUCCA CCUGGGCGUGAACG AGAGCCUGACCGAC ACCGCCAGAGUGCU GAGCAGCAUGGCUG ACGCCGUGCUGGCC AGAGUGUACAAGCA GUCCGACCUGGAUA CCCUGGCCAAGGAG GCCAGCAUCCCUAU CAUCAACGGCCUGA GCGACCUGUACCAC CCUAUCCAGAUCCU GGCCGACUACCUGA CCCUGCAGGAGCAC UACAGCAGCCUGAA GGGCCUGACGCUGA GCUGGAUCGGCGAC GGCAACAACAUCCU GCACAGCAUCAUGA UGAGCGCCGCCAAG UUCGGCAUGCACUU GCAAGCCGCCACCC CUAAGGGCUACGAG CCUGACGCCUCCGU GACCAAGCUCGCCG AGCAGUACGCCAAG GAGAACGGCACCAA GCUGCUGCUGACCA ACGACCCUCUGGAG GCCGCCCACGGCGG CAACGUGCUGAUCA CCGACACCUGGAUC AGCAUGGGCCAGGA GGAGGAGAAGAAG AAGAGACUGCAGGC CUUCCAGGGCUACC AGGUGACCAUGAAG ACCGCCAAGGUGGC CGCCAGCGACUGGA CCUUCCUGCACUGC CUGCCUAGAAAGCC UGAGGAGGUGGACG ACGAGGUGUUCUAC AGCCCUAGAAGCCU GGUGUUCCCUGAGG CCGAGAACAGAAAG UGGACCAUCAUGGC CGUGAUGGUGAGCC UGCUGACCGAUUAC AGCCCACAGCUGCA GAAGCCUAAGUUC | | GUCUUU GAAUAA AGUCUG AGUGGG CGGC | |
| SEQ ID NO: | 1 | 12 | 3 | 4 | 38 |
| OTC-10 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD | AUGCUGUUCAACCU GAGAAUCCUGCUGA ACAACGCCGCCUUC AGAAACGCCACAA CUUCAUGGUGAGA ACUUCAGGUGCGGC CAGCCUCUGCAGAA CAAGGUGCAGCUGA AGGGCCGCGAUCUG CUGACUCUGAAGAA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC | SEQ ID NO: 38 consists from 5' to 3' end: 5' UTR of SEQ ID NO: 3, ORF Sequence |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | CUUCACCGGCGAGG AGAUCAAGUACAUG CUCUGGCUGAGCGC AGACCUGAAAUUCA GAAUCAAGCAGAAG GGCGAGUACCUGCC CCUGCUCCAAGGCA AGAGCCUGGGCAUG AUCUUCGAGAAGAG AAGCACCAGAACCA GACUGAGCACCGAA ACCGGCUUCGCCCU GCUGGGAGGCCACC CUUGCUUCCUGACC ACCCAGGACAUCCA CCUCGGCGUGAACG AAUCCCUGACCGAU ACGGCCAGAGUCCU GAGCUCAAUGGCCG ACGCCGUCCUGGCG AGAGUGUACAAGCA GUCCGACCUCGACA CCCUGGCCAAAGAG GCCAGCAUCCCUAU CAUCAACGGCCUGA GCGACCUGUACCAC CCUAUCCAGAUUCU CGCUGACUAUCUGA CCCUGCAGGAGCAC UACUCCAGCCUAAA GGGCCUCACCCUUA GCUGGAUCGGCGAC GGCAACAACAUCCU GCACAGCAUCAUGA UGAGCGCCGCCAAG UUCGGCAUGCACCU CCAGGCCGCCACAC CGAAGGGGUACGAA CCGGACGCCAGCGU GACUAAGCUCGCCG AGCAGUACGCCAAG GAGAACGGCACCAA GCUGCUGCUGACCA ACGACCCUCUGGAG GCCGCUCACGGCGG CAACGUUCUGAUUA CCGACACCUGGAUC AGCAUGGGCCAGGA GGAGGAGAAGAAG AAGAGACUGCAGGC CUUCCAGGGCUACC AGGUGACUAUGAAG ACGGCCAAAGUGGC CGCCUCCGACUGGA CCUUCCUCCACUGC CUGCCUAGAAAGCC UGAGGAGGUGGACG ACGAGGUGUUCUAC AGCCCUAGAAGCCU GGUGUUCCCUGAGG CCGAGAACAGAAAG UGGACCAUCAUGGC CGUGAUGGUGUCCC UGCUCACCGAUUAC UCCCCUCAGCUCCA GAAGCCUAAGUUC | | CUCCUC CCCUUC CUGCAC CCGUAC CCCCUC CAUAAA GUAGGA AACACU ACAGUG GUCUUU GAAUAA AGUCUG AGUGGG CGGC | of SEQ ID NO: 12, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 13 | 3 | 4 | 39 |
| OTC-11 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GAGAAUCCUGCUGA ACAACGCCGCCUUC AGAAACGGCCACAA CUUCAUGGUGAGAA ACUUCAGGUGCGGC CAGCCUCUGCAGAA CAAGGUGCAGCUGA AGGGCAGAGAUCUG CUGACCCUGAAGAA CUUCACCGGCGAGG AGAUCAAGUACAUG CUGUGGCUGAGCGC CGACCUGAAGUUCA GAAUCAAGCAGAAG GGCGAGUACCUGCC UCUGCUGCAGGGCA AGAGCCUGGGCAUG AUCUUCGAGAAGAG AAGCACCAGAACCA GACUGAGCACCGAG ACGGGCUUCGCCCU GCUGGGCGGCCACC CUUGCUUCCUGACC ACCCAGGACAUCCA CCUGGGCGUGAACG AGAGCCUGACCGAC ACCGCCAGAGUGCU GAGCAGCAUGGCCG ACGCCGUGCUGGCU AGAGUGUACAAGCA GAGCGACCUGGACA CCCUGGCCAAGGAG GCCAGCAUCCCUAU CAUCAACGGCCUUA GUGAUCUGUACCAC CCUAUCCAGAUCCU GGCCGACUACCUAA CCCUGCAGGAGCAC UACAGCAGCCUGAA GGGUCUUACGCUGA GCUGGAUCGGCGAC GGCAACAACAUCCU GCACAGCAUCAUGA UGUCCGCCGCCAAG UUCGGCAUGCACCU GCAGGCCGCCACCC CUAAGGGCUACGAA CCAGACGCCAGCGU GACCAAGCUGGCCG AGCAGUACGCCAAG GAGAACGGCACCAA GCUUCUGCUUACCA ACGACCCUCUGGAG GCCGCCCACGGCGG CAACGUGCUGAUCA CGGACACCUGGAUC AGCAUGGGCCAGGA GGAGGAGAAGAAG AAGAGACUCCAAGC UUUCCAGGGCUACC AGGUGACCAUGAAG ACCGCCAAGGUGGC CGCCAGCGACUGGA CCUUCCUGCACUGC CUGCCUAGAAAGCC UGAGGAGGUGGACG ACGAGGUGUUCUAC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 39 consists from 5' to 3' end: 5' UTR of SEQ ID NO: 3, ORF Sequence of SEQ ID NO: 13, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCCCUAGAAGCCU GGUGUUCCCUGAGG CCGAGAACAGAAAG UGGACCAUCAUGGC CGUGAUGGUGUCCU UGCUUACAGACUAU AGUCCUCAGCUGCA GAAGCCUAAGUUC | | | |
| SEQ ID NO: | 1 | 14 | 3 | 4 | 40 |
| OTC-12 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGGAUCCUGCUGA ACAACGCCGCCUUC CGGAACGGCCACAA CUUCAUGGUGCGGA ACUUCCGGUGCGGC CAGCCCCUGCAGAA CAAGGUGCAGCUGA AGGGCCGGGACCUG CUGACCCUGAAGAA CUUCACCGGCGAGG AGAUCAAGUACAUG CUGUGGCUGAGCGC CGACCUGAAGUUCC GGAUCAAGCAGAAG GGCGAGUACCUGCC CCUGCUGCAGGGCA AGAGCCUGGGCAUG AUCUUCGAGAAGCG GAGCACCCGGACCC GGCUGAGCACCGAG ACCGGCUUCGCCCU GCUGGGCGGCCACC CCUGCUUCCUGACC ACCCAGGACAUCCA CCUGGGCGUGAACG AGAGCCUGACCGAC ACCGCCCGGGUGCU GAGCAGCAUGGCCG ACGCCGUGCUGGCC CGGGUGUACAAGCA GAGCGACCUGGACA CCCUGGCCAAGGAG GCCAGCAUCCCCAU CAUCAACGGCCUGA GCGACCUGUACCAC CCCAUCCAGAUCCU GGCCGACUACCUGA CCCUGCAGGAGCAC UACAGCAGCCUGAA GGGCCUGACCCUGA GCUGGAUCGGCGAC GGCAACAACAUCCU GCACAGCAUCAUGA UGAGCGCCGCCAAG UUCGGCAUGCACCU GCAGGCCGCCACGC CCAAGGGCUACGAG CCCGACGCCAGCGU GACCAAGCUGGCCG AGCAGUACGCCAAG GAGAACGGCACCAA GCUGCUGCUGACCA ACGACCCGCUGGAG GCCGCCCACGGCGG CAACGUGCUGAUCA CCGACACCUGGAUC AGCAUGGGCCAGGA GGAGGAGAAGAAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 40 consists from 5' to 3' end: 5' UTR of SEQ ID NO: 3, ORF Sequence of SEQ ID NO: 14, and 3' UTR of SEQ ID NO: 4 |

-continued

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AAGCGGCUGCAGGC CUUCCAGGGCUACC AGGUGACCAUGAAG ACCGCCAAGGUGGC CGCCAGCGACUGGA CCUUCCUGCACUGC CUGCCCCGGAAGCC CGAGGAGGUGGACG ACGAGGUGUUCUAC AGCCCACGGAGCCU GGUGUUCCCCGAGG CCGAGAACCGGAAG UGGACCAUCAUGGC CGUGAUGGUGAGCC UGCUGACCGACUAC AGCCCACAGCUGCA GAAGCCCAAGUUC | | | |

| SEQ ID NO: | 1 | 15 | 3 | 4 | 41 |
|---|---|---|---|---|---|
| OTC-13 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GAGGAUACUGCUGA ACAACGCCGCCUUC AGAAACGGCCAUAA CUUCAUGGUCCGGA ACUUCCGGUGCGGC CAGCCCCUCCAGAA UAAAGUGCAGCUGA AGGGCAGGGACCUG CUUACCCUGAAGAA CUUCACCGGCGAGG AGAUCAAGUACAUG CUGUGGCUCAGCGC CGACUUGAAGUUUA GGAUCAAGCAGAAG GGCGAGUACCUGCC CCUGCUGCAAGGCA AGAGCCUGGGCAUG AUUUUCGAGAAGAG AUCAACCCCGGACUA GGCUGAGCACGGAG ACUGGCUUCGCCCU GCUCGGCGGCCACC CCUGCUUCCUGACC ACCCAGGACAUCCA CCUGGGCGUGAACG AGUCCCUGACCGAC ACGGCCCGCGUCCU CAGCAGCAUGGCCG ACGCCGUCCUGGCC CGGGUGUACAAGCA GUCCGACCUGGACA CCCUGGCCAAGGAA GCCAGCAUCCCGAU CAUCAACGGCCUGA GCGAUCUGUACCAU CCCAUCCAGAUCCU CGCCGACUACCUGA CCCUCCAGGAGCAC UACAGCAGCCUGAA GGGGCUGACCCUGA GCUGGAUAGGCGAC GGCAAUAACAUCCU GCACUCGAUCAUGA UGAGCGCCGCGAAG UUCGGCAUGCACCU GCAGGCCGCCACCC CAAAGGGCUACGAA CCCGACGCCAGCGU GACCAAGCUGGCGG | GGGAAA UAAGAG AGAAAA GAAGAG UAAGAG GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 41 consists from 5' to 3' end: 5' UTR of SEQ ID NO: 3, ORF Sequence of SEQ ID NO: 15, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCAGUACGCCAAG GAGAACGGCACCAA GCUCCUGCUGACCA ACGACCCGCUGGAA GCCGCCCACGGCGG CAACGUGCUGAUCA CCGAUACGUGGAUC UCCAUGGGGCAGGA GGAGGAGAAGAAG AAGAGGCUCCAAGC CUUCCAGGGCUACC AAGUGACAAUGAAG ACCGCCAAGGUUGC CGCCAGCGACUGGA CCUUCCUCCACUGC CUGCCUCGGAAGCC CGAGGAGGUGGACG ACGAGGUGUUCUAC UCCCCUCGGAGCCU GGUGUUCCCCGAGG CCGAGAAUAGGAAG UGGACCAUCAUGGC CGUGAUGGUGAGUC UGCUGACGGAUUAC AGCCCGCAGCUCCA GAAGCCCAAGUUC | | | |

| SEQ ID NO: | 1 | 16 | 3 | 4 | 42 |
|---|---|---|---|---|---|
| OTC-14 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGCAUCCUGCUGA ACAACGCCGCCUUC CGGAACGGCCACAA CUUCAUGGUGCGGA ACUUCCGGUGCGGC CAGCCCCUGCAGAA CAAAGUCCAGCUCA AAGGCAGGGACCUC CUCACCCUGAAGAA CUUCACCGGCGAGG AGAUCAAGUACAUG CUCUGGCUGUCCGA CGACCUGAAGUUCC GCAUCAAGCAGAAG GGCGAGUACCUGCC CCUGCUGCAGGGCA AGAGCCUGGGCAUG AUCUUCGAGAAGAG AUCCACCCGCACUA GGCUGUCAACCGAG ACUGGCUUUGCCCU GCUGGGCGGCCACC CCUGCUUCCUCACC ACCCAGGACAUUCA CCUGGGUGUGAACG AGAGCCUGACCGAU ACGGCCAGAGUCCU GUCGUCCAUGGCCG ACGCCGUGCUCGCC AGAGUGUAUAAACA GUCAGACCUGGACA CGCUGGCCAAGGAG GCCAGUAUUCCAAU CAUCAACGGCCUGA GCGACCUGUAUCAU CCCAUCCAGAUCCU GGCCGACUACCUGA CCCUGCAGGAACAC UACUCUAGCCUGAA GGGUCUGACACUGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 42 consists from 5' to 3' end: 5' UTR of SEQ ID NO: 3, ORF Sequence of SEQ ID NO: 16, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GCUGGAUCGGCGAC GGGAAUAACAUCCU GCACAGCAUCAUGA UGAGCGCCGCCAAG UUUGGGAUGCACCU CCAGGCCGCCACAC CUAAGGGCUACGAG CCCGACGCCAGCGU GACCAAGCUCGCCG AGCAGUACGCAAAG GAGAACGGCACCAA GCUGCUCCUGACCA ACGACCCUCUGGAA GCCGCCCACGGAGG CAACGUGCUGAUCA CCGACACCUGGAUC AGCAUGGGUCAGGA AGAGGAGAAGAAG AAGCGGCUGCAAGC CUUCCAGGGAUACC AGGUGACUAUGAAG ACCGCCAAGGUGGC GGCCUCCGACUGGA CCUUCCUCCAUUGC CUCCCCAGGAAGCC UGAGGAGGUGGACG ACGAGGUGUUCUAU UCACCCCGUUCCCU GGUGUUCCCCGAGG CCGAGAACCGAAAG UGGACCAUCAUGGC CGUGAUGGUGAGCC UGCUCACCGACUAC AGCCCUCAACUGCA GAAGCCCAAGUUC | | | |

| SEQ ID NO: | 1 | 17 | 3 | 4 | 43 |
|---|---|---|---|---|---|
| OTC-15 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGGAUCCUGCUGA ACAACGCCGCCUUC CGGAACGGCCACAA CUUCAUGGUGCGGA ACUUCCGGUGCGGC CAGCCCCUGCAGAA CAAGGUGCAGCUGA AGGGCCGGGACCUG CUGACCCUGAAGAA CUUCACCGGCGAGG AGAUCAAGUACAUG CUGUGGCUGAGCGC CGACCUGAAGUUCC GGAUCAAGCAGAAG GGCGAGUACCUGCC CCUGCUGCAGGGCA AGAGCCUGGGCAUG AUCUUCGAGAAGCG GAGCACCCGGACCC GGCUGAGCACCGAG ACGGGCUUCGCCCU GCUGGGCGGCCACC CCUGCUUCCUGACC ACCCAGGACAUCCA CCUGGGCGUGAACG AGAGCCUGACCGAC ACCGCCCGGGUGCU GAGCAGCAUGGCCG ACGCCGUGCUGGCC AGGGUGUACAAGCA GAGCGACCUGGACA | GGGAAA UAAGAG AGAAAA GAAGAC UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 43 consists from 5' to 3' end: 5' UTR of SEQ ID NO: 3, ORF Sequence of SEQ ID NO: 17, and 3' UTR of SEQ ID NO: 4 |

-continued

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCCUGGCCAAGGAG GCCAGCAUCCCCAU CAUCAACGGCCUUA GCGAUCUGUACCAC CCCAUCCAGAUCCU GGCCGACUACCUGA CCCUCCAGGAGCAC UACAGCAGCCUGAA AGGCCUGACGCUGA GCUGGAUCGGCGAC GGCAACAACAUCCU GCACAGCAUCAUGA UGAGCGCAGCCAAG UUCGGCAUGCACCU GCAGGCCGCCACCC CGAAGGGCUACGAG CCCGACGCCAGCGU GACCAAGCUGGCCG AGCAGUACGCCAAG GAGAACGGCACGAA GCUCCUGCUCACGA ACGAUCCCCUGGAG GCCGCCCACGGCGG CAACGUGCUGAUCA CCGAUACCUGGAUC AGCAUGGGCCAGGA GGAGGAGAAGAAG AAGCGGCUCCAGGC CUUCCAGGGCUACC AGGUGACCAUGAAG ACCGCCAAGGUGGC CGCCAGCGACUGGA CCUUCCUGCACUGC CUGCCCCGGAAGCC CGAGGAGGUGGACG ACGAGGUGUUCUAC AGCCCUCGGAGCCU GGUGUUCCCCGAGG CCGAGAACCGGAAG UGGACCAUCAUGGC CGUGAUGGUGAGCC UCCUGACGGAUUAC UCACCCCAGCUGCA GAAGCCCAAGUUC | | | |
| SEQ ID NO: | 1 | 18 | 3 | 4 | 44 |
| OTC-16 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD | AUGCUGUUCAACCU GCGGAUCCUGCUGA ACAACGCCGCCUUC CGGAACGGCCACAA CUUCAUGGUGCGGA ACUUCCGGUGCGGC CAGCCCCUGCAGAA CAAGGUGCAGCUGA AGGGCCGGGACCUG CUGACCCUGAAGAA CUUCACCGGCGAGG AGAUCAAGUACAUG CUGUGGCUGAGCGC CGACCUGAAGUUCC GGAUCAAGCAGAAG GGCGAGUACCUGCC CCUGCUGCAGGGCA AGAGCCUGGGCAUG AUCUUCGAGAAGCG GAGCACCCGGACCC | GGGAAA UAAGAG AGAAAA GAAGAG GAAUAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU | SEQ ID NO: 44 consists from 5' to 3' end: 5' UTR of SEQ ID NO: 3, ORF Sequence of SEQ ID NO: 18, and 3' UTR of SEQ ID NO: 4 |

-continued

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | WTFLHCLPRKPEEVD DEVFYSPRSLVFPEAE NRKWTIMAVMVSLL TDYSPQLQKPKF | GGCUGAGCACCGAA ACCGGCUUCGCCCU GCUGGGCGGCCACC CCUGCUUCCUGACC ACCCAGGACAUCCA CCUGGGCGUGAACG AGAGCCUGACCGAC ACCGCCCGGGUGCU GAGCAGCAUGGCCG ACGCCGUGCUGGCC CGCGUGUACAAGCA GAGCGACCUGGACA CCCUGGCCAAGGAG GCCAGCAUCCCCAU CAUCAACGGCCUGU CCGACCUGUACCAC CCCAUCCAGAUCCU GGCCGACUACCUGA CCCUCCAGGAGCAC UACAGCAGCCUGAA GGGGCUGACCCUCA GCUGGAUCGGCGAC GGCAACAACAUCCU GCACAGCAUCAUGA UGAGCGCGGCCAAG UUCGGCAUGCACCU GCAGGCCGCCACGC CCAAGGGCUACGAG CCCGACGCCAGCGU GACCAAGCUGGCCG AGCAGUACGCCAAG GAGAACGGCACCAA ACUGCUACUGACCA ACGACCCGCUGGAG GCCGCCCACGGCGG CAACGUGCUGAUCA CCGAUACCUGGAUC AGCAUGGGCCAGGA GGAGGAGAAGAAG AAGCGGCUGCAAGC UUUCCAGGGCUACC AGGUGACCAUGAAG ACCGCCAAGGUGGC CGCCAGCGACUGGA CCUUCCUGCACUGC CUGCCCCGGAAGCC CGAGGAGGUGGACG ACGAGGUGUUCUAC AGCCCGCGGAGCCU GGUGUUCCCCGAGG CCGAGAACCGGAAG UGGACCAUCAUGGC CGUGAUGGUGAGCC UGCUCACCGACUAC AGCCCUCAGCUGCA GAAGCCCAAGUUC | | GAAUAA AGUCUG AGUGGG CGGC | |
| SEQ ID NO: | 1 | 19 | 3 | 4 | 45 |
| OTC-17 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL | AUGCUGUUCAACCU GCGGAUCCUGCUGA ACAACGCCGCCUUC CGGAACGGCCACAA CUUCAUGGUGCGGA ACUUCCGGUGCGGC CAGCCCCUCCAGAA CAAGGUCCAGCUCA AGGGCCGCGACCUC CUCACCCUCAAGAA CUUCACCGGCGAGG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC | SEQ ID NO: 45 consists from 5' to 3' end: 5' UTR of SEQ ID NO: 3, ORF Sequence of SEQ ID |

| | | CONSTRUCT SEQUENCES | | | |
|---|---|---|---|---|---|
| | By "G-5" is meant that all uracils (U) in the mRNA are replaced by N1-methylpseudouracils. | | | | |
| | By "G6" is meant that all uracils (U) in the mRNA are replaced by 5-methoxyuracils. | | | | |
| mRNA Name | ORF Sequence (Amino Acid) | ORF Sequence (Nucleotide) | 5' UTR Sequence | 3' UTR Sequence | Construct Sequence |
| | YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AGAUCAAGUACAUG CUCUGGCUCUCCGC CGACCUCAAGUUCC GCAUCAAGCAGAAG GGCGAGUACCUGCC CCUCCUCCAGGGCA AGUCCCUCGGCAUG AUCUUCGAGAAGCG CUCCACCCGCACCC GCCUCUCCACCGAG ACUGGCUUCGCCCU CCUCGGCGGCCACC CCUGCUUCCUCACC ACCCAGGACAUCCA CCUCGGCGUCAACG AGUCCCUCACCGAC ACCGCCCGCGUCCU CUCCUCCAUGGCCG ACGCCGUCCUGGCC AGGGUGUACAAGCA GUCCGACCUCGACA CCCUCGCCAAGGAG GCCUCCAUCCCCAU CAUCAACGGCCUCU CCGAUCUGUACCAC CCCAUCCAGAUCCU CGCCGACUACCUGA CUCUGCAGGAGCAC UACUCCUCCCUGAA GGGCCUGACCCUGU CCUGGAUCGGCGAC GGCAACAACAUCCU CCACUCCAUCAUGA UGUCCGCCGCCAAG UUCGGCAUGCACCU CCAGGCCGCCACGC CCAAGGGCUACGAG CCCGACGCCUCCGU CACCAAGCUCGCCG AGCAGUACGCUAAG GAGAACGGCACGAA GCUGCUCCUGACCA ACGACCCGCUCGAG GCCGCCCACGGCGG CAACGUCCUCAUUA CCGAUACCUGGAUC UCCAUGGGCCAGGA GGAGGAGAAGAAG AAGAGGUUGCAGGC CUUCCAGGGCUACC AGGUCACCAUGAAG ACCGCCAAGGUCGC CGCCUCCGACUGGA CCUUCCUGCACUGC CUGCCGCGCAAGCC CGAGGAGGUCGACG ACGAGGUCUUCUAC AGCCCACGCUCCCU CGUCUUCCCCGAGG CCGAGAACCGCAAG UGGACCAUCAUGGC CGUCAUGGUCAGCC UGCUGACCGAUUAC UCCCCGCAGCUCCA GAAGCCCAAGUUC | | CCCUUC CUGCAC CCGUAC CCCCUC CAUAAA GUAGGA AACACU ACAGUG GUCUUU GAAUAA AGUCUG AGUGGG CGGC | NO: 19, and 3' UTR of SEQ ID NO: 4 |

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 20 | 3 | 4 | 46 |
| OTC-18 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GAGAAUCCUGCUGA ACAACGCCGCCUUC AGAAACGGCCACAA CUUCAUGGUUCGAA AUUUUCGGUGUGGA CAACCACUACAGAA CAAAGUGCAGCUGA AGGGCAGAGACCUG CUGACCCUGAAGAA CUUCACCGGCGAGG AGAUCAAGUACAUG CUGUGGCUGAGCGC CGACCUGAAGUUCA GAAUCAAGCAGAAG GGCGAGUAUUUGCC UUUAUUGCAAGGGA AGUCCUUAGGCAUG AUCUUCGAGAAGAG AAGCACCAGAACCA GACUGAGCACCGAG ACCGGCUUCGCCCU GCUGGGCGGCCACC CCUGCUUCCUGACC ACCCAGGACAUCCA CCUGGGCGUGAACG AGAGCCUGACCGAC ACCGCCAGAGUGCU GAGCAGCAUGGCCG ACGCCGUGCUGGCC AGAGUGUACAAGCA GAGCGACCUGGACA CCCUGGCCAAGGAG GCCAGCAUCCCCAU CAUCAACGGCCUGA GCGACCUGUACCAC CCCAUCCAGAUCCU GGCCGACUACCUGA CCCUGCAGGAGCAC UACAGCAGCCUGAA GGGCCUGACCCUGA GCUGGAUCGGCGAC GGCAACAACAUCCU GCACAGCAUCAUGA UGAGCGCCGCCAAG UUCGGCAUGCACCU GCAGGCCGCCACUC CCAAGGGCUACGAG CCCGACGCCAGCGU GACCAAGCUGGCCG AGCAGUACGCCAAG GAGAACGGCACCAA GCUGCUGCUGACAA ACGAUCCAUUGGAA GCAGCGCACGGAGG CAACGUGCUGAUCA CCGACACCUGGAUC AGCAUGGGCCAGGA GGAGGAGAAGAAG AAGAGACUGCAGGC CUUCCAGGGCUACC AGGUGACCAUGAAG ACCGCCAAGGUGGC CGCCAGCGACUGGA CCUUCCUGCACUGC CUGCCCAGAAAGCC CGAGGAGGUGGACG ACGAGGUGUUCUAC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 46 consists from 5' to 3' end: 5' UTR of SEQ ID NO: 3, ORF Sequence of SEQ ID NO: 20, and 3' UTR of SEQ ID NO: 4 |

| | CONSTRUCT SEQUENCES | | | | |
|---|---|---|---|---|---|
| | By "G-5" is meant that all uracils (U) in the mRNA are replaced by N1-methylpseudouracils. | | | | |
| | By "G6" is meant that all uracils (U) in the mRNA are replaced by 5-methoxyuracils. | | | | |
| mRNA Name | ORF Sequence (Amino Acid) | ORF Sequence (Nucleotide) | 5' UTR Sequence | 3' UTR Sequence | Construct Sequence |
| | | AGCCCCAGAAGCCU GGUGUUCCCCGAGG CCGAGAACAGAAAG UGGACCAUCAUGGC CGUGAUGGUGAGCC UGCUGACCGACUAC AGCCCUCAGCUGCA GAAGCCCAAGUUC | | | |
| SEQ ID NO: | 1 | 21 | 3 | 4 | 47 |
| OTC-19 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GAGAAUCUGCGGA ACAACGCCGCCUUC AGAAACGGCCACAA CUUCAUGGUGAGAA ACUUCCGGUGCGGC CAGCCUCUGCAGAA CAAGGUGCAGCUGA AGGGCAGAGAUCUG CUGACCCUGAAGAA CUUCACCGGCGAGG AGAUCAAGUACAUG CUGUGGCUGAGCGC CGACCUGAAGUUCA GAAUCAAGCAGAAG GGCGAGUACCUGCC UCUGCUGCAGGGCA AGAGCCUGGGCAUG AUCUUCGAGAAGAG AAGCACCAGAACCA GACUGAGCACCGAA ACCGGCUUCGCCCU GCUGGGCGGACACC CUUGCUUCCUGACC ACCCAGGACAUCCA CCUGGGCGUGAACG AGAGCCUGACCGAC ACCGCCAGAGUGCU GAGCAGCAUGGCUG ACGCCGUGCUGGCC AGAGUGUACAAGCA GUCCGACCUGGAUA CCCUGGCCAAGGAG GCCAGCAUCCCUAU CAUCAACGGCCUGA GCGACCUGUACCAC CCUAUCCAGAUCCU GGCCGACUACCUGA CCCUGCAGGAGCAC UACAGCAGCCUGAA GGGCCUGACGCUGA GCUGGAUCGGCGAC GGCAACAACAUCCU GCACAGCAUCAUGA UGAGCGCCGCCAAG UUCGGCAUGCACUU GCAAGCCGCCACCC CUAAGGGCUACGAG CCUGACGCCUCCGU GACCAAGCUCGCCG AGCAGUACGCCAAG GAGAACGGCACCAA GCUGCUGCUGACCA ACGACCCUCUGGAG GCCGCCCACGGCGG CAACGUGCUGAUCA CCGACACCUGGAUC AGCAUGGGCCAGGA GGAGGAGAAGAAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 47 consists from 5' to 3' end: 5' UTR of SEQ ID NO: 3, ORF Sequence of SEQ ID NO: 21, and 3' UTR of SEQ ID NO: 4 |

-continued

| | | | | | |
|---|---|---|---|---|---|
| | | CONSTRUCT SEQUENCES | | | |
| | | By "G-5" is meant that all uracils (U) in the mRNA are replaced by N1-methylpseudouracils. | | | |
| | | By "G6" is meant that all uracils (U) in the mRNA are replaced by 5-methoxyuracils. | | | |
| mRNA Name | ORF Sequence (Amino Acid) | ORF Sequence (Nucleotide) | 5' UTR Sequence | 3' UTR Sequence | Construct Sequence |
| | | AAGAGACUGCAGGC CUUCCAGGGCUACC AGGUGACCAUGAAG ACCGCCAAGGUGGC CGCCAGCGACUGGA CCUUCCUGCACUGC CUGCCUAGAAAGCC UGAGGAGGUGGACG ACGAGGUGUUCUAC AGCCCUAGAAGCCU GGUGUUCCCUGAGG CCGAGAACAGAAAG UGGACCAUCAUGGC CGUGAUGGUGAGCC UGCUGACCGAUUAC AGCCCACAGCUGCA GAAGCCUAAGUUC | | | |
| SEQ ID NO: | 1 | 22 | 3 | 4 | 48 |
| OTC-20 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GAGAAUCCUGCUGA ACAACGCCGCCUUC AGAAACGGCCACAA CUUCAUGGUGAGA ACUUCAGGUGCGGC CAGCCUCUGCAGAA CAAGGUGCAGCUGA AGGGCCGCGAUCUG CUGACUCUGAAGAA CUUCACCGGCGAGG AGAUCAAGUACAUG CUCUGGCUGAGCGC AGACCUGAAAUUCA GAAUCAAGCAGAAG GGCGAGUACCUGCC CCUGCUCCAAGGCA AGAGCCUGGGCAUG AUCUUCGAGAAGAG AAGCACCAGAACCA GACUGAGCACCGAA ACCGGCUUCGCCCU GCUGGGAGGCCACC CUUGCUUCCUGACC ACCCAGGACAUCCA CCUCGGCGUGAACG AAUCCCUGACCGAU ACGGCCAGAGUCCU GAGCUCAAUGGCCG ACGCCGUCCUGGCG AGAGUGUACAAGCA GUCCGACCUCGACA CCCUGGCCAAAGAG GCCAGCAUCCCUAU CAUCAACGGCCUGA GCGACCUGUACCAC CCUAUCCAGAUUCU CGCUGACUAUCUGA CCCUGCAGGAGCAC UACUCCAGCCUAAA GGGCCUCACCCUUA GCUGGAUCGGCGAC GGCAACAACAUCCU GCACAGCAUCAUGA UGAGCGCCGCCAAG UUCGGCAUGCACCU CCAGGCCGCCACAC CGAAGGGGUACGAA CCGGACGCCAGCGU GACUAAGCUCGCCG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 48 consists from 5' to 3' end: 5' UTR of SEQ ID NO: 3, ORF Sequence of SEQ ID NO: 22, and 3' UTR of SEQ ID NO: 4 |

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCAGUACGCCAAG GAGAACGGCACCAA GCUGCUGCUGACCA ACGACCCUCUGGAG GCCGCUCACGGCGG CAACGUUCUGAUUA CCGACACCUGGAUC AGCAUGGGCCAGGA GGAGGAGAAGAAG AAGAGACUGCAGGC CUUCCAGGGCUACC AGGUGACUAUGAAG ACGGCCAAAGUGGC CGCCUCCGACUGGA CCUUCCUCCACUGC CUGCCUAGAAAGCC UGAGGAGGUGGACG ACGAGGUGUUCUAC AGCCCUAGAAGCCU GGUGUUCCCUGAGG CCGAGAACAGAAAG UGGACCAUCAUGGC CGUGAUGGUGUCCC UGCUCACCGAUUAC UCCCCUCAGCUCCA GAAGCCUAAGUUC | | | |

| SEQ ID NO: | | 1 | 23 | 3 | 4 | 49 |
|---|---|---|---|---|---|---|
| | OTC-21 (hOTC: G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPPEAE NRKWTIMAVMVSLL TDYSPQLQKPKF | AUGCUGUUCAACCU GAGAAUCCUGCUGA ACAACGCCGCCUUC AGAAACGGCCACAA CUUCAUGGUGAGAA ACUUCAGGUGCGGC CAGCCUCUGCAGAA CAAGGUGCAGCUGA AGGGCAGAGAUCUG CUGACCCUGAAGAA CUUCACCGGCGAGG AGAUCAAGUACAUG CUGUGGCUGAGCGC CGACCUGAAGUUCA GAAUCAAGCAGAAG GGCGAGUACCUGCC UCUGCUGCAGGGCA AGAGCCUGGGCAUG AUCUUCGAGAAGAG AAGCACCAGAACCA GACUGAGCACCGAG ACGGGCUUCGCCCU GCUGGGCGGCCACC CUUGCUUCCUGACC ACCCAGGACAUCCA CCUGGGCGUGAACG AGAGCCUGACCGAC ACCGCCAGAGUGCU GAGCAGCAUGGCCG ACGCCGUGCUGGCU AGAGUGUACAAGCA GAGCGACCUGGACA CCCUGGCCAAGGAG GCCAGCAUCCCUAU CAUCAACGGCCUUA GUGAUCUGUACCAC CCUAUCCAGAUCCU GGCCGACUACCUAA CCCUGCAGGAGCAC UACAGCAGCCUGAA GGGUCUUACGCUGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 49 consists from 5' to 3' end: 5' UTR of SEQ ID NO: 3, ORF Sequence of SEQ ID NO: 23, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GCUGGAUCGGCGAC GGCAACAACAUCCU GCACAGCAUCAUGA UGUCCGCCGCCAAG UUCGGCAUGCACCU GCAGGCCGCCACCC CUAAGGGCUACGAA CCAGACGCCAGCGU GACCAAGCUGGCCG AGCAGUACGCCAAG GAGAACGGCACCAA GCUUCUGCUUACCA ACGACCCUCUGGAG GCCGCCCACGGCGG CAACGUGCUGAUCA CGGACACCUGGAUC AGCAUGGGCCAGGA GGAGGAGAAGAAG AAGAGACUCCAAGC UUUCCAGGGCUACC AGGUGACCAUGAAG ACCGCCAAGGUGGC CGCCAGCGACUGGA CCUUCCUGCACUGC CUGCCUAGAAAGCC UGAGGAGGUGGACG ACGAGGUGUUCUAC AGCCCUAGAAGCCU GGUGUUCCCUGAGG CCGAGAACAGAAAG UGGACCAUCAUGGC CGUGAUGGUGUCCU UGCUUACAGACUAU AGUCCUCAGCUGCA GAAGCCUAAGUUC | | | |

| SEQ ID NO: | 1 | 24 | 3 | 4 | 50 |
|---|---|---|---|---|---|
| OTC-22 (hOTC; G6) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGGAUCCUGCUGA ACAACGCCGCCUUC CGGAACGGCCACAA CUUCAUGGUGCGGA ACUUCCGGUGCGGC CAGCCCCUGCAGAA CAAGGUGCAGCUGA AGGGCCGGGACCUG CUGACCCUGAAGAA CUUCACCGGCGAGG AGAUCAAGUACAUG CUGUGGCUGAGCGC CGACCUGAAGUUCC GGAUCAAGCAGAAG GGCGAGUACCUGCC CCUGCUGCAGGGCA AGAGCCUGGGCAUG AUCUUCGAGAAGCG GAGCACCCGGACCC GGCUGAGCACCGAG ACCGGCUUCGCCCU GCUGGGCGGCCACC CCUGCUUCCUGACC ACCCAGGACAUCCA CCUGGGCGUGAACG AGAGCCUGACCGAC ACCGCCCGGGUGCU GAGCAGCAUGGCCG ACGCCGUGCUGGCC CGGGUGUACAAGCA GAGCGACCUGGACA | GGGAAA UAAGAG AGAAAA GAAGAG UCGGUG UAAGAA GAAAUA UAAGAG CCACC | UGAUAA UAGGCU GGAGCC UCGGUG CCUUCU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 50 consists from 5' to 3' end: 5' UTR of SEQ ID NO: 3, ORF Sequence of SEQ ID NO: 24, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCCUGGCCAAGGAG GCCAGCAUCCCCAU CAUCAACGGCCUGA GCGACCUGUACCAC CCCAUCCAGAUCCU GGCCGACUACCUGA CCCUGCAGGAGCAC UACAGCAGCCUGAA GGGCCUGACCCUGA GCUGGAUCGGCGAC GGCAACAACAUCCU GCACAGCAUCAUGA UGAGCGCCGCCAAG UUCGGCAUGCACCU GCAGGCCGCCACGC CCAAGGGCUACGAG CCCGACGCCAGCGU GACCAAGCUGGCCG AGCAGUACGCCAAG GAGAACGGCACCAA GCUGCUGCUGACCA ACGACCCGCUGGAG GCCGCCCACGGCGG CAACGUGCUGAUCA CCGACACCUGGAUC AGCAUGGGCCAGGA GGAGGAGAAGAAG AAGCGGCUGCAGGC CUUCCAGGGCUACC AGGUGACCAUGAAG ACCGCCAAGGUGGC CGCCAGCGACUGGA CCUUCCUGCACUGC CUGCCCCGGAAGCC CGAGGAGGUGGACG ACGAGGUGUUCUAC AGCCCACGGAGCCU GGUGUUCCCCGAGG CCGAGAACCGGAAG UGGACCAUCAUGGC CGUGAUGGUGAGCC UGCUGACCGACUAC AGCCCACAGCUGCA GAAGCCCAAGUUC | | | |
| SEQ ID NO: | 1 | 25 | 3 | 4 | 51 |
| OTC-02-001 (hOTC; G5) Cap: C1 PolyA tail: 100 nt | MVFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD | AUGGUGUUCAACCU GAGAAUCCUGCUGA ACAACGCCGCCUUC AGAAACGGCCACAA CUUCAUGGUGAGAA ACUUCAGGUGCGGC CAGCCUCUGCAGAA CAAGGUGCAGCUGA AGGGCCGCGAUCUG CUGACUCUGAAGAA CUUCACCGGCGAGG AGAUCAAGUACAUG CUCUGGCUGAGCGC AGACCUGAAAUUCA GGCGAGUACCUGCC CCUGCUCCAAGGCA AGAGCCUGGGCAUG AUCUUCGAGAAGAG AAGCACCAGAACCA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU | SEQ ID NO: 51 consists from 5' to 3' end: 5' UTR of SEQ ID NO: 3, ORF Sequence of SEQ ID NO: 25, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | WTFLHCLPRKPEEVD DEVFYSPRSLVFPEAE NRKWTIMAVMVSLL TDYSPQLQKPKF | GACUGAGCACCGAA ACCGGCUUCGCCCU GCUGGGAGGCCACC CUUGCUUCCUGACC ACCCAGGACAUCCA CCUCGGCGUGAACG AAUCCCUGACCGAU ACGGCCAGAGUCCU GAGCUCAAUGGCCG ACGCCGUCCUGGCG AGAGUGUACAAGCA GUCCGACCUCGACA CCCUGGCCAAAGAG GCCAGCAUCCCUAU CAUCAACGGCCUGA GCGACCUGUACCAC CCUAUCCAGAUUCU CGCUGACUAUCUGA CCCUGCAGGAGCAC UACUCCAGCCUAAA GGGCCUCACCCUUA GCUGGAUCGGCGAC GGCAACAACAUCCU GCACAGCAUCAUGA UGAGCGCCGCCAAG UUCGGCAUGCACCU CCAGGCCGCCACAC CGAAGGGGUACGAA CCGGACGCCAGCGU GACUAAGCUCGCCG AGCAGUACGCCAAG GAGAACGGCACCAA GCUGCUGCUGACCA ACGACCCUCUGGAG GCCGCUCACGGCGG CAACGUUCUGAUUA CCGACACCUGGAUC AGCAUGGGCCAGGA GGAGGAGAAGAAG AAGAGACUGCAGGC CUUCCAGGGCUACC AGGUGACUAUGAAG ACGGCCAAAGUGGC CGCCUCCGACUGGA CCUUCCUCCACUGC CUGCCUAGAAAGCC UGAGGAGGUGGACG ACGAGGUGUUCUAC AGCCCUAGAAGCCU GGUGUUCCCUGAGG CCGAGAACAGAAAG UGGACCAUCAUGGC CGUGAUGGUGUCCC UGCUCACCGAUUAC UCCCCUCAGCUCCA GAAGCCUAAGUUC | | GAAUAA AGUCUG AGUGGG CGGC | |
| SEQ ID NO: | 1 | 26 | 3 | 4 | 52 |
| OTC-03-001 (hOTC; G5) Cap: C1 PolyA tail: 100 nt | MLSNLRILLNNAALR KGHTSVVRHFWCGK PVQNKVQLKGRDLL TLKNFTGEEIKYMLW LSADLKFRIKQKGEY LPLLQGKSLGMIFEK RSTRTRLSTETGFALL GGHPCFLTTQDIHLG VNESLTDTARVLSSM ADAVLARVYKQSDL DTLAKEASIPIINGLS | AUGCUGAGCAACCU GAGAAUCCUGCUGA ACAACGCCCUCUG AGAAAGGGACAUAC CUCCGUGGUGAGAC ACUUCUGGUGCGGA AAGCCCGUGCAGAA CAAGGUGCAGCUGA AGGGCCGCAUCUG CUGACUCUGAAGAA CUUCACCGGCGAGG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC | SEQ ID NO: 52 consists from 5' to 3' end: 5' UTR of SEQ ID NO: 3, ORF Sequence of SEQ ID |

| CONSTRUCT SEQUENCES |||||| 
|||||||
| | By "G-5" is meant that all uracils (U) in the mRNA are replaced by N1-methylpseudouracils. |
| | By "G6" is meant that all uracils (U) in the mRNA are replaced by 5-methoxyuracils. |
| mRNA Name | ORF Sequence (Amino Acid) | ORF Sequence (Nucleotide) | 5' UTR Sequence | 3' UTR Sequence | Construct Sequence |
|---|---|---|---|---|---|
| | DLYHPIQILADYLTLQ EHYSSLKGLTLSWIG DGNNILHSIMMSAAK FGMHLQAATPKGYE PDASVTKLAEQYAKE NGTKLLLTNDPLEAA HGGNVLITDTWISMG QEEEKKKRLQAFQG YQVTMKTAKVAASD WTFLHCLPRKPEEVD DEVFYSPRSLVFPEAE NRKWTIMAVMVSLL TDYSPQLQKPKF | AGAUCAAGUACAUG CUCUGGCUGAGCGC AGACCUGAAAUUCA GAAUCAAGCAGAAG GGCGAGUACCUGCC CCUGCUCCAAGGCA AGAGCCUGGGCAUG AUCUUCGAGAAGAG AAGCACCAGAACCA GACUGAGCACCGAA ACCGGCUUCGCCCU GCUGGGAGGCCACC CUUGCUUCCUGACC ACCCAGGACAUCCA CCUCGGCGUGAACG AAUCCCUGACCGAU ACGGCCAGAGUCCU GAGCUCAAUGGCCG ACGCCGUCCUGGCG AGAGUGUACAAGCA GUCCGACCUCGACA CCCUGGCCAAAGAG GCCAGCAUCCCUAU CAUCAACGGCCUGA GCGACCUGUACCAC CCUAUCCAGAUUCU CGCUGACUAUCUGA CCCUGCAGGAGCAC UACUCCAGCCUAAA GGGCCUCACCCUUA GCUGGAUCGGCGAC GGCAACAACAUCCU GCACAGCAUCAUGA UGAGCGCCGCCAAG UUCGGCAUGCACCU CCAGGCCGCCACAC CGAAGGGGUACGAA CCGGACGCCAGCGU GACUAAGCUCGCCG AGCAGUACGCCAAG GAGAACGGCACCAA GCUGCUGCUGACCA ACGACCCUCUGGAG GCCGCUCACGGCGG CAACGUUCUGAUUA CCGACACCUGGAUC AGCAUGGGCCAGGA GGAGGAGAAGAAG AAGAGACUGCAGGC CUUCCAGGGCUACC AGGUGACAUGAAG ACGGCCAAAGUGGC CGCCUCCGACUGGA CCUUCCUCCACUGC CUGCCUAGAAAGCC UGAGGAGGUGGACG ACGAGGUGUUCUAC AGCCCUAGAAGCCU GGUGUUCCCUGAGG CCGAGAACAGAAAG UGGACCAUCAUGGC CGUGAUGGUGUCCC UGCUCACCGAUUAC UCCCCUCAGCUCCA GAAGCCUAAGUUC | | CCCUUC CUGCAC CCGUAC CCCCUC CAUAAA GUAGGA AACACU ACAGUG GUCUUU GAAUAA AGUCUG AGUGGG CGGC | NO: 26, and 3' UTR of SEQ ID NO: 4 |

-continued

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 27 | 3 | 4 | 53 |
| OTC-01-023 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUCUUUAACCU CCGCAUCCUGUUGA AUAACGCUGCGUUC CGAAACGGGCAUAA CUUCAUGGUACGCA ACUUCAGGUGCGGC CAGCCACUCCAGAA CAAGGUGCAGCUUA AAGGUCGGGACCUC CUUACUCUGAAGAA CUUUACCGGAGAAG AGAUCAAGUACAUG CUGUGGCUUUCAGC GGAUUUGAAGUUUC GCAUUAAACAGAAG GGAGAGUAUCUUCC CCUCUUGCAAGGGA AGUCGCUCGGGAUG AUCUUCGAGAAGCG CUCGACAAGGACCC GGCUCAGCACCGAA ACCGGAUUUGCGCU GUUGGGAGGGCACC CGUGUUUUCUCACG ACGCAAGACAUUCA CUUGGGAGUGAACG AGUCGUUGACAGAC ACUGCCAGAGUCCU UUCAUCGAUGGCCG ACGCGGUGCUUGCG AGGGUCUACAAACA GUCGGAUCUUGACA CACUGGCCAAGGAA GCCUCGAUCCCGAU CAUUAACGGGCUCU CGGAUUUGUACCAC CCAAUCCAGAUCUU GGCGGAUUAUCUUA CAUUGCAAGAGCAU UAUUCCUCCCUCAA GGGGCUGACUCUCA GCUGGAUUGGUGAC GGAAAUAACAUCCU CCAUUCAAUCAUGA UGAGCGCAGCGAAA UUCGGAAUGCACCU CCAAGCGGCCACGC CCAAAGGUUACGAA CCUGACGCGAGCGU AACUAAACUCGCGG AGCAGUACGCAAAG GAGAACGGCACGAA ACUCUUGCUCACAA ACGACCCCUUGGAG GCAGCACACGGUGG UAACGUCCUGAUUA CAGACACGUGGAUC UCCAUGGGGCAGGA GGAGGAGAAGAAG AAGAGACUUCAGGC AUUUCAGGGAUACC AGGUAACGAUGAAG ACGGCGAAGGUCGC CGCCUCAGACUGGA CUUUCCUCCAUUGC CUGCCGAGGAAGCC GGAAGAAGUCGACG ACGAGGUGUUUUAC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 53 consists from 5' to 3' end: 5' UTR of SEQ ID NO: 3, ORF Sequence of SEQ ID NO: 27, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCCCGCGAUCCCU GGUGUUCCCUGAAG CCGAGAAUCGGAAG UGGACAAUUAUGGC AGUGAUGGUGUCCC UUCUUACGGACUAC UCGCCCCAGCUGCA GAAACCGAAAUUC | | | |
| SEQ ID NO: | 1 | 28 | 3 | 150 | 54 |
| OTC-01-024 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUCUUUAACCU CCGCAUCCUGUUGA AUAACGCUGCGUUC CGAAAUGGGCAUAA CUUCAUGGUACGCA ACUUCAGAUGCGGC CAGCCACUCCAGAA CAAGGUCGGGACCUC CUUACUCUGAAGAA CUUUACCGGAGAAG AGAUCAAGUACAUG CUGUGGCUUUCAGC GGAUUUGAAGUUUC GCAUUAAACAGAAG GGAGAGUAUCUUCC CCUCUUGCAAGGGA AGUCGCUCGGGAUG AUCUUCGAGAAGCG CUCGACAAGGACCC GGCUCAGCACCGAA ACCGGAUUUGCGCU GUUGGGAGGGCACC CGUGUUUUCUCACG ACGCAAGACAUUCA CUUGGGAGUGAAUG AGUCGUUGACAGAC ACUGCCAGAGUCCU UUCAUCGAUGGCCG AUGCGGUGCUUGCG AGGGUCUACAAACA GUCGGAUCUUGACA CACUGGCCAAGGAA GCCUCGAUCCCGAU CAUUAACGGGCUCU CGGAUUUGUACCAC CCAAUCCAGAUCUU GGCGGAUUAUCUUA CAUUGCAAGAGCAU UAUUCCUCCCUCAA GGGGCUGACUCUCA GCUGGAUUGGUGAC GGAAAUAACAUCCU CCAUUCAAUCAUGA UGAGCGCAGCGAAA UUCGGAAUGCACCU CCAAGCGGCCACGC CCAAAGGUUAUGAA CCUGAUGCGAGCGU AACUAAACUCGCGG AGCAGUAUGCAAAG GAAAAUGGCACGAA ACUCUUGCUCACAA AUGACCCCUUGGAG GCAGCACACGGUGG UAAUGUCCUGAUUA CAGACACAUGGAUC UCCAUGGGGCAGGA GGAGGAGAAAAAG | GGGAAA UAAGAG AGAAAA GAAGAG UAAGAA GAAAUA UAAGAG CCACC | UGAUAA UAGGCU GGAGCC UCGGUG GCCAUG CUUCUU GCCCCU UGGGCC UCCCCC CAGCCC CUCCUC CCCUUC CUGCAC CCGUAC CCCCGU GGUCUU UGAAUA AAGUCU GAGUGG GCGGC | SEQ ID NO: 54 consists from 5' to 3' end: 5' UTR of SEQ ID NO: 3, ORF Sequence of SEQ ID NO: 28, and 3' UTR of SEQ ID NO: 150 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AAAAGACUUCAGGC AUUUCAGGGAUACC AGGUAACGAUGAAA ACGGCGAAGGUCGC CGCCUCAGACUGGA CUUUCCUCCAUUGC CUGCCGAGGAAGCC GGAAGAAGUCGAUG AUGAGGUGUUUUAC AGCCCCCGAUCCCU GGUGUUCCCUGAAG CCGAAAAUCGGAAG UGGACAAUUAUGGC AGUGAUGGUGUCCC UUCUUACGGACUAC UCGCCCCAGCUGCA AAAACCGAAAUUC | | | |
| SEQ ID NO: | 1 | 29 | 3 | 4 | 55 |
| OTC-01-025 (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUGUUCAACCU GCGAAUCCUGCUGA ACAAUGCCGCUUUU CGGAACGGGCACAA UUUCAUGGUGAGGA ACUUCGCUGCGGA CAGCCCCUCCAGAA CAAGGUCCAGCUGA AGGGCAGGGACCUG CUGACCCUGAAAAA UUUCACAGGGGAGG AAAUCAAGUACAUG CUGUGGCUGUCAGC CGAUCUGAAGUUCC GGAUCAAGCAGAAG GGCGAAUAUCUGCC UCUGCUCCAGGGCA AAAGCCUGGGGAUG AUCUUCGAAAAGCG CAGUACUCGGACCA GACUGUCAACAGAG ACUGGAUUCGCACU GCUGGGAGGACACC CAUGUUUUCUGACC ACACAGGACAUUCA UCUGGGAGUGAACG AGUCCCUGACCGAC ACAGCACGCGUCCU GAGCUCCAUGGCUG AUGCAGUGCUGGCU CGAGUCUACAAACA GUCUGACCUGGAUA CCCUGGCCAAGGAA GCUUCUAUCCCAAU CAUUAAUGGCCUGA GUGACCUGUAUCAC CCCAUCCAGAUUCU GGCCGAUUACCUGA CCCUCCAGGAGCAU UAUUCUAGUCUGAA AGGGCUGACACUGA GCUGGAUUGGGGAC GGAAACAAUAUCCU GCACUCCAUUAUGA UGAGCGCCGCCAAG UUUGGAAUGCACCU CCAGGCUGCAACCC CAAAAGGCUACGAA CCCGAUGCCUCCGU GACAAAGCUGGCAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 55 consists from 5' to 3' end: 5' UTR of SEQ ID NO: 3, ORF Sequence of SEQ ID NO: 29, and 3' UTR of SEQ ID NO: 4 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AACAGUAUGCCAAA GAGAACGGCACUAA GCUGCUGCUGACCA AUGACCCUCUGGAG GCCGCUCACGGAGG CAACGUGCUGAUCA CUGAUACCUGGAUU AGUAUGGGACAGGA GGAAGAGAAGAAG AAGCGGCUCCAGGC CUUCCAGGGCUACC AGGUGACAAUGAAA ACUGCUAAGGUCGC AGCCAGCGACUGGA CCUUUCUGCAUUGC CUGCCCAGAAAGCC UGAAGAGGUGGACG AUGAGGUCUUCUAC UCACCCAGAAGCCU GGUGUUUCCUGAAG CUGAGAAUAGGAAG UGGACAAUCAUGGC AGUGAUGGUCAGCC UGCUGACUGAUUAU UCCCCUCAGCUCCA GAAACCAAAGUUC | | | |
| SEQ ID NO: | 1 | 56 | | | |
| 894-hFOTC hOTC-Flag; G5) | | AUGCUGUUUAAUCU GAGGAUCCUGUUAA ACAAUGCAGCUUUU AGAAAUGGUCACAA CUUCAUGGUUCGAA AUUUUCGGUGUGGA CAACCACUACAAGA CUACAAGGACGAUG ACGACAAGAAUAAA GUGCAGCUGAAGGG CCGUGACCUUCUCA CUCUAAAAAACUUU ACCGGAGAAGAAAU UAAAUAUAUGCUAU GGCUAUCAGCAGAU CUGAAAUUUAGGAU AAAACAGAAAGGAG AGUAUUUGCCUUUA UUGCAAGGGAAGUC CUUAGGCAUGAUUU UUGAGAAAAGAAG UACUCGAACAAGAU UGUCUACAGAAACA GGCUUUGCACUUCU GGGAGGACAUCCUU GUUUUCUUACCACA CAAGAUAUUCAUUU GGGUGUGAAUGAA AGUCUCACGGACAC GGCCCGUGUAUUGU CUAGCAUGGCAGAU GCAGUAUUGGCUCG AGUGUAUAAACAAU CAGAUUUGGACACC CUGGCUAAAGAAGC AUCCAUCCCAAUUA UCAAUGGGCUGUCA GAUUUGUACCAUCC UAUCCAGAUCCUGG CUGAUUACCUCACG CUCCAGGAACACUA | | | |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UAGCUCUCUGAAAG GUCUUACCCUCAGC UGGAUCGGGGAUGG GAACAAUAUCCUGC ACUCCAUCAUGAUG AGCGCAGCGAAAUU CGGAAUGCACCUUC AGGCAGCUACUCCA AAGGGUUAUGAGCC GGAUGCUAGUGUAA CCAAGUUGGCAGAG CAGUAUGCCAAAGA GAAUGGUACCAAGC UGUUGCUGACAAAU GAUCCAUUGGAAGC AGCGCAUGGAGGCA AUGUAUUAAUUACA GACACUUGGAUAAG CAUGGGACAAGAAG AGGAGAAGAAAAA GCGGCUCCAGGCUU UCCAAGGUUACCAG GUUACAAUGAAGAC UGCUAAAGUUGCUG CCUCUGACUGGACA UUUUUACACUGCUU GCCCAGAAAGCCAG AAGAAGUGGAUGA UGAAGUCUUUUAUU CUCCUCGAUCACUA GUGUUCCCAGAGGC AGAAAACAGAAAGU GGACAAUCAUGGCU GUCAUGGUGUCCCU GCUGACAGAUUACU CACCUCAGCUCCAG AAGCCUAAAUUU | | | |
| SEQ ID NO: | 1 | 57 | | | |
| 895-mOTC Mouse OTC; G5) | | AUGCUGUCUAAUUU GAGGAUCCUGCUCA ACAAUGCAGCUCUU AGAAAGGGUCACAC UUCUGUGGUUCGAC AUUUUUGGUGUGG GAAGCCAGUCCAAA GUCAAGUACAGCUG AAAGGCCGUGACCU CCUCACCUUGAAGA ACUUCACAGGAGAG GAGAUUCAGUACAU GCUAUGGCUCUCUG CAGAUCUGAAAUUC AGGAUCAAGCAGAA AGGAGAAUAUUUAC CUUUAUUGCAAGGG AAAUCCUUAGGAAU GAUUUUUGAGAAA AGAAGUACUCGAAC AAGACUGUCCACAG AAACAGGCUUUGCU CUGCUGGGAGGACA CCCUUCCUUUCUUA CCACACAAGACAUU CACUUGGGUGUGAA UGAAAGUCUCACAG ACACCGCUCUGUC UUAUCUAGCAUGAC AGAUGCAGUGUUAG | | | |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CUCGAGUGUAUAAA CAAUCAGAUCUGGA CACCCUGGCUAAAG AAGCAUCCAUCCCA AUUGUCAAUGGACU GUCAGACUUGUAUC AUCCUAUCCAGAUC CUGGCUGAUUACCU UACACUCCAGGAAC ACUAUGGCUCUCUC AAAGGUCUUACCCU CAGCUGGAUAGGGG AUGGGAACAAUAUC UUGCACUCUAUCAU GAUGAGUGCUGCAA AAUUCGGGAUGCAC CUUCAAGCAGCUAC UCCAAAGGGUUAUG AGCCAGAUCCUAAU AUAGUCAAGCUAGC AGAGCAGUAUGCCA AGGAGAAUGGUACC AAGUUGUCAAUGAC AAAUGAUCCACUGG AAGCAGCACGUGGA GGCAAUGUAUUAAU UACAGAUACUUGGA UAAGCAUGGGACAA GAGGAUGAGAAGA AAAAGCGUCUUCAA GCUUUCCAAGGUUA CCAGGUUACGAUGA AGACUGCCAAAGUG GCUGCGUCUGACUG GACAUUUUACACU GUUUGCCUAGAAAG CCAGAAGAAGUGGA UGAUGAAGUAUUU UAUUCUCCACGGUC AUUAGUGUUCCCAG AGGCAGAGAAUAGA AAGUGGACAAUCAU GGCUGUCAUGGUAU CCCUGCUGACAGAC UACUCACCUGUGCU CCAGAAGCCAAAGU UU | | | |
| SEQ ID NO: | 1 | 58 | | | |
| 896-mFOTC (mouse OTC-Flag; G5) | | AUGCUGUCUAAUUU GAGGAUCCUGCUCA ACAAUGCAGCUCUU AGAAAGGGUCACAC UUCUGUGGUUCGAC AUUUUUGGUGUGG GAAGCCAGUCCAAG ACUACAAGGACGAU GACGACAAGAGUCA AGUACAGCUGAAAG GCCGUGACCUCCUC ACCUUGAAGAACUU CACAGGAGAGGAGA UUCAGUACAUGCUA UGGCUCUCUGCAGA UCUGAAAUUCAGGA UCAAGCAGAAAGGA GAAUAUUUACCUUU AUUGCAAGGGAAAU CCUUAGGAAUGAUU | | | |

-continued

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UUUGAGAAAAGAA GUACUCGAACAAGA CUGUCCACAGAAAC AGGCUUUGCUCUGC UGGGAGGACACCCU UCCUUUCUUACCAC ACAAGACAUUCACU UGGGUGUGAAUGA AAGUCUCACAGACA CCGCUCGUGUCUUA UCUAGCAUGACAGA UGCAGUGUUAGCUC GAGUGUAUAAACAA UCAGAUCUGGACAC CCUGGCUAAAGAAG CAUCCAUCCCAAUU GUCAAUGGACUGUC AGACUUGUAUCAUC CUAUCCAGAUCCUG GCUGAUUACCUUAC ACUCCAGGAACACU AUGGCUCUCUCAAA GGUCUUACCCUCAG CUGGAUAGGGGAUG GGAACAAUAUCUUG CACUCUAUCAUGAU GAGUGCUGCAAAAU UCGGGAUGCACCUU CAAGCAGCUACUCC AAAGGGUUAUGAGC CAGAUCCUAAUAUA GUCAAGCUAGCAGA GCAGUAUGCCAAGG AGAAUGGUACCAAG UUGUCAAUGACAAA UGAUCCACUGGAAG CAGCACGUGGAGGC AAUGUAUUAAUUAC AGAUACUUGGAUAA GCAUGGGACAAGAG GAUGAGAAGAAAA AGCGUCUUCAAGCU UUCCAAGGUUACCA GGUUACGAUGAAGA CUGCCAAAGUGGCU GCGUCUGACUGGAC AUUUUUACACUGUU UGCCUAGAAAGCCA GAAGAAGUGGAUG AUGAAGUAUUUUA UUCUCCACGGUCAU UAGUGUUCCCAGAG GCAGAGAAUAGAAA GUGGACAAUCAUGG CUGUCAUGGUAUCC CUGCUGACAGACUA CUCACCUGUGCUCC AGAAGCCAAAGUUU | | | |
| SEQ ID NO: | | 59 | | | |
| 893-hOTC (hOTC; G5) | | AUGCUGUUUAAUCU GAGGAUCCUGUUAA ACAAUGCAGCUUUU AGAAAUGGUCACAA CUUCAUGGUUCGAA AUUUUCGGUGUGGA CAACCACUACAAAA UAAAGUGCAGCUGA AGGGCCGUGACCUU | | | |

| | | CONSTRUCT SEQUENCES | | | |
|---|---|---|---|---|---|
| | By "G-5" is meant that all uracils (U) in the mRNA are replaced by N1-methylpseudouracils. By "G6" is meant that all uracils (U) in the mRNA are replaced by 5-methoxyuracils. | | | | |
| mRNA Name | ORF Sequence (Amino Acid) | ORF Sequence (Nucleotide) | 5' UTR Sequence | 3' UTR Sequence | Construct Sequence |
| | | CUCACUCUAAAAAA CUUUACCGGAGAAG AAAUUAAAUAUAU GCUAUGGCUAUCAG CAGAUCUGAAAUUU AGGAUAAAACAGAA AGGAGAGUAUUUGC CUUUAUUGCAAGGG AAGUCCUUAGGCAU GAUUUUUGAGAAA AGAAGUACUCGAAC AAGAUUGUCUACAG AAACAGGCUUUGCA CUUCUGGGAGGACA UCCUUGUUUUCUUA CCACACAAGAUAUU CAUUUGGGUGUGAA UGAAAGUCUCACGG ACACGGCCCGUGUA UUGUCUAGCAUGGC AGAUGCAGUAUUGG CUCGAGUGUAUAAA CAAUCAGAUUUGGA CACCCUGGCUAAAG AAGCAUCCAUCCCA AUUAUCAAUGGGCU GUCAGAUUUGUACC AUCCUAUCCAGAUC CUGGCUGAUUACCU CACGCUCCAGGAAC ACUAUAGCUCUCUG AAAGGUCUUACCCU CAGCUGGAUCGGGG AUGGGAACAAUAUC CUGCACUCCAUCAU GAUGAGCGCAGCGA AAUUCGGAAUGCAC CUUCAGGCAGCUAC UCCAAAGGGUUAUG AGCCGGAUGCUAGU GUAACCAAGUUGGC AGAGCAGUAUGCCA AAGAGAAUGGUACC AAGCUGUUGCUGAC AAAUGAUCCAUUGG AAGCAGCGCAUGGA GGCAAUGUAUUAAU UACAGACACUUGGA UAAGCAUGGGACAA GAAGAGGAGAAGA AAAAGCGGCUCCAG GCUUUCCAAGGUUA CCAGGUUACAAUGA AGACUGCUAAAGUU GCUGCCUCUGACUG GACAUUUUUACACU GCUUGCCCAGAAAG CCAGAAGAAGUGGA UGAUGAAGUCUUUU AUUCUCCUCGAUCA CUAGUGUUCCCAGA GGCAGAAAACAGAA AGUGGACAAUCAUG GCUGUCAUGGUGUC CCUGCUGACAGAUU ACUCACCUCAGCUC CAGAAGCCUAAAUU U | | | |

-continued

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 60 | 3 | 150 | 61 |
| ahOTC (hOTC; G5) Cap: C1 PolyA tail: 100 nt | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AUGCUCUUUAACCU CCGCAUCCUGUUGA AUAACGCUGCGUUC CGAAAUGGGCAUAA CUUCAUGGUACGCA ACUUCAGAUGCGGC CAGCCACUCCAGAA CAAGGUGCAGCUUA AAGGUCGGGACCUC CUUACUCUGAAGAA CUUUACCGGAGAAG AGAUCAAGUACAUG CUGUGGCUUUCAGC GGAUUUGAAGUUUC GCAUUAAACAGAAG GGAGAGUAUCUUCC CCUCUUGCAAGGGA AGUCGCUCGGGAUG AUCUUCGAGAAGCG CUCGACAAGGACCC GGCUCAGCACCGAA ACCGGAUUUGCGCU GUUGGGAGGGCACC CGUGUUUUCUCACG ACGCAAGACAUUCA CUUGGGAGUGAAUG AGUCGUUGACAGAC ACUGCCAGAGUCCU UUCAUCGAUGGCCG AUGCGGUGCUUGCG AGGGUCUACAAACA GUCGGAUCUUGACA CACUGGCCAAGGAA GCCUCGAUCCCGAU CAUUAACGGGCUCU CGGAUUUGUACCAC CCAAUCCAGAUCUU GGCGGAUUAUCUUA CAUUGCAAGAGCAU UAUUCCUCCCUCAA GGGGCUGACUCUCA GCUGGAUUGGUGAC GGAAAUAACAUCCU CCAUUCAAUCAUGA UGAGCGCAGCGAAA UUCGGAAUGCACCU CCAAGCGGCCACGC CCAAAGGUUAUGAA CCUGAUGCGAGCGU AACUAAACUCGCGG AGCAGUAUGCAAAG GAAAAUGGCACGAA ACUCUUGCUCACAA AUGACCCCUUGGAG GCAGCACACGGUGG UAAUGUCCUGAUUA CAGACACAUGGAUC UCCAUGGGGCAGGA GGAGGAGAAAAAG AAAAGACUUCAGGC AUUUCAGGGAUACC AGGUAACGAUGAAA ACGGCGAAGGUCGC CGCCUCAGACUGGA CUUUCCUCCAUUGC CUGCCGAGGAAGCC GGAAGAAGUCGAUG AUGAGGGUGUUUUAC | GGGAAA UAAGAG AGAAAA GAAGAG UAAGAA GAAAUA UAAGAG CCACC | UGAUAA UAGGCU GGAGCC UCGGUG GCCAUG CUUCUU GCCCCU UGGGCC UCCCCC CAGCCC CUCCUC CCCUUC CUGCAC CCGUAC CCCCGU GGUCUU UGAAUA AAGUCU GAGUGG GCGGC | SEQ ID NO: 61 consists from 5' to 3' end: 5' UTR of SEQ ID NO: 3, ORF Sequence of SEQ ID NO: 60, and 3' UTR of SEQ ID NO: 150 |

CONSTRUCT SEQUENCES

By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCCCCCGAUCCCU GGUGUUCCCUGAAG CCGAAAAUCGGAAG UGGACAAUUAUGGC AGUGAUGGUGUCCC UUCUUACGGACUAC UCGCCCCAGCUGCA AAAACCGAAAUUC | | | |
| SEQ ID NO: | 1 | 62 | | | |
| Human ornithine carbamoyl-transferase (OTC), mRNA NCBI Ref. Seq. NM_000531.5 | MLFNLRILLNNAAFR NGHNFMVRNFRCGQ PLQNKVQLKGRDLLT LKNFTGEEIKYMLWL SADLKFRIKQKGEYL PLLQGKSLGMIFEKR STRTRLSTETGFALLG GHPCFLTTQDIHLGV NESLTDTARVLSSMA DAVLARVYKQSDLD TLAKEASIPIINGLSDL YHPIQILADYLTLQEH YSSLKGLTLSWIGDG NNILHSIMMSAAKFG MHLQAATPKGYEPD ASVTKLAEQYAKEN GTKLLLTNDPLEAAH GGNVLITDTWISMGQ EEEKKKRLQAFQGY QVTMKTAKVAASD WTFLHCLPRKPEEVD DEVFYSPRSLVFPEAE NRKWTIMAVMVSLL TDYSPQLQKPKF | AGCGGUGGAGCUUG GCAUAAAGUUCAAA UGCUCCUACACCCU GCCCUGCAGUAUCU CUAACCAGGGGACU UUGAUAAGGAAGCU GAAGGGUGAUAUU ACCUUUGCUCCCUC ACUGCAACUGAACA CAUUUCUUAGUUUU UAGGUGGCCCCCGC UGGCUAACUUGCUG UGGAGUUUUCAAGG GCAUAGAAUCGUCC UUUACACAAUUAAA AGAAGAUGCUGUUU AAUCUGAGGAUCCU GUUAAACAAUGCAG CUUUUAGAAAUGGU CACAACUUCAUGGU UCGAAAUUUCGGU GUGGACAACCACUA CAAAAUAAAGUGCA GCUGAAGGGCCGUG ACCUUCUCACUCUA AAAACUUUACCGG AGAAGAAAUUAAA UAUAUGCUAUGGCU AUCAGCAGAUCUGA AAUUUAGGAUAAA ACAGAAAGGAGAGU AUUUGCCUUUAUUG CAAGGGAAGUCCUU AGGCAUGAUUUUUG AGAAAAGAAGUACU CGAACAAGAUUGUC UACAGAAACAGGCU UUGCACUUCUGGGA GGACAUCCUUGUUU UCUUACCACACAAG AUAUUCAUUUGGGU GUGAAUGAAAGUCU CACGGACACGGCCC GUGUAUUGUCUAGC AUGGCAGAUGCAGU AUUGGCUCGAGUGU AUAAACAAUCAGAU UUGGACACCCUGGC UAAAGAAGCAUCCA UCCCAAUUAUCAAU GGGCUGUCAGAUUU GUACCAUCCUAUCC AGAUCCUGGCUGAU UACCUCACGCUCCA GGAACACUAUAGCU CUCUGAAAGGUCUU ACCCUCAGCUGGAU CGGGGAUGGGAACA AUAUCCUGCACUCC | | | |

CONSTRUCT SEQUENCES
By "G-5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AUCAUGAUGAGCGC AGCGAAAUUCGGAA UGCACCUUCAGGCA GCUACUCCAAAGGG UUAUGAGCCGGAUG CUAGUGUAACCAAG UUGGCAGAGCAGUA UGCCAAAGAGAAUG GUACCAAGCUGUUG CUGACAAAUGAUCC AUUGGAAGCAGCGC AUGGAGGCAAUGUA UUAAUUACAGACAC UUGGAUAAGCAUGG GACAAGAAGAGGAG AAGAAAAAGCGGCU CCAGGCUUUCCAAG GUUACCAGGUUACA AUGAAGACUGCUAA AGUUGCUGCCUCUG ACUGGACAUUUUUA CACUGCUUGCCCAG AAAGCCAGAAGAAG UGGAUGAUGAAGUC UUUUAUUCUCCUCG AUCACUAGUGUUCC CAGAGGCAGAAAAC AGAAAGUGGACAAU CAUGGCUGUCAUGG UGUCCCUGCUGACA GAUUACUCACCUCA GCUCCAGAAGCCUA AAUUUUGAUGUUG UGUUACUUGUCAAG AAAGAAGCAAUGUU CUUCAGUAACAGAA UGAGUUGGUUUAU GGGGAAAAGAGAA GAGAAUCUAAAAAA UAAACAAAUCCCUA ACACGUGGUAUGGG UGAACCGUAUGAUA UGCUUUGCCAUUGU GAAACUUUCCUUAA GCCUUUAAUUUAAG UGCUGAUGCACUGU AAUACGUGCUUAAC UUUGCUUAAACUCU CUAAUUCCCAAUUU CUGAGUUACAUUUA GAUAUCAUAUUAAU UAUCAUAUACAUUU ACUUCAACAUAAAA UACUGUGUUCAUAA UGUAUAAUGUCUAA GCCAUUAAGUGUAA UCUAUGCUUAUUAC CUAAAUAAAUUAUC ACCCAUGCUAAUUU A | | | |

EXAMPLES

Example 1: Chimeric Polynucleotide Synthesis

A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:
(a) Capped and protected 5' segment comprising a normal 3'OH (SEG. 1)
(b) 5' triphosphate segment which can include the coding region of a polypeptide and comprising a normal 3'OH (SEG. 2)
(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG.2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5' UTR (SEG. 1), open reading frame or ORF (SEG. 2) and 3' UTR+PolyA (SEG. 3).

The yields of each step can be as much as 90-95%.

Example 2: PCR for cDNA Production

PCR procedures for the preparation of cDNA can be performed using 2×KAPA HIFI™ HotStart ReadyMix by Kapa Biosystems (Woburn, MA). This system includes 2× KAPA ReadyMix12.5 µl; Forward Primer (10 µM) 0.75 IA; Reverse Primer (10 µM) 0.75 µl; Template cDNA –100 ng; and dH$_2$O diluted to 25.0 µl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-T$_{120}$ for a poly-A$_{120}$ in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, CA) per manufacturer's instructions (up to 5 µg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3: In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:
1 Template cDNA—1.0
2 10× transcription buffer (400 mM Tris-HCl pH 8.0, 190 mM MgCl$_2$, 50 mM DTT, mM Spermidine)—2.0
3 Custom NTPs (25 mM each)—7.2 µl
4 RNase Inhibitor—20 U
5 T7 RNA polymerase—3000 U
6 dH$_2$O—Up to 20.0 µl. and
7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 µg of RNA. Following the cleanup, the RNA can be quantified using the NanoDrop and analyzed by agarose gel electrophoresis to confirm the RNA is the proper size and that no degradation of the RNA has occurred.

Example 4: Enzymatic Capping

Capping of a polynucleotide can be performed with a mixture includes: IVT RNA µg-180 µg and dH$_2$O up to 72 µl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM MgCl$_2$) (10.0 IA); 20 mM GTP (5.0 IA); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$O (Up to 28 µl); and incubation at 37° C. for 30 minutes for 60 µg RNA or up to 2 hours for 180 µg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5: PolyA Tailing Reaction

Without a poly-T in the cDNA, a poly-A tailing reaction must be performed before cleaning the final product. This can be done by mixing Capped IVT RNA (100 µl); RNase Inhibitor (20 U); 10×Tailing Buffer (0.5 M Tris-HCl (pH 8.0), 2.5 M NaCl, 100 mM MgCl$_2$)(12.0 µl); 20 mM ATP (6.0 µl); Poly-A Polymerase (20 U); dH$_2$O up to 123.5 µl and incubating at 37° C. for 30 min. If the poly-A tail is already in the transcript, then the tailing reaction can be skipped and proceed directly to cleanup with Ambion's MEGA-CLEAR™ kit (Austin, TX) (up to 500 µg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6: Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap];G(5')ppp(5')A; G(5')ppp(5')G; m7G(5')ppp(5')A; m7G(5')ppp(5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England BioLabs, Ipswich, MA). Cap 1 structure can be generated using both Vaccinia Virus Capping Enzyme and a 2'-O methyltransferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7: Capping Assays

A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8: Agarose Gel Electrophoresis of Modified RNA or RT PCR Products

Individual polynucleotides (200-400 ng in a 20 µl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 9: Nanodrop Modified RNA Quantification and UV Spectral Data

Modified polynucleotides in TE buffer (1 µl) can be used for Nanodrop UV absorbance readings to quantitate the yield of each polynucleotide from an chemical synthesis or in vitro transcription reaction.

Example 10: Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11: Method of Screening for Protein Expression

A. Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

B. Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI). Patterns of protein fragments, or whole proteins, can be compared to known controls for a given protein and identity can be determined by comparison.

C. Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 12: Synthesis of mRNA Encoding OTC

Sequence optimized polynucleotides encoding OTC polypeptides, i.e., SEQ ID NO:62, are synthesized and characterized as described in Examples 1 to 11, and prepared for the Examples described below.

An mRNA encoding human OTC can be constructed, e.g., by using the ORF sequence provided in any of SEQ ID NOs:2 and 5-29. The mRNA sequence includes both 5' and 3' UTR regions flanking the ORF sequence (nucleotide). In an exemplary construct, the 5' UTR and 3' UTR sequences are SEQ ID NO: 3 and SEQ ID NO: 4, respectively (see Sequence Listing).

5'UTR:
(SEQ ID NO: 3)
GGGAAAUAAGAGAGAAAAGAAGAGUAAGAAGAAAUAUAAGAGCCACC

3'UTR:
(SEQ ID NO: 4)
UGAUAAUAGGCUGGAGCCUCGGUGGCCUAGCUUCUUGCCCCUUGGGCCUC
CCCCCAGCCCCUCCUCCCCUUCCUGCACCCGUACCCCUCCAUAAAGUAG
GAAACACUACAGUGGUCUUUGAAUAAAGUCUGAGUGGGCGGC

In another exemplary construct, the 5' UTR and 3' UTR sequences are below:
5'UTR:
(SEQ ID NO: 3)
GGGAAAUAAGAGAGAAAAGAAGAGUAAGAAGAAAUAUAAGAGCCACC 3'UTR:
(SEQ ID NO: 150)
UGAUAAUAGGCUGGAGCCUCGGUGGCCAUGCUUCUUGCCCCUUGGGCCUC
CCCCCAGCCCCUCCUCCCCUUCCUGCACCCGUACCCCGUGGUCUUUGAA
UAAAGUCUGAGUGGGCGGC The OTC mRNA sequence is prepared as modified mRNA. Specifically, during in vitro translation, modified mRNA can be generated using N1-methylpseudouridine-5'-Triphosphate or 5-methoxy-UTP to ensure that the mRNAs contain 100% N1-methylpseudouridine-5'-Triphosphate or 5-methoxy-uridine instead of uridine. Further, OTC-mRNA can be synthesized with a primer that introduces a polyA-tail, and a Cap 1 structure is generated on both mRNAs using Vaccinia Virus Capping Enzyme and a 2'-O methyl-transferase to generate: m7G(5)ppp(5')G-2'-O-methyl.

Example 13: Detecting Endogenous OTC Expression In Vitro

OTC expression is characterized in a variety of cell lines derived from both mice and human sources. Cell are cultured in standard conditions and cell extracts are obtained by placing the cells in lysis buffer. For comparison purposes, appropriate controls are also prepared. To analyze OTC expression, lysate samples are prepared from the tested cells and mixed with lithium dodecyl sulfate sample loading buffer and subjected to standard Western blot analysis. For detection of OTC, the antibody used is a commercial rabbit polyclonal anti-OTC antibody (ab91418, Abcam). For detection of a load control, the antibody used is anti-citrase synthase (rabbit polyclonal; PA5-22126; Thermo-Fisher Scientific®). To examine the localization of endogenous OTC, immunofluorescence analysis is performed on cells. OTC expression is detected using a commercial anti-OTC. The location of specific organelles can be detected with existing commercial products. For example, mitochondria can be detected using Mitotracker, and the nucleus can be stained with DAPI. Image analysis is performed on a Zeiss ELYRA imaging system.

Endogenous OTC expression can be used as a base line to determine changes in OTC expression resulting from transfection with mRNAs comprising nucleic acids encoding OTC.

Example 14: In Vitro Expression of OTC in HeLa Cells

To measure in vitro expression of human OTC in HeLa cells, those cells were seeded on 12-well plates (BD Biosciences, San Jose, USA) one day prior to transfection. mRNA formulations comprising human OTC or a GFP control was transfected using 800 ng mRNA and 2 µL Lipofectamin 2000 in 60 µL OPTI-MEM per well and incubated.

After 24 hours, the cells in each well were lysed using a consistent amount of lysis buffer. Appropriate controls were used, including citrate synthesase, a mitochondrial marker. Protein concentrations of each were determined using a BCA assay according to manufacturer's instructions. To analyze OTC expression, equal loads of each lysate (24 µg)

were prepared in a loading buffer and subjected to standard Western blot analysis. For detection of OTC, a commercial anti-OTC antibody was used according to the manufacturer's instructions. The mRNA expressed OTC was compared to loaded recombinant human OTC protein (10, 5, and 2.5 ng).

Figure 1A:
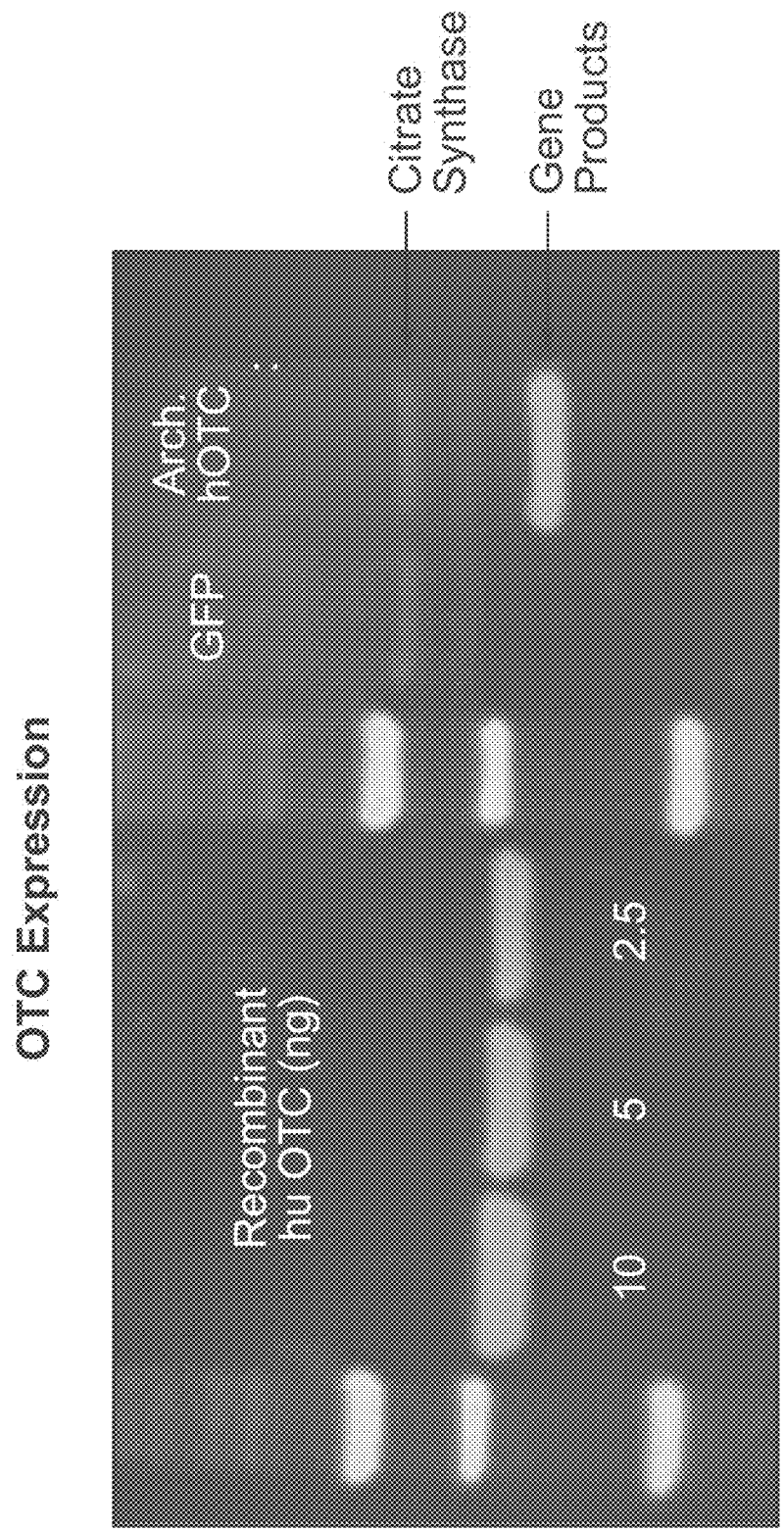
FIG. 1B shows immunohistochemical staining of human OTC expressed in HeLa cells 24 hours post transfection.
FIG. 1C is a bar graph showing the activity of OTC expressed from human or mouse OTC mRNA. Constructs used are shown on the graph (left to right) in the order shown in the legend (top to bottom).
Figure 1B:
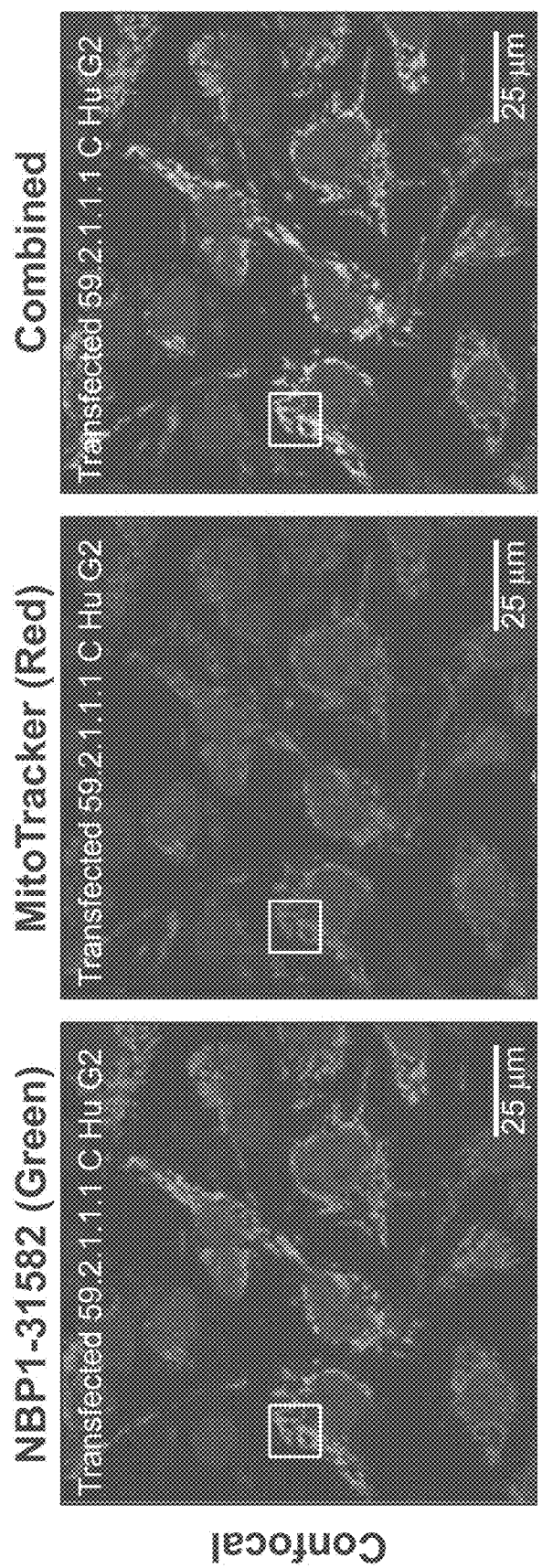

FIG. 1A shows the expression level of human OTC (construct ahOTC; SEQ ID NO: 61) and the citrate synthesase mitochondrial protein control. FIG. 1B shows that the expressed human OTC (construct ahOTC; SEQ ID NO: 61) co-localizes with the mitotracker mitochondrial marker, and is therefore present in the mitochondria of cells.

Example 15: In Vitro OTC Activity in HeLa Cells

An in vitro OTC activity assay was performed to determine whether OTC exogenously-expressed after introduction of mRNA comprising a OTC sequence is active.

A. Expression Assay

HeLa cells were transfected with mRNA formulations comprising human OTC or mouse OTC. Cells were transfected with Lipofectamin 2000 and lysed as described in Example 14 above. Appropriate controls were also prepared.

B. Activity Assay

To assess whether exogenous human and mouse OTC can function, an in vitro activity assay was performed using transfected HeLa cell lysates as the source of enzymatic activity. OTC catalyzes the reaction between carbamyl phosphate and ornithine to produce citrulline and phosphate. OTC activity was measured by a colorimetric assay which detects the formation of L-citrulline. Cells were lysed as described in Example 13. Assays were performed in 50 mM Tris acetate, 2 mM EDTA, pH 8.3 at 25° C. and normalized to cellular protein. Results were expressed as pmol citrulline/g protein/hour.

Figure 1C:
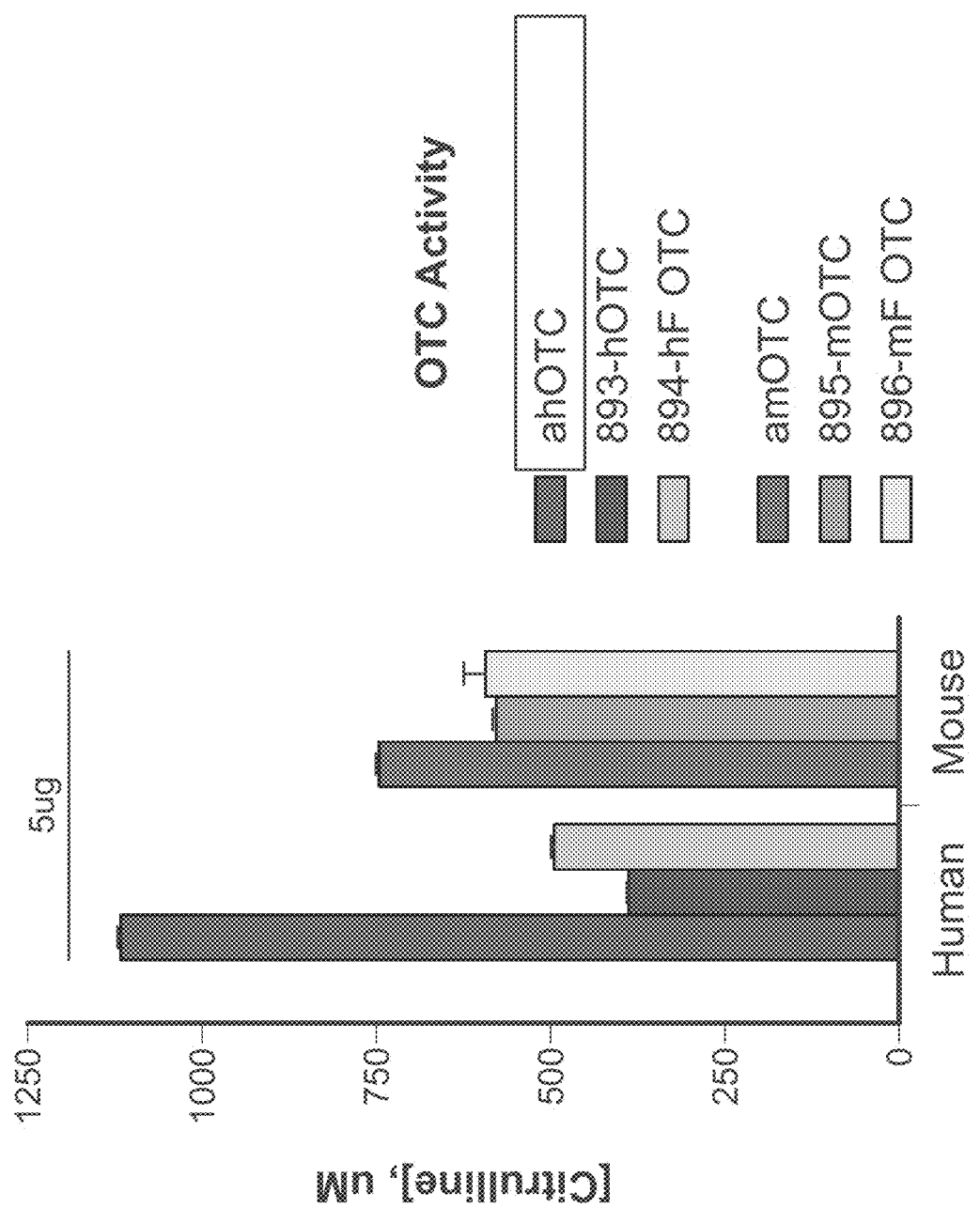

The OTC activity results are shown in FIG. 1C. The OTC activity resulted from transfection of mRNAs encoding human or mouse OTC, by using the ORF sequence provided in any of SEQ ID NOs: 56-59 or a 1-methyl-pseudouridine modified mRNA construct encoding OTC (construct ahOTC; SEQ ID NO: 61). Transfection of HeLa cells with the ahOTC codified OTC mRNA construct (SEQ ID NO: 61) resulted in the highest OTC activity.

Example 16: Human OTC Mutant and Chimeric Constructs

A polynucleotide of the present invention can comprise at least a first region of linked nucleosides encoding human OTC, which can be constructed, expressed, and characterized according to the examples above. Similarly, the polynucleotide sequence can contain one or more mutations that results in the expression of a OTC with increased or decreased activity. Furthermore, the polynucleotide sequence encoding OTC can be part of a construct encoding a chimeric fusion protein.

Example 17: In Vitro OTC Protein Expression and Activity in Animal Model Primary Hepatocytes OTC protein expression was determined for spf$^{ash}$ mouse primary hepatocytes after transfection of cells with an mRNA encoding human OTC (SEQ ID NOs: 30-55 and 61) or control GFP. Some of the OTC mRNA constructs were 1-methyl-pseudouridine modified and some OTC mRNA constructs were 5-methoxyuridine modified. Cells were plated in 6 well plate and transfected with 1 μg of mRNA per well (ThermoFisher Lipofectamine MessengerMAX). Cells were lysed at 24-hours post-transfection, as described in Example 13, and OTC protein expression was determined using rabbit polyclonal anti-OTC NBP1-87408 (NovusBio) for capillary electrophoresis. OTC activity was measured by a colorimetric assay which detects the formation of L-citrulline, as described in Example 15.

Figure 2:
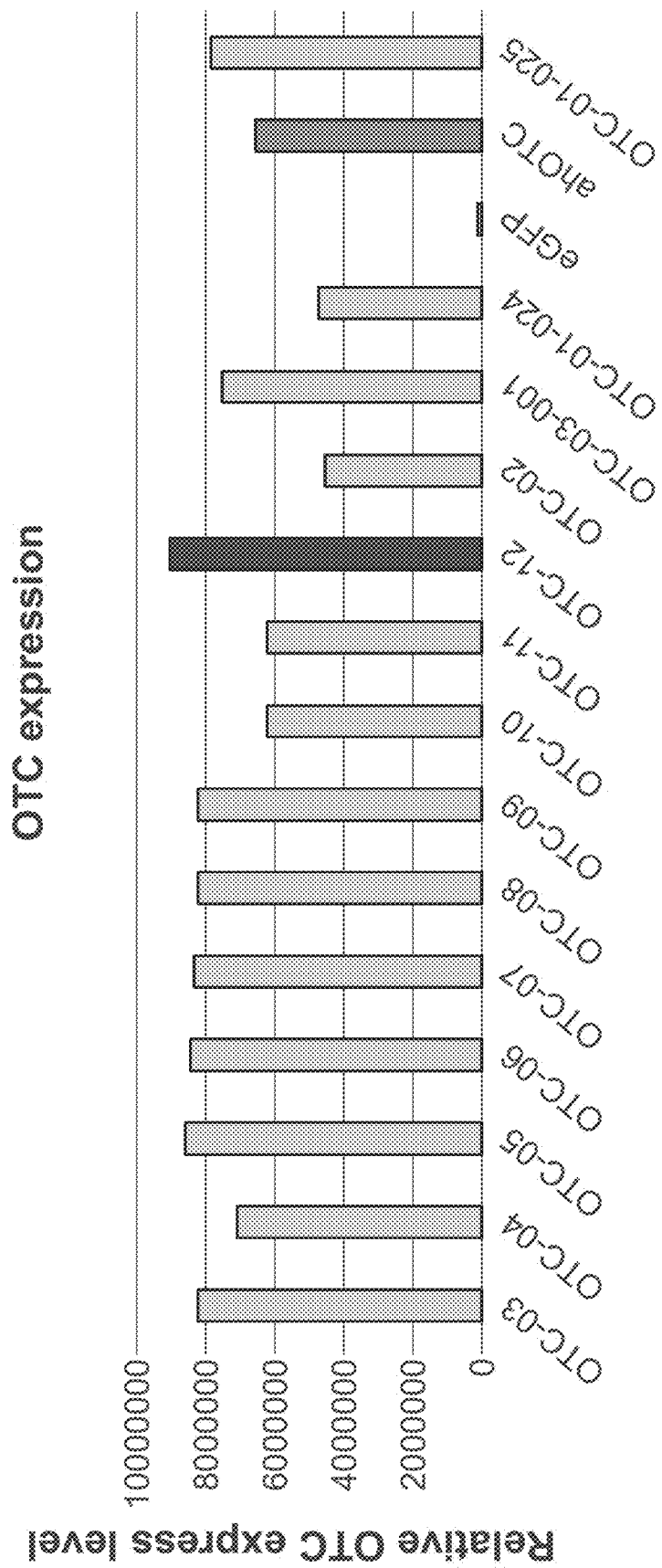
FIG. 2 shows the levels of OTC expression from human OTC mRNA constructs transfected in spf$^{ash}$ hepatocytes.
Figure 3:
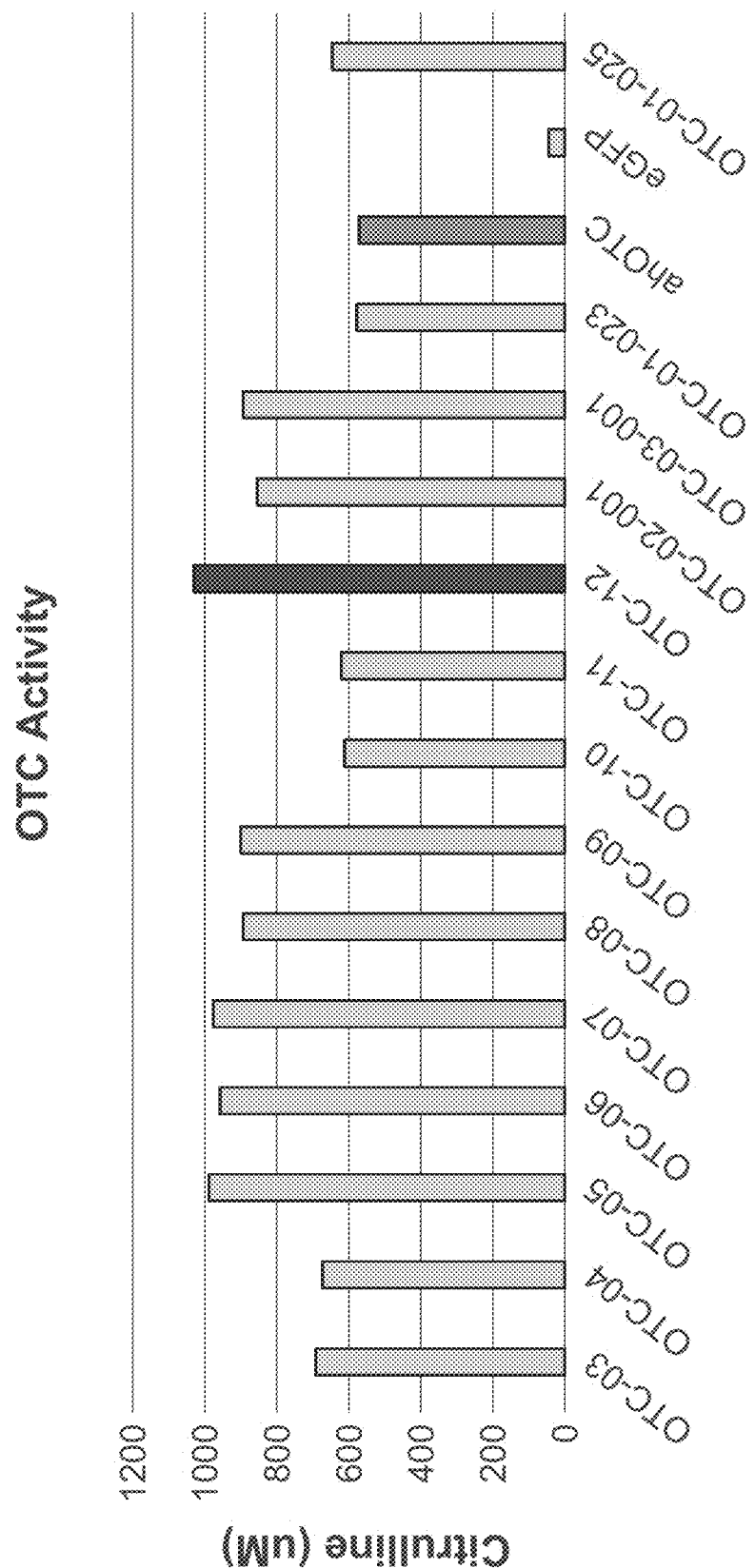
FIG. 3 shows the activity levels of OTC expressed in FIG. 2.

FIG. 2 presents the OTC expression results for a subset of the 1-methyl-pseudouridine modified human OTC mRNA constructs. OTC was expressed from the human OTC mRNA constructs, while the mRNA encoding GFP did not result in OTC expression. Construct OTC-12 (SEQ ID NO:40) exhibited the highest expression level. In general the 1-methyl-pseudouridine modified constructs were expressed more highly than the 5-methoxyuridine modified constructs (data not shown). FIG. 3 presents the OTC activity results for a subset of the 1-methyl-pseudouridine modified human OTC mRNA constructs. The OTC activity correlated with the OTC expression levels depicted in FIG. 2. Construct OTC-12 (SEQ ID NO:40) exhibited the highest activity level. In general the 1-methyl-pseudouridine modified constructs exhibited higher activity levels than the 5-methoxyuridine modified constructs (data not shown).

Figure 4A:
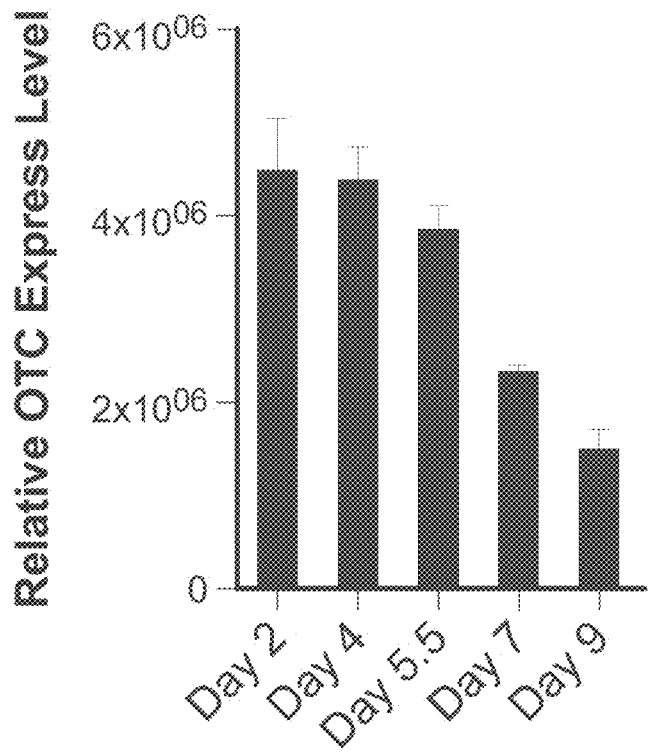
FIG. 4A shows the levels of OTC expression at 2, 4, 5.5, 7, and 9 days following transfection of spf$^{ash}$ hepatocytes with the human OTC mRNA construct OTC-12.
Figure 4B:
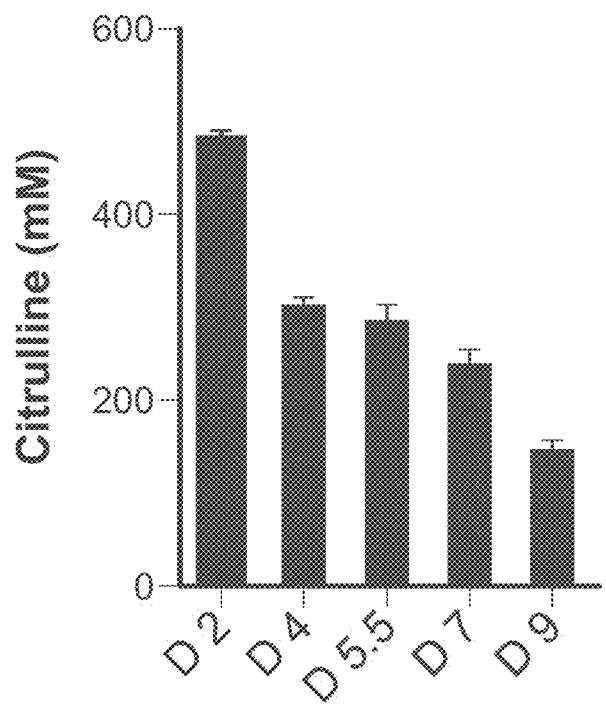
FIG. 4B shows OTC activity levels at 2, 4, 5.5, 7, and 9 days following transfection of spf$^{ash}$ hepatocytes with the human OTC mRNA construct OTC-12.

A time course study was also conducted to determine the protein half life of OTC and duration of OTC activity using the OTC mRNA construct that exhibited the highest expression level (construct OTC-12, SEQ ID NO:40). Spf$^{ash}$ primary hepatocytes were transfected with 1 μg of human OTC mRNA (construct OTC-12, SEQ ID NO:40) or a control mRNA encoding eGFP, and OTC expression and activity (citrulline levels) were measured at 2, 4, 5.5, 7, and 9 days following mRNA transfection, as described above. FIG. 4A shows that OTC expression was detected for at least 9 days in spf$^{ash}$ primary hepatocytes following transfection with human OTC mRNA. FIG. 4B shows that OTC activity (citrulline (μM)) was detected for at least 9 days in spf$^{ash}$ primary hepatocytes following transfection with human OTC mRNA. 9 days after transfection, around 40% OTC protein expression and activity compared day 2 were detected.

Example 18: Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining an ionizable amino lipid disclosed herein, e.g., a lipid according to Formula (I) such as Compound II or a lipid according to Formula (III) such as Compound VI, a phospholipid (such as DOPE or DSPC, obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 µm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2% Triton X-100 solution is added to the wells. The plate is incubated at a temperature of 37° C. for 15 minutes. The RIBOGREEN® reagent is diluted 1:100 in TE buffer, and 100 µL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in Table 6 below. The term "Compound" refers to an ionizable lipid such as MC3, Compound II, or Compound VI. "Phospholipid" can be DSPC or DOPE. "PEG-lipid" can be PEG-DMG or Compound I.

TABLE 6

Exemplary Formulations of Nanoparticles

| Composition (mol %) | Components |
| --- | --- |
| 40:20:38.5:1.5 | Compound:Phospholipid:Chol:PEG-lipid |
| 45:15:38.5:1.5 | Compound:Phospholipid:Chol:PEG-lipid |
| 50:10:38.5:1.5 | Compound:Phospholipid:Chol:PEG-lipid |
| 55:5:38.5:1.5 | Compound:Phospholipid:Chol:PEG-lipid |
| 60:5:33.5:1.5 | Compound:Phospholipid:Chol:PEG-lipid |
| 45:20:33.5:1.5 | Compound:Phospholipid:Chol:PEG-lipid |
| 50:20:28.5:1.5 | Compound:Phospholipid:Chol:PEG-lipid |
| 55:20:23.5:1.5 | Compound:Phospholipid:Chol:PEG-lipid |
| 60:20:18.5:1.5 | Compound:Phospholipid:Chol:PEG-lipid |
| 40:15:43.5:1.5 | Compound:Phospholipid:Chol:PEG-lipid |
| 50:15:33.5:1.5 | Compound:Phospholipid:Chol:PEG-lipid |
| 55:15:28.5:1.5 | Compound:Phospholipid:Chol:PEG-lipid |
| 60:15:23.5:1.5 | Compound:Phospholipid:Chol:PEG-lipid |
| 40:10:48.5:1.5 | Compound:Phospholipid:Chol:PEG-lipid |
| 45:10:43.5:1.5 | Compound:Phospholipid:Chol:PEG-lipid |
| 55:10:33.5:1.5 | Compound:Phospholipid:Chol:PEG-lipid |
| 60:10:28.5:1.5 | Compound:Phospholipid:Chol:PEG-lipid |
| 40:5:53.5:1.5 | Compound:Phospholipid:Chol:PEG-lipid |
| 45:5:48.5:1.5 | Compound:Phospholipid:Chol:PEG-lipid |
| 50:5:43.5:1.5 | Compound:Phospholipid:Chol:PEG-lipid |
| 40:20:40:0 | Compound:Phospholipid:Chol:PEG-lipid |
| 45:20:35:0 | Compound:Phospholipid:Chol:PEG-lipid |
| 50:20:30:0 | Compound:Phospholipid:Chol:PEG-lipid |
| 55:20:25:0 | Compound:Phospholipid:Chol:PEG-lipid |
| 60:20:20:0 | Compound:Phospholipid:Chol:PEG-lipid |
| 40:15:45:0 | Compound:Phospholipid:Chol:PEG-lipid |
| 45:15:40:0 | Compound:Phospholipid:Chol:PEG-lipid |
| 50:15:35:0 | Compound:Phospholipid:Chol:PEG-lipid |
| 55:15:30:0 | Compound:Phospholipid:Chol:PEG-lipid |
| 60:15:25:0 | Compound:Phospholipid:Chol:PEG-lipid |
| 40:10:50:0 | Compound:Phospholipid:Chol:PEG-lipid |
| 45:10:45:0 | Compound:Phospholipid:Chol:PEG-lipid |
| 50:10:40:0 | Compound:Phospholipid:Chol:PEG-lipid |
| 55:10:35:0 | Compound:Phospholipid:Chol:PEG-lipid |
| 60:10:30:0 | Compound:Phospholipid:Chol:PEG-lipid |

Example 19: In Vivo OTC Expression in Animal Models

To assess the ability of OTC-encoding mRNAs to facilitate OTC expression in vivo, mRNA encoding human OTC is introduced into an animal model of human urea cycle disorders caused by OTC-deficiency.

A genetic model of OTC deficiency is the spf$^{ash}$ mutant mouse (Veres et al., Science, 415-417, 1987; Rosenberg et al., Science, 426-428, 1983; Hodges and Rosenberg, Proc. Natl. Acad. Sci. USA, 4142-4146, 1989; Quereshi et al., Pediat. Res., 807-811, 1979). spf$^{ash}$ mice have an x-linked mutation that causes a partial deficiency in OTC. These mice only have about 5-10% of the OTC activity of wild type mice, and have a phenotype of sparse fur and abnormal skin and hair. The spf$^{ash}$ mutation is a guanine to adenine transition of the last nucleotide of the fourth exon of the gene that inefficient pre-mRNA splicing and causes two mutant proteins to be translated from the RNA. One mutant protein has an arginine-to-histidine substitution at amino acid 129, but appears to function normally. The second mutant protein is an elongated non-functional protein that is the product of mis-splicing of the RNA.

The spf$^{ash}$ mutant mice are injected intravenously with 0.5 mg/kg of either control mRNA (non-translated Factor IX (NT-FIX)) or human OTC mRNA. The mRNA is formulated in lipid nanoparticles for delivery into the mice. Mice are sacrificed after 24 hours and OTC protein levels in liver lysates are determined by capillary electrophoresis (CE). Citrate synthase expression is examined for use as a load control. OTC activity is determined using a colorimetric assay, as described in Example 15. Four mice are tested for each human OTC mRNA injection, and for control NT-FIX injections. Treatment with mRNA encoding OTC is expected to reliably induce expression and activity of OTC. Orotic acid levels are also tested in mouse urine (Agilux).

Figure 5:
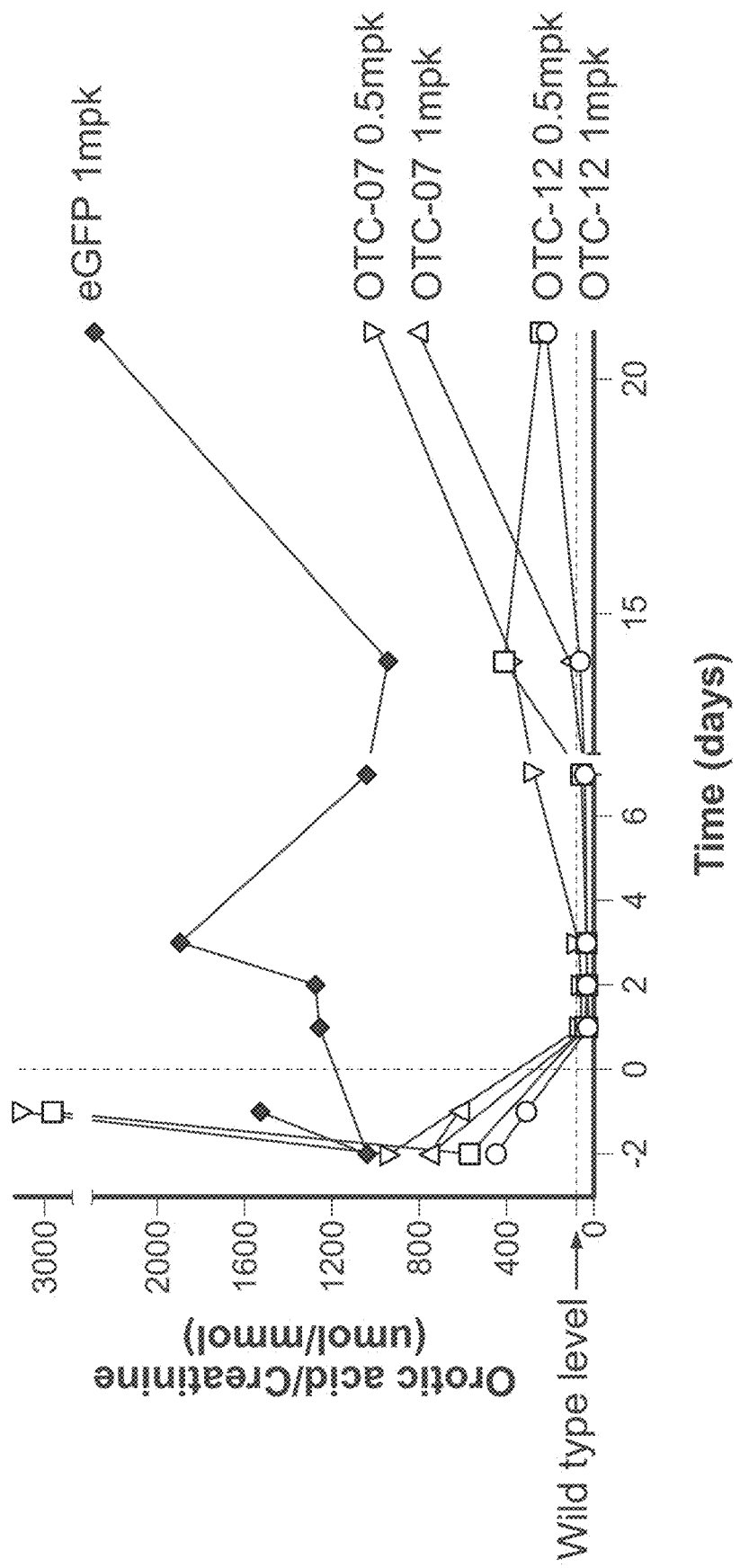
FIG. 5 is a graph showing urinary orotic acid/creatinine levels (μmol/mmol) in spf$^{ash}$ mice for 21 days following injection of the mice with a single 0.5 mg/kg or 1.0 mg/kg dose of a human OTC mRNA construct (OTC-07 or OTC-12) or 1 mg/kg of a control mRNA encoding GFP.

Example 20: In Vivo Duration of Efficacy in Animal Model Following a Single-Dose of OTC mRNA The spf$^{ash}$ mutant mice were injected intravenously with a single dose of human OTC mRNA (either construct OTC-07 (SEQ ID NO:35) or OTC-12 (SEQ ID NO:40)) at either 0.5 mg/kg or 1.0 mg/kg, or a control mRNA encoding eGFP at a dose of 1 mg/kg, via tail vein injection. The mRNA was formulated in lipid nanoparticles (Compound II) for delivery into the mice. Urine was collected from mice 48 hours and 24 hours prior to mRNA injection for urinary orotic acid/creatinine analysis. All mice urine was collected for urinary orotic acid/creatinine levels 24 hours, 48 hours, 72 hours, 7 days, 14 days, or 21 days after dosing for each injected human OTC mRNA and for the injected eGFP control. FIG. 5 shows that administering a single dose of mRNA encoding human OTC (either construct OTC-07 or OTC-12) to spf$^{ash}$ mice led to a substantial and sustained decrease in orotic acid levels for at least 21 days following the mRNA injection.

Figure 6B:
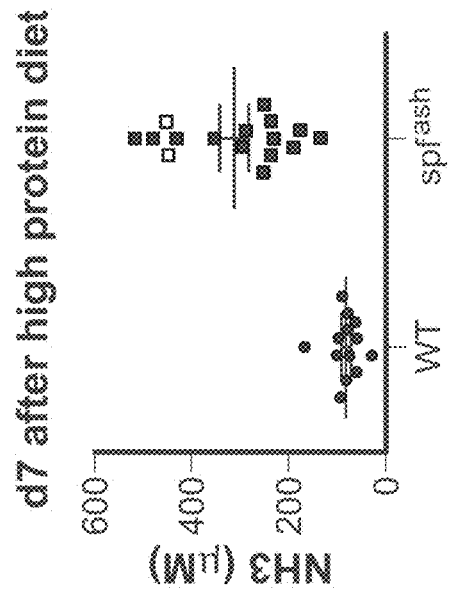
FIG. 6B shows the plasma ammonia levels of wild type and spf$^{ash}$ mice after 7 days of being fed a high protein diet.
Figure 6A:
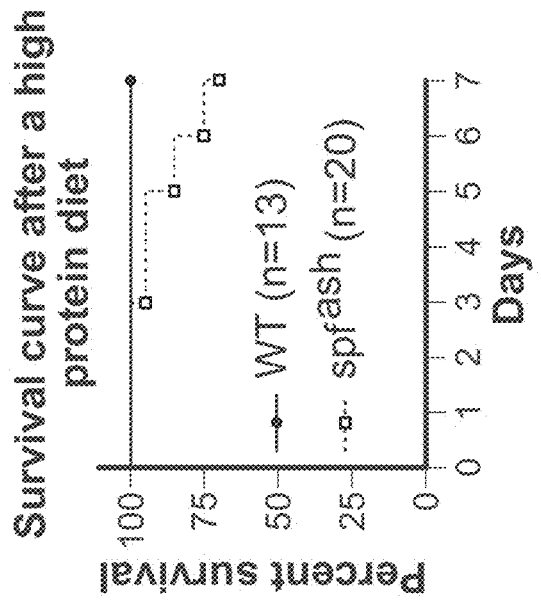
FIG. 6A shows the percent survival of wild type and spf$^{ash}$ mice fed a high protein diet over the course of 7 days.
Figure 6C:
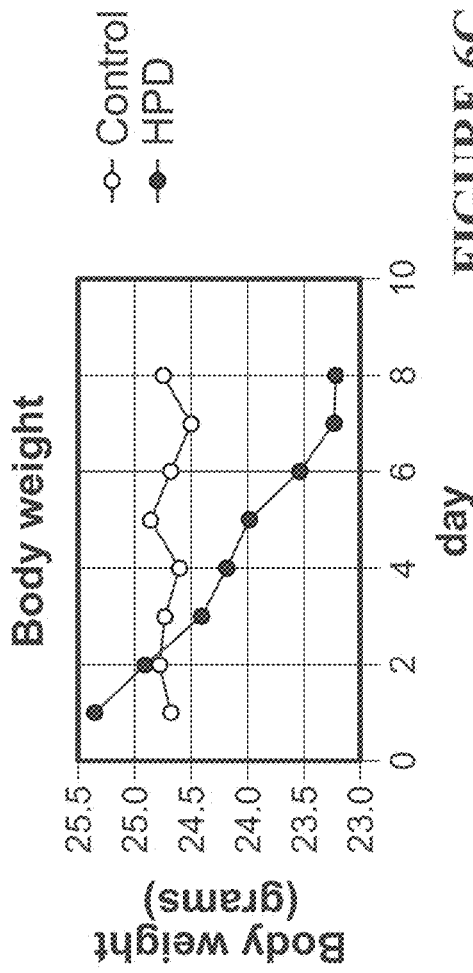
FIG. 6C shows the body weight of spf$^{ash}$ mice fed a high protein diet over the course of 8 days.

Example 21: In Vivo Duration of OTC Activity in Animal Models Maintained on a High Protein Diet Following a Single-Dose of OTC mRNA Spf$^{ash}$ mice have approximately 5-10% of the OTC activity of wild type mice, exhibit elevated urine orotic acid, but have normal plasma ammonia levels. In humans, OTCD can be managed by maintaining a low protein diet. Therefore, spf$^{ash}$ mice were fed a high protein diet to test whether OTCD symptoms in these mice would get worse. FIGS. 6A-C show that a high protein diet exacerbates OTCD in spf$^{ash}$ mice. FIG. 6A shows that spf$^{ash}$ mice given a high protein diet exhibited mortality levels of 10-20% over a span of 7 days. FIG. 6B shows that plasma ammonia levels were elevated in Spf$^{ash}$ mice at 7 days of being fed a high protein diet relative to plasma ammonia levels in wild-type mice. FIG. 6C shows that spf$^{ash}$ mice on a high protein diet ("HPD"; bottom line at 8 days) lose body weight rapidly relative to control mice (top line at 8 days).

Figure 7:
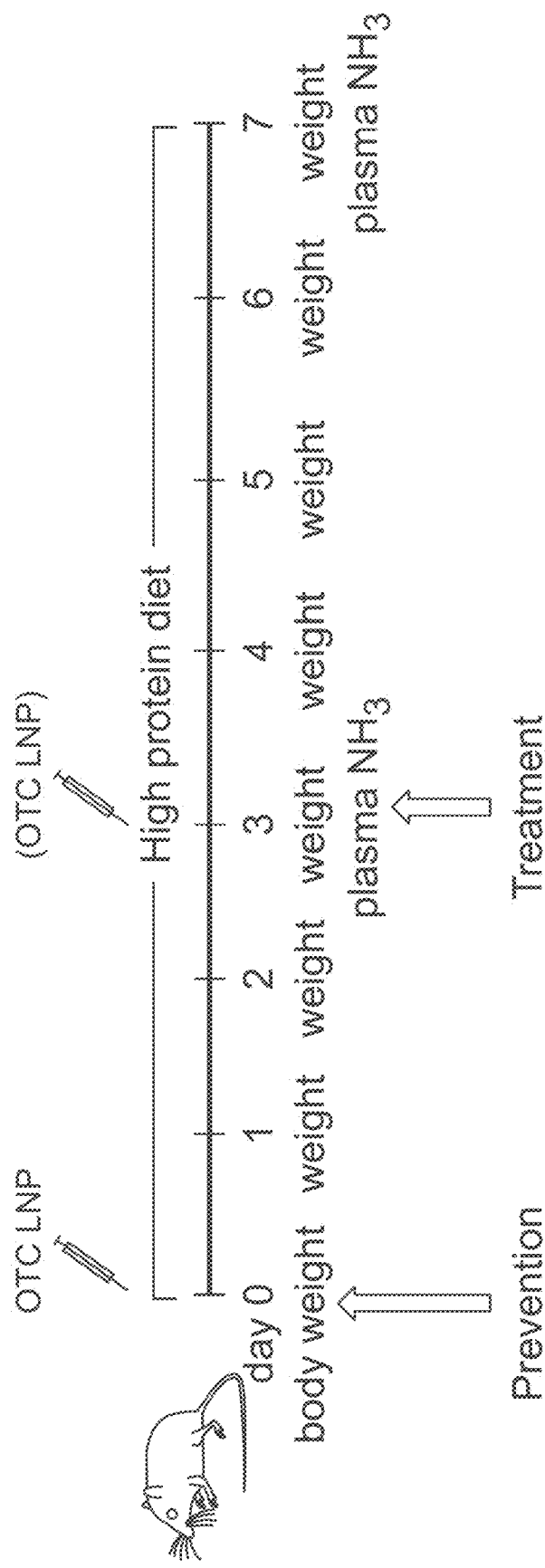
FIG. 7 shows a schematic of an experimental design to test whether administering mRNA encoding human OTC into spf$^{ash}$ mice fed a high protein diet can prevent or treat OTCD symptoms in the mice.

To test whether human OTC mRNA can prevent or treat OTCD in Spf$^{ash}$ mice, spf$^{ash}$ mice were fed a high protein diet (starting at day 0) and administered 1 mg/kg of 1-methyl-pseudouridine modified human OTC mRNA (construct OTC-12; SEQ ID NO:40), or 1 mg/kg mRNA encoding GFP, as a control, via IV tail vein injection. The mRNA encoding OTC, or mRNA encoding GFP, was administered at day 0 to the mice to test whether the OTC mRNA can prevent OTCD. Alternatively, the mRNA encoding OTC was administered to the mice at day 3 to test whether OTC mRNA can treat OTCD. A total of 9-10 mice were included in each group. The mRNA was formulated in lipid nanoparticles (Compound II) for delivery into the mice. The mice were bled for plasma to test ammonia levels (Sigma AA0100-1KT) at day 3 and at day 7 following mRNA injection. Weight loss and mortality were also monitored during the course of the experiment. Test results were compared to results in wild-type mice. FIG. 7 presents the overall design of the experiment.

FIG. 8A shows that spf$^{ash}$ mice on a high protein diet that were administered mRNA encoding human OTC exhibited 100% survival, like the wild-type control mice, over the 7-day course of the study. Mice that were administered the mRNA encoding human OTC at day 3 exhibited over 80% survival. By contrast, spf$^{ash}$ control mice that did not receive an OTC mRNA injection exhibited less than 60% survival over 7 days of high protein diet. The results show that administering human OTC mRNA early (at day 0) can prevent mortality due to OTCD in spf$^{ash}$ mice on a high protein diet. Administering human OTC mRNA later (at day 3) can treat OTCD, reducing mortality in these mice.

FIG. 8B shows that spf$^{ash}$ mice on a high protein diet that were administered mRNA encoding human OTC exhibited no weight loss, similar to the wild-type control mice, over the 7-day course of the study. Mice that were administered the mRNA encoding human OTC at day 3 exhibited significant weight loss, similar to spf$^{ash}$ control mice that did not receive an OTC mRNA injection, from day 0 to day 3, during the period of time before mRNA injection. However, the mRNA-injected mice began to rapidly gain weight after day 3, following the mRNA injection (see arrow; weight gain beginning at about day 4). The spf$^{ash}$ control mice continued to rapidly lose weight during the entire 7-day course of the study. The results show that administering human OTC mRNA early (at day 0) can prevent weight loss due to OTCD in spf$^{ash}$ mice on a high protein diet. Administering human OTC mRNA later (at day 3) can treat OTCD, reversing weight loss in these mice.

FIG. 8C shows that plasma ammonia levels measured at day 3 were elevated in control spf$^{ash}$ mice that were fed a high protein diet and administered mRNA encoding GFP at day 0. Administering human OTC mRNA at day 0 significantly lowered plasma ammonia levels at day 3 in the spf$^{ash}$ mice fed the high protein diet, showing that administering OTC mRNA early (at day 0) can prevent the elevation of ammonia in plasma. FIG. 8D shows that plasma ammonia levels were significantly reduced in spf$^{ash}$ mice at day 7 (after 7 days of being fed a high protein diet) when human OTC mRNA was administered to the mice at either day 0 or at day 3. By comparison, spf$^{ash}$ mice administered GFP mRNA exhibited elevated plasma ammonia levels at day 7. These results show that administering OTC mRNA early (at day 0) can prevent plasma ammonia levels from increasing for at least 7 days, while administering OTC mRNA later (at day 3) can lead to a sharp reduction in elevated plasma ammonia by day 7 (compare FIGS. 8C and 8D).

In addition, OTC protein levels in liver lysates from the injected mice were determined by capillary electrophoresis (CE). Citrate synthase (mitochondrial marker) expression was examined for use as a load control. A commercial rabbit polyclonal anti-OTC antibody (Novus NBP 1-87408) was used to detect OTC, and an anti-citrase synthase antibody (rabbit polyclonal; Abcam ab96600) was used to detect the citrate synthase (mitochondrial marker) load control. Immunohistochemistry of liver cells from mRNA-injected mice was used to confirm the high OTC protein expression, compared to OTC levels and localization in control spf-ash mice (homozygote mutant mice and heterozygous mice) and wild-type mice.

FIG. 9 shows that a high level of mRNA-encoded human OTC protein was expressed in spf$^{ash}$ mice at 6 hours following injection of 1.0 mg/kg of mRNA (construct OTC-12, SEQ ID NO:40) and lasted over the course of at least 7 days. A high level of OTC positive hepatocytes also was detected in the livers of spf$^{ash}$ mice for a duration of at least 7 days following injection of mRNA encoding human OTC (data not shown).

Example 22: In Vivo Duration of Action and Dose Dependency Study in Animal Models Maintained on a High Protein Diet Following a Single-Dose of OTC mRNA To assess the efficacy of OTC mRNA (OTC-12; SEQ ID NO:40) formulated in Compound II/PEG-DMG LNPs on survival, a single dose, one-month study was performed with 10-week-old spf$^{ash}$ mice fed a high protein diet, as described in Example 10. FIG. 10 shows the study outline. Mice were switched to high protein diet three days before mRNA injection (on day −3) and then dosed with 1, 0.5, 0.2 or 0.05 mg/kg of OTC mRNA, or 1 mg/kg of control mRNA encoding eGFP, on day 0 by IV bolus injection (n=14 mice/group). Four mice from each group were sacrificed the next day to assess OTC expression and activity. Capillary electrophoresis was used to measure OTC expression in the liver homogenates of the sacrificed mice using a rabbit polyclonal anti-OTC antibody (NBP1-87408 (NovusBio)). OTC enzymatic activity was determined in liver mitochondrial extracts using the colorimetric assay measuring L-citrulline formation from carbamyl phosphate and ornithine substrates, as described in Example 15. The remaining groups of 10 mice were continued on the high protein diet to determine percent survival over time, and were sacrificed 31 days after mRNA injection (day 31). Plasma was collected from mice one day before mRNA injection (day −1), and at 3, 10, 17, 24, and 31 days after mRNA injection, and plasma ammonia levels were assessed at each time point using a commercially-available kit (Sigma). Body weight was also measured throughout the study.

FIGS. 11A and 11B show the OTC expression and activity results for the groups of 4 mice sacrificed one day after mRNA injection. FIG. 11A shows that there was a dose dependent increase in OTC expression in mice injected with OTC mRNA over the baseline expression in control mice (eGFP mRNA injected). These differences were significant by Student's paired, two-tailed t-Test between control eGFP and the 1 mg/kg and 0.2 mg/kg OTC mRNA dose groups. FIG. 11B shows that OTC activity increased in mice injected with OTC mRNA relative to control mice. An increase in citrulline levels was observed in the two highest OTC mRNA dose groups (1 mg/kg and 0.5 mg/kg) compared to control mice injected with eGFP mRNA. The results were significant for the highest dose group (1 mg/kg OTC mRNA) by Student's two-tailed paired t-Test.

FIG. 12A shows that plasma ammonia increased in the 5 mice in the GFP control group that survived until the end of the study, as expected. Ammonia levels increased from normal levels (~50 μM) to 184 μM at the end of the study, and was significantly higher from the pre-bleed levels of ammonia within 13 days following the switch to a high protein diet (day 10 after mRNA was administered). Mice that were administered the 0.05 mg/kg dose of OTC mRNA had similar plasma ammonia levels as the mice in the eGFP mRNA dose control group at the same time point. By contrast, the remaining three groups of mice that were administered 1, 0.5, and 0.2 mg/kg doses of OTC mRNA exhibited significantly less plasma ammonia levels relative to the eGFP mRNA control mice, and had ammonia levels at or below normal levels (ammonia levels in wild type mice not on a high protein diet; dotted line in graph) at day 10 following mRNA injection. Mice injected with the highest dose of OTC mRNA (1 mg/kg) had plasma ammonia levels that were significantly reduced relative to eGFP control mice at all time points. For the highest dosing group, ammonia levels were significantly lowered relative to the pre-dose ammonia levels on both Day 3 and Day 10 post dosing. Mice injected with 0.5 mg/kg of OTC mRNA had significantly lower plasma ammonia levels only on day 3 post dosing relative to pre-dose levels. For this study, three data points in the pre-dose animals, with values over 200 μM when the average was 58±39 μM, were excluded by Iglewicz and Hoaglin's robust test with a modified Z score of 3.5.

FIG. 12B shows that body weight decreased for the spf$^{ash}$ mice following the switch to high protein diet compared to three wild-type control animals that were not on a high protein diet (Student's t-test, two-tailed, heteroscedastic). Mice that were injected with 0.2 mg/kg or 0.05 mg/kg of OTC mRNA and mice injected with eGFP mRNA continued to lose body mass over time, although the two lower dose groups of OTC mRNA mice exhibited a non-significant trend towards a reduced rate of body mass loss. (Student's t-Test, two-tailed, paired). By contrast, the two higher dose groups of mice that were injected with 1 mg/kg or 0.5 mg/kg of OTC mRNA exhibited a rebound in body weight after mRNA injection, and returned to about the same body weight as the wild-type control animals (not on a high protein diet) within 2 days. The body mass for these mice in the two highest OTC mRNA dose groups matched the body mass of wild-type control mice for several more days before beginning to decease again, and only became significantly lower than the wild-type control mice at 22 days post dosing (Student's t-test, two-tailed, heteroscedastic).

FIG. 13 shows that mice injected with 1 mg/kg of OTC mRNA exhibited a statistically significant increase in survival compared to the control mice injected with eGFP mRNA (by Log-rank (Mantel-Cox) and Gehan-Breslow-Wilsoxon tests ($p<0.05$)). There was a trend towards a dose-dependent change in survival for the other OTC mRNA dose levels relative to the control mice, although none of these differences in survival was statistically significant.

Example 23: Effects of Different Lipid Nanoparticle Formulations on Hepatic Expression of mRNA in Neonatal Mice When mRNA is administered to mice in a formulation of Compound II/PEG-DMG LNPs, the uptake of the injected mRNA into the hepatocytes of the mice is dependent on the cell surface expression of Low-Density Lipoprotein (LDL) Receptor (LDLR). To determine the extent to which mRNA formulations with Compound II/PEG-DMG LNPs are compatible with dosing neonatal mice, the amounts of LDLR in neonatal mice liver cell homogenates were compared to the amounts of LDLR in liver cell homogenates from adult mice. Capillary electrophoresis (CE) was performed on liver cell homogenates from adult (3 mice), versus 1, 4 and 7 day old neonatal mice (4 mice in each group). LDLR expression was normalized to membrane protein ERP72. FIG. 14 shows that the LDLR expression levels were higher in the liver cells of adult mice compared to each group of neonatal mice. For example, expression of LDLR in adult liver cells was approximately 8-fold higher than the expression of LDLR in neonatal mice that were 1 day old.

To test the efficiency of liver uptake of mRNA in neonatal mice using different LNP formulations, a comparative study was performed using mRNA encoding eGFP formulated into three LNP formulations: Compound VI/Compound I, Compound VI/PEG-DMG and Compound II/PEG-DMG. All eGFP mRNA formulations were dosed on Day 0 neonatal mice (shortly after birth) and eGFP expression relative to ERP72 loading control in liver homogenates was determined by CE after sacrificing the mice the next day (as Day 1 neonates). Compound VI/Compound I and Compound II/PEG-DMG LNP formulations were dosed at 1 and 3 mg/kg of eGFP mRNA, and Compound VI/PEG-DMG LNP formulation was dosed at 1 mg/kg of eGFP mRNA only. Five animals were administered Compound IV/Compound I and Compound VI/PEG-DMG, and four animals were administered Compound II/PEG-DMG. One animal was left untreated as a control. FIG. 15 shows that mRNA-expressed eGFP was much lower in Day 1 neonate mice injected with mRNA formulations with Compound II/PEG-DMG LNPs compared to Day 1 neonate mice injected with mRNA formulations with Compound VI/Compound I or Compound VI/PEG-DMG LNPs. Indeed, eGFP expression was approximately 44-fold lower in the liver homogenates of neonatal mice that were injected with 3 mg/kg mRNA formulated in Compound II/PEG-DMG LNPs relative liver homogenates of mice injected with 3 mg/kg mRNA formulated in Compound VI/Compound I LNPs. eGFP was not detected in 3 of 4 animals dosed with 1 mg/kg of mRNA formulated in Compound II/PEG-DMG LNPs.

To assess the duration of eGFP expression in neonatal animals dosed with eGFP mRNA formulated in Compound VI/Compound I and Compound VI/PEG-DMG lipid nanoparticles, groups of 8 day 0 animals were dosed and four animals each were sacrificed on day 1 and day 7 (Day 1 and Day 7 neonates, respectively) to assess eGFP expression relative to ERP72 loading control in liver homogenates by CE. eGFP mRNA was dosed at 1 and 3 mg/kg in Compound VI/Compound I LNP formulations/PEG-DMG and eGFP mRNA was dosed at 1 mg/kg in Compound VI/PEG-DMG LNP formulations. FIG. 16 shows that the levels of mRNA-expressed eGFP were similar when formulated with Compound VI/Compound I or Compound VI/PEG-DMG, with slightly higher expression observed when 1 mg/kg of mRNA was formulated in Compound VI/PEG-DMG LNPs relative to Compound VI/Compound I LNPs at both day 1 and day 7. In all cases, mRNA expression was markedly decreased in day 7 neonate mice compared to in day 1 neonatal mice.

Example 24: Repeat Dose Study Assessing Response Due to OTC mRNA in an Animal Model Maintained on a High Protein Diet A repeat dose study is performed to evaluate whether repeat administration of OTC mRNA could improve the symptoms of OTCD. Spf$^{ash}$ mice are administered either 0.25 mg/kg or 0.5 mg/kg of OTC mRNA, or 0.5 mg/kg of mRNA encoding eGFP as a control, via tail vein injection (n=12 mice per group) every 2 weeks, starting 3 days after the mice are switched to a high protein diet. As another control, wild-type mice are administered 0.5 mg/kg of mRNA encoding eGFP (n=12 mice) every two weeks, starting 3 days after beginning a high protein diet. The survival, body weight, plasma ammonia, and urine orotic acid levels are evaluated throughout the study (daily for survival, twice a week for body weight, and weekly for the other parameters). At the end of the study, liver OTC expression and activity are determined. In addition, clinical chemistry measurements are performed on terminal plasma, and anti-OTC antibody and anti-PEG IgM levels are determined.

All of the wild-type control mice are expected to survive and gain weight over the course of the study, plasma ammonia levels are expected to remain at approximately 50 uM, and orotic acid levels are expected to remain constant. OTC expression and activity are expected to be at normal endogenous levels at the end of study, no anti-OTC antibodies are expected to be present, and few anti-PEG antibodies are expected to be in circulation.

Spf$^{ash}$ mice dosed with eGFP mRNA are expected to lose weight following the switch to high protein diet and the majority of the animals are not anticipated to survive the course of the study. Plasma ammonia and urine orotic acid levels are expected to increase during the study. OTC expression and activity levels are expected to be undetectable, or at around 5-10% of the levels in wild-type mice, when the mice are terminated. It is also anticipated that there will be no anti-OTC antibodies and very low anti-PEG IgM levels in these mice.

The spf$^{ash}$ mice dosed with OTC mRNA are expected to lose body weight following the switch to high protein diet, and then, following injection of OTC mRNA, the body weight of these mice is expected to either rebound (increase) or be maintained at approximately 10% lower than the weight of wild-type control animals. It is anticipated that the weight of these mice will probably increase for the first three days after dosing with mRNA, and possibly drop off a little in the last few days before the next mRNA dose is administered. Plasma ammonia levels are expected to initially rise after the spf$^{ash}$ mice are switched to a high protein diet, but then decrease after the first dose of OTC mRNA and remain below 50 uM between mRNA injections. A similar trend is expected for urine orotic acid levels, wherein orotic acid levels are expected to rise after the mice are switched to a high protein diet, and then decrease after mRNA injections (and remain lower between injections). Both plasma ammonia and urine orotic acid levels may begin to rise again in the last few days before the next mRNA dose. At end of study, the presence of OTC expression and activity are expected to be confirmed and the levels one day after the last dose of OTC mRNA are anticipated to be comparable to the levels in wild-type animals. Most animal are expected to survive the course of the study if the administered OTC mRNA consistently lowers ammonia after each repeated dose. In this scenario, no anti-OTC or anti-PEG antibodies are expected to be detected.

Example 25: Development of an Inducible OTC Knockout Animal Model

An OTC mutant animal model is developed that allows for tamoxifen-induced knockout of the Spf gene in mice. Normal endogenous OTC protein in expressed in these mutant mice, until tamoxifen is administered. Administration of tamoxifen induces Cre-mediated recombination that leads to knockout of Spf, and the prevention of further endogenous OTC protein expression in particular tissues, including in the liver. The expression and activity of human OTC mRNA is tested in this mutant mouse background, as described in Examples 21 and 22.

Example 26: In Vivo Duration of Action Study in an Inducible OTC Knockout Animal Model Following a Single-Dose of OTC mRNA In this study, the effects of administering OTC mRNA are tested in the inducible mouse model described in Example 25, that is engineered to have OTC knocked out in liver following exposure to tamoxifen. To induce the OTC phenotype, mice will be treated with 75 mg/kg tamoxifen by intraperitoneal injection each day for 5 days. Animals will then be monitored for up to 3 weeks to determine whether, and to what extent, plasma ammonia levels increased. After approximately 3 weeks, plasma ammonia levels are expected to be elevated. At this time, 3 groups (8 inducible animals per group) will be administered 0.5 mg/kg of eGFP mRNA (control), 0.25 mg/kg of OTC mRNA, or 0.5 mg/kg of OTC mRNA via tail vein injection. As another control, a group of 8 wild type mice will be injected with 0.5 mg/kg of eGFP mRNA. Animals will then be followed for up to 4 weeks for survival, changes in body weight, and changes in plasma ammonia and urine orotic acid levels.

It is anticipated that the wild-type control mice dosed with mRNA encoding eGFP will all survive and gain weight over the course of the study. The plasma ammonia levels are expected to stay at approximately 50 uM, and the orotic acid levels are expected to be constant, in these mice throughout the study.

The inducible OTC knockout mice that are dosed with eGFP mRNA (and exposed to tamoxifen) are expected to lose weight over the course of the study, and the majority of animals are not expected to survive. The plasma ammonia and urine orotic acid levels are expected to increase over time.

The inducible OTC knockout mice that are dosed with OTC mRNA (and exposed to tamoxifen) are expected have higher survival rates, and decreased plasma ammonia and urine orotic acid levels, relative to the inducible OTC knockout mice that are dosed with eGFP mRNA (and exposed to tamoxifen). The inducible OTC knockout mice that are dosed with OTC mRNA are also expected to better maintain body weight throughout the study compared to the mice that are dosed with eGFP mRNA.

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

What is claimed is:

1. A polynucleotide comprising a messenger RNA (mRNA) comprising:
   (i) a 5' UTR;
   (ii) an open reading frame (ORF) encoding a human ornithine transcarbamylase (OTC) polypeptide, wherein the ORF has at least 99% sequence identity to the nucleic acid sequence of SEQ ID NO:14;
   (iii) a stop codon; and
   (iv) a 3' UTR.

2. The polynucleotide of claim 1, wherein the ORF comprises the nucleic acid sequence of SEQ ID NO:14.

3. The polynucleotide of claim 2, wherein all uracils in the polynucleotide are N1-methylpseudouracils.

4. A pharmaceutical composition comprising the polynucleotide of claim 3 and a delivery agent.

5. A method of treating ornithine transcarbamylase deficiency (OTCD) in a human subject in need thereof, the method comprising administering to the human subject an effective amount of the pharmaceutical composition of claim 4.

6. The method of claim 5, wherein the pharmaceutical composition is administered intravenously.

7. A pharmaceutical composition comprising the polynucleotide of claim 2 and a delivery agent.

8. A method of treating ornithine transcarbamylase deficiency (OTCD) in a human subject in need thereof, the method comprising administering to the human subject an effective amount of the pharmaceutical composition of claim 7.

9. The method of claim 8, wherein the pharmaceutical composition is administered intravenously.

10. The polynucleotide of claim 1, wherein the OTC polypeptide consists of the amino acid sequence of SEQ ID NO:1.

11. The polynucleotide of claim 10, wherein all uracils in the polynucleotide are N1-methylpseudouracils.

12. A pharmaceutical composition comprising the polynucleotide of claim 11 and a delivery agent.

13. A method of treating ornithine transcarbamylase deficiency (OTCD) in a human subject in need thereof, the method comprising administering to the human subject an effective amount of the pharmaceutical composition of claim 12.

14. The method of claim 13, wherein the pharmaceutical composition is administered intravenously.

15. A pharmaceutical composition comprising the polynucleotide of claim 10 and a delivery agent.

16. A method of treating ornithine transcarbamylase deficiency (OTCD) in a human subject in need thereof, the method comprising administering to the human subject an effective amount of the pharmaceutical composition of claim 15.

17. The method of claim 16, wherein the pharmaceutical composition is administered intravenously.

18. The polynucleotide of claim 1, wherein the mRNA comprises a 5' terminal cap.

19. The polynucleotide of claim 18, wherein the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

20. The polynucleotide of claim 1, wherein the mRNA comprises a poly-A region.

21. The polynucleotide of claim 20, wherein the poly-A region has about 10 to about 200, about 20 to about 180, about 50 to about 160, about 70 to about 140, or about 80 to about 120 nucleotides in length.

22. The polynucleotide of claim 1, wherein the mRNA comprises at least one chemically modified nucleobase, sugar, backbone, or any combination thereof.

23. The polynucleotide of claim 22, wherein the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

24. The polynucleotide of claim 23, wherein all uracils in the polynucleotide are N1-methylpseudouracils.

25. A pharmaceutical composition comprising the polynucleotide of claim 1 and a delivery agent.

26. A method of treating ornithine transcarbamylase deficiency (OTCD) in a human subject in need thereof, the method comprising administering to the human subject an effective amount of the pharmaceutical composition of claim 25.

27. The method of claim 26, wherein multiple administrations of the pharmaceutical composition are administered to the human subject.

28. The method of claim 26, wherein the administration to the subject is about once a week, about once every two weeks, or about once a month.

29. The method of claim 26, wherein the pharmaceutical composition is administered intravenously.

* * * * *

SEQUENCE LISTING

```
<160> NUMBER OF SEQ ID NOS: 226

<210> SEQ ID NO 1
<211> LENGTH: 354
<212> TYPE: PRT
<213> ORGANISM: Homo sapiens

<400> SEQUENCE: 1

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
```

```
                65                  70                  75                  80
Ser Leu Gly Met Ile Phe Glu Lys Arg Ser Thr Arg Thr Arg Leu Ser
                    85                  90                  95

Thr Glu Thr Gly Phe Ala Leu Leu Gly Gly His Pro Cys Phe Leu Thr
                100                 105                 110

Thr Gln Asp Ile His Leu Gly Val Asn Glu Ser Leu Thr Asp Thr Ala
                115                 120                 125

Arg Val Leu Ser Ser Met Ala Asp Ala Val Leu Ala Arg Val Tyr Lys
            130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
                180                 185                 190

Trp Ile Gly Asp Gly Asn Asn Ile Leu His Ser Ile Met Met Ser Ala
            195                 200                 205

Ala Lys Phe Gly Met His Leu Gln Ala Ala Thr Pro Lys Gly Tyr Glu
210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
                260                 265                 270

Glu Lys Lys Lys Arg Leu Gln Ala Phe Gln Gly Tyr Gln Val Thr Met
            275                 280                 285

Lys Thr Ala Lys Val Ala Ala Ser Asp Trp Thr Phe Leu His Cys Leu
290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

<210> SEQ ID NO 2
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
augcuguuua aucugaggau ccuguuaaac aacgcagcuu uuagaaacgg ucacaacuuc    60
augguucgaa auuucggug uggacaacca cuacagaaua aagugcagcu gaagggccgu    120
gaccuucuca cuuugaagaa cuuuaccgga gaagaaauua aauauaugcu cuggcuauca    180
gcagaucuga aauuuaggau uaagcagaaa ggagaguauu ugccuuuauu gcaagggaag    240
uccuuaggca ugauuuucga gaagagaagu acucgaacaa gauugcuac agaaacaggc    300 uuugcacuuc ugggaggaca uccuuguuuu cuuaccacac aagauauuca uuugggugug    360
```

-continued

| | |
|---|---|
| aacgaaaguc ucacggacac ggcccgugua uugucuagca uggcagacgc aguauuggcu | 420 |
| cgaguguaua aacaaucaga uuuggacacc cuggcuaaag aagcauccau cccaauuauc | 480 |
| aacgggcugu cagauuugua ccauccuauc cagauccugg cugauuaccu cacgcuccag | 540 |
| gaacacuaua gcucucugaa aggucuuacc cucagcugga ucggggacgg gaacaauauc | 600 |
| cugcacucca ucaugaugag cgcagcgaaa uucggaaugc accuucaggc agcuacucca | 660 |
| aaggguuacg agccggacgc uaguguaacc aaguuggcag agcaguacgc caaagagaac | 720 |
| gguaccaagc uguugcugac aaacgaucca uggaagcag cgcacggagg caacguauua | 780 |
| auuacagaca cuuggauaag cauggggacaa gaagaggaga agaagaagcg gcuccaggcu | 840 |
| uccaagguu accagguuac aaugaagacu gcuaaaguug cugccucuga cuggacauuc | 900 |
| uuacacugcu ugcccagaaa gccagaagaa guggacgacg aagucuuuua uucuccucga | 960 |
| ucacuagugu ucccagaggc agagaacaga aaguggacaa ucauggcugu caugguguca | 1020 |
| cugcugacag auuacucacc ucagcuccag aagccuaaau uu | 1062 |

<210> SEQ ID NO 3
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 3
gggaaauaag agagaaaaga agaguaagaa gaaauauaag agccacc        47

<210> SEQ ID NO 4
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 4

| | |
|---|---|
| ugauaauagg cuggagccuc gguggccuag cuucuugccc cuugggccuc ccccagccc | 60 |
| cuccuccccu uccugcaccc guaccccuc cauaaaguag gaaacacuac agugucuuu | 120 |
| gaauaaaguc ugagugggcg gc | 142 |

<210> SEQ ID NO 5
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 5

| | |
|---|---|
| augcuguuua accugcggau ccuccugaac aacgccgccu uucggaacgg ccacaacuuc | 60 |
| auggugcgga acuucaggug uggucagccu cugcagaaca aggugcagcu uaaaggcaga | 120 |
| gaucuguuga cccugaagaa cuucacuggc gaggagauca aguacaugcu cuggcugucc | 180 |
| gcagaccuaa aguccgcau caagcagaag ggagaguacc ugccacugcu gcagggcaag | 240 |
| agccugggca ugauuuucga gaagagagc acaaggacca gacugucuac agagacagga | 300 |
| uuugcccugu ugggaggaca ucccugcuuc cugaccaccc aggauaucca ucuggcguc | 360 |

```
aacgagagcc ugaccgacac cgccagaguu cucuccagca uggccgacgc ugugcuggcc    420
cggguguaca aacaaagcga ccuggauacc cuggcaaagg aggccaguau ccccauuauc    480
aacggucuga gcgaucuuua ccaucccaua cagauccugg ccgauuaccu gacccuccag    540
gaacacuaca gcagccucaa agggcugacg cucagcugga ucggcgacgg aaacaacauu    600
cuucacucca ucaugaugag cgcugccaag uucgggaugc accugcaggc cgccacaccc    660
aagggcuacg agcccgacgc uucggucacu aagcuggccg agcaguacgc caaggagaac    720
ggcacaaagc ugcugcugac caacgauccu cuggaagccg cccacggcgg caacgugcug    780
aucacagaca cuuggaucag cauggggcag gaggaggaga agaagaagag acugcaggcu    840 uccagggcu aucaggugac caugaagacu gccaaggugg ccgcgagcga cuggaccuuc    900
cugcauuguc ugccuagaaa gcccgaggag guggacgacg aggguucua cucucccagg    960 ucccuggugu ucccagaggc cgagaauaga aaguggacua uuauggccgu gauggugucu   1020
cugcucaccg auuauccccc ucagcugcag aagccaaagu uu                      1062
```

<210> SEQ ID NO 6
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
augcuguuua accucaggau ccugcugaac aacgccgcau ucagaaacgg acacaacuuu     60
auggugagga acuuccggug cggacagccu cugcagaaca agguucaacu gaagggccgg    120
gaccugcuga cccucaagaa cuucaccggc gaagagauca aauacaugcu cuggcugagc    180
gccgaccuga aguucagaau caaacagaag ggagaguacu ugccccugcu ucagggaaag    240
agccucggca ugaucuuuga agaggagc acccggaccc ggcugagcac cgagacgggu    300
uuugcccucu uggcggguca ucccugcuuu ucaccacac aggacaucca ccugggugug    360
aacgagagcc ucaccgacac cgcaagggug cugagcagca uggcagacgc cgucuggcu    420 cgcguguaua agcaguccga ucucgauacc cuggccaaag aggcaagcau cccuauuauc    480
aacggccuga gcgauuugua ccauccaauc cagauccuug ccgacuaucu gacccugcag    540
gagcacuaca gcuccgaa ggggcucacc cugucuugga ugggacgg uaacaauauu       600 cugcacagca ucaugaugag ugccgccaag uucggcaugc accugcaggc cgcaccccu    660 aagggcuacg agccgacgc cuccgugacc aagcuggcug aacaguacgc aaaggagaac    720
ggaaccaagc uucugcucac caacgaucca cuggaggccg cccacggcgg caacgugcug    780
aucacagaca ccuggauuag caugggcag gaggaggaga agaagaagag acugcaggca    840
uuucagggau accaaguuac caugaagacc gccaaggugg ccgcuucaga uuggacauuc    900
cugcauugcc ugccacggaa accagaggag gucgacgacg aggguucua cagccccaga    960 agccucgugu uccccgaggc ugagaacaga aaguggacga ucauggccgu gauggugagu   1020
uuacugaccg acuauucgcc ccagcuccag aaaccaaagu uc                      1062
```

<210> SEQ ID NO 7
<211> LENGTH: 1062
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 7
augcuguuca accugcggau ccugcugaac aacgccgccu uccggaacgg ccacaacuuc      60
auggugcgga acuuccggug cggccagccc cugcagaaca aggugcagcu gaagggccgg     120
gaccugcuga cccugaagaa cuucaccggc gaggagauca aguacaugcu guggcugagc     180
gccgaccuga aguuccggau caagcagaag ggcgaguacc ugccccugcu gcagggcaag     240
agccugggca ugaucuucga agcggagc acccggaccc ggcugagcac cgagacuggc       300
uucgcccugc ugggcggcca ccccugcuuc cugaccaccc aggacaucca ccugggcgug     360
aacgagagcc ugaccgacac cgcccggguc ugagcagca uggccgacgc cgucuggcc       420 agaguguaca agcagagcga ccuggacacc cuggccaagg aggccagcau ccccaucauc     480
aacggcuuga ugaccuguga ccaccccauc cagauccugg ccgacuaccu cacccugcag     540
gagcacuaca gcagccucaa ggggcugaca cucagcugga ucggcgacgg caacaacauc     600
cugcacagca ucaugaugag cgcugccaag uucggcaugc accugcaggc cgccacaccc     660
aagggcuacg agcccgacgc cagcgugacc aagcuggccg agcaguacgc uaaggagaac     720
ggcacaaagc ugcugcugac aaacgaccca cuggaggccg cccacggcgg caacgugcug     780
aucacagaua cuuggaucag cauggggcag gaggaggaga agaagaagcg gcugcaggcg     840 uccagggcu accaggugac caugaagacc gccaaggugg ccgccagcga cuggaccuuc     900
cugcacugcc ugccccggaa gcccgaggag guggacgacg aggguuucua cagcccucgg     960
agccuggugu uccccgaggc cgagaaccgg aaguggacca ucauggccgu gauggugagu    1020
cugcugacug acuacagucc ucagcugcag aagcccaagu uc                       1062

<210> SEQ ID NO 8
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
augcuguuca accugcggau ccugcugaac aacgccgccu uccggaacgg ccacaacuuc      60
auggugcgga acuuccggug cggccagccc cugcagaaca aggugcagcu gaagggccgg     120
gaccugcuga cccugaagaa cuucaccggc gaggagauca aguacaugcu guggcugagc     180
gccgaccuga aguuccggau caagcagaag ggcgaguacc ugccccugcu gcagggcaag     240
agccugggca ugaucuucga agcggagc acccggaccc ggcugagcac cgaaaccggc      300
uucgcccugc ugggcggcca ccccugcuuc cugaccaccc aggacaucca ccugggcgug     360
aacgagagcc ugaccgacac cgcccggguc ugagcagca uggccgacgc cgucuggcu       420 aggguguaca agcagagcga ccuggacacc cuggccaagg aggccagcau ccccaucauc     480
aacggccugu ccgacuugua ccaccccauc cagauccugg ccgacuaccu gacccuucag     540
gagcacuaca gcagccugaa aggucugaca cugagcugga ucggcgacgg caacaacauc     600
cugcacagca ucaugaugag cgcugccaag uucggcaugc accugcaggc cgccacgccg     660
aagggcuacg agcccgacgc cagcgugacc aagcuggccg agcaguacgc caaggagaac     720
ggcacuaagc uacugcucac caacgauccc cuggaggccg cccacggcgg caacgugcug     780
```

```
aucacagaca ccuggaucag caugggccag gaggaggaga agaagaagcg gcugcaggcu    840
uuccagggcu accaggugac caugaagacc gccaaggugg ccgccagcga cuggaccuuc    900
cugcacugcc ugccccggaa gcccgaggag guggacgacg aggusucua cagcccacgg    960 agccuggugu uccccgaggc cgagaaccgg aaguggacca ucauggccgu gauggugagc   1020
cucuugaccg auuacucacc ccagcugcag aagcccaagu uc                     1062

<210> SEQ ID NO 9
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
augcuguuca accugcggau ccugcugaac aacgccgccu uccggaacgg ccacaacuuc     60
auggugcgga acuuccggug cggccagccc cuccagaaca agguccagcu caagggccgc    120
gaccuccuca cccucaagaa cuucaccggc gaggagauca aguacaugcu cuggcucucc    180
gccgaccuca aguccgcau caagcagaag ggcgaguacc ugccccuccu ccagggcaag    240
ucccucggca ugaucuucga gaagcgcucc acccgcaccc gcucuccac cgaaaccggc    300 uucgcccucc ucggcggcca ccccugcuuc cucaccaccc aggacaucca ccucggcguc    360
aacgagcccc ucaccgacac cgcccgcguc cucuccucca uggccgacgc cguccuggcu    420
agaguguaca agcagguccga ccucgacacc cucgccaagg aggccuccau ccccaucauc    480
aacggccuca gcgaucucua ccaccccauc cagauccucg ccgacuacu ugacccugcag    540 gagcacuacu ccucccucaa ggguuuaacg cuguccugga ucggcgacgg caacaacauc    600
cuccacucca ucaugauguc cgccgccaag uucggcaugc accuccagge cgccacacca    660 aagggcuacg agcccgacgc cuccgucacc aagcucgccg agcaguacgc caaagagaac    720
ggcacgaagc ugcugcugac uaacgauccc cucgaggccg cccacggcgg caacguccuc    780
aucaccgaua ccuggaucuc caugggccag gaggaggaga agaagaaga gcugcaggcc    840 uuccagggcu accaggucac caugaagacc gccaaggucg ccgccuccga cuggaccuuu    900
cuccacugcc ugcucucgcaa gcccgaggag gucgacgacg agucuucua cucaccucgc    960 ucccucgucu uccccgaggc cgagaaccgc aaguggacca ucauggccgu caugugucu   1020 cuccuaacug acuacagucc ccagcuccag aagcccaagu uc                     1062

<210> SEQ ID NO 10
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
augcuguuca accugagaau ccugcugaac aacgccgccu ucagaaacgg ccacaacuuc     60
augguucgaa auuucggug uggacaacca cuacagaaca aagugcagcu gaagggcaga    120
gaccugcuga cccugaagaa cuucaccggc gaggagauca aguacaugcu guggcugagc    180
gccgaccuga aguucagaau caagcagaag ggcgaguauu ugccuuuauu gcaagggaag    240
```

| | |
|---|---|
| uccuuaggca ugaucuucga gaagagaagc accagaaccagacugagcac cgagaccggc | 300 |
| uucgcccugc ugggcggcca ccccugcuuc cugaccacccaggacaucca ccugggcgug | 360 |
| aacgagagcc ugaccgacac cgccagagug cugagcagcauggccgacgc cgugcuggcc | 420 |
| agaguguaca agcagagcga ccuggacacc cuggccaaggaggccagcau ccccaucauc | 480 |
| aacggccuga gcgaccugua cccccccaucagauccuggccgacuaccugacccugcag | 540 |
| gagcacuaca gcagccugaa gggcugaccc ugagcuggaucggcgacgg caacaacauc | 600 |
| cugcacagca ucaugaugag cgccgccaag uucggcaugcaccugcaggc cgccacuccc | 660 |
| aagggcuacg agcccgacgc cagcgugacc aagcuggccgagcaguacgc caaggagaac | 720 |
| ggcaccaagc ugcugcugac aaacgauccauuggaagcagcgcacggaggcaacgugcug | 780 |
| aucaccgaca ccuggaucag caugggccag gaggaggagaagaagaagagacugcaggcc | 840 |
| uccagggcuaccaggugac caugaagacc gccaaggugg ccgccagcga cuggaccuuc | 900 |
| cugcacugcc ugcccagaaa gcccgaggag guggacgacgagguguucua cagcccccaga | 960 |
| agccuggugu uccccgaggc cgagaacaga aaguggaccaucauggccgu gauggugagc | 1020 |
| cugcugaccg acuacagccc ucagcugcag aagcccaagu uc | 1062 |

<210> SEQ ID NO 11
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 11

| | |
|---|---|
| augcuguuca accugagaau ccugcugaac aacgccgccuucagaaacgg ccacaacuuc | 60 |
| auggugagaa acuuccggug cggccagccu cugcagaacaaggugcagcu gaagggcaga | 120 |
| gaucugcuga cccugaagaa cuucaccggc gaggagaucaaguacaugcu guggcugagc | 180 |
| gccgaccuga aguucagaau caagcagaag ggcgaguaccugccucugcu gcagggcaag | 240 |
| agccugggca ugaucuucga agagaagc accagaaccagacugagcac cgaaaccggc | 300 |
| uucgcccugc ugggcggaca cccuugcuuc cugaccacccaggacaucca ccugggcgug | 360 |
| aacgagagcc ugaccgacac cgccagagug cugagcagcaggcugacgc cgugcuggcc | 420 |
| agaguguaca agcaguccga ccuggauacc cuggccaagg aggccagcau cccuaucauc | 480 |
| aacggccuga gcgaccugua cccccccaucagauccuggccgacuaccugacccugcag | 540 |
| gagcacuaca gcagccugaa gggcugacgc ugagcuggaucggcgacgg caacaacauc | 600 |
| cugcacagca ucaugaugag cgccgccaag uucggcaugcacuugcaagccgccaccccu | 660 |
| aagggcuacg agccugacgc cuccgugacc aagcucgccgagcaguacgc caaggagaac | 720 |
| ggcaccaagc ugcugcugac caacgacccu cuggaggccgcccacggcgg caacgugcug | 780 |
| aucaccgaca ccuggaucag caugggccag gaggaggagaagaagaagagacugcaggcc | 840 |
| uuccagggcu accaggugac caugaagacc gccaaggugg ccgccagcga cuggaccuuc | 900 |
| cugcacugcc ugccuagaaa gcccgaggag guggacgacg agguguucua cagcccuaga | 960 |
| agccuggugu ucccugaggc cgagaacaga aaguggaccaucauggccgu gauggugagc | 1020 |
| cugcugaccg auuacagccc acagcugcag aagccuaagu uc | 1062 |

<210> SEQ ID NO 12
<211> LENGTH: 1062

<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
augcuguuca accugagaau ccugcugaac aacgccgccu cagaaacgg ccacaacuuc      60 auggugagaa acuucaggug cggccagccu cugcagaaca aggugcagcu gaagggccgc     120
gaucugcuga cucugaagaa cuucaccggc gaggagauca aguacaugcu cuggcugagc     180
gcagaccuga aauucagaau caagcagaag ggcgaguacc ugccccugcu ccaaggcaag     240
agccugggca ugaucuucga aagagaagc accagaacca gacugagcac cgaaaccggc     300
uucgcccugc ugggaggcca cccuugcuuc cugaccaccc aggacaucca ccucggcgug     360
aacgaauccc ugaccgauac ggccagaguc cugagcucaa uggccgacgc cguccuggcg     420
agaguguaca agcaguccga ccucgacacc cuggccaaag aggccagcau cccuaucauc     480
aacggccuga gcgaccugua ccacccuauc cagauucucg cugacuaucu gacccugcag     540
gagcacuacu ccagccuaaa gggccucacc cuuagcugga ucggcgacgg caacaacauc     600
cugcacagca ucaugaugag cgccgccaag uucggcaugc accuccaggc cgccacaccg     660 aaggguacg aaccggacgc cagcgugacu aagcucgccg agcaguacgc caaggagaac     720
ggcaccaagc ugcugcugac caacgacccu cuggaggccc ucacggcgg caacguucug     780 auuaccgaca ccuggaucag caugggccag gaggaggaga agaagaagag acugcaggcc     840
uuccagggcu accaggugac uaugaagacg gccaaagugg ccgccuccga cuggaccuuc     900
cuccacugcc ugccuagaaa gccugaggag guggacgacg agguguucua cagcccuaga     960
agccuggugu cccugaggc cgagaacaga aaguggacca ucauggccgu gaugguguccc    1020 cugcucaccg auuacucccc ucagcuccag aagccuaagu uc                       1062
```

<210> SEQ ID NO 13
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
augcuguuca accugagaau ccugcugaac aacgccgccu cagaaacgg ccacaacuuc      60 auggugagaa acuucaggug cggccagccu cugcagaaca aggugcagcu gaagggcaga     120
gaucugcuga cccugaagaa cuucaccggc gaggagauca aguacaugcu guggcugagc     180
gccgaccuga aguucagaau caagcagaag ggcgaguacc ugccucugcu gcagggcaag     240
agccugggca ugaucuucga aagagaagc accagaacca gacugagcac cgagacgggc     300
uucgcccugc ugggcggcca cccuugcuuc cugaccaccc aggacaucca ccugggcgug     360
aacgagagcc ugaccgacac cgccagagug cugagcagca uggccgacgc cgugcuggcu     420
agaguguaca agcagagcga ccuggacacc cuggccaagg aggccagcau cccuaucauc     480
aacggccuua gugaucugua ccacccuauc cagauccugg ccgacuaccu aacccugcag     540
gagcacuaca gcagccugaa gggucuuacc cugagcugga ucggcgacgg caacaacauc     600
cugcacagca ucaugaugua cgccgccaag uucggcaugc accugcaggc cgccacccu     660
```

| aagggcuacg aaccagacgc cagcgugacc aagcuggccg agcaguacgc caaggagaac | 720 |
| ggcaccaagc uucugcuuac caacgacccu cuggaggccg cccacggcgg caacgugcug | 780 |
| aucacggaca ccuggaucag cauggggccag gaggaggaga agaagaagag acuccaagcu | 840 |
| uuccagggcu accaggugac caugaagacc gccaaggugg ccgccagcga cuggaccuuc | 900 |
| cugcacugcc ugccuagaaa gccugaggag guggacgacg agguguucua cagcccuaga | 960 |
| agccuggugu ucccugaggc cgagaacaga aaguggacca ucauggccgu gauggugucc | 1020 |
| uugcuuacag acuauagucc ucagcugcag aagccuaagu uc | 1062 |

<210> SEQ ID NO 14
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

| augcuguuca accugcggau ccugcugaac aacgccgccu uccggaacgg ccacaacuuc | 60 |
| auggugcgga acuuccggug cggccagccc cugcagaaca aggugcagcu gaagggccgg | 120 |
| gaccugcuga cccugaagaa cuucaccggc gaggagauca aguacaugcu guggcugagc | 180 |
| gccgaccuga aguccggau caagcagaag ggcgaguacc ugcccccugcu gcagggcaag | 240 |
| agccugggca ugaucuucga gaagcggagc acccggaccc ggcugagcac cgagaccggc | 300 |
| uucgcccugc ugggcggcca ccccugcuuc cugaccaccc aggacaucca ccugggcgug | 360 |
| aacgagagcc ugaccgacac cgcccggggug cugagcagca uggccgacgc cgugcuggcc | 420 |
| cggguguaca agcagagcga ccuggacacc cuggccaagg aggccagcau ccccaucauc | 480 |
| aacggccuga gcgaccugua ccaccccauc cagauccugg ccgacuaccu gacccugcag | 540 |
| gagcacuaca gcagccugaa gggccugacc cugagcugga ucggcgacgg caacaacauc | 600 |
| cugcacagca ucaugaugag cgccgccaag uucggcaugc accugcaggc cgccacgccc | 660 |
| aagggcuacg agcccgacgc cagcgugacc aagcuggccg agcaguacgc caaggagaac | 720 |
| ggcaccaagc ugcugcugac caacgacccg cuggaggccg cccacggcgg caacgugcug | 780 |
| aucaccgaca ccuggaucag caugggccag gaggaggaga agaagaagcg gcugcaggcc | 840 |
| uuccagggcu accaggugac caugaagacc gccaaggugg ccgccagcga cuggaccuuc | 900 |
| cugcacugcc ugcccggaa gccgaggag guggacgacg agguguucua cagcccacgg | 960 |
| agccuggugu uccccgaggc cgagaaccgg aaguggacca ucauggccgu gauggugagc | 1020 |
| cugcugaccg acuacagccc acagcugcag aagcccaagu uc | 1062 |

<210> SEQ ID NO 15
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

| augcuguuca accugaggau acugcugaac aacgccgccu ucagaaacgg ccauaacuuc | 60 |
| auggucecgga acuuccggug cggccagccc cuccagaaua aagugcagcu gaagggcagg | 120 |
| gaccugcuua cccugaagaa cuucaccggc gaggagauca aguacaugcu guggcucagc | 180 |

```
gccgacuuga aguuuaggau caagcagaag ggcgaguacc ugccccugcu gcaaggcaag      240
agccugggca ugauuuucga gaagagauca acccggacua ggcugagcac ggagacuggc      300
uucgcccugc ucggcggcca ccccugcuuc cugaccaccc aggacaucca ccugggcgug      360
aacgaguccc ugaccgacac ggcccgcguc ucagcagca uggccgacgc cguccuggcc       420
cggguguaca agcaguccga ccuggacacc cuggccaagg aagccagcau cccgaucauc      480
aacggccuga gcgaucugua ccaucccauc cagauccucg ccgacuaccu gacccuccag      540
gagcacuaca gcagccugaa ggggcugacc cugagcugga uaggcgacgg caauaacauc     600
cugcacucga ucaugaugag cgccgcgaag uucggcaugc accugcaggc cgccacccca      660
aagggcuacg aacccgacgc cagcgugacc aagcuggcgg agcaguacgc caaggagaac      720
ggcaccaagc uccugcugac caacgacccg cuggaagccg cccacggcgg caacgugcug      780
aucaccgaua cguggaucuc caugggggcag gaggaggaga agaagaagag gcuccaagcc    840
uuccagggcu accaagugac aaugaagacc gccaagguug ccgccagcga cuggaccuuc      900
cuccacugcc ugccucggaa gcccgaggag guggacgacg agguguucua cuccccucgg    960
agccuggugu uccccgaggc cgagaauagg aaguggacca ucauggccgu gauggugagu   1020
cugcugacgg auuacagccc gcagcuccag aagcccaagu uc                          1062

<210> SEQ ID NO 16
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
augcuguuca accugcgcau ccugcugaac aacgccgccu ccggaacgg ccacaacuuc        60 augguggcgga acuuucgggug cggccagccc cugcagaaca aaguccagcu caaaggcagg    120
gaccucuuca cccugaagaa cuucaccggc gaggagauca aguacaugcu cuggcugucc      180
gccgaccuga aguccgcau caagcagaag ggcgaguacc ugccccugcu gcagggcaag       240
agccugggca ugaucuucga gaagagaucc acccgcacua ggcugucaac cgagacuggc     300
uuugcccugc ugggcggcca ccccugcuuc ucaccaccc aggacauuca ccuggguguyg       360 aacgagagcc ugaccgauac ggccagaguc cugucguccca uggccgacgc cgugcucgcc    420
agaguguaua aacagucaga ccuggacacg cuggccaagg aggccaguau ccaaucauc        480 aacggccuga gcgaccugua ucaucccauc cagauccugg ccgacuaccu gacccugcag      540
gaacacuacu cuagccugaa ggguucugaca cugagcugga ucggcgacgg aauaacauc     600 cugcacagca ucaugaugag cgccgccaag uuuggggugc accuccagggc cgccacaccu      660 aagggcuacg agccccgacgc cagcgugacc aagcucgccg agcaguacgc aaaggagaac      720
ggcaccaagc ugucccugac caacgacccu cuggaagccg cccacggagg caacgugcug      780
aucaccgaca ccuggaucag cauggugucag gaagaggaga agaagaagcg gcugcaagcc    840
uuccagggau accaggugac uaugaagacc gccaagguugg cggccuccga cuggaccuuc    900
cuccauugcc uccccaggaa gccugaggag guggacgacg agguguucua uucccccgu     960 ucccuggugu uccccgaggc cgagaaccga aaguggacca ucauggccgu gauggugagc      1020
cugcucaccg acuacagccc ucaacugcag aagcccaagu uc                          1062
```

<210> SEQ ID NO 17
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

```
augcuguuca accugcggau ccugcugaac aacgccgccu uccggaacgg ccacaacuuc        60
auggugcgga acuuccggug cggccagccc cugcagaaca aggugcagcu gaagggccgg       120
gaccugcuga cccugaagaa cuucaccggc gaggagauca aguacaugcu guggcugagc       180
gccgaccuga aguccggau caagcagaag ggcgaguacc ugccccugcu gcagggcaag        240
agccugggca ugaucuucga aagcggagc acccggaccc ggcugagcac cgagacgggc        300
uucgcccugc ugggcggcca ccccugcuuc cugaccaccc aggacaucca ccugggcgug       360
aacgagagcc ugaccgacac cgcccgggug cugagcagca uggccgacgc cgugcuggcc       420
agggguacaa gcagagcga ccuggacacc cuggccaagg aggccagcau ccccaucauc        480
aacgccuua gcgaucugua ccaccccauc cagauccugg ccgacuaccu gacccuccag        540
gagcacuaca gcagccugaa aggccugacg cugagcugga ucggcgacgg caacaacauc       600
cugcacagca ucaugaugag cgcagccaag uucggcaugc accugcaggc cgccaccccg       660
aagggcuacg agcccgacgc cagcgugacc aagcuggccg agcaguacgc caaggagaac       720
ggcacgaagc uccugcucac gaacgauccc cuggaggccg cccacggcgg caacgugcug       780
aucaccgaua ccuggaucag cauggggcag gaggaggaga agaagaagcg gcuccaggcc       840
uuccaggggcu accaggugac cauagaagacc gccaaggugg ccgccagcga cuggaccuuc       900
cugcacugcc ugccccggaa gcccgaggag guggacgacg agguguucua cagcccucgg       960
agccuggugu ccccgaggc cgagaaccgg aaguggacca ucauggccgu gauggugagc      1020
cuccugacgg auuacucacc ccagcugcag aagcccaagu uc                          1062
```

<210> SEQ ID NO 18
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
augcuguuca accugcggau ccugcugaac aacgccgccu uccggaacgg ccacaacuuc        60
auggugcgga acuuccggug cggccagccc cugcagaaca aggugcagcu gaagggccgg       120
gaccugcuga cccugaagaa cuucaccggc gaggagauca aguacaugcu guggcugagc       180
gccgaccuga aguccggau caagcagaag ggcgaguacc ugccccugcu gcagggcaag        240
agccugggca ugaucuucga aagcggagc acccggaccc ggcugagcac cgaaaccggc        300
uucgcccugc ugggcggcca ccccugcuuc cugaccaccc aggacaucca ccugggcgug       360
aacgagagcc ugaccgacac cgcccgggug cugagcagca uggccgacgc cgugcuggcc       420
cgcguguaca gcagagcga ccuggacacc cuggccaagg aggccagcau ccccaucauc        480
aacgccugu ccgaccugua ccaccccauc cagauccugg ccgacuaccu gacccuccag        540
gagcacuaca gcagccugaa ggggcugacc cucagcugga ucggcgacgg caacaacauc       600
```

```
cugcacagca ucaugaugag cgcggccaag uucggcaugc accugcaggc cgccacgccc    660
aagggcuacg agcccgacgc cagcgugacc aagcuggccg agcaguacgc caaggagaac    720
ggcaccaaac ugcuacugac caacgacccg cuggaggccg cccacggcgg caacgugcug    780
aucaccgaua ccuggaucag caugggccag gaggaggaga agaagaagcg gcugcaagcu    840
uuccagggcu accaggugac caugaagacc gccaaggugg ccgccagcga cuggaccuuc    900
cugcacugcc ugccccggaa gcccgaggag guggacgacg agguguucua cagcccgcgg    960
agccuggugu ccccgaggc cgagaaccgg aaguggacca ucauggccgu gauggugagc   1020
cugcucaccg acuacagccc ucagcugcag aagcccaagu uc                     1062

<210> SEQ ID NO 19
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
augcuguuca accugcggau ccugcugaac aacgccgccu uccggaacgg ccacaacuuc     60
auggugcgga acuuccggug cggccagccc cuccagaaca agguccagcu caagggccgc    120
gaccuccuca cccucaagaa cuucaccggc gaggagauca aguacaugcu cuggcucucc    180
gccgaccuca aguccgcau caagcagaag ggcgaguacc ugccccuccu ccagggcaag    240
ucccucggca ugaucuucga gaagcgcucc acccgcaccc gccucccac cgagacuggc    300 uucgccuucc ucggcggcca ccccugcuuc cucaccaccc aggacaucca ccucggcguc    360
aacgagcccc ucaccgacac cgcccgcguc cucuccucca uggccgacgc cguccuggcc    420
aggguguaca agcaguccga ccucgacacc cucgccaagg aggccuccau ccccaucauc    480
aacggccucu ccgaucugua ccaccccauc cagauccucg ccgacuaccu gacucugcag    540
gagcacuacu ccucccugaa gggccugacc cuguccugga ucggcgacgg caacaacauc    600
cuccacucca ucaugauguc cgccgccaag uucggcaugc accuccaggc cgccacgccc    660
aagggcuacg agcccgacgc cuccgucacc aagcucgccg agcaguacgc uaaggagaac    720
ggcacgaagc ugccucugac caacgacccg cucgaggccg cccacggcgg caacguccuc    780
auuaccgaua ccuggaucuc caugggccag gaggaggaga agaagaagag guugcaggcc    840
uuccagggcu accaggucac caugaagacc gccaaggucg ccgccuccga cuggaccuuc    900
cugcacugcc ugccgcgcaa gcccgaggag gucgacgacg agguguucua cagcccacgc    960 uccccgucu ccccgaggc cgagaaccgc aaguggacca ucauggccgu caugaucagc   1020
cugcugaccg auuacucccc gcagcuccag aagcccaagu uc                     1062

<210> SEQ ID NO 20
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
augcuguuca accugagaau ccugcugaac aacgccgccu ucagaaacgg ccacaacuuc     60
```

| | |
|---|---|
| augguucgaa auuuucggug uggacaacca cuacagaaca aagugcagcu gaagggcaga | 120 |
| gaccugcuga cccugaagaa cuucaccggc gaggagauca aguacaugcu guggcugagc | 180 |
| gccgaccuga aguucagaau caagcagaag ggcgaguauu ugccuuuauu gcaagggaag | 240 |
| uccuuaggca ugaucuucga aagagaagc accagaacca gacugagcac cgagaccggc | 300 |
| uucgcccugc ugggcggcca ccccugcuuc cugaccaccc aggacaucca ccugggcgug | 360 |
| aacgagagcc ugaccgacac cgccagagug cugagcagca uggccgacgc cgucuggcc | 420 |
| agaguguaca agcagagcga ccuggacacc cuggccaagg aggccagcau ccccaucauc | 480 |
| aacggccuga cgaccugua caccccauc cagauccugg ccgacuaccu gacccugcag | 540 |
| gagcacuaca gcagccugaa gggccugacc cugagcugga ucggcgacgg caacaacauc | 600 |
| cugcacagca ucaugaugag cgccgccaag uucggcaugc accugcaggc cgccacuccc | 660 |
| aagggcuacg agcccgacgc cagcgugacc aagcuggccg agcaguacgc caaggagaac | 720 |
| ggcaccaagc ugcugcugac aaacgaucca uuggaagcag cgcacggagg caacgugcug | 780 |
| aucaccgaca ccuggaucag cauggggcag gaggaggaga agaagaagag acugcaggcc | 840 |
| uuccagggcu accaggugac caugaagacc gccaagguggg ccgccagcga cuggaccuuc | 900 |
| cugcacugcc ugcccagaaa gcccgaggag guggacgacg agguguucua cagccccaga | 960 |
| agccuggugu uccccgaggc cgagaacaga aaguggacca ucauggccgu gauggugagc | 1020 |
| cugcugaccg acuacagccc ucagcugcag aagcccaagu uc | 1062 |

<210> SEQ ID NO 21
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

| | |
|---|---|
| augcuguuca accugagaau ccugcugaac aacgccgccu ucagaaacgg ccacaacuuc | 60 |
| auggugagaa acuuccggug cggccagccu cugcagaaca aggugcagcu gaagggcaga | 120 |
| gaucugcuga cccugaagaa cuucaccggc gaggagauca aguacaugcu guggcugagc | 180 |
| gccgaccuga aguucagaau caagcagaag ggcgaguacc ugccucugcu gcagggcaag | 240 |
| agccugggca ugaucuucga aagagaagc accagaacca gacugagcac cgaaaccggc | 300 |
| uucgcccugc ugggcggaca cccuugcuuc cugaccaccc aggacaucca ccugggcgug | 360 |
| aacgagagcc ugaccgacac cgccagagug cugagcagca uggcugacgc cgucuggcc | 420 |
| agaguguaca agcaguccga ccuggauacc cuggccaagg aggccagcau cccuaucauc | 480 |
| aacgccuga gcgaccugua caccccuauc cagauccugg ccgacuaccu gacccugcag | 540 |
| gagcacuaca gcagccugaa gggccugacg cugagcugga ucggcgacgg caacaacauc | 600 |
| cugcacagca ucaugaugag cgccgccaag uucggcaugc acuugcaagc cgccaccccu | 660 |
| aagggcuacg agccugacgc cuccgugacc aagcucgccg agcaguacgc caaggagaac | 720 |
| ggcaccaagc ugcugcugac caacgacccu cuggaggccg cccacggcgg caacgugcug | 780 |
| aucaccgaca ccuggaucag cauggggccag gaggaggaga agaagaagag acugcaggcc | 840 |
| uuccagggcu accaggugac caugaagacc gccaagguggg ccgccagcga cuggaccuuc | 900 |
| cugcacugcc ugccuagaaa gcccgaggag guggacgacg agguguucua cagcccuaga | 960 |
| agccuggugu ucccugaggc cgagaacaga aaguggacca ucauggccgu gauggugagc | 1020 |

```
cugcugaccg auuacagccc acagcugcag aagccuaagu uc            1062
```

<210> SEQ ID NO 22
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
augcuguuca accugagaau ccugcugaac aacgccgccu ucagaaacgg ccacaacuuc   60
auggugagaa acuucaggug cggccagccu cugcagaaca aggugcagcu gaagggccgc  120
gaucugcuga cucugaagaa cuucaccggc gaggagauca aguacaugcu cuggcugagc  180
gcagaccuga aauucagaau caagcagaag ggcgaguacc ugccccugcu ccaaggcaag  240
agccugggca ugaucuucga aagagaagcc accagaacca gacugagcac cgaaaccggc  300
uucgcccugc ugggaggcca cccuugcuuc cugaccaccc aggacaucca ccucggcgug  360
aacgaauccc ugaccgauac ggccagaguc cugagcucaa uggccgacgc cguccuggcg  420
agaguguaca agcaguccga ccucgacacc cuggccaaag aggccagcau cccuaucauc  480
aacggccuga cgaccugua cacccuauc cagauucucg cugacuaucu gacccugcag  540
gagcacuacu ccagccuaaa gggccucacc cuuagcugga ucggcgacgg caacaacauc  600
cugcacagca ucaugaugag cgccgccaag uucggcaugc accuccaggc cgccacaccg  660
aagggguacg aaccggacgc cagcgugacu aagcucgccg agcaguacgc caaggagaac  720
ggcaccaagc ugcugcugac caacgacccu cuggaggccg cucacggcgg caacguucug  780
auuaccgaca ccuggaucag cauggccag gaggaggaga agaagaagag acugcaggcc  840 uccagggcu accaggugac uaugaagacg gccaaagugg ccgccuccga cuggaccuuc  900
cuccacugcc ugccuagaaa gccugaggag guggacgacg agguguucua cagcccuaga  960
agccuggugu ucccugaggc cgagaacaga aaguggacca ucauggccgu gaugugucc  1020 cugcucaccg auuacucccc ucagcuccag aagccuaagu uc             1062
```

<210> SEQ ID NO 23
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

```
augcuguuca accugagaau ccugcugaac aacgccgccu ucagaaacgg ccacaacuuc   60
auggugagaa acuucaggug cggccagccu cugcagaaca aggugcagcu gaagggcaga  120
gaucugcuga cccugaagaa cuucaccggc gaggagauca aguacaugcu guggcugagc  180
gccgaccuga aguucagaau caagcagaag ggcgaguacc ugccucugcu gcagggcaag  240
agccugggca ugaucuucga aagagaagcc accagaacca gacugagcac cgagacgggc  300
uucgcccugc ugggcggcca cccuugcuuc cugaccaccc aggacaucca ccugggcgug  360
aacgagagcc ugaccgacac cgccagagug cugagcagca uggccgacgc cgugcuggcu  420
agaguguaca agcagagcga ccuggacacc cuggccaagg aggccagcau cccuaucauc  480
```

| aacggccuua gugaucugua ccacccuauc cagauccugg ccgacuaccu aacccugcag | 540 |
| gagcacuaca gcagccugaa gggucuuacg cugagcugga ucggcgacgg caacaacauc | 600 |
| cugcacagca ucaugaugug cgccgccaag uucggcaugc accugcaggc cgccacccu | 660 |
| aagggcuacg aaccagacgc cagcgugacc aagcuggccg agcaguacgc caaggagaac | 720 |
| ggcaccaagc uucugcuuac caacgacccu cuggaggccg cccacggcgg caacgugcug | 780 |
| aucacggaca ccuggaucag cauggggccag gaggaggaga agaagaagag acuccaagcu | 840 |
| uccagggcu accaggugac caugaagacc gccaaggugg ccgccagcga cuggaccuuc | 900 |
| cugcacugcc ugccuagaaa gccugaggag guggacgacg aguguucua cagcccuaga | 960 |
| agccuggugu ucccugaggc cgagaacaga aaguggacca ucauggccgu gauggugucc | 1020 |
| uugcuuacag acuauagucc ucagcugcag aagccuaagu uc | 1062 |

```
<210> SEQ ID NO 24
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
```

| augcuguuca accugcggau ccugcugaac aacgccgccu uccggaacgg ccacaacuuc | 60 |
| auggugcgga acuuccggug cggccagccc cugcagaaca aggugcagcu gaagggccgg | 120 |
| gaccugcuga cccugaagaa cuucaccggc gaggagauca aguacaugcu guggcugagc | 180 |
| gccgaccuga aguuccggau caagcagaag ggcgaguacc ugccccugcu gcagggcaag | 240 |
| agccuggca ugaucuucga gaagcggagc acccggaccc ggcugagcac cgagaccggc | 300 |
| uucgcccugc ugggcggcca ccccugcuuc cugaccaccc aggacauccca ccugggcgug | 360 |
| aacgagagcc ugaccgacac cgcccggguug cugagcagca uggccgacgc cgucgucggcc | 420 |
| cgggguguaca agcagagcga ccuggacacc cuggccaagg aggccagcau ccccaucauc | 480 |
| aacgccuga gcgaccugua ccaccccauc cagauccugg ccgacuaccu gacccugcag | 540 |
| gagcacuaca gcagccugaa gggccugacc cugagcugga ucggcgacgg caacaacauc | 600 |
| cugcacagca ucaugaugag cgccgccaag uucggcaugc accugcaggc cgccacgccc | 660 |
| aagggcuacg agcccgacgc cagcgugacc aagcuggccg agcaguacgc caaggagaac | 720 |
| ggcaccaagc ugcugcugac caacgacccc cuggaggccg cccacggcgg caacgugcug | 780 |
| aucaccgaca ccuggaucag cauggggccag gaggaggaga agaagagcg gcugcaggcc | 840 |
| uccagggcu accaggugac caugaagacc gccaaggugg ccgccagcga cuggaccuuc | 900 |
| cugcacugcc ugccccggaa gcccgaggag guggacgacg aguguucua cagcccacgg | 960 |
| agccuggugu uccccgaggc cgagaaccgg aaguggacca ucauggccgu gauggugagc | 1020 |
| cugcugaccg acuacagccc acagcugcag aagcccaagu uc | 1062 |

```
<210> SEQ ID NO 25
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
```

| | |
|---|---|
| auggucuuca accugagaauu ccugcugaac aacgccgccu ucagaaacgg ccacaacuuc | 60 |
| auggugagaa acuucaggug cggccagccu cugcagaaca aggugcagcu gaagggccgc | 120 |
| gaucugcuga cucugaagaa cuucaccggc gaggagauca aguacaugcu cuggcugagc | 180 |
| gcagaccuga aauucagaau caagcagaag ggcgaguacc ugccccugcu ccaaggcaag | 240 |
| agccugggca ugaucuucga gaagagaagc accagaacca gacugagcac cgaaaccggc | 300 |
| uucgcccugc ugggaggcca cccuugcuuc cugaccaccc aggacaucca ccucggcgug | 360 |
| aacgaauccc ugaccgauac ggccagaguc cugagcucaa uggccgacgc cguccuggcg | 420 |
| agaguguaca agcaguccga ccucgacacc cuggccaaag aggccagcau cccuaucauc | 480 |
| aacggccuga gcgaccugua ccacccuauc cagauucucg cugacuaucu gacccugcag | 540 |
| gagcacuacu ccagccuaaa gggccucacc cuuagcugga ucggcgacgg caacaacauc | 600 |
| cugcacagca ucaugaugag cgccgccaag uucggcaugc accuccaggc cgccacaccg | 660 |
| aaggggguacg aaccggacgc cagcgugacu aagcucgccg agcaguacgc caaggagaac | 720 |
| ggcaccaagc ugcugcugac caacgacccu cuggaggccg cucacggcgg caacguucug | 780 |
| auuaccgaca ccuggaucag cauggggccag gaggaggaga agaagaagag acugcaggcc | 840 |
| uccagggcu accaggugac uaugaagacg gccaaagugg ccgccuccga cuggaccuuc | 900 |
| cuccacugcc ugccuagaaa gccugaggag guggacgacg aggugoucua cagcccuaga | 960 |
| agccuggugu cccugaggc cgagaacaga aaguggacca ucauggccgu gauggugucc | 1020 |
| cugcucaccg auuacucccc ucagcuccag aagccuaagu uc | 1062 |

<210> SEQ ID NO 26
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

| | |
|---|---|
| augcugagca accugagaau ccugcugaac aacgccgcuc ugagaaaggg acauaccucc | 60 |
| guggugagac acuucggug cggaaagccc gugcagaaca aggugcagcu gaagggccgc | 120 |
| gaucugcuga cucugaagaa cuucaccggc gaggagauca aguacaugcu cuggcugagc | 180 |
| gcagaccuga aauucagaau caagcagaag ggcgaguacc ugccccugcu ccaaggcaag | 240 |
| agccugggca ugaucuucga gaagagaagc accagaacca gacugagcac cgaaaccggc | 300 |
| uucgcccugc ugggaggcca cccuugcuuc cugaccaccc aggacaucca ccucggcgug | 360 |
| aacgaauccc ugaccgauac ggccagaguc cugagcucaa uggccgacgc cguccuggcg | 420 |
| agaguguaca agcaguccga ccucgacacc cuggccaaag aggccagcau cccuaucauc | 480 |
| aacggccuga gcgaccugua ccacccuauc cagauucucg cugacuaucu gacccugcag | 540 |
| gagcacuacu ccagccuaaa gggccucacc cuuagcugga ucggcgacgg caacaacauc | 600 |
| cugcacagca ucaugaugag cgccgccaag uucggcaugc accuccaggc cgccacaccg | 660 |
| aaggggguacg aaccggacgc cagcgugacu aagcucgccg agcaguacgc caaggagaac | 720 |
| ggcaccaagc ugcugcugac caacgacccu cuggaggccg cucacggcgg caacguucug | 780 |
| auuaccgaca ccuggaucag cauggggccag gaggaggaga agaagaagag acugcaggcc | 840 |
| uccagggcu accaggugac uaugaagacg gccaaagugg ccgccuccga cuggaccuuc | 900 |

| | |
|---|---|
| cuccacugcc ugccuagaaa gccugaggag guggacgacg agguguucua cagcccuaga | 960 |
| agccuggugu ucccugaggc cgagaacaga aaguggacca ucauggccgu gaugguglucc | 1020 |
| cugcucaccg auuacuccccc ucagcuccag aagccuaagu uc | 1062 |

<210> SEQ ID NO 27
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

| | |
|---|---|
| augcucuuua accuccgcau ccuguugaau aacgcugcgu uccgaaacgg gcauaacuuc | 60 |
| augguacgca acuucaggug cggccagcca cuccagaaca aggugcagcu uaaaggucgg | 120 |
| gaccuccuua cucugaagaa cuuuaccgga gaagagauca aguacaugcu uggcuuuca | 180 |
| gcggauuuga aguuucgcau uaaacagaag ggagaguauc uuccccucuu gcaagggaag | 240 |
| ucgcucggga ugaucuucga gaagcgcucg acaaggaccc ggcucagcac cgaaaccgga | 300 |
| uuugcgcugu ugggagggca cccguguuuu cucacgacg aagacauuca cuugggagug | 360 |
| aacgagucgu ugacagacac ugccagaguc cuuucaucga uggccgacgc ggugcuugcg | 420 |
| agggucuaca aacagucgga ucuugacaca cuggccaagg aagccucgau cccgaucauu | 480 |
| aacgggcucu cggauuugua ccacccaauc cagaucuugg cggauuaucu uacauugcaa | 540 |
| gagcauuauu ccucccucaa ggggcugacu cucagcugga uuggugacgg aaauaacauc | 600 |
| cuccauucaa ucaugaugag cgcagcgaaa uucggaaugc accucaagc ggccacgccc | 660 |
| aaagguuacg aaccgacgc gagcguaacu aaacucgcgg agcaguacgc aaaggagaac | 720 |
| ggcacgaaac ucuugcucac aaacgacccc uuggaggcag cacacggugg uaacguccug | 780 |
| auuacagaca cguggaucuc cauggggcag gaggaggaga agaagaagag acuucaggca | 840 |
| uuucagggau accagguaac gaugaagacg gcgaaggucg ccgccucaga cuggacuuuc | 900 |
| cuccauugcc ugccgaggaa gccggaagaa gucgacgacg aggguguuua cagcccgcga | 960 |
| ucccuggugu ucccugaagc cgagaaucgg aaguggacaa uuauggcagu gaugguglucc | 1020 |
| cuucuuacgg acuacucgcc ccagcugcag aaaccgaaau uc | 1062 |

<210> SEQ ID NO 28
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

| | |
|---|---|
| augcucuuua accuccgcau ccuguugaau aacgcugcgu uccgaaaugg gcauaacuuc | 60 |
| augguacgca acuucagaug cggccagcca cuccagaaca aggugcagcu uaaaggucgg | 120 |
| gaccuccuua cucugaagaa cuuuaccgga gaagagauca aguacaugcu uggcuuuca | 180 |
| gcggauuuga aguuucgcau uaaacagaag ggagaguauc uuccccucuu gcaagggaag | 240 |
| ucgcucggga ugaucuucga gaagcgcucg acaaggaccc ggcucagcac cgaaaccgga | 300 |
| uuugcgcugu ugggagggca cccguguuuu cucacgacg aagacauuca cuugggagug | 360 |
| aaugagucgu ugacagacac ugccagaguc cuuucaucga uggccgaugc ggugcuugcg | 420 |

| | | |
|---|---|---|
| agggucuaca aacagucgga ucuugacaca cuggccaagg aagccucgau cccgaucauu | 480 | |
| aacgggcucu cggauuugua ccacccaauc cagaucuugg cggauuaucu uacauugcaa | 540 | |
| gagcauuauu ccucccucaa ggggcugacu cucagcugga uuggugacgg aaauaacauc | 600 | |
| cuccauucaa ucaugaugag cgcagcgaaa ucggaaugc accuccaagc ggccacgccc | 660 | |
| aaagguuaug aaccugaugc gagcguaacu aaacucgcgg agcaguaugc aaaggaaaau | 720 | |
| ggcacgaaac ucuugcucac aaaugacccc uggaggcag cacacggugg uaauguccug | 780 | |
| auuacagaca caugaucuc caugggcag gaggaggaga aaaagaaaag acuucaggca | 840 | |
| uuucagggau accagguaac gaugaaaacg gcgaaggucg ccgccucaga cuggacuuuc | 900 | |
| cuccauugcc ugccgaggaa gccggaagaa gucgaugaug aggguuuua cagcccccga | 960 | |
| ucccuggugu ucccugaagc cgaaaaucgg aaguggacaa uuauggcagu gaugguguccc | 1020 | |
| cuucuuacgg acuacucgcc ccagcugcaa aaccgaaau uc | 1062 | |

<210> SEQ ID NO 29
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

| | | |
|---|---|---|
| augcuguuca accugcgaau ccugcugaac aaugccgcuu ucggaacgg gcacaauuuc | 60 | |
| auggugagga acuuucgcug cggacagccc cuccagaaca agguccagcu gaagggcagg | 120 | |
| gaccugcuga cccugaaaaa uuucacaggg gaggaaauca aguacaugcu guggcuguca | 180 | |
| gccgaucuga aguccggau caagcagaag ggcgaauauc ugccucugcu ccagggcaaa | 240 | |
| agccugggga ugaucuucga aaagcgcagu acucggacca gacugucaac agagacugga | 300 | |
| uucgcacugc ugggaggaca cccauguuuu cugaccacac aggacauuca ucugggagug | 360 | |
| aacgagucc ugaccgacac agcacgcguc cugagcucca uggcugaugc agugcuggcu | 420 | |
| cgagucuaca acagucuga ccuggauacc cuggccaagg aagcuucuau cccaaucauu | 480 | |
| aauggccuga gugaccugua caccccauc cagauucugg ccgauuaccu gacccuccag | 540 | |
| gagcauuauu cuagucugaa agggcugaca cugagcugga uuggggacgg aaacaauauc | 600 | |
| cugcacucca uuaugaugag cgccgccaag uuuggaaugc accuccaggc ugcaaccca | 660 | |
| aaaggcuacg aacccgaugc cuccgugaca agcuggcag aacaguaugc caaagagaac | 720 | |
| ggcacuaagc ugcugcugac caaugacccu cuggaggccg cucacggagg caacgugcug | 780 | |
| aucacugaua ccuggauuag uaugggacag gaggaagaga agaagagcg gcuccaggcc | 840 | |
| uuccaggcu accaggugac aaugaaaacu gcuaaggucg cagccagcga cuggaccuuu | 900 | |
| cugcauugcc ugcccagaaa gccugaagag guggacgau aggucuucua cucacccaga | 960 | |
| agccuggugu uccugaagc ugagaauagg aaguggacaa ucauggcagu gaugguccagc | 1020 | |
| cugcugacug auuauuccc ucagcuccag aaaccaaagu uc | 1062 | |

<210> SEQ ID NO 30
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 30

| | |
|---|---|
| gggaaauaag agagaaaaga agaguaagaa gaaauauaag agccaccaug cuguuuaauc | 60 |
| ugaggauccu guuaaacaac gcagcuuuua gaaacgguca caacuucaug guucgaaauu | 120 |
| uucggugugg acaaccacua cagaauaaag ugcagcugaa gggccgugac cuucucacuu | 180 |
| ugaagaacuu uaccggagaa gaaauuaaau auaugcucug gcuaucagca gaucugaaau | 240 |
| uuaggauuaa gcagaaagga gaguauuugc cuuuauugca agggaagucc uuaggcauga | 300 |
| uuuucgagaa gagaaguacu cgaacaagau ugucuacaga aacaggcuuu gcacuucugg | 360 |
| gaggacaucc uuguuucuu accacacaag auauucauuu gggugugaac gaaagucuca | 420 |
| cggacacggc ccguguauug ucuagcaugg cagacgcagu auuggcucga guguauaaac | 480 |
| aaucagauuu ggacacccug gcuaaagaag cauccauccc aauuaucaac gggcugucag | 540 |
| auuuguacca uccuauccag auccuggcug auuaccucac gcuccaggaa cacuauagcu | 600 |
| cucugaaagg ucuuacccuc agcuggaucg gggacgggaa caauauccug cacuccauca | 660 |
| ugaugagcgc agcgaaauuc ggaaugcacc uucaggcagc uacuccaaag gguuacgagc | 720 |
| cggacgcuag uguaaccaag uuggcagagc aguacgccag agaacgggu accaagcugu | 780 |
| ugcugacaaa cgauccauug gaagcagcgc acggaggcaa cguauuaauu acagacacuu | 840 |
| ggauaagcau gggacaagaa gaggagaaga agaagcggcu ccaggcuuuc caagguuacc | 900 |
| agguuacaau gaagacugcu aaaguugcug ccucugacug gacauucuua cacugcuugc | 960 |
| ccagaaagcc agaagaagug gacgacgaag ucuuuuauuc uccucgauca cuaguguucc | 1020 |
| cagaggcaga gaacagaaag uggacaauca uggcugucau ggugucccug cugacagauu | 1080 |
| acucacccuca gcuccagaag ccuaaauuuu gauaauaggc uggagcccucg guggccuagc | 1140 |
| uucuugcccc uugggccucc ccccagcccc uccucccccuu ccugcacccg uaccccucc | 1200 |
| auaaaguagg aaacacuaca gugguucuuug aauaaagucu gaguggggcgg c | 1251 |

<210> SEQ ID NO 31
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

| | |
|---|---|
| gggaaauaag agagaaaaga agaguaagaa gaaauauaag agccaccaug cuguuuaacc | 60 |
| ugcggauccu ccugaacaac gccgccuuuc ggaacggcca caacuucaug gugcggaacu | 120 |
| ucaggugugg ucagccucug cagaacaagg ugcagcuuaa aggcagagau cuguugaccc | 180 |
| ugaagaacuu cacuggcgag gagaucaagu acaugcucug gcuguccgca gaccuaaagu | 240 |
| uccgcaucaa gcagaaggga gaguaccgc cacugcugca gggcaagagc cugggcauga | 300 |
| uuuucgagaa gagaagcaca aggaccagac ugucuacaga gacaggauuu gcccuguugg | 360 |
| gaggacaucc cugcuuccug accacccagg auaccaucu uggcgucaac gagagccuga | 420 |
| ccgacaccgc cagaguucuc uccagcaugg ccgacgcugu gcuggcccgg guguacaaac | 480 |
| aaagcgaccu ggauacccug gcaaggagg ccaguaucc cauuaucaac ggucugagcg | 540 |
| aucuuuacca ucccauacag auccggccg auuaccugac ccuccaggaa cacuacagca | 600 |
| gcccucaaagg gcugacgcuc agcuggaucg gcgacggaaa caacauucuu cacuccauca | 660 |

```
ugaugagcgc ugccaaguuc gggaugcacc ugcaggccgc cacacccaag ggcuacgagc      720
ccgacgcuuc ggucacuaag cuggccgagc aguacgccaa ggagaacggc acaaagcugc      780
ugcugaccaa cgauccucug gaagccgccc acggcggcaa cgugcugauc acagacacuu      840
ggaucagcau gggccaggag gaggagaaga agaagagacu gcaggcuuuc cagggcuauc      900
aggugaccau gaagacugcc aagguggccg cgagcgacug gaccuuccug cauugucugc      960
cuagaaagcc cgaggaggug gacgacgagg uguucuacuc ucccaggucc cugguguucc     1020
cagaggccga gaauagaaag uggacuauua uggccgugau ggugucucug cucaccgauu     1080
auuccccuca gcugcagaag ccaaaguuuu gauaauaggc uggagccucg guggccuagc     1140
uucuugcccc uugggccucc cccagccccu ccuccccuu ccugcacccg uaccccuccc       1200
auaaaguagg aaacacuaca guggucuuug aauaaagucu gaguggggcgg c              1251

<210> SEQ ID NO 32
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
gggaauaaag agagaaaaga agaguaagaa gaaauauaag agccaccaug cuguuuaacc        60
ucaggauccu gcugaacaac gccgcauuca gaaacggaca caacuuuaug gugaggaacu       120
uccggugcgg acagccucug cagaacaagg uucaacugaa gggccgggac cugcugaccc       180
ucaagaacuu caccggcgaa gagaucaaau acaugcucug gcugagcgcc gaccugaagu       240
ucagaaucaa acagaaggga gaguacuugc cccugcuuca gggaaagagc cucggcauga       300
ucuuugagaa gaggagcacc cggacccggc ugagcaccga cgggguuuu gcccucuugg        360 gcggucaucc cugcuuucuc accacacagg acauccaccu ggggugugaac gagagccuca     420 ccgacaccgc aagggugcug agcagcaugg cagacgccgu gcuggcucgc guguauaagc       480
aguccgaucu cgauacccug gccaaagagg caagcauccc uauuaucaac ggccugagcg       540
auuuguacca uccaauccag auccuugccg acuaucugac ccugcaggag cacuacagcu       600
cccugaaggg gcucacccug ucuuggauug ggacgguaa caauauucug cacagcauca      660
ugaugagugc cgccaaguuc ggcaugcacc ugcaggccgc caccccuaag ggcuacgagc       720
cugacgccuc cgugaccaag cuggcugaac aguacgcaaa ggagaacgga accaagcuuc       780
ugcucaccaa cgauccacug gaggccgccc acggcggcaa cgugcugauc acagacaccu       840
ggauuagcau ggggcaggag gaggagaaga agaagagacu gcaggcauuu cagggauacc       900
aaguuaccau gaagaccgcc aagguggccg cuucagauug gacauuccug cauugccugc       960
cacgaaaacc agaggagguc gacgacgagg uguucuacag ccccagaagc cucguguucc      1020
ccgaggcuga aacagaaaag uggacgauca uggccgugau ggugaguuua cugaccgacu      1080
auucgcccca gcuccagaaa ccaaaguucu gauaauaggc uggagccucg guggccuagc      1140
uucuugcccc uugggccucc cccagccccu ccuccccuu ccugcacccg uaccccuccc       1200
auaaaguagg aaacacuaca guggucuuug aauaaagucu gaguggggcgg c              1251

<210> SEQ ID NO 33
<211> LENGTH: 1251
<212> TYPE: RNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

```
gggaaauaag agagaaaaga agaguaagaa gaaauauaag agccaccaug cuguucaacc    60
ugcggauccu gcugaacaac gccgccuucc ggaacggcca caacuucaug gugcggaacu   120
uccggugcgg ccagccccug cagaacaagg ugcagcugaa gggccgggac cugcugaccc   180
ugaagaacuu caccggcgag gagaucaagu acaugcugug gcugagcgcc gaccugaagu   240
uccggaucaa gcagaagggc gaguaccugc cccugcugca gggcaagagc cugggcauga   300
ucuucgagaa gcggagcacc cggacccggc ugagcaccga acuggcuuc gcccugcugg   360
gcggccaccc cugcuuccug accacccagg acauccaccu gggcgugaac gagagccuga   420
ccgacaccgc ccgggugcug agcagcaugg ccgacgccgu gcuggccaga guguacaagc   480
agagcgaccu ggacacccug gccaaggagg ccagcauccc caucaucaac ggcuugagug   540
accuguacca ccccauccag auccuggccg acuaccucac ccugcaggag cacuacagca   600
gccucaaggg gcugacacuc agcuggaucg gcgacggcaa caacauccug cacagcauca   660
ugaugagcgc ugccaaguuc ggcaugcacc ugcaggccgc cacacccaag ggcuacgagc   720
ccgacgccag cgugaccaag cuggccgagc aguacgcuaa ggagaacggc acaaagcugc   780
ugcugacaaa cgacccacug gaggccgccc acggcggcaa cgugcugauc acagauacuu   840
ggaucagcau gggccaggag gaggagaaga agaagcggcu gcaggcguuc cagggcuacc   900
aggugaccau gaagaccgcc aagguggccg ccagcgacug gaccuuccug cacugccugc   960
cccggaagcc cgaggaggug gacgacgagg uguucuacag ccccggagc cugguguucc  1020
ccgaggccga gaaccggaag uggaccauca uggccgugau ggugagucug cugacugacu  1080
acaguccuca gcugcagaag cccaaguucu gauaauaggc uggagccucg guggccagc   1140
uucuugccc uuugggccucc ccccagccc uccuccccuu ccugcacccg uaccccucc   1200
auaaaguagg aaacacuaca guggucuuug aauaaagucu gaguggcgg c            1251
```

<210> SEQ ID NO 34
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34

```
gggaaauaag agagaaaaga agaguaagaa gaaauauaag agccaccaug cuguucaacc    60
ugcggauccu gcugaacaac gccgccuucc ggaacggcca caacuucaug gugcggaacu   120
uccggugcgg ccagccccug cagaacaagg ugcagcugaa gggccgggac cugcugaccc   180
ugaagaacuu caccggcgag gagaucaagu acaugcugug gcugagcgcc gaccugaagu   240
uccggaucaa gcagaagggc gaguaccugc cccugcugca gggcaagagc cugggcauga   300
ucuucgagaa gcggagcacc cggacccggc ugagcaccga aaccggcuuc gcccugcugg   360
gcggccaccc cugcuuccug accacccagg acauccaccu gggcgugaac gagagccuga   420
ccgacaccgc ccgggugcug agcagcaugg ccgacgccgu gcuggcuagg guguacaagc   480
agagcgaccu ggacacccug gccaaggagg ccagcauccc caucaucaac ggccuguccg   540
```

```
acuuguacca cccccauccag auccuggccg acuaccugac ccuucaggag cacuacagca        600
gccugaaagg ucugacacug agcuggaucg gcgacggcaa caacauccug cacagcauca        660
ugaugagcgc ugccaaguuc ggcaugcacc ugcaggccgc cacgccgaag ggcuacgagc        720
ccgacgccag cgugaccaag cuggccgagc aguacgccaa ggagaacggc acuaagcuac        780
ugcucaccaa cgaucccug gaggccgccc acggcggcaa cgugcugauc acagacaccu         840
ggaucagcau gggccaggag gaggagaaga agaagcggcu gcaggcuuuc cagggcuacc        900
aggugaccau gaagaccgcc aaggugccg ccagcgacug gaccuuccug cacugccugc         960
cccggaagcc cgaggaggug gacgacgagg uguucuacag cccacggagc cugguguucc       1020
ccgaggccga aaccggaag uggaccauca uggccgugau ggugagccuc uugaccgauu        1080
acucaccccca gcugcagaag cccaaguucu gauaauaggc uggagccucg guggccuagc      1140
uucuugcccc uugggccucc ccccagcccc uccuccccuu ccugcacccg uacccccucc       1200
auaaaguagg aaacacuaca guggucuuug aauaaagucu gaguggggcgg c               1251
```

<210> SEQ ID NO 35
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 35

```
gggaauaaag agagaaaaga agaguaagaa gaaauauaag agccaccaug cuguucaacc         60
ugcggauccu gcugaacaac gccgccuucc ggaacggcca caacuucaug gugcggaacu       120
uccggugcgg ccagccccuc cagaacaagg uccagcucaa gggccgcgac cuccucaccc       180
ucaagaacuu caccggcgag gagaucaagu acaugcucug cucuccgcc gaccucaagu        240
uccgcaucaa gcagaagggc gaguaccugc cccuccucca gggcaaguccc ucggcauga        300
ucuucgagaa gcgcuccacc cgcacccgcc ucuccaccga aaccggcuuc gcccucucg        360
gcggccaccc cugcuuccuc accacccagg acauccaccu cggcgucaac gagucccuca       420
ccgacaccgc ccgcguccuc uccuccaugg ccgacgccgu ccuggcuaga guguacaagc       480
aguccgaccu cgacacccuc gccaaggagg ccuccauccc caucaucaac ggccucagcg       540
aucucuacca cccccauccag auccucgccg acuacuugac ccugcaggag cacuacuccu       600
cccucaaggg uuuaacgcug uccuggaucg gcgacggcaa caacauccuc cacuccauca       660
ugaugucccgc cgccaaguuc ggcaugcacc uccaggccgc cacaccaaag ggcuacgagc       720
ccgacgccuc cgucaccaag cucgccgagc aguacgccaa agagaacggc acgaagcugc       780
ugcugacuaa cgauccccuc gaggccgccc acggcggcaa cguccucauc accgauaccu       840
ggaucuccau gggccaggag gaggagaaga agaagaggcu gcaggccuuc cagggcuacc       900
aggucaccau gaagaccgcc aaggucgcgg ccuccgacug gaccuuucuc cacugccugc       960
cucgcaagcc cgaggagguc gacgacgagg ucuucuacuc accucgcucc cucgucuucc      1020
ccgaggccga aaccgcaag uggaccauca uggccgucau gguucucuc cuaacugacu        1080
acaguccccca gcuccagaag cccaaguucu gauaauaggc uggagccucg guggccuagc      1140
uucuugcccc uugggccucc ccccagcccc uccuccccuu ccugcacccg uacccccucc       1200
auaaaguagg aaacacuaca guggucuuug aauaaagucu gaguggggcgg c               1251
```

<210> SEQ ID NO 36
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

| | | |
|---|---|---|
| gggaaauaag agagaaaaga agaguaagaa gaaauauaag agccaccaug cuguucaacc | 60 |
| ugagaauccu gcugaacaac gccgccuuca gaaacggcca caacuucaug guucgaaauu | 120 |
| uucggugugg acaaccacua cagaacaaag ugcagcugaa gggcagagac cugcugaccc | 180 |
| ugaagaacuu caccggcgag gagaucaagu acaugcugug gcugagcgcc gaccugaagu | 240 |
| ucagaaucaa gcagaagggc gaguauuugc cuuuauugca agggaagucc uuaggcauga | 300 |
| ucuucgagaa gaagcacc agaaccagac ugagcaccga gaccggcuuc gcccugcugg | 360 |
| gcggccaccc cugcuuccug accacccagg acauccaccu gggcgugaac gagagccuga | 420 |
| ccgacaccgc cagagugcug agcagcaugg ccgacgccgu gcuggccaga guguacaagc | 480 |
| agagcgaccu ggacacccug gccaaggagg ccagcauccc caucaucaac ggccugagcg | 540 |
| accuguacca ccccauccag auccuggccg acuaccugac ccugcaggag cacuacagca | 600 |
| gccugaaggg ccugcccug agcuggaucg gcgacggcaa caacauccug cacagcauca | 660 |
| ugaugagcgc cgccaaguuc ggcaugcacc ugcaggccgc cacucccaag ggcuacgagc | 720 |
| ccgacgccag cgugaccaag cuggccgagc aguacgccaa ggagaacggc accaagcugc | 780 |
| ugcugacaaa cgauccauug gaagcagcgc acggaggcaa cgugcugauc accgacaccu | 840 |
| ggaucagcau gggccaggag gaggagaaga agaagagacu gcaggccuuc cagggcuacc | 900 |
| aggugaccau gaagaccgcc aagguggccg ccagcgacug gaccuuccug cacugccugc | 960 |
| ccagaaagcc cgaggaggug gacgacgagg uguucuacag ccccagaagc cugguguucc | 1020 |
| ccgaggccga gaacagaaag uggaccauca uggccgugau ggugagccug cugaccgacu | 1080 |
| acagcccuca gcugcagaag cccaaguucu gauaauaggc uggagccucg guggccagc | 1140 |
| uucuugcccc uugggccucc ccccagcccc uccucccuu ccugcacccg uaccccucc | 1200 |
| auaaaguagg aaacacuaca guggucuuug aauaaagucu gaguggggg c | 1251 |

<210> SEQ ID NO 37
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

| | | |
|---|---|---|
| gggaaauaag agagaaaaga agaguaagaa gaaauauaag agccaccaug cuguucaacc | 60 |
| ugagaauccu gcugaacaac gccgccuuca gaaacggcca caacuucaug gugagaaacu | 120 |
| uccggugcgg ccagccucug cagaacaagg ugcagcugaa gggcagagau cugcugaccc | 180 |
| ugaagaacuu caccggcgag gagaucaagu acaugcugug gcugagcgcc gaccugaagu | 240 |
| ucagaaucaa gcagaagggc gaguaccugc cucugcugca gggcaagagc cugggcauga | 300 |
| ucuucgagaa gaagcacc agaaccagac ugagcaccga aaccggcuuc gcccugcugg | 360 |
| gcggacaccc uugcuuccug accacccagg acauccaccu gggcgugaac gagagccuga | 420 |

```
ccgacaccgc cagagugcug agcagcaugg cugacgccgu gcuggccaga guguacaagc    480
aguccgaccu ggauacccug gccaaggagg ccagcauccc uaucaucaac ggccugagcg    540
accuguacca cccuauccag auccuggccg acuaccugac ccugcaggag cacuacagca    600
gccugaaggg ccugacgcug agcuggaucg gcgacggcaa caacauccug cacagcauca    660
ugaugagcgc cgccaaguuc ggcaugcacu ugcaagccgc caccccuaag ggcuacgagc    720
cugacgccuc cgugaccaag cucgccgagc aguacgccaa ggagaacggc accaagcugc    780
ugcugaccaa cgacccucug gaggccgccc acggcggcaa cgugcugauc accgacaccu    840
ggaucagcau gggccaggag gaggagaaga agaagagacu gcaggccuuc cagggcuacc    900
aggugaccau gaagaccgcc aagguggccg ccagcgacug gaccuuccug cacugccugc    960
cuagaaagcc ugaggaggug gacgacgagg uguucuacag cccuagaagc cugguguucc   1020
cugaggccga gaacagaaag uggaccauca uggccgugau ggugagccug cugaccgauu   1080
acagcccaca gcugcagaag ccuaaguucu gauaauaggc uggagccucg guggccuagc   1140
uucuugcccc uugggccucc ccccagcccc uccuccccuu ccugcacccg uaccccaucc   1200
auaaaguagg aaacacuaca guggucuuug aauaaagucu gaguggggcgg c           1251
```

<210> SEQ ID NO 38
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
gggaaauaag agagaaaaga agaguaagaa gaaauauaag agccaccaug cuguucaacc     60
ugagaauccu gcugaacaac gccgccuuca gaaacggcca caacuucaug gugagaaacu    120
ucaggugcgg ccagccucug cagaacaagg ugcagcugaa gggccgcgau cugcugacuc    180
ugaagaacuu caccggcgag gagaucaagu acaugcucug gcugagcgca gaccugaaau    240
ucagaaucaa gcagaagggc gaguaccugc cccugcucca aggcaagagc cugggcauga    300
ucuucgagaa gagaagcacc agaaccagac ugagcaccga aaccggcuuc gcccugcugg    360 gaggccacccc uugcuuccug accacccagg acauccaccu cggcgugaac gaaucccuga    420
ccgauacggc cagagucccug agcucaaugg ccgacgccgu ccuggcgaga guguacaagc    480
aguccgaccu cgacacccug gccaagagag ccagcauccc uaucaucaac ggccugagcg    540
accuguacca cccuauccag auucucgcug acuaucugac ccugcaggag cacuacucca    600
gccuaaaggg ccucaccccuu agcuggaucg gcgacggcaa caacauccug cacagcauca    660
ugaugagcgc cgccaaguuc ggcaugcacu uccaggccgc cacaccgaag ggguacgaac    720
cggacgccag cgugacuaag cucgccgagc aguacgccaa ggagaacggc accaagcugc    780
ugcugaccaa cgacccucug gaggccgcuc acggcggcaa cguucugauu accgacaccu    840
ggaucagcau gggccaggag gaggagaaga agaagagacu gcaggccuuc cagggcuacc    900
aggugacuau gaagacggcc aaguggccg ccucgacug gaccuuccuc acugccugc       960 cuagaaagcc ugaggaggug gacgacgagg uguucuacag cccuagaagc cugguguucc   1020
cugaggccga gaacagaaag uggaccauca uggccgugau ggugucccug cucaccgauu   1080 acucccccuca gcuccagaag ccuaaguucu gauaauaggc uggagccucg guggccuagc  1140
```
uucuugcccc uugggccucc ccccagcccc uccuccccuu ccugcacccg uaccccucc    1200 auaaaguagg aaacacuaca guggucuuug aauaaagucu gaguggcgg c    1251

<210> SEQ ID NO 39
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
gggaaauaag agagaaaaga agaguaagaa gaaauauaag agccaccaug cuguucaacc      60
ugagaauccu gcugaacaac gccgccuuca gaaacggcca caacuucaug gugagaaacu     120
ucaggugcgg ccagccucug cagaacaagg ugcagcugaa gggcagagau cugcugaccc     180
ugaagaacuu caccggcgag gagaucaagu acaugcugug gcugagcgcc gaccugaagu     240
ucagaaucaa gcagaagggc gaguaccugc cucugcugca gggcaagagc cugggcauga     300
ucuucgagaa gagaagcacc agaaccagac ugagcaccga cgggcuuc gcccugcugg     360 gcggccaccc uugcuuccug accacccagg acauccaccu gggcgugaac gagagccuga     420
ccgacaccgc cagagugcug agcagcaugg ccgacgccgu gcuggcuaga guguacaagc     480
agagcgaccu ggacacccug gccaaggagg ccagcauccc uaucaucaac ggccuuagug     540
aucuguacca cccuauccag auccuggccg acuaccuaac ccugcaggag cacuacagca     600
gccugaaggg ucuuacgcug agcuggaucg gcgacggcaa caacauccug cacagcauca     660
ugauguccgc cgccaaguuc ggcaugcacc ugcaggccgc caccccuaag ggcuacgaac     720
cagacgccag cgugaccaag cuggccgagc aguacgccag ggagaacggc accaagcuuc     780
ugcuuaccaa cgacccucug gaggccgccc acggcggcaa cgugcugauc acggacaccu     840
ggaucagcau gggccaggag gaggagaaga agaagagacu ccaagcuuuc cagggcuacc     900
aggugaccau gaagaccgcc aagguggccg ccagcgacug gaccuuccug cacugccugc     960
cuagaaagcc ugaggaggug gacgacgagg uguucuacag cccuagaagc cugguguucc    1020
cugaggccga aacagaaag uggaccauca uggccgugau ggugccuug cuuacagacu    1080 auaguccuca gcugcagaag ccuaaguucu gauaauaggc uggagccucg guggccuagc    1140
uucuugcccc uugggccucc ccccagcccc uccuccccuu ccugcacccg uaccccucc    1200 auaaaguagg aaacacuaca guggucuuug aauaaagucu gaguggcgg c    1251

<210> SEQ ID NO 40
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
gggaaauaag agagaaaaga agaguaagaa gaaauauaag agccaccaug cuguucaacc      60
ugcggauccu gcugaacaac gccgccuucc ggaacggcca caacuucaug gugcggaacu     120
uccggugcgg ccagccccug cagaacaagg ugcagcugaa gggccgggac cugcugaccc     180
ugaagaacuu caccggcgag gagaucaagu acaugcugug gcugagcgcc gaccugaagu     240
uccggaucaa gcagaagggc gaguaccugc cccugcugca gggcaagagc cugggcauga     300

-continued

| | |
|---|---|
| ucuucgagaa gcggagcacc cggacccggc ugagcaccga gaccggcuuc gcccugcugg | 360 |
| gcggccaccc cugcuuccug accacccagg acauccaccu gggcgugaac gagagccuga | 420 |
| ccgacaccgc ccgggugcug agcagcaugg ccgacgccgu gcuggccgg guguacaagc | 480 |
| agagcgaccu ggacacccug gccaaggagg ccagcauccc caucaucaac ggccugagcg | 540 |
| accuguacca ccccauccag auccuggccg acuaccugac ccugcaggag cacuacagca | 600 |
| gccugaaggg ccugacccug agcuggaucg gcgacggcaa caacauccug cacagcauca | 660 |
| ugaugagcgc cgccaaguuc ggcaugcacc ugcaggccgc cacgcccaag ggcuacgagc | 720 |
| ccgacgccag cgugaccaag cuggccgagc aguacgccaa ggagaacggc accaagcugc | 780 |
| ugcugaccaa cgacccgcug gaggccgccc acggcggcaa cgucugauc accgacaccu | 840 |
| ggaucagcau gggccaggag gaggagaaga agaagcggcu gcaggccuuc cagggcuacc | 900 |
| aggugaccau gaagaccgcc aagguggccg ccagcgacug gaccuuccug cacugccugc | 960 |
| cccggaagcc cgaggaggug gacgacgagg uguucuacag cccacggagc cuggguguucc | 1020 |
| ccgaggccga gaaccggaag uggaccauca uggccgugau ggugagccug cugaccgacu | 1080 |
| acagcccaca gcugcagaag cccaaguucu gauaauaggc uggagccucg guggccuagc | 1140 |
| uucuugcccc uugggccucc ccccagcccc uccucccuu ccugcacccg uaccccucc | 1200 |
| auaaaguagg aaacacuaca guggucuuug aauaaagucu gaguggcgg c | 1251 |

<210> SEQ ID NO 41
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41

| | |
|---|---|
| gggaaauaag agagaaaaga agaguaagaa gaaauauaag agccaccaug cuguucaacc | 60 |
| ugaggauacu gcugaacaac gccgccuuca gaaacggcca uaacuucaug guccggaacu | 120 |
| uccggugcgg ccagccccuc cagaauaaag ugcagcugaa gggcagggac cugcuuaccc | 180 |
| ugaagaacuu caccggcgag gagaucaagu acaugcugug gcucagcgcc gacuugaagu | 240 |
| uuaggaucaa gcagaagggc gaguaccugc cccugcugca aggcaagagc cugggcauga | 300 |
| uuuucgagaa gagaucaacc cggacuaggc ugagcacgga gacuggcuuc gcccugcucg | 360 |
| gcggccaccc cugcuuccug accacccagg acauccaccu gggcgugaac gagucccuga | 420 |
| ccgacacggc ccgcguccuc agcagcaugg ccgacgccgu ccuggccgg guguacaagc | 480 |
| aguccgaccu ggacacccug gccaaggaag ccagcauccc gaucaucaac ggccugagcg | 540 |
| aucuguacca ucccauccag auccucgccg acuaccugac ccuccaggag cacuacagca | 600 |
| gccugaaggg gcugacccug agcuggauag gcgacggcaa uaacauccug cacucgauca | 660 |
| ugaugagcgc cgcgaaguuc ggcaugcacc ugcaggccgc caccccaaag ggcuacgaac | 720 |
| ccgacgccag cgugaccaag cuggcggagc aguacgccaa ggagaacggc accaagcucc | 780 |
| ugcugaccaa cgacccgcug gaagccgccc acggcggcaa cgucugauc accgauacgu | 840 |
| ggaucuccau ggggcaggag gaggagaaga agaagaggcu ccaagccuuc cagggcuacc | 900 |
| aagugacaau gaagaccgcc aagguugccg ccagcgacug gaccuuccuc cacugccugc | 960 |
| cucggaagcc cgaggaggug gacgacgagg uguucuacuc cccucggagc cugguguucc | 1020 |

```
ccgaggccga gaauaggaag uggaccauca uggccgugau ggugagucug cugacggauu    1080
acagcccgca gcuccagaag cccaaguucu gauaauaggc uggagccucg guggccuagc    1140
uucuugcccc uugggccucc ccccagcccc uccuccccuu ccugcacccg uaccccucc     1200 auaaaguagg aaacacuaca guggucuuug aauaaagucu gagugggcgg c             1251
```

<210> SEQ ID NO 42
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42

```
gggaaauaag agagaaaaga agaguaagaa gaaauauaag agccaccaug cuguucaacc      60
ugcgcauccu gcugaacaac gccgccuucc ggaacggcca caacuucaug gugcggaacu     120
uucggugcgg ccagccccug cagaacaaag uccagcucaa aggcagggac cuccucaccc     180
ugaagaacuu caccggcgag gagaucaagu acaugcucug gcuguccgcc gaccugaagu     240
uccgcaucaa gcagaagggc gaguaccugc cccugcugca gggcaagagc cugggcauga     300
ucuucgagaa gagauccacc cgcacuaggc ugucaaccga dacuggcuuu gcccugcugg     360
gcggccaccc cugcuuccuc accacccagg acauucaccu ggugugaac gagagccuga     420 ccgauacggc cagaguccug ucguccaugg ccgacgccgu gcucgccaga guguauaaac     480
agucagaccu ggacacgcug gccaaggagg ccaguauucc aaucaucaac ggccugagcg     540
accuguauca ucccauccag auccuggccg acuaccugac ccugcaggaa cacuacucua     600
gccugaaggg ucugacacug agcuggaucg gcgacgggaa uaacauccug cacagcauca     660
ugaugagcgc cgccaaguuu gggaugcacc uccaggccgc cacaccuaag ggcuacgagc     720
ccgacgccag cgugaccaag cucgccgagc auacgcaaa ggagaacggc accaagcugc     780
uccugaccaa cgacccucug gaagccgccc acggaggcaa cgugcugauc accgacaccu     840
ggaucagcau gggucaggaa gaggagaaga agaagcggcu gcaagccuuc cagggauacc     900
aggugacuau gaagaccgcc aagguggcgg ccuccgacug gaccuuccuc cauugccucc     960
ccaggaagcc ugaggaggug gacgacgagg uguucuauuc accccguucc cugguguucc    1020
ccgaggccga gaaccgaaag uggaccauca uggccgugau ggugagccug cucaccgacu    1080
acagcccuca acugcagaag cccaaguucu gauaauaggc uggagccucg guggccuagc    1140
uucuugcccc uugggccucc ccccagcccc uccuccccuu ccugcacccg uaccccucc     1200 auaaaguagg aaacacuaca guggucuuug aauaaagucu gagugggcgg c             1251
```

<210> SEQ ID NO 43
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43

```
gggaaauaag agagaaaaga agaguaagaa gaaauauaag agccaccaug cuguucaacc      60
ugcggauccu gcugaacaac gccgccuucc ggaacggcca caacuucaug gugcggaacu     120
uccggugcgg ccagccccug cagaacaagg ugcagcugaa gggccgggac cugcugaccc     180
```

```
ugaagaacuu caccggcgag gagaucaagu acaugcugug gcugagcgcc gaccugaagu      240
uccggaucaa gcagaagggc gaguaccugc cccugcugca gggcaagagc cugggcauga      300
ucuucgagaa gcggagcacc cggacccggc ugagcaccga cacgggcuuc gcccugcugg      360
gcggccaccc cugcuuccug accacccagg acauccaccu gggcgugaac gagagccuga      420
ccgacaccgc ccgggugcug agcagcaugg ccgacgccgu gcuggccagg guguacaagc      480
agagcgaccu ggacacccug gccaaggagg ccagcauccc caucaucaac ggccuuagcg      540
aucuguacca ccccauccag auccuggccg acuaccugac ccuccaggag cacuacagca      600
gccugaaagg ccugacgcug agcuggaucg gcgacggcaa caacauccug cacagcauca      660
ugaugagcgc agccaaguuc ggcaugcacc ugcaggccgc caccccgaag ggcuacgagc      720
ccgacgccag cgugaccaag cuggccgagc aguacgccaa ggagaacggc acgaagcucc      780
ugcucacgaa cgaucccccug gaggccgccc acggcggcaa cgugcugauc accgauaccu      840
ggaucagcau gggccaggag gaggagaaga agaagcggcu ccaggccuuc cagggcuacc      900
aggugaccau gaagaccgcc aagguggccg ccagcgacug gaccuuccug cacugccugc      960
cccggaagcc cgaggaggug gacgacgagg uguucuacag cccucggagc cugguguucc     1020
ccgaggccga gaaccggaag uggaccauca uggccgugau ggugagccuc cugacggauu     1080 acucaccccca gcugcagaag cccaaguucu gauaauaggc uggagccucg guggccuagc     1140
uucuugcccc uugggccucc cccagccccc uccucccccuu ccugcacccg uaccccoucc     1200 auaaaguagg aaacacuaca guggucuuug aauaaagucu gaguggcgg c                1251
```

<210> SEQ ID NO 44
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

```
gggaaauaag agagaaaaga agaguaagaa gaaauauaag agccaccaug cuguucaacc       60
ugcggauccu gcugaacaac gccgccuucc ggaacggcca caacuucaug gugcggaacu      120 uccgugcgg ccagccccug cagaacaagg ugcagcugaa gggccgggac cugcugaccc      180
ugaagaacuu caccggcgag gagaucaagu acaugcugug gcugagcgcc gaccugaagu      240
uccggaucaa gcagaagggc gaguaccugc cccugcugca gggcaagagc cugggcauga      300
ucuucgagaa gcggagcacc cggacccggc ugagcaccga aaccggcuuc gcccugcugg      360
gcggccaccc cugcuuccug accacccagg acauccaccu gggcgugaac gagagccuga      420
ccgacaccgc ccgggugcug agcagcaugg ccgacgccgu gcuggccogc guguacaagc      480 agagcgaccu ggacacccug gccaaggagg ccagcauccc caucaucaac ggccugccg       540 accuguacca ccccauccag auccuggccg acuaccugac ccuccaggag cacuacagca      600
gccugaaggg gcugacccuc agcuggaucg gcgacggcaa caacauccug cacagcauca      660
ugaugagcgc ggccaaguuc ggcaugcacc ugcaggccgc cacgcccaag ggcuacgagc      720
ccgacgccag cgugaccaag cuggccgagc aguacgccaa ggagaacggc accaaacugc      780
uacugaccaa cgaccgcug gaggccgccc acggcggcaa cgugcugauc accgauaccu       840
ggaucagcau gggccaggag gaggagaaga agaagcggcu gcaagcuuuc cagggcuacc      900
```

| | |
|---|---:|
| aggugaccau gaagaccgcc aaggugggccg ccagcgacug gaccuuccug cacugccugc | 960 |
| cccggaagcc cgaggaggug gacgacgagg uguucuacag cccgcggagc cugguguucc | 1020 |
| ccgaggccga gaaccggaag uggaccauca uggccgugau ggugagccug cucaccgacu | 1080 |
| acagcccuca gcugcagaag cccaaguucu gauaauaggc uggagccucg guggccuagc | 1140 |
| uucuugcccc uugggccucc cccagcccc uccucccuu ccugcacccg uaccccucc | 1200 |
| auaaaguagg aaacacuaca guggucuuug aauaaagucu gagugggcgg c | 1251 |

<210> SEQ ID NO 45
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45

| | |
|---|---:|
| gggaauaaag agagaaaaga agaguaagaa gaaauauaag agccaccaug cuguucaacc | 60 |
| ugcggauccu gcugaacaac gccgccuucc ggaacggcca caacuucaug gugcggaacu | 120 |
| uccggugcgg ccagccccuc cagaacaagg uccagcucaa gggccgcgac cuccucaccc | 180 |
| ucaagaacuu caccggcgag gagaucaagu acaugcucug gcucuccgcc gaccucaagu | 240 |
| uccgcaucaa gcagaagggc gaguaccugc cccucccca gggcaagucc cucggcauga | 300 |
| ucuucgagaa gcgcuccacc cgcacccgcc ucuccaccga gacuggcuuc gcccuccucg | 360 |
| gcggccaccc cugcuuccuc accacccagg acauccaccu cggcgucaac gagucccuca | 420 |
| ccgacaccgc ccgcguccuc uccuccaugg ccgacgccgu ccuggccagg guguacaagc | 480 |
| agguccgaccu cgacacccuc gccaaggagg ccuccauccc caucaucaac ggccucuccg | 540 |
| aucuguacca ccccauccag auccucgccg acuaccugac ucugcaggag cacuacuccu | 600 |
| cccugaaggg ccugacccug uccuggaucg gcgacggcaa caacauccuc acuccauca | 660 |
| ugauguccgc cgccaaguuc ggcaugcacc uccaggccgc cacgcccaag ggcuacgagc | 720 |
| ccgacgccuc cgucaccaag cucgccgagc aguacgcuaa ggagaacggc acgaagcugc | 780 |
| uccugaccaa cgaccgcuc gaggccgccc acggcggcaa cguccucauu accgauaccu | 840 |
| ggaucuccau gggccaggag gaggagaaga agaagagguu gcaggccuuc cagggcuacc | 900 |
| aggucaccau gaagaccgcc aaggucgccg ccuccgacug gaccuuccug cacugccugc | 960 |
| cgcgcaagcc cgaggagguc gacgacgagg ucuucuacag cccacgcucc cucgucuucc | 1020 |
| ccgaggccga gaaccgcaag uggaccauca uggccgucau ggucagccug cugaccgauu | 1080 |
| acucccccgca gcuccagaag cccaaguucu gauaauaggc uggagccucg guggccuagc | 1140 |
| uucuugcccc uugggccucc cccagcccc uccucccuu ccugcacccg uaccccucc | 1200 |
| auaaaguagg aaacacuaca guggucuuug aauaaagucu gagugggcgg c | 1251 |

<210> SEQ ID NO 46
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

| | |
|---|---:|
| gggaauaaag agagaaaaga agaguaagaa gaaauauaag agccaccaug cuguucaacc | 60 |

-continued

```
ugagaauccu gcugaacaac gccgccuuca gaaacggcca caacuucaug guucgaaauu      120
uucggugugg acaaccacua cagaacaaag ugcagcugaa gggcagagac cugcugaccc      180
ugaagaacuu caccggcgag gagaucaagu acaugcugug gcugagcgcc gaccugaagu      240
ucagaaucaa gcgaagggc gaguauugc cuuuauugca agggaagucc uuaggcauga       300
ucuucgagaa gagaagcacc agaaccagac ugagcaccga gaccggcuuc gcccugcugg      360
gcggccaccc cugcuuccug accacccagg acauccaccu gggcgugaac gagagccuga      420
ccgacaccgc cagagugcug agcagcaugg ccgacgccgu gcuggccaga guguacaagc      480
agagcgaccu ggacacccug gccaaggagg ccagcauccc caucaucaac ggccugagcg      540
accuguacca ccccauccag auccuggccg acuaccugac ccugcaggag cacuacagca      600
gccugaaggg ccugacccug agcuggaucg gcgacggcaa caacauccug cacagcauca      660
ugaugagcgc cgccaaguuc ggcaugcacc ugcaggccgc cacucccaag ggcuacgagc      720
ccgacgccag cgugaccaag cuggccgagc aguacgccaa ggagaacggc accaagcugc      780
ugcugacaaa cgauccauug gaagcagcgc acggaggcaa cgugcugauc accgacaccu      840
ggaucagcau gggccaggag gaggagaaga agaagagacu gcaggccuuc cagggcuacc      900
aggugaccau gaagaccgcc aaggugggcg ccagcgacug gaccuuccug cacugccugc      960
ccagaaagcc cgaggaggug gacgacgagg uguucuacag ccccagaagc cuggugaucc     1020
ccgaggccga aacagaaag uggaccauca uggccgugau ggugagccug cugaccgacu     1080
acagcccuca gcugcagaag cccaaguucu gauaauaggc uggagcccg guggccuagc     1140 uucuugcccc uugggccucc ccccagcccc uccuccccuu ccugcacccg uaccccucc      1200 auaaaguagg aaacacuaca guggucuuug aauaaagucu gagugggcgg c              1251
```

<210> SEQ ID NO 47
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 47

```
gggaauaaag agagaaaaga agaguaagaa gaaauauaag agccaccaug cuguucaacc       60
ugagaauccu gcugaacaac gccgccuuca gaaacggcca caacuucaug gugagaaacu      120
uccggugcgg ccagccucug cagaacaagg ugcagcugaa gggcagagau cugcugaccc      180
ugaagaacuu caccggcgag gagaucaagu acaugcugug gcugagcgcc gaccugaagu      240
ucagaaucaa gcgaagggc gaguaccugc cucugcugca gggcaagagc cugggcauga      300
ucuucgagaa gagaagcacc agaaccagac ugagcaccga aaccggcuuc gcccugcugg      360
gcggacaccc uugcuuccug accacccagg acauccaccu gggcgugaac gagagccuga      420
ccgacaccgc cagagugcug agcagcaugg cugacgccgu gcuggccaga guguacaagc      480
aguccgaccu ggauacccug gccaaggagg ccagcauccc uaucaucaac ggccugagcg      540
accuguacca cccauccag auccuggccg acuaccugac ccugcaggag cacuacagca      600
gccugaaggg ccugacgcug agcuggaucg gcgacggcaa caacauccug cacagcauca      660
ugaugagcgc cgccaaguuc ggcaugcacu ugcaagccgc caccccuaag ggcuacgagc      720
cugacgccuc cgugaccaag cucgccgagc aguacgccaa ggagaacggc accaagcugc      780
```

```
ugcugaccaa cgacccucug gaggccgccc acggcggcaa cgugcugauc accgacaccu     840
ggaucagcau gggccaggag gaggagaaga agaagagacu gcaggccuuc cagggcuacc     900
aggugaccau gaagaccgcc aagguggccg ccagcgacug gaccuuccug cacugccugc     960
cuagaaagcc ugaggaggug gacgacgagg uguucuacag cccuagaagc cuggugiuucc   1020 cugaggccga aacagaaag uggaccauca uggccgugau ggugagccug cugaccgauu    1080
acagcccaca gcugcagaag ccuaaguucu gauaauaggc uggagccucg guggccuagc    1140
uucuugcccc uugggccucc ccccagcccc uccuccccuu ccugcacccg uaccccucc    1200 auaaaguagg aaacacuaca guggucuuug aauaaagucu gaugugggcgg c            1251
```

<210> SEQ ID NO 48
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 48

```
gggaauaaag agagaaaaga agaguaagaa gaaauauaag agccaccaug cuguucaacc      60
ugagaauccu gcugaacaac gccgccuuca gaaacggcca caacuucaug gugagaaacu    120
ucaggugcgg ccagccucug cagaacaagg ugcagcugaa gggccgcgau cugcugacuc    180
ugaagaacuu caccggcgag gagaucaagu acaugcucug gcugagcgca gaccugaaau    240
ucagaaucaa gcagaagggc gaguaccugc cccugccuca aggcaagagc cugggcauga    300
ucuucgagaa gaagaagcacc agaaccagac ugagcaccga aaccggcuuc gcccugcugg    360
gaggccaccc uugcuuccug accacccagg acauccaccu cggcgugaac gaaucccuga    420
ccgauacggc cagaguccug agcucaaugg ccgacgccgu ccuggcgaga guguacaagc    480
aguccgaccu cgacacccug gccaaagagg ccagcauccc uaucaucaac ggccugagcg    540
accuguacca cccuauccag auucucgcug acuaucugac ccugcaggag cacuacucca    600
gccuaaaggg ccucaccccuu agcuggaucg gcgacggcaa caacauccug cacagcauca    660
ugaugagcgc cgccaaguuc ggcaugcacc uccaggccgc cacaccgaag ggguacgaac    720
cggacgccag cgugacuaag cucgccgagc aguacgccaa ggagaacggc accaagcugc    780
ugcugaccaa cgacccucug gaggccgcuc acggcggcaa cguucugauu accgacaccu    840
ggaucagcau gggccaggag gaggagaaga agaagagacu gcaggccuuc cagggcuacc    900
aggugacuau gaagacggcc aaaguggccg ccuccgacug gaccuuccuc cacugccugc    960
cuagaaagcc ugaggaggug gacgacgagg uguucuacag cccuagaagc cuggugiuucc   1020 cugaggccga aacagaaag uggaccauca uggccgugau ggugucccug cucaccgauu    1080 acucccccuca gcuccagaag ccuaaguucu gauaauaggc uggagccucg guggccuagc   1140
uucuugcccc uugggccucc ccccagcccc uccuccccuu ccugcacccg uaccccucc    1200 auaaaguagg aaacacuaca guggucuuug aauaaagucu gaugugggcgg c            1251
```

<210> SEQ ID NO 49
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49

```
gggaaauaag agagaaaaga agaguaagaa gaaauauaag agccaccaug cuguucaacc      60
ugagaauccu gcugaacaac gccgccuuca gaaacggcca caacuucaug gugagaaacu     120
ucaggugcgg ccagccucug cagaacaagg ugcagcugaa gggcagagau cugcugaccc     180
ugaagaacuu caccggcgag gagaucaagu acaugcugug gcugagcgcc gaccugaagu     240
ucagaaucaa gcgaagggc gaguaccugc cucugcugca gggcaagagc cugggcauga     300
ucuucgagaa gagaagcacc agaaccagac ugagcaccga cgggcuuc gcccugcugg      360
gcggccaccc uugcuuccug accccaggg acauccaccu gggcgugaac gagagccuga     420
ccgacaccgc cagagugcug agcagcaugg ccgacgccgu gcuggcuaga guguacaagc     480
agagcgaccu ggacacccug gccaaggagg ccagcauccc uaucaucaac ggccuuagug     540
aucuguacca cccuauccag auccuggccg acuaccuaac ccugcaggag cacuacagca     600
gccugaaggg ucuuacgcug agcuggaucg gcgacggcaa caacauccug cacagcauca     660
ugaugucccgc cgccaaguuc ggcaugcacc ugcaggccgc caccccuaag ggcuacgaac     720
cagacgccag cgugaccaag cuggccgagc aguacgccaa ggagaacggc accaagcuuc     780
ugcuuaccaa cgacccucug gaggccgccc acggcggcaa cgugcugauc acggacaccu     840
ggaucagcau gggccaggag gaggagaaga agaagagacu ccaagcuuuc cagggcuacc     900
aggugaccau gaagaccgcc aagguggccg ccagcgacug gaccuuccug cacugccugc     960
cuagaaagcc ugaggaggug gacgacgagg uguucuacag cccuagaagc cugguguucc    1020
cugaggccga aacagaaag uggaccauca uggccgugau ggugccuug cuuacagacu     1080
auaguccuca gcugcagaag ccuaaguucu gauaauaggc uggagccucg guggccuagc    1140
uucuugcccc uugggccucc ccccagcccc uccuccccuu ccugcacccg uaccccuccc    1200
auaaaguagg aaacacuaca guggucuuug aauaaagucu gaguggggcgg c            1251
```

<210> SEQ ID NO 50
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50

```
gggaaauaag agagaaaaga agaguaagaa gaaauauaag agccaccaug cuguucaacc      60
ugcggauccu gcugaacaac gccgccuucc ggaacggcca caacuucaug gugcggaacu     120
uccggugcgg ccagccccug cagaacaagg ugcagcugaa gggccgggac cugcugaccc     180
ugaagaacuu caccggcgag gagaucaagu acaugcugug gcugagcgcc gaccugaagu     240
uccggaucaa gcgaagggc gaguaccugc cccugcugca gggcaagagc cugggcauga     300
ucuucgagaa gcggagcacc cggaccggc ugagcaccga cggccuuc gcccugcugg       360
gcggccaccc cugcuuccug accccaggg acauccaccu gggcgugaac gagagccuga     420
ccgacaccgc ccgggugcug agcagcaugg ccgacgccgu gcuggccgg guguacaagc      480
agagcgaccu ggacacccug gccaaggagg ccagcauccc caucaucaac ggccugagcg     540
accuguacca cccuauccag auccuggccg acuaccugac ccugcaggag cacuacagca     600
gccugaaggg ccugacccug agcuggaucg gcgacggcaa caacauccug cacagcauca     660
```

| | |
|---|---|
| ugaugagcgc cgccaaguuc ggcaugcacc ugcaggccgc cacgcccaag ggcuacgagc | 720 |
| ccgacgccag cgugaccaag cuggccgagc aguacgccaa ggagaacggc accaagcugc | 780 |
| ugcugaccaa cgacccgcug gaggccgccc acggcggcaa cgugcugauc accgacaccu | 840 |
| ggaucagcau gggccaggag gaggagaaga agaagcggcu gcaggccuuc cagggcuacc | 900 |
| aggugaccau gaagaccgcc aagguggccg ccagcgacug gaccuuccug cacugccugc | 960 |
| cccggaagcc cgaggaggug gacgacgagg uguucuacag cccacggagc cugguguucc | 1020 |
| ccgaggccga gaaccggaag uggaccauca uggccgugau ggugagccug cugaccgacu | 1080 |
| acagcccaca gcugcagaag cccaaguucu gauaauaggc uggagccucg guggccuagc | 1140 |
| uucuugcccc uugggccucc ccccagcccc uccuccccuu ccugcacccg uaccccuccc | 1200 |
| auaaaguagg aaacacuaca guggucuuug aauaaagucu gagugggcgg c | 1251 |

<210> SEQ ID NO 51
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 51

| | |
|---|---|
| gggaaauaag agagaaaaga agaguaagaa gaaauauaag agccaccaug guguucaacc | 60 |
| ugagaauccu gcugaacaac gccgccuuca gaaacggcca caacuucaug gugagaaacu | 120 |
| ucaggugcgg ccagccucug cagaacaagg ugcagcugaa gggccgcgau cgcugacuc | 180 |
| ugaagaacuu caccggcgag gagaucaagu acaugcucug gcugagcgca gaccugaaau | 240 |
| ucagaaucaa gcagaagggc gaguaccugc cccugcucca aggcaagagc cugggcauga | 300 |
| ucuucgagaa gaagagcacc agaaccagac ugagcaccga aaccggcuuc gcccugcugg | 360 |
| gaggccaccc uugcuuccug accacccagg acauccaccu cggcgugaac gaaucccuga | 420 |
| ccgauacggc cagagaccug agcucaaugg ccgacgccgu ccuggcgaga guguacaagc | 480 |
| aguccgaccu cgacacccug gccaaagagg ccagcauccc uaucaucaac ggccugagcg | 540 |
| accuguacca cccuauccag auucucgcug acuaucugac ccugcaggag cacuacucca | 600 |
| gccuaaaggg ccuaccccuu agcuggaucg gcgacggcaa caacauccug cacagcauca | 660 |
| ugaugagcgc cgccaaguuc ggcaugcacc uccaggccgc cacaccgaag ggguacgaac | 720 |
| cggacgccag cgugacuaag cucgccgagc aguacgccaa ggagaacggc accaagcugc | 780 |
| ugcugaccaa cgacccucug gaggccgcuc acggcggcaa cguucugauu accgacaccu | 840 |
| ggaucagcau gggccaggag gaggagaaga agaagagacu gcaggccuuc cagggcuacc | 900 |
| aggugacuau gaagacggcc aaaguggccg ccuccgacug gaccuuccuc cacugccugc | 960 |
| cuagaaagcc ugaggaggug gacgacgagg uguucuacag cccuagaagc cugguguucc | 1020 |
| cugaggccga gaacagaaag uggaccauca uggccgugau ggugcccug cucaccgauu | 1080 |
| acuccccuca gcuccagaag ccuaaguucu gauaauaggc uggagccucg guggccuagc | 1140 |
| uucuugcccc uugggccucc ccccagcccc uccuccccuu ccugcacccg uaccccuccc | 1200 |
| auaaaguagg aaacacuaca guggucuuug aauaaagucu gagugggcgg c | 1251 |

<210> SEQ ID NO 52
<211> LENGTH: 1251
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 52
gggaauuaag agagaaaaga agaguaagaa gaaauauaag agccaccaug cugagcaacc      60
ugagaauccu gcugaacaac gccgcucuga gaaagggaca uaccuccgug gugagacacu     120
ucuggugcgg aaagcccgug cagaacaagg ugcagcugaa gggccgcgau cugcugacuc     180
ugaagaacuu caccggcgag gagaucaagu acaugcucug gcugagcgca gaccugaaau     240
ucagaaucaa gcagaagggc gaguaccugc cccugcucca aggcaagagc cugggcauga     300
ucuucgagaa gagaagcacc agaaccagac ugagcaccga aaccggcuuc gcccugcugg     360
gaggccaccc uugcuuccug accacccagg acauccaccu cggcgugaac gaaucccuga     420
ccgauacggc cagaguccug agcucaaugg ccgacgccgu ccuggcgaga guguacaagc     480
aguccgaccu cgacacccug gccaaagagg ccagcauccc uaucaucaac ggccugagcg     540
accuguacca cccuauccag auucucgcug acuaucugac ccugcaggag cacuacucca     600
gccuaaaggg ccucacccuu agcuggaucg gcgacggcaa caacauccug cacagcauca     660
ugaugagcgc cgccaaguuc ggcaugcacc uccaggccgc cacaccgaag ggguacgaac     720
cggacgccag cgugacuaag cucgccgagc aguacgccaa ggagaacggc accaagcugc     780
ugcugaccaa cgacccucug gaggccgcuc acggcggcaa cguucugauu accgacaccu     840
ggaucagcau gggccaggag gaggagaaga agaagagacu gcaggccuuc agggcuacc      900 aggugacuau gaagacggcc aaaguggccg ccuccgacug gaccuuccuc cacugccugc     960
cuagaaagcc ugaggaggug gacgacgagg uguucuacag cccuagaagc cugguguucc    1020
cugaggccga gaacagaaag uggaccauca uggccgugau ggugucccug cucaccgauu    1080 acucccccuca gcuccagaag ccuaaaguucu gauaauaggc uggagcccg guggccuagc   1140 uucuugcccc uugggccucc ccccagcccc uccucccuu ccugcacccg uaccccucc     1200 auaaaguagg aaacacuaca guggucuuug aauaaagucu gagugggcgg c             1251

<210> SEQ ID NO 53
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
gggaauuaag agagaaaaga agaguaagaa gaaauauaag agccaccaug cucuuuaacc      60
uccgcauccu guugaauaac gcugcguucc gaaacgggca uaacuucaug guacgcaacu     120
ucaggugcgg ccagccacuc cagaacaagg ugcagcuuaa aggucgggac cuccuuacuc     180
ugaagaacuu uaccggagaa gagaucaagu acaugcugug gcuuucagcg gauuugaagu     240
uucgcauuaa acagaaggga gaguaucuuc cccucuugca agggaagucg cucgggauga     300
ucuucgagaa gcgcucgaca aggacccggc ucagcaccga aaccggauuu gcgcuguugg     360
gagggcaccc cguguuucuc acgacgcaag acauucacuu gggagugaac gagucguuga     420
cagacacugc cagaguccuu ucaucgaugg ccgacgcggu gcuugcgagg gucuacaaac     480
agucggaucu ugacacacug gccaaggaag ccucgauccc gaucauuaac gggcucucgg     540
```

| | |
|---|---|
| auuuguacca cccaauccag aucuuggcgg auuaucuuac auugcaagag cauuauuccu | 600 |
| cccucaaggg gcugacucuc agcuggauug gugacggaaa uaacauccuc cauucaauca | 660 |
| ugaugagcgc agcgaaauuc ggaaugcacc uccaagcggc cacgcccaaa gguuacgaac | 720 |
| cugacgcgag cguaacuaaa cucgcggagc aguacgcaaa ggagaacggc acgaaacucu | 780 |
| ugcucacaaa cgacccucuug gaggcagcac acggugguaa cguccugauu acagacacgu | 840 |
| ggaucuccau ggggcaggag gaggagaaga agaagagacu ucaggcauuu cagggauacc | 900 |
| agguaacgau gaagacggcg aaggucgccg ccucagacug gacuuuccuc cauugccugc | 960 |
| cgaggaagcc ggaagaaguc gacgacgagg uguuuacag cccgcgaucc cugguguucc | 1020 |
| cugaagccga gaaucggaag uggacaauua uggcagugau ggugucccuu cuuacggacu | 1080 |
| acucgcccca gcugcagaaa ccgaaauucu gauaauaggc uggagccucg guggccuagc | 1140 |
| uucuugcccc uugggccucc ccccagcccc uccucccuu ccugcacccg uaccccucc | 1200 |
| auaaaguagg aaacacuaca guggucuuug aauaaagucu gaguggggcgg c | 1251 |

```
<210> SEQ ID NO 54
<211> LENGTH: 1228
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
```

| | |
|---|---|
| gggaauaag agagaaaga agaguaagaa gaaauauaag agccaccaug cucuuuaacc | 60 |
| uccgcauccu guugaauaac gcugcguucc gaaaugggca uaacuucaug guacgcaacu | 120 |
| ucagaugcgg ccagccacuc cagaacaagg ugcagcuuaa aggucgggac cuccuuacuc | 180 |
| ugaagaacuu uaccggagaa gagaucaagu acaugcugug gcuuucagcg gauuugaagu | 240 |
| uucgcauuaa acagaaggga gaguaucuuc cccucuugca agggaagucg cucgggauga | 300 |
| ucuucgagaa gcgcucgaca aggacccggc ucagcaccga aaccggauuu gcgcuguugg | 360 |
| gagggcaccc cguguuuucuc acgacgcaag acauucacuu gggagugaau gagucguuga | 420 |
| cagacacugc cagaguccuu ucaucgaugg ccgaugcggu gcuugcgagg gucuacaaac | 480 |
| agucggaucu ugacacacug gccaaggaag ccucgauccc gaucauuaac gggcucucgg | 540 |
| auuuguacca cccaauccag aucuuggcgg auuaucuuac auugcaagag cauuauuccu | 600 |
| cccucaaggg gcugacucuc agcuggauug gugacggaaa uaacauccuc cauucaauca | 660 |
| ugaugagcgc agcgaaauuc ggaaugcacc uccaagcggc cacgcccaaa gguuaugaac | 720 |
| cugaugcgag cguaacuaaa cucgcggagc aguaugcaaa ggaaaauggc acgaaacucu | 780 |
| ugcucacaaa ugacccucuug gaggcagcac acggugguaa uguccugauu acagacacau | 840 |
| ggaucuccau ggggcaggag gaggagaaaa agaaaagacu ucaggcauuu cagggauacc | 900 |
| agguaacgau gaaacggcg aaggucgccg ccucagacug gacuuuccuc cauugccugc | 960 |
| cgaggaagcc ggaagaaguc gaugaugagg uguuuacag ccccgaucc cugguguucc | 1020 |
| cugaagccga aaaucggaag uggacaauua uggcagugau ggugucccuu cuuacggacu | 1080 |
| acucgcccca gcugcaaaaa ccgaaauucu gauaauaggc uggagccucg guggccaugc | 1140 |
| uucuugcccc uugggccucc ccccagcccc uccucccuu ccugcacccg uaccccgug | 1200 |
| gucuuugaau aaagucugag ugggcggc | 1228 |

```
<210> SEQ ID NO 55
<211> LENGTH: 1251
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
gggaauuaag agagaaaaga agaguaagaa gaaauauaag agccaccaug cguucaacc      60 ugcgaauccu gcugaacaau gccgcuuuuc ggaacgggca caauuucaug gugaggaacu   120
uucgcugcgg acagcccuc cagaacaagg uccagcugaa gggcagggac cugcugaccc    180
ugaaaaauuu cacaggggag gaaaucaagu acaugcugug gcugucagcc gaucugaagu   240
uccggaucaa gcagaagggc gaauaucugc cucugcucca gggcaaaagc cuggggauga   300
ucuucgaaaa gcgcaguacu cggaccagac ugucaacaga gacuggauuc gcacugcugg   360
gaggacaccc auguuuucug accacacagg acauucaucu gggagugaac gagucccuga   420
ccgacacagc acgcguccug agcuccaugg cugaugcagu gcuggcucga gucuacaaac   480
agucugaccu ggauacccug gccaaggaag cuucuauccc aaucauuaau ggccugagug   540
accuguauca ccccauccag auucuggccg auuaccugac ccuccaggag cauuauucua   600
gucugaaagg gcugacacug agcuggauug gggacggaaa caauauccug cacuccauua   660
ugaugagcgc cgccaaguuu ggaaugcacc uccaggcugc aaccccaaaa ggcuacgaac   720
ccgaugccuc cgugacaaag cuggcagaac aguaugccaa agagaacggc acuaagcugc   780
ugcugaccaa ugacccucug gaggccgcuc acggaggcaa cgucugauc acugauaccu    840 ggauuaguau gggacaggag gaagagaaga agaagcggcu ccaggccuuc cagggcuacc   900
aggugacaau gaaaacugcu aaggucgcag ccagcgacug gaccuuucug cauugccugc   960
ccagaaagcc ugaagaggug gacgaugagg ucuucuacuc acccagaagc cugguguuuc  1020
cugaagcuga gaauaggaag uggacaauca uggcagugau ggucagccug cugacugauu  1080
auucccucca gcuccagaaa ccaaaguucu gauaauaggc uggagccucg guggccuagc  1140
uucuugcccc uugggccucc ccccagcccc uccuccccuu ccugcacccg uaccccuccc  1200
auaaaguagg aaacacuaca gugguucuuug aauaaagucu gagugggcgg c          1251

<210> SEQ ID NO 56
<211> LENGTH: 1086
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
augcuguuua aucugaggau ccuguuaaac aaugcagcuu uuagaaaugg ucacaacuuc      60
augguucgaa auuucgggug uggacaacca cuacaagacu acaaggacga ugacgacaag   120
aauaaagugc agcugaaggg ccgugaccuu cucacucuaa aaacuuuac cggagaagaa     180 auuaauauau ugcuauggcu aucagcagau cugaaauuua ggauaaaaca gaaggagag    240 uauuugccuu uauugcaagg gaaguccuua ggcaugauuu uugagaaaag aaguacucga   300
acaagauugu cuacagaaac aggcuuugca cuucggggag gacauccuug uuuucuuacc   360
acacaagaua uucauuuggg ugugaaugaa agucucacgg acacggcccg uguauugucu   420
```

| | |
|---|---|
| agcauggcag augcaguauu ggcucgagug uauaaacaau cagauuugga cacccuggcu | 480 |
| aaagaagcau ccaucccaau uaucaauggg cugucagauu uguaccaucc uauccagauc | 540 |
| cuggcugauu accucacgcu ccaggaacac uauagcucuc ugaaaggucu acccucagc | 600 |
| uggaucgggg augggaacaa uauccugcac uccaucauga ugagcgcagc gaaauucgga | 660 |
| augcaccuuc aggcagcuac uccaaagggu uaugagccgg augcuagugu aaccaaguug | 720 |
| gcagagcagu augccaaaga gaauggauacc aagcuguugc ugacaaauga uccauuggaa | 780 |
| gcagcgcaug gaggcaaugu auuaauuaca gacacuugga uaagcauggg acaagaagag | 840 |
| gagaagaaaa agcggcucca ggcuuuccaa gguuaccagg uuacaaugaa gacugcuaaa | 900 |
| guugcugccu cugacuggac auuuuuacac ugcuugccca gaaagccaga agaaguggau | 960 |
| gaugaagucu uuuauucucc ucgaucacua uguuucccag aggcagaaaa cagaaagugg | 1020 |
| acaaucaugg cugucauggu gucccugcug acagauuacu caccucagcu ccagaagccu | 1080 |
| aaauuu | 1086 |

<210> SEQ ID NO 57
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

| | |
|---|---|
| augcugucua auuugaggau ccugcucaac aaugcagcuc uuagaaaggg ucacacuucu | 60 |
| gugguucgac auuuuuggug ugggaagcca guccaaaguc aaguacagcu gaaaggccgu | 120 |
| gaccuccuca ccuugaagaa cuucacagga gaggagauuc aguacaugcu auggcucucu | 180 |
| gcagaucuga aauucaggau caagcagaaa ggagaauauu uaccuuuauu gcaagggaaa | 240 |
| uccuuaggaa ugauuuuuga gaaaagaagu acucgaacaa gacugccac agaaacaggc | 300 |
| uuugcucugc ugggaggaca cccuuccuuu cuuaccacac aagacauuca cuugggugug | 360 |
| aaugaaaguc ucacagacac cgcucgguguc uuaucuagca ugacagaugc aguguuagcu | 420 |
| cgaguguaua aacaaucaga ucuggacacc cuggcuaaag aagcauccau cccaauuguc | 480 |
| aauggacugu cagacuugua ucauccuauc cagauccugg cugauuaccu uacacuccag | 540 |
| gaacacuaug gcucucucaa aggucuuacc cucagcugga uaggggaugg gaacaauauc | 600 |
| uugcacucua ucaugaugag ugcugcaaaa ucgggaugc accuucaagc agcuacucca | 660 |
| aagguuaug agccagaucc uaauauaguc aagcuagcag agcaguugc caaggagaau | 720 |
| gguaccaagu ugucaaugac aaaugaucca cuggaagcag cacguggagg caauguauua | 780 |
| auuacagaua cuuggauaag cauggacaa gaggaugaga agaaaagcg ucuucaagcu | 840 |
| uuccaagguu accagguuac gaugaagacu gccaaaguggg cugcgucuga cuggacauuu | 900 |
| uuacacuguu ugccuagaaa gccagaagaa guggaugaug aaguauuuua uucuccacgg | 960 |
| ucauuagugu ucccagaggc agagaauaga aguggacaa ucauggcugu caugguaucc | 1020 |
| cugcugacag acuacucacc ugugcuccag aagccaaagu uu | 1062 |

<210> SEQ ID NO 58
<211> LENGTH: 1086
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58

```
augcugucua auuugaggau ccugcucaac aaugcagcuc uuagaaaggg ucacacuucu      60
gugguucgac auuuuggug ugggaagcca guccaagacu acaaggacga ugacgacaag      120
agucaaguac agcugaaagg ccgugaccuc ucaccuuga agaacuucac aggagaggag      180
auucaguaca ugcuauggcu cucugcagau cugaaauuca ggaucaagca gaaaggagaa      240
uauuuaccuu uauugcaagg gaaauccuua ggaaugauuu ugagaaaag aaguacucga       300 acaagacugu ccacagaaac aggcuuugcu cugcugggag acacccuuc cuuucuuacc       360 acacaagaca uucacuuggg ugugaaugaa agucucacag acaccgcucg ugucuuaucu      420
agcaugacag augcaguguu agcucgagug uauaaacaau cagaucugga cacccuggcu      480
aaagaagcau ccaucccaau ugucaaugga cugucagacu uguaucaucc uaccagauc      540 cuggcugauu accuuacacu ccaggaacac uauggcucuc ucaaaggucu acccucagc       600 uggauagggg augggaacaa uaucuugcac ucuaucauga ugagugcugc aaaauucggg      660
augcaccuuc aagcagcuac uccaaagggu uaugagccag auccuaauau agucaagcua      720
gcagagcagu augccaagga gaauggua cc aaguugucaa ugacaaauga uccacuggaa     780
gcagcacgug gaggcaaugu auuaauuaca gauacuugga uaagcauggg acaagaggau      840
gagaagaaaa agcgucuuca agcuuuccaa gguuaccagg uuacgaugaa gacugccaaa     900
guggcugcgu cugacuggac auuuuuacac uguuugccua gaaagccaga agaaguggau      960
gaugaaguau uuuauucucc acggucauua guguccag aggcagagaa uagaaaguggg     1020 acaaucaugg cugucauggu aucccugcug acagacuacu caccugugcu ccagaagcca     1080
aaguuu                                                             1086
```

<210> SEQ ID NO 59
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59

```
augcuguuua aucugaggau ccuguuaaac aaugcagcuu uuagaaaugg ucacaacuuc      60
augguucgaa auuuucggug uggacaacca cuacaaaaua aagugcagcu gaagggccgu     120
gaccuucuca cucuaaaaaa cuuuaccgga gaagaaauua aauauaugcu auggcuauca     180
gcagaucuga aauuuaggau aaaacagaaa ggagaguauu ugccuuuauu gcaagggaag     240
uccuuaggca ugauuuuuga gaaagaagu acucgaacaa gauugcuac agaaacaggc      300 uuugcacuuc ugggaggaca uccuuguuuu cuuaccacac aagauauuca uuuggguguag  360 aaugaaaguc ucacggacac ggcccgugua uugucuagca uggcagaugc aguauuggcu     420
cgaguguaua aacaaucaga uuuggacacc cuggcuaaag aagcauccau cccaauuauc     480
aaugggcugu cagauuugua ccauccuauc cagauccugg cugauuaccu cacgcuccag     540
gaacacuaua gcucucugaa aggucuuacc cucagcugga ucggggaugg gaacaauauc     600
cugcacucca ucaugaugag cgcagcgaaa uucggaaugc accuucaggc agcuacucca     660
aaggguuaug agccggaugc uaguguaacc aaguuggcag agcaguaugc caaagagaau    720
```

| | |
|---|---|
| gguaccaagc uguugcugac aaaugaucca uuggaagcag cgcauggagg caauguauua | 780 |
| auuacagaca cuuggauaag caugggacaa gaagaggaga agaaaaagcg gcuccaggcu | 840 |
| uuccaagguu accagguuac aaugaagacu gcuaaaguug cugccucuga cuggacauuu | 900 |
| uuacacugcu ugcccagaaa gccagaagaa guggaugaug aagucuuuua uucuccucga | 960 |
| ucacuagugu ucccagaggc agaaaacaga aaguggacaa ucauggcugu caugguglucc | 1020 |
| cugcugacag auuacucacc ucagcuccag aagccuaaau uu | 1062 |

<210> SEQ ID NO 60
<211> LENGTH: 1062
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 60

| | |
|---|---|
| augcucuuua accuccgcau ccuguugaau aacgcugcgu uccgaaaugg gcauaacuuc | 60 |
| augguacgca acuucagaug cggccagcca cuccagaaca aggugcagcu uaaaggucgg | 120 |
| gaccuccuua cucugaagaa cuuuaccgga gaagagauca aguacaugcu guggcuuuca | 180 |
| gcggauuuga aguuucgcau uaaacagaag ggagaguauc uuccccucuu gcaagggaag | 240 |
| ucgcucggga ugaucuucga gaagcgcucg acaaggaccc ggcucagcac cgaaaccgga | 300 |
| uuugcgcugu ugggagggca cccguguuuu ucacgacgc aagacauuca cuugggagug | 360 |
| aaugagucgu ugacagacac ugccagaguc cuuucaucga uggccgaugc ggugcuugcg | 420 |
| agggucuaca aacagucgga ucuugacaca cuggccaagg aagccucgau cccgaucauu | 480 |
| aacgggcucu cggauuugua ccacccaauc cagaucuugg cggauuaucu uacauugcaa | 540 |
| gagcauuauu ccucccucaa ggggcugacu cucagcugga uuggugacgg aaauaacauc | 600 |
| cuccauucaa ucaugaugag cgcagcgaaa uucggaaugc accuccaagc ggccacgccc | 660 |
| aaagguuaug aaccugaugc gagcguaacu aaacucgcgg agcaguaugc aaaggaaaau | 720 |
| ggcacgaaac ucuugcucac aaaugacccc uuggaggcag cacacggugg uaaugcccug | 780 |
| auuacagaca cauggaucuc cauggggcag gaggaggaga aaagaaaag acuucaggca | 840 |
| uuucagggau accagguaac gaugaaaacg gcgaaggucg ccgccucaga cuggacuuuc | 900 |
| cuccauugcc ugccgaggaa gccggaagaa gucgaugaug agguguuuua cagcccccga | 960 |
| ucccuggugu ucccugaagc cgaaaaucgg aaguggacaa uuauggcagu gaugguglucc | 1020 |
| cuucuuacgg acuacucgcc ccagcugcaa aaaccgaaau uc | 1062 |

<210> SEQ ID NO 61
<211> LENGTH: 1228
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 61

| | |
|---|---|
| gggaauaaag agagaaaaga agaguaagaa gaaauauaag agccaccaug cucuuuaacc | 60 |
| uccgcauccu guugaauaac gcugcguucc gaaaugggca uaacuucaug guacgcaacu | 120 |
| ucagaugcgg ccagcacucu cagaacaagg ugcagcuuaa aggucgggac cuccuuacuc | 180 |
| ugaagaacuu uaccggagaa gagaucaagu acaugcugug gcuuucagcg gauuugaagu | 240 |

```
uucgcauuaa acagaaggga gaguaucuuc cccucuugca agggaagucg cucgggauga    300
ucuucgagaa gcgcucgaca aggacccggc ucagcaccga aaccggauuu gcgcuguugg    360
gagggcaccc uguuuucuc acgacgcaag acauucacuu gggagugaau gagucguuga    420
cagacacugc cagagaccuu ucaucgaugg ccgaugcggu gcuugcgagg ucuacaaac     480 agucggaucu ugacacacug gccaaggaag ccucgauccc gaucauuaac gggcucucgg    540
auuuguacca cccaauccag aucuuggcgg auuaucuuac auugcaagag cauuauuccu    600
cccucaaggg gcugacucuc agcuggauug ugacggaaa uaacauccuc cauucaauca    660
ugaugagcgc agcgaaauuc ggaaugcacc uccaagcggc cacgcccaaa gguuaugaac    720
cugaugcgag cguaacuaaa cucgcggagc aguaugcaaa ggaaaauggc acgaaacucu    780
ugcucacaaa ugaccccuug gaggcagcac acggugguaa uguccugauu acagacacau    840
ggaucuccau ggggcaggag gaggagaaaa agaaaagacu ucaggcauuu cagggauacc    900
agguaacgau gaaaacggcg aaggucgccg cccagacug gacuuuccuc cauugccugc     960
cgaggaagcc ggaagaaguc gaugaugagg uguuuacag cccccgaucc cugguguucc     1020
cugaagccga aaaucggaag uggacaauua uggcagugau ggugucccuu cuuacggacu    1080
acucgcccca gcugcaaaaa ccgaaauucu gauaauaggc uggagccucg guggccaugc    1140
uucuugcccc uugggccucc ccccagcccc uccuccccuu ccugcacccg uaccccgug    1200 gucuuugaau aaagucugag ugggcggc                                     1228
```

<210> SEQ ID NO 62
<211> LENGTH: 1647
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

```
agcgguggag cuuggcauaa aguucaaaug cuccuacacc cugcccugca guaucucuaa     60
ccaggggacu uugauaagga agcugaaggg ugauauuacc uuugcucccu cacugcaacu    120
gaacacauuu cuuaguuuuu agguggcccc cgcuggcuaa cuugcuguga aguuuucaag    180
ggcauagaau cguccuuuac acaauuaaaa gaagaugcug uuuaaucuga ggauccuguu    240
aaacaaugca gcuuuuagaa augguccacaa cuucaugguu cgaaauuuuc ggugugaaca    300
accacuacaa aauaaagugc agcugaaggg ccgugaccuu cucacucuaa aaacuuuuac    360
cggagaagaa auuaaauaua ugcuauggcu aucagcagau cugaaauuua ggauaaaaca    420 gaaggagag uauuugccuu uauugcaagg gaaguccuua gcaugauuu uugagaaaag    480 aaguacucga acaagauugu cuacagaaac aggcuuugca cuucugggag acauccuug     540 uuuucuuacc acacaagaua ucauuuggg ugugaaugaa agucucacgg acacggcccg    600
uguauugucu agcauggcag augcaguauu ggcucgagug uauaaacaau cagauuugga    660
cacccuggcu aaagaagcau ccaucccaau uaucaauggg cugucagauu uguaccaucc    720
uauccagauc cuggcugauu accucacgcu ccaggaacac uauagcucuc ugaaaggucu    780
uacccucagc uggaucgggg augggaacaa uauccugcac uccaucauga ugagcgcagc    840
gaaauucgga augcaccuuc aggcagcuac uccaaagggu uauagccgg augcuagugu    900 aaccaaguug gcagagcagu augccaaaga gaauggguacc aagcguuugc ugacaaauga    960
```

| | | | | |
|---|---|---|---|---|
| uccauuggaa | gcagcgcaug | gaggcaaugu | auuaauuaca | gacacuugga uaagcauggg | 1020 |
| acaagaagag | gagaagaaaa | agcggcucca | ggcuuccaa | gguuaccagg uuacaaugaa | 1080 |
| gacugcuaaa | guugcugccu | cugacuggac | auuuuacac | ugcuugccca gaaagccaga | 1140 |
| agaaguggau | gaugaagucu | uuuauucucc | ucgaucacua | guuucccag aggcagaaaa | 1200 |
| cagaaagugg | acaaucaugg | cugucauggu | gucccugcug | acagauuacu caccucagcu | 1260 |
| ccagaagccu | aaauuuugau | guuguguuac | uugucaagaa | agaagcaaug uucuucagua | 1320 |
| acagaaugag | uugguuuaug | gggaaaagag | aagagaaucu | aaaaaauaaa caaaucccua | 1380 |
| acacgguua | ugggugaacc | guaugauaug | cuuugccauu | gugaaacuuu ccuuaagccu | 1440 |
| uuaauuuaag | ugcugaugca | cuguaauacg | ugcuuaacuu | ugcuuaaacu cucuaauucc | 1500 |
| caauuucuga | guuacauuua | gauaucauau | uaauuaucau | auacauuuac uucaacauaa | 1560 |
| aauacugugu | ucauaaugua | uaaugucuaa | gccauuaagu | guaaucuaug cuuauuaccu | 1620 |
| aaauaaauua | ucacccaugc | uaauuua | | | 1647 |

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

```
<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85
<211> LENGTH: 41
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85 gggaauaag agagaaaaga agaguaagaa gaaauauaag a                    41

<210> SEQ ID NO 86
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Gly Gly Gly Ser
1               5

<210> SEQ ID NO 87
<211> LENGTH: 9
<212> TYPE: RNA
<213> ORGANISM: Unknown
<220> FEATURE:
<221> NAME/KEY: source
<223> OTHER INFORMATION: /note="Description of Unknown:
      Kozak sequence"

<400> SEQUENCE: 87 ccrccaugg                                                        9

<210> SEQ ID NO 88
<211> LENGTH: 92
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
ucaagcuuuu ggacccucgu acagaagcua auacgacuca cuauagggaa auaagagaga    60
aaagaagagu aagaagaaau auaagagcca cc                                 92
```

```
<210> SEQ ID NO 89
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
gggagaucag agagaaaaga agaguaagaa gaaauauaag agccacc              47

<210> SEQ ID NO 90
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gggagacaag cuuggcauuc cgguacuguu gguaaagcca cc                   42

<210> SEQ ID NO 91

<400> SEQUENCE: 91

000

<210> SEQ ID NO 92

<400> SEQUENCE: 92

000

<210> SEQ ID NO 93
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
gggaauuaac agagaaaaga agaguaagaa gaaauauaag agccacc              47

<210> SEQ ID NO 94
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
gggaaauuag acagaaaaga agaguaagaa gaaauauaag agccacc              47

<210> SEQ ID NO 95
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 95
gggaaauaag agaguaaaga acaguaagaa gaaauauaag agccacc    47

<210> SEQ ID NO 96
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
gggaaaaaag agagaaaaga agacuaagaa gaaauauaag agccacc    47

<210> SEQ ID NO 97
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gggaaauaag agagaaaaga agaguaagaa gauauauaag agccacc    47

<210> SEQ ID NO 98
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
gggaaauaag agacaaaaca agaguaagaa gaaauauaag agccacc    47

<210> SEQ ID NO 99
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
gggaaauuag agaguaaaga acaguaagua gaauuaaaag agccacc    47

<210> SEQ ID NO 100
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gggaaauaag agagaauaga agaguaagaa gaaauauaag agccacc    47

<210> SEQ ID NO 101
<211> LENGTH: 47
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
gggaaauaag agagaaaaga agaguaagaa gaaaauuaag agccacc    47

<210> SEQ ID NO 102
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
gggaaauaag agagaaaaga agaguaagaa gaaauuuaag agccacc    47

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

```
<210> SEQ ID NO 111
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111
ugauaauagu ccauaaagua ggaaacacua cagcuggagc cucgguggcc augcuucuug      60
ccccuugggc cucccccag ccccuccucc ccuuccugca cccguacccc ccgcauuauu      120
acucacggua cgaguggucu uugaauaaag ucgagugggg cggc                      164

<210> SEQ ID NO 112
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112
ugauaauagu ccauaaagua ggaaacacua cagcuggagc cucgguggcc uagcuucuug      60
ccccuugggc cucccccag ccccuccucc ccuuccugca cccguacccc ccgcauuauu      120
acucacggua cgaguggucu uugaauaaag ucgagugggg cggc                      164

<210> SEQ ID NO 113

<400> SEQUENCE: 113

000

<210> SEQ ID NO 114
<211> LENGTH: 87
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gacagugcag ucacccauaa aguagaaagc acuacuaaca gcacuggagg guguaguguu      60
uccuacuuua uggaugagug uacugug                                         87

<210> SEQ ID NO 115
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
uguaguguuu ccuacuuuau gga                                             23

<210> SEQ ID NO 116
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 116
uccauaaagu aggaaacacu aca                                        23

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
cauaaaguag aaagcacuac u                                          21

<210> SEQ ID NO 118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
aguagugcuu ucuacuuuau g                                          21

<210> SEQ ID NO 119
<211> LENGTH: 85
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
cgcuggcgac gggacauuau uacuuuuggu acgcgcugug acacuucaaa cucguaccgu   60
gaguaauaau gcgccgucca cggca                                        85

<210> SEQ ID NO 120
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
ucguaccgug aguaauaaug cg                                         22

<210> SEQ ID NO 121
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
```
cgcauuauua cucacgguac ga                                      22

<210> SEQ ID NO 122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
cauuauuacu uuugguacgc g                                       21

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
cgcguaccaa aaguaauaau g                                       21

<210> SEQ ID NO 124
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124 ugauaauag                                                      9

<210> SEQ ID NO 125
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125 ugauaguaa                                                      9

<210> SEQ ID NO 126
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126 uaaugauag                                                      9

<210> SEQ ID NO 127
<211> LENGTH: 9
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 127 ugauaauaa                                                                9

<210> SEQ ID NO 128
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128 ugauaguag                                                                9

<210> SEQ ID NO 129
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129 uaaugauga                                                                9

<210> SEQ ID NO 130
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130 uaauaguag                                                                9

<210> SEQ ID NO 131
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131 ugaugauga                                                                9

<210> SEQ ID NO 132
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132 uaauaauaa                                                                9

<210> SEQ ID NO 133
```

```
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133 uaguaguag                                                                   9

<210> SEQ ID NO 134
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
gcuggagccu cgguggccau gcuucuugcc ccuugggccu cccccagcc ccuccuccc            60 uuccugcacc cguaccccu ccauaaagua ggaaacacua caguggucuu ugaauaaagu          120
cugagugggc ggc                                                           133

<210> SEQ ID NO 135
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
ccucugaaau ucaguucuuc ag                                                  22

<210> SEQ ID NO 136
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
ugagaacuga auuccauggg uu                                                  22

<210> SEQ ID NO 137
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
cuccuacaua uuagcauuaa ca                                                  22

<210> SEQ ID NO 138
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 138
uuaaugcuaa ucgugauagg ggu                                              23

<210> SEQ ID NO 139
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
ccaguauuaa cugugcugcu ga                                               22

<210> SEQ ID NO 140
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
uagcagcacg uaaauauugg cg                                               22

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
caacaccagu cgaugggcug u                                                21

<210> SEQ ID NO 142
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
uagcuuauca gacugauguu ga                                               22

<210> SEQ ID NO 143
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
ugucaguuug ucaaauaccc ca                                               22

<210> SEQ ID NO 144
```

```
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
cguguauuug acaagcugag uu                                              22

<210> SEQ ID NO 145
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
uggcucaguu cagcaggaac ag                                              22

<210> SEQ ID NO 146
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ugccuacuga gcugauauca gu                                              22

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
uucacagugg cuaaguuccg c                                               21

<210> SEQ ID NO 148
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
agggcuuagc ugcuugugag ca                                              22

<210> SEQ ID NO 149
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 149
```

```
ugauaauagg cuggagccuc gguggccaug cuucuugccc cuugggccuc ccccagccc      60 cuccucccccu uccugcaccc guacccccccg cauuauuacu cacgguacga guggucuuug   120
aauaaagucu gagugggcgg c                                               141
```

<210> SEQ ID NO 150
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 150

```
ugauaauagg cuggagccuc gguggccaug cuucuugccc cuugggccuc ccccagccc      60 cuccucccccu uccugcaccc guaccccccgu ggucuuugaa uaaagucuga gugggcggc    119
```

<210> SEQ ID NO 151
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 151

```
ugauaauagg cuggagccuc gguggccaug cuucuugccc cuugggccuc ccccagccc      60 cuccucccccu uccugcaccc guacccccuc cauaaaguag gaaacacuac aguggucuuu    120
gaauaaaguc ugagugggcg gc                                              142
```

<210> SEQ ID NO 152

<400> SEQUENCE: 152

000

<210> SEQ ID NO 153
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153

```
uuaaugcuaa uugugauagg ggu                                             23
```

<210> SEQ ID NO 154
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154

```
accccuauca caauuagcau uaa                                             23
```

<210> SEQ ID NO 155
<211> LENGTH: 188

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 155
ugauaauagu ccauaaagua ggaaacacua cagcuggagc cucgguggcc augcuucuug      60
ccccuugggc cuccauaaag uaggaaacac uaucccccc cagccccucc ucccuuccu       120 gcacccguac ccccuccaua aaguaggaaa cacuacagug gucuuugaau aaagucugag    180
ugggcggc                                                              188

<210> SEQ ID NO 156
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
ugauaauagg cuggagccuc ggguggccaug cuucuugccc cuugggccuc ccccagccc      60 cuccucccu uccugcaccc guaccccag uagugcuuuc uacuuuaugg uggucuuuga      120
auaaagucug agugggcggc                                                 140

<210> SEQ ID NO 157
<211> LENGTH: 182
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157
ugauaauaga guagugcuuu cuacuuuaug gcuggagccu cgguggccau gcuucuugcc      60
ccuugggcca guagugcuuu cuacuuuaug ucccccagc cccuccuccc cuccugcac     120 ccguacccc aguagugcuu ucuacuuuau gguggucuuu gaauaaaguc ugagugggcg    180
gc                                                                    182

<210> SEQ ID NO 158
<211> LENGTH: 184
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 158
ugauaauaga guagugcuuu cuacuuuaug gcuggagccu cgguggccau gcuucuugcc      60
ccuugggccu ccauaaagua ggaaacacua cauccccca gccccuccuc cccuccugc      120 acccguaccc ccaguagugc uuucuacuuu auggugguculu ugaauaaag ucgagugggg   180 cggc                                                                 184

<210> SEQ ID NO 159
<211> LENGTH: 142
<212> TYPE: RNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 159

```
ugauaauagg cuggagccuc gguggccaug cuucuugccc cuugggccuc ccccagccc       60
cuccucccu uccugcaccc guaccccac cccaucaca auuagcauua aguggucuuu         120
gaauaaaguc ugagugggcg gc                                              142
```

<210> SEQ ID NO 160
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 160

```
ugauaauaga ccccuaucac aauuagcauu aagcuggagc cucgguggcc augcuucuug       60
ccccuugggc caccccuauc acaauuagca uuaauccccc cagccccucc ucccuuccu       120
gcacccguac ccccaccccu aucacaauua gcauuaagug gucuuugaau aaagucugag     180
ugggcggc                                                               188
```

<210> SEQ ID NO 161
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 161

```
ugauaauaga ccccuaucac aauuagcauu aagcuggagc cucgguggcc augcuucuug       60
ccccuugggc cuccauaaag uaggaaacac uacauccccc cagccccucc ucccuuccu       120
gcacccguac ccccaccccu aucacaauua gcauuaagug gucuuugaau aaagucugag     180
ugggcggc                                                               188
```

<210> SEQ ID NO 162
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 162

```
ugauaauagu ccauaaagua ggaaacacua cagcuggagc cucgguggcc augcuucuug       60
ccccuugggc cuccccccag ccccuccucc ccuuccugca cccguacccc cguggucuuu      120
gaauaaaguc ugagugggcg gc                                              142
```

<210> SEQ ID NO 163
<211> LENGTH: 142
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic polynucleotide"

<400> SEQUENCE: 163
ugauaauagg cuggagccuc gguggcucca uaaaguagga aacacuacac augcuucuug      60
ccccuugggc cuccccccag ccccuccucc ccuuccugca cccguacccc cguggucuuu     120
gaauaaaguc ugagugggcg gc                                              142

<210> SEQ ID NO 164
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
ugauaauagg cuggagccuc gguggccaug cuucuugccc cuugggccuc cauaaaguag      60
gaaacacuac auccccccag ccccuccucc ccuuccugca cccguacccc cguggucuuu     120
gaauaaaguc ugagugggcg gc                                              142

<210> SEQ ID NO 165
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
gggaaauaag aguccauaaa guaggaaaca cuacaagaaa agaagaguaa gaagaaauau      60
aagagccacc                                                             70

<210> SEQ ID NO 166
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
gggaaauaag agagaaaaga agaguaaucc auaaaguagg aaacacuaca gaagaaauau      60
aagagccacc                                                             70

<210> SEQ ID NO 167
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
gggaaauaag agagaaaaga agaguaagaa gaaauauaau ccauaaagua ggaaacacua      60
cagagccacc                                                             70

<210> SEQ ID NO 168
```

<400> SEQUENCE: 168

000

<210> SEQ ID NO 169
<211> LENGTH: 181
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 169
ugauaauaga guagugcuuu cuacuuuaug gcuggagccu cgguggccau gcuucuugcc      60
ccuugggcca guagugcuuu cuacuuuaug uccccccagc cccucuccc uuccugcacc      120 cguaccccca guagugcuuu cuacuuuaug guggucuuug aauaaagucu gagugggcgg   180
c                                                                     181

<210> SEQ ID NO 170
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 170
ugauaauagg cuggagccuc gguggccaug cuucuugccc cuuccauaaa guaggaaaca   60
cuacaugggc cucccccag ccccuccucc ccuuccugca cccguacccc cguggucuuu   120
gaauaaaguc ugagugggcg gc                                              142

<210> SEQ ID NO 171
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 171
ugauaauagg cuggagccuc gguggccaug cuucuugccc cuugggccuc ccccagucc    60 auaaaguagg aaacacuaca ccccuccucc ccuuccugca cccguacccc cguggucuuu   120
gaauaaaguc ugagugggcg gc                                              142

<210> SEQ ID NO 172
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 172
ugauaauagg cuggagccuc gguggccaug cuucuugccc cuugggccuc ccccagccc    60 cuccucccu ucuccauaaa guaggaaaca cuacacugca cccguacccc cguggucuuu    120
gaauaaaguc ugagugggcg gc                                              142

<210> SEQ ID NO 173
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 173
ugauaauagg cuggagccuc gguggccaug cuucuugccc cuugggccuc ccccagccc      60 cuccuccccu uccugcaccc guaccccgu ggucuuugaa uaaaguucca uaaaguagga     120
aacacuacac ugaguggggcg gc                                            142

<210> SEQ ID NO 174

<400> SEQUENCE: 174

000

<210> SEQ ID NO 175
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 175
ugauaauagg cuggagccuc gguggccuag cuucuugccc cuugggccuc ccccagccc      60 cuccuccccu uccugcaccc guaccccgu ggucuuugaa uaaagucuga gugggcggc     119

<210> SEQ ID NO 176

<400> SEQUENCE: 176

000

<210> SEQ ID NO 177
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 177
ugauaauagg cuggagccuc gguggccuag cuucuugccc cuugggccuc ccccagccc      60 cuccuccccu uccugcaccc guacccccg cauuauuacu cacgguacga guggucuuug    120
aauaaagucu gagugggcgg c                                             141

<210> SEQ ID NO 178
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 178
ugauaauagu ccauaaagua ggaaacacua cagcuggagc cucgguggcc uagcuucuug     60

```
ccccuugggc ucccauaaag uaggaaacac uacaucccc cagccccucc uccccuuccu    120
gcacccguac cccuccaua aaguaggaaa cacuacagug gucuuugaau aaagucugag    180
ugggcggc                                                             188
```

<210> SEQ ID NO 179
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 179

```
ugauaauagu ccauaaagua ggaaacacua cagcuggagc cucgguggcc uagcuucuug    60
ccccuugggc ucccccccag ccccuccucc ccuuccugca cccguacccc cguggucuuu   120
gaauaaaguc ugaguggggcg gc                                           142
```

<210> SEQ ID NO 180
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 180

```
ugauaauagg cuggagccuc gguggcucca uaaaguagga aacacuacac uagcuucuug    60
ccccuugggc ucccccccag ccccuccucc ccuuccugca cccguacccc cguggucuuu   120
gaauaaaguc ugaguggggcg gc                                           142
```

<210> SEQ ID NO 181
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 181

```
ugauaauagg cuggagccuc gguggccuag cuucuugccc cuuggccuc cauaaaguag     60 gaaacacuac auccccccag ccccuccucc ccuuccugca cccguacccc cguggucuuu   120
gaauaaaguc ugaguggggcg gc                                           142
```

<210> SEQ ID NO 182
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 182

```
ugauaauagg cuggagccuc gguggccuag cuucuugccc cuuggccuc ccccagccc     60 cucccccccu uccugcaccc guaccccac cccuaucaca auuagcauua aguggucuuu   120
gaauaaaguc ugaguggggcg gc                                           142
```

<210> SEQ ID NO 183
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183
ugauaauaga cccucuaucac aauuagcauu aagcuggagc cucgguggcc uagcuucuug      60 ccccuuggggc caccccuauc acaauuagca uuaauccccc cagccccucc ucccuuccu     120 gcacccguac ccccaccccu aucacaauua gcauuaagug gucuuugaau aaagucgag     180 ugggcggc                                                                188

<210> SEQ ID NO 184
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
ugauaauaga cccucuaucac aauuagcauu aagcuggagc cucgguggcc uagcuucuug      60 ccccuuggggc cuccauaaag uaggaaacac uacauccccc cagccccucc ucccuuccu     120 gcacccguac ccccaccccu aucacaauua gcauuaagug gucuuugaau aaagucgag     180 ugggcggc                                                                188

<210> SEQ ID NO 185
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
attgggcacc cgtaaggg                                                      18

<210> SEQ ID NO 186

<400> SEQUENCE: 186

000

<210> SEQ ID NO 187

<400> SEQUENCE: 187

000

<210> SEQ ID NO 188
<211> LENGTH: 66
<212> TYPE: RNA
<213> ORGANISM: Unknown
<220> FEATURE:
<221> NAME/KEY: source
<223> OTHER INFORMATION: /note="Description of Unknown:
      2A sequence"

<400> SEQUENCE: 188

```
ggaagcggag cuacuaacuu cagccugcug aagcaggcug gagacgugga ggagaacccu    60
ggaccu                                                              66

<210> SEQ ID NO 189

<400> SEQUENCE: 189

000

<210> SEQ ID NO 190
<211> LENGTH: 54
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
gggaaauaag agagaaaaga agaguaagaa gaaauauaag accccggcgc cacc          54

<210> SEQ ID NO 191
<211> LENGTH: 57
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
gggaaauaag agagaaaaga agaguaagaa gaaauauaag accccggcgc cgccacc       57

<210> SEQ ID NO 192
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192 gccrcc                                                               6

<210> SEQ ID NO 193
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193 gccgcc                                                               6

<210> SEQ ID NO 194
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
```

```
ccccggcgcc                                                          10

<210> SEQ ID NO 195
<211> LENGTH: 7
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195 ccccggc                                                             7

<210> SEQ ID NO 196
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
aggaaauaag agagaaaaga agaguaagaa gaaauauaag agccacc                 47

<210> SEQ ID NO 197
<211> LENGTH: 57
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
aggaaauaag agagaaaaga agaguaagaa gaaauauaag accccggcgc cgccacc      57

<210> SEQ ID NO 198
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 198
ugauaauagg cuggagccuc gguggccaug cuucuugccc cuugggccuc ccccagccc    60 cuccuccccu uccugcaccc guaccccca aacaccauug ucacaucca guggucuuug     120 aauaaagucu gagugggcgg c                                             141

<210> SEQ ID NO 199
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 199
ugauaauagg cuggagccuc gguggccuag cuucuugccc cuugggccuc ccccagccc    60 cuccuccccu uccugcaccc guaccccca aacaccauug ucacaucca guggucuuug     120
```

```
aauaaagucu gagugggcgg c                                                    141

<210> SEQ ID NO 200
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 200
uccggacuca gauccgggga ucucaaaauu gucgcuccug ucaaacaaac ucuuaacuuu   60
gauuuacuca aacuggcugg ggauguagaa agcaauccag gtccacuc              108

<210> SEQ ID NO 201
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 50-150
      nucleotides"

<400> SEQUENCE: 201
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa                                   150

<210> SEQ ID NO 202
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(120)
<223> OTHER INFORMATION: /note="This sequence may encompass 90-120
      nucleotides"

<400> SEQUENCE: 202
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa  120

<210> SEQ ID NO 203
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(130)
<223> OTHER INFORMATION: /note="This sequence may encompass 90-130
```

-continued nucleotides"

<400> SEQUENCE: 203
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa                                                            130

<210> SEQ ID NO 204
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 204
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa                           100

<210> SEQ ID NO 205
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Gly Gly Gly Ser
1

<210> SEQ ID NO 206
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 2-5 'Gly
      Gly Gly Ser' repeating units"

<400> SEQUENCE: 206

Gly Gly Gly Ser Gly Gly Gly Ser Gly Gly Gly Ser Gly Gly Gly Ser
1               5                   10                  15

Gly Gly Gly Ser
            20

<210> SEQ ID NO 207
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Gly Ser Gly Val Lys Gln Thr Leu Asn Phe Asp Leu Leu Lys Leu Ala
1               5                   10                  15

-continued

Gly Asp Val Glu Ser Asn Pro Gly Pro
            20                  25

<210> SEQ ID NO 208
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 209
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 210
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 211
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      2A sequence"

<400> SEQUENCE: 211

Asn Pro Gly Pro
1

<210> SEQ ID NO 212
<211> LENGTH: 30
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: misc_feature
<222> LOCATION: (1)..(30)
<223> OTHER INFORMATION: /note="This sequence may encompass 1-10 'ccg'
      repeating units

<400> SEQUENCE: 212
ccgccgccgc cgccgccgcc gccgccgccg                                          30

<210> SEQ ID NO 213
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(24)
<223> OTHER INFORMATION: /note="This sequence may encompass 2-8 'ccg'
      repeating units

<400> SEQUENCE: 213
ccgccgccgc cgccgccgcc gccg                                                24

<210> SEQ ID NO 214
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(18)
<223> OTHER INFORMATION: /note="This sequence may encompass 3-6 'ccg'
      repeating units

<400> SEQUENCE: 214
ccgccgccgc cgccgccg                                                       18

<210> SEQ ID NO 215
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(15)
<223> OTHER INFORMATION: /note="This sequence may encompass 4-5 'ccg'
      repeating units

<400> SEQUENCE: 215
ccgccgccgc cgccg                                                          15

<210> SEQ ID NO 216
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 216
ccgccgccgc cg                                                          12

<210> SEQ ID NO 217
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(30)
<223> OTHER INFORMATION: /note="This sequence may encompass 1-10 'gcc'
      repeating units

<400> SEQUENCE: 217
gccgccgccg ccgccgccgc cgccgccgcc                                       30

<210> SEQ ID NO 218
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218
tttttttttt tttttttttt tttttttttt tttttttttt tttttttttt tttttttttt     60
tttttttttt tttttttttt tttttttttt tttttttttt tttttttttt tttttttttt    120

<210> SEQ ID NO 219
<211> LENGTH: 354
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219
```

Met Val Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile

```
                    145                 150                 155                 160
Asn Gly Leu Ser Asp Leu Tyr His Pro Ile Gln Ile Leu Ala Asp Tyr
            165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
            195                 200                 205

Ala Lys Phe Gly Met His Leu Gln Ala Ala Thr Pro Lys Gly Tyr Glu
            210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                    245                 250                 255

Gly Asn Val Leu Ile Thr Asp Thr Trp Ile Ser Met Gly Gln Glu Glu
                    260                 265                 270

Glu Lys Lys Lys Arg Leu Gln Ala Phe Gln Gly Tyr Gln Val Thr Met
                    275                 280                 285

Lys Thr Ala Lys Val Ala Ala Ser Asp Trp Thr Phe Leu His Cys Leu
            290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                    325                 330                 335

Val Met Val Ser Leu Leu Thr Asp Tyr Ser Pro Gln Leu Gln Lys Pro
                    340                 345                 350

Lys Phe
```

<210> SEQ ID NO 220
<211> LENGTH: 354
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 220

```
Met Leu Ser Asn Leu Arg Ile Leu Leu Asn Asn Ala Ala Leu Arg Lys
1               5                   10                  15

Gly His Thr Ser Val Val Arg His Phe Trp Cys Gly Lys Pro Val Gln
                20                  25                  30

Asn Lys Val Gln Leu Lys Gly Arg Asp Leu Leu Thr Leu Lys Asn Phe
            35                  40                  45

Thr Gly Glu Glu Ile Lys Tyr Met Leu Trp Leu Ser Ala Asp Leu Lys
        50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
                100                 105                 110

Thr Gln Asp Ile His Leu Gly Val Asn Glu Ser Leu Thr Asp Thr Ala
            115                 120                 125

Arg Val Leu Ser Ser Met Ala Asp Ala Val Leu Ala Arg Val Tyr Lys
        130                 135                 140
```

-continued

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
                260                 265                 270

Glu Lys Lys Lys Arg Leu Gln Ala Phe Gln Gly Tyr Gln Val Thr Met
            275                 280                 285

Lys Thr Ala Lys Val Ala Ala Ser Asp Trp Thr Phe Leu His Cys Leu
290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

<210> SEQ ID NO 221
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 75-150
      nucleotides"

<400> SEQUENCE: 221
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                      150

<210> SEQ ID NO 222
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 85-150
      nucleotides"

<400> SEQUENCE: 222
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                     150

<210> SEQ ID NO 223
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 90-150
      nucleotides"

<400> SEQUENCE: 223
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                     150

<210> SEQ ID NO 224
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(15)
<223> OTHER INFORMATION: /note="This sequence may encompass 1-5 'ccg'
      repeating units

<400> SEQUENCE: 224
ccgccgccgc cgccg                                                      15

<210> SEQ ID NO 225
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
ccgccgccgc cgccg                                                      15

<210> SEQ ID NO 226
<211> LENGTH: 120
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 226
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
```